(12) United States Patent
Yoshimi et al.

(10) Patent No.: US 11,473,071 B2
(45) Date of Patent: Oct. 18, 2022

(54) METHOD FOR TREATING MUSCULAR DYSTROPHY BY TARGETING UTROPHIN GENE

(71) Applicants: ASTELLAS PHARMA INC., Tokyo (JP); MODALIS THERAPEUTICS CORPORATION, Tokyo (JP)

(72) Inventors: Eiji Yoshimi, Tokyo (JP); Katsuro Yoshioka, Tokyo (JP); Tetsuya Yamagata, Cambridge, MA (US); Yuanbo Qin, Cambridge, MA (US); Iain Robert Thompson, Cambridge, MA (US); Nidhi Khanna, Cambridge, MA (US)

(73) Assignees: ASTELLAS PHARMA INC., Tokyo (JP); MODALIS THERAPEUTICS CORPORATION, Tokyo (JP)

( * ) Notice: Subject to any disclaimer, the term of this patent is extended or adjusted under 35 U.S.C. 154(b) by 0 days.

(21) Appl. No.: 17/320,643

(22) Filed: May 14, 2021

(65) Prior Publication Data
US 2021/0355464 A1 Nov. 18, 2021

Related U.S. Application Data

(63) Continuation of application No. PCT/JP2019/045716, filed on Nov. 15, 2019.

(60) Provisional application No. 62/931,925, filed on Nov. 7, 2019, provisional application No. 62/861,039, filed on Jun. 13, 2019, provisional application No. 62/768,474, filed on Nov. 16, 2018.

(51) Int. Cl.
| | | |
|---|---|---|
| *C12N 9/22* | (2006.01) | |
| *C12N 15/113* | (2010.01) | |
| *C07K 14/47* | (2006.01) | |
| *C12N 15/11* | (2006.01) | |
| *A61K 48/00* | (2006.01) | |

(52) U.S. Cl.
CPC ............ *C12N 9/22* (2013.01); *C07K 14/4705* (2013.01); *C12N 15/11* (2013.01); *A61K 48/00* (2013.01); *C07K 2319/00* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | | |
|---|---|---|---|---|
| 2018/0163188 A1* | 6/2018 | Xie | .......... | C12N 15/86 |
| 2021/0102206 A1* | 4/2021 | Liao | .......... | C12N 9/22 |

FOREIGN PATENT DOCUMENTS

| | | |
|---|---|---|
| WO | WO 2009/044383 | 4/2009 |
| WO | WO 2013/176772 | 11/2013 |
| WO | WO 2014/197748 | 12/2014 |
| WO | WO 2015/018503 | 2/2015 |
| WO | WO 2017/049407 | 3/2017 |
| WO | WO 2017/139505 | 8/2017 |
| WO | WO 2018/148256 | 8/2018 |
| WO | WO 2018/169983 | 9/2018 |
| WO | WO 2018/204764 | 11/2018 |

OTHER PUBLICATIONS

Boyle et al., High-throughput biochemical profiling reveals sequence determinants of dCas9 off-target binding and unbinding (PNAS, 2017, 114:5461-5466) (Year: 2017).*
Yi-Li Min et al: "CRISPR Correction of Duchenne Muscular Dystrophy", Annual Review of Medicine, Oct. 31, 2018, pp. 239-255, XP055662016.
Wojtal Daria et al: "Spell Checking Nature: Versatility of CRISPR/Cas9 for Developing Treatments for Inherited Disorders", American Journal of Human Genetics, American Society of Human Genetics, vol. 98, No. 1, Dec. 10, 2015, pp. 90-101, XP029381495.
Yi-Li Min et al: "CRISPR Correction of Duchenne Muscular Dystrophy", Annual Review of Medicine : Selected Topics in the Clinicalsciences, vol. 70, No. 1, Jan. 27, 2019 (Jan. 27, 2019), pp. 239-255, XP055661993.
Sakamoto et al, "Micro-dystrophin cDNA ameliorates dystrophic phenotypes when introduced into mdx mice as a transgene", *Biochemical and Biophysical Research Communications* 293 (2002) 1265-1272.
Gilbert et al, "Adenovirus-Mediated Utrophin Gene Transfer Mitigates the Dystrophic Phenotype of mdx Mouse Muscles", *Human Gene Therapy*, 10 (1999) :1299-1310.
Liao et al, "In Vivo Target Gene Activation via CRISPR/Cas9-Mediated Trans-epigenetic Modulation", *Cell* 171 (2017) 1495-1507.
Dominguez et al, "Beyond editing: repurposing CRISPR-Cas9 for precision genome regulation and interrogation", *Nature*, 17 (2016) 5-15.

(Continued)

*Primary Examiner* — Arthur S Leonard
(74) *Attorney, Agent, or Firm* — Oblon, McClelland, Maier & Neustadt, L.L.P.

(57) ABSTRACT

Polynucleotides comprising the following base sequences:
(a) a base sequence encoding a fusion protein of a nuclease-deficient CRISPR effector protein and a transcription activator, and
(b) a base sequence encoding a guide RNA targeting a continuous region of 18 to 24 nucleotides in length in a region set forth in SEQ ID NO: 104, 105, 135, 141, 153, 167, or 172 in the expression regulatory region of human Utrophin gene
are expected to be useful for treating or preventing DUCHENNE muscular dystrophy or BECKER muscular dystrophy.

17 Claims, 17 Drawing Sheets

Specification includes a Sequence Listing.

(56) References Cited

OTHER PUBLICATIONS

Office Action dated Jan. 4, 2022, in JP patent application No. 2021-551108, with English translation—9 pages.
Search Report dated Feb. 10, 2020, in international application No. PCT/JP2019/045716, 6 pages.
Written Opinion of the International Searching Authority dated Feb. 10, 2020, in International application No. PCT/JP2019/045716, 11 pages.
Suhani Vora et al: "Rational design of a compact CRISPR-Cas9 activator for AAV-mediated delivery", bioRxiv, Apr. 15, 2018, XP055657794 34 pages.
Kenji Lim et al: "Applications of CRISPR/Cas9 for the Treatment of Duchenne Muscular Dystrophy", Journal of Personalized Medicine, vol. 8, No. 4, Nov. 24, 2018, p. 38, XP055661985 20 pages.

* cited by examiner

Figure 8

Experimental setup for single sgRNA and combinations thereof

5 targeting sequences

| Guide# | Cyno match | Target |
|---:|---|---|
| 145 | Yes | Enhancer (E2) |
| 146 | Yes | Enhancer (E2) |
| 205 | No | Promoter (P1) |
| 208 | Yes | Promoter (P1) |
| 210 | No | Promoter (P1) |

Combinations

| combos | Cyno match | Target |
|---|---|---|
| 205+145 | No | Enhancer (E2) + Promoter (P1) |
| 208+145 | Yes | Enhancer (E2) + Promoter (P1) |
| 210+145 | No | Enhancer (E2) + Promoter (P1) |
| 205+146 | No | Enhancer (E2) + Promoter (P1) |
| 208+146 | Yes | Enhancer (E2) + Promoter (P1) |
| 210+146 | No | Enhancer (E2) + Promoter (P1) |

UTRN upregulation in 5 HSMM donors - single sgRNA vs combinations thereof

METHOD FOR TREATING MUSCULAR DYSTROPHY BY TARGETING UTROPHIN GENE

CROSS REFERENCE TO RELATED APPLICATIONS

The present application is a Continuation of International Application No. PCT/JP2019/045716, filed Nov. 15, 2019, which claims the benefit of U.S. Provisional Patent Application No. 62/768,474, filed on Nov. 16, 2018, U.S. Provisional Patent Application No. 62/861,039, filed on Jun. 13, 2019, and U.S. Provisional Patent Application No. 62/931,925, filed on Nov. 7, 2019, the contents of each of which are incorporated herein by reference in their entireties.

BACKGROUND OF THE INVENTION

FIELD OF THE INVENTION

The present invention relates to methods for treating muscular dystrophy by targeting the human Utrophin (UTRN) gene, and the like. More particularly, the present invention relates to methods and agents for treating or preventing muscular dystrophy by activating expression of human UTRN gene by using a guide RNA targeting a particular sequence of human UTRN gene and a fusion protein of a transcription activator and a CRISPR effector protein, and the like.

DISCUSSION OF THE BACKGROUND

Muscular dystrophy is a generic term for hereditary diseases associated with progressive muscular atrophy and muscle weakness. Among muscular dystrophies, those caused by mutation of the dystrophin gene on the X chromosome include DUCHENNE muscular dystrophy (DMD) and its mild type, BECKER muscular dystrophy (BMD).

DMD is the most frequent hereditary progressive muscular disease that one in about 3,500 newborn males develops. The clinical symptoms thereof include muscle weakness from around 2 to 5 years of age, progression of muscle weakness thereafter, abasia by about 10 years of age, and death in the twenties due to cardiac failure or respiratory failure (see WO 2009/044383, which is incorporated herein by reference in its entirety).

It is known that DMD is caused by a mutation in the dystrophin gene. The dystrophin gene is present on the X chromosome, and is a huge gene consisting of about 2.2 million bases of DNA. It is transcribed from DNA to mRNA precursor, introns are further removed by splicing, and mRNA composed of 79 exons is produced (about 14kb). This mRNA is translated into 3685 amino acids to generate dystrophin protein. Dystrophin protein is involved in the maintenance of membrane stability of muscle cells. In DMD patients, since the mutation occurs in the dystrophin gene, the dystrophin protein is hardly expressed and the structure of the muscle cell cannot be maintained, thus leading to muscle weakness.

BMD is also caused by mutation in dystrophin gene; however, the symptoms thereof are generally mild compared to DMD. The difference between the clinical symptoms of DMD and BMD is based on that functional dystrophin protein is hardly expressed in DMD whereas incomplete but functional dystrophin protein is produced in BMD.

Even now, there is no effective drug as causal therapy for muscular dystrophy and symptomatic therapies such as administration of steroid are performed. A plurality of therapeutic strategies have been proposed to treat DMD and BMD, and the gene therapy approach has been attracting attention as one of the strategies. The purpose of gene therapy is to achieve expression of normal dystrophin protein by supplementing normal dystrophin gene to muscle cells having mutation. However, the full-length dystrophin cDNA is relatively large with a length of about 14 kb; therefore the size limitation of DNA that can be packaged may be a problem for certain vectors like adeno-associated virus (AAV) vector. As one solution to this problem, a method using a truncated dystrophin gene (mini/microdystrophin gene) which has a minimum functional domain has been proposed (see Sakamoto M. et al., Biochem Biophys Res Commun. 2002 May 17; 293(4):1265-72, which is incorporated herein by reference in its entirety). In view of the possibility of an immune response being induced by the introduction of dystrophin into DMD patients who lack dystrophin, a means using utrophin (sometimes also described as "Utrophin", "UTRN" etc. in the present specification) for reducing this immune response has also been reported (see Gilbert R. et al., Hum Gene Ther. 1999 May 20; 10(8):1299-310, which is incorporated herein by reference in its entirety). Utrophin is a cytoskeletal protein highly homologous to dystrophin, and is present in normal and DMD muscle, albeit at a low level. Utrophin cDNA is very large (over 10 kb) as with dystrophin. Utrophin is also known to be able to compensate the muscle cell membrane stabilizing function of dystrophin (see Gilbert R. et al., Hum Gene Ther. 1999 May 20; 10(8):1299-310 and Liao H. et al., Cell. 2017 Dec 14; 171(7): 1495-507, which are incorporated herein by reference in their entireties).

As a gene therapy targeting utrophin, for example, WO2015/018503 discloses an invention directed to a recombinant adeno-associated virus (AAV) vector for expression of a gene in skeletal or cardiac muscle tissue, comprising a muscle-specific promoter and a gene encoding a fusion protein, wherein said fusion protein comprises:
a) a transcriptional activation element and
b) a DNA binding element,
wherein said fusion protein, when expressed in said skeletal or cardiac muscle tissue, is capable of increasing utrophin expression (see WO2015/018503, which is incorporated herein by reference in its entirety). In the invention, zinc finger protein is used as a DNA binding element.

On the other hand, a system using a combination of Cas9 with deactivated nuclease activity (dCas9) and a transcription activation domain or transcription repression domain has been developed in recent years, in which expression of a target gene is controlled through targeting of the protein to the gene by using guide RNA and without cleaving DNA sequence of the gene (WO2013/176772, which is incorporated herein by reference in its entirety). Its clinical application is expected (see Dominguez A. et al., Nat Rev Mol Cell Biol. 2016 January; 17(1): 5-15, which is incorporated herein by reference in its entirety). However, a problem exists in that a sequence encoding a complex of dCas9, guide RNA and a co-transcription activator exceeds the capacity of the most common viral vectors (e.g., AAV), which represent the most promising method for gene delivery in vivo (see Liao H. et al., Cell. 2017 Dec 14; 171(7): 1495-507, which is incorporated herein by reference in its entirety).

In 2017, it was reported that (a) by administration of AAV carrying a guide RNA targeting mouse UTRN and inhibiting the DNA cleavage ability of Cas9 (dgUtrn) and a transcription activation domain to DMD model mouse (mdx mouse) into which Cas9 gene was introduced, the expression level of UTRN was increased and grip strength was also improved, and (b) by co-injection of AAV carrying Cas9 and AAV carrying the aforementioned dgUtrn and a transcription activation domain to mdx mouse, grip strength was improved (see Liao H. et al., Cell. 2017 Dec 14; 171(7): 1495-507, which is incorporated herein by reference in its entirety).

SUMMARY OF THE INVENTION

Accordingly, it is one object of the present invention to provide novel therapeutic approaches to muscular dystrophy (particularly, DMD and BMD).

This and other objects, which will become apparent during the following detailed description, have been achieved by the inventors' discovery that the expression of human UTRN gene (Gene ID:7402) can be strongly activated by using a guide RNA targeting a particular sequence of human UTRN gene and a fusion protein of a transcription activator and a nuclease-deficient CRISPR effector protein. In addition, the present inventors have found that the expression of human UTRN gene can be strongly activated by a single AAV vector carrying a base sequence encoding the fusion protein and a base sequence encoding the guide RNA, using a compact nuclease-deficient CRISPR effector protein and a compact transcription activator.

Thus, the present invention provides:

(1) A polynucleotide comprising the following base sequences:

(a) a base sequence encoding a fusion protein of a nuclease-deficient CRISPR effector protein and a transcription activator, and (b) a base sequence encoding a guide RNA targeting a continuous region of 18 to 24 nucleotides in length in a region set forth in SEQ ID NO: 104, 105, 135, 141, 153, 167, or 172 in the expression regulatory region of human Utrophin gene.

(2) The polynucleotide of (1), wherein the base sequence encoding the guide RNA comprises the base sequence set forth in SEQ ID NO: 45, 46, 58, 59, 60, 135, 141, 153, 155, 156, 157, 159, 167, or 172, or the base sequence set forth in SEQ ID NO: 45, 46, 58, 59, 60, 135, 141, 153, 155, 156, 157, 159, 167, or 172 in which 1 to 3 bases are deleted, substituted, inserted, and/or added.

(3) The polynucleotide of (1) or (2), comprising at least two different base sequences encoding the guide RNA.

(4) The polynucleotide of any of (1) to (3), wherein the transcription activator is a peptide comprising VP64 and a transcription activation domain of RTA. (5) The polynucleotide of (4), wherein the transcription activator comprises an amino acid sequence set forth in SEQ ID NO: 117, or an amino acid sequence which is at least 90% identical to the amino acid sequence set forth in SEQ ID NO: 117.

(6) The polynucleotide of any of (1) to (5), wherein the nuclease-deficient CRISPR effector protein is dCas9.

(7) The polynucleotide of (6), wherein the dCas9 is derived from *Staphylococcus aureus*.

(8) The polynucleotide of any of (1) to (7), further comprising a promoter sequence for the base sequence encoding the guide RNA and/or a promoter sequence for the base sequence encoding the fusion protein of the nuclease-deficient CRISPR effector protein and the transcription activator.

(9) The polynucleotide of (8), wherein the promoter sequence for the base sequence encoding the guide RNA is selected from the group U6 promoter, SNR6 promoter, SNR52 promoter, SCR1 promoter, RPR1 promoter, U3 promoter, and H1 promoter.

(10) The polynucleotide of (8) or (9), wherein the promoter sequence for the base sequence encoding the fusion protein of the nuclease-deficient CRISPR effector protein and the transcription activator is selected from the group EFS promoter, EF-1a promoter, CMV promoter, CK8 promoter, MHC promoter, Des promoter, CAG promoter and MYOD promoter.

(11) The polynucleotide of any of (8) to (10),
wherein the base sequence encoding the guide RNA comprises the base sequence set forth in SEQ ID NO: 45, 46, or 59, or the base sequence set forth in SEQ ID NO: 45, 46, or 59 in which 1 to 3 bases are deleted, substituted, inserted, and/or added, the transcription activator comprises an amino acid sequence set forth in SEQ ID NO: 117, or an amino acid sequence which is at least 90% identical to the amino acid sequence set forth in SEQ ID NO: 117, the nuclease-deficient CRISPR effector protein is dCas9 derived from *Staphylococcus aureus*, the promoter sequence for the base sequence encoding the guide RNA is U6 promoter, and the promoter sequence for the base sequence encoding the fusion protein of the nuclease-deficient CRISPR effector protein and the transcription activator is CK8 promoter.

(12) The polynucleotide of (11),
wherein the base sequence encoding the guide RNA comprises the base sequence set forth in SEQ ID NO: 59, or the base sequence set forth in SEQ ID NO: 59 in which 1 to 3 bases are deleted, substituted, inserted, and/or added.

(13) A vector comprising a polynucleotide of any of (1) to (12).

(14) The vector of (13), wherein the vector is a plasmid vector or a viral vector.

(15) The vector of (14), wherein the viral vector is selected from the group consisting of adeno-associated virus (AAV) vector, adenovirus vector, and lentivirus vector.

(16) The vector of (15), wherein the AAV vector is selected from the group consisting of AAV1, AAV2, AAV6, AAV7, AAV8, AAV9, $AAV_{587}MTP$, $AAV_{588}MTP$, AAV-B1, AAVM41, AAVrh74, AAVS1_P1, and AAVS10_P1.

(17) The vector of (16), wherein the AAV vector is AAV9.

(18) A pharmaceutical composition comprising a polynucleotide of any of (1) to (12) or a vector of any of (13) to (17).

(19) The pharmaceutical composition of (18) for treating or preventing DUCHENNE muscular dystrophy or BECKER muscular dystrophy.

(20) A method for treating or preventing DUCHENNE muscular dystrophy or BECKER muscular dystrophy, comprising administering a polynucleotide of any of (1) to (12) or a vector of any of (13) to (17) to a subject in need thereof.

(21) Use of a polynucleotide of any of (1) to (12) or a vector of any of (13) to (17) for the treatment or prevention of DUCHENNE muscular dystrophy or BECKER muscular dystrophy.

(22) Use of a polynucleotide of any of (1) to (12) or a vector of any of (13) to (17) in the manufacture of a pharmaceutical composition for the treatment or prevention of DUCHENNE muscular dystrophy or BECKER muscular dystrophy.

(23) A ribonucleoprotein comprising the following:

(c) a fusion protein of a nuclease-deficient CRISPR effector protein and a transcription activator, and (d) a guide RNA targeting a continuous region of 18 to 24 nucleotides in length in a region set forth in SEQ ID NO: 104, 105, 135, 141, 153, 167, or 172 in the expression regulatory region of human Utrophin gene.

(24) The ribonucleoprotein of (23), wherein the guide RNA comprises the base sequence set forth in SEQ ID NO: 194, 195, 196, 197, 198, 199, 200, 201, 202, 203, 204, 205, 206 or 207, or the base sequence set forth in SEQ ID NO: 194, 195, 196, 197, 198, 199, 200, 201, 202, 203, 204, 205, 206 or 207 in which 1 to 3 bases are deleted, substituted, inserted, and/or added.

(25) The ribonucleoprotein of (23) or (24), wherein the transcription activator is a peptide comprising VP64 and a transcription activation domain of RTA.

(26) The ribonucleoprotein of (25), wherein the transcription activator comprises an amino acid sequence set forth in SEQ ID NO: 117, or an amino acid sequence which is at least 90% identical to the amino acid sequence set forth in SEQ ID NO: 117.

(27) The ribonucleoprotein of any of (23) to (26), wherein the nuclease-deficient CRISPR effector protein is dCas9.

(28) The ribonucleoprotein of (27), wherein the dCas9 is derived from *Staphylococcus aureus*.

(29) The ribonucleoprotein of any of (23) to (28), wherein the guide RNA comprises the base sequence set forth in SEQ ID NO: 194, 195, or 197, or the base sequence set forth in SEQ ID NO: 194, 195, or 197 in which 1 to 3 bases are deleted, substituted, inserted, and/or added,
wherein the transcription activator comprises an amino acid sequence set forth in SEQ ID NO: 117, or an amino acid sequence which is at least 90% identical to the amino acid sequence set forth in SEQ ID NO: 117, and
wherein the nuclease-deficient CRISPR effector protein is dCas9 derived from *Staphylococcus aureus*.

(30) The ribonucleoprotein of (29), wherein the guide RNA comprises the base sequence set forth in SEQ ID NO: 197, or the base sequence set forth in SEQ ID NO: 197 in which 1 to 3 bases are deleted, substituted, inserted, and/or added. (31) A composition or kit comprising the following for activation of the expression of the human Utrophin gene:

(e) a fusion protein of a nuclease-deficient CRISPR effector protein and a transcription activator, or a polynucleotide encoding the fusion protein, and (f) a guide RNA targeting a continuous region of 18 to 24 nucleotides in length in a region set forth in SEQ ID NO: 104, 105, 135, 141, 153, 167, or 172 in the expression regulatory region of human Utrophin gene, or a polynucleotide encoding the guide RNA.

(32) The composition or kit of (31), wherein the guide RNA comprises the base sequence set forth in SEQ ID NO: 194, 195, 196, 197, 198, 199, 200, 201, 202, 203, 204, 205, 206 or 207, or the base sequence set forth in SEQ ID NO: 194, 195, 196, 197, 198, 199, 200, 201, 202, 203, 204, 205, 206 or 207 in which 1 to 3 bases are deleted, substituted, inserted, and/or added.

(33) The composition or kit of (31) or (32), comprising at least two different guide RNAs.

(34) The composition or kit of any of (31) to (33), wherein the transcription activator is a peptide comprising VP64 and a transcription activation domain of RTA.

(35) The composition or kit of (34), wherein the transcription activator comprises an amino acid sequence set forth in SEQ ID NO: 117, or an amino acid sequence which is at least 90% identical to the amino acid sequence set forth in SEQ ID NO: 117.

(36) The composition or kit of any of (31) to (35), wherein the nuclease-deficient CRISPR effector protein is dCas9.

(37) The composition or kit of (36), wherein the dCas9 is derived from *Staphylococcus aureus*.

(38) The composition or kit of any of (31) to (37),
wherein the composition or kit comprises a polynucleotide encoding the fusion protein and a polynucleotide encoding the guide RNA and
wherein the polynucleotide encoding the fusion protein further comprises a promoter sequence for the fusion protein and/or the polynucleotide encoding the guide RNA further comprises a promoter sequence for the guide RNA.

(39) The composition or kit of (38), wherein the promoter sequence for the guide RNA is selected from the group U6 promoter, SNR6 promoter, SNR52 promoter, SCR1 promoter, RPR1 promoter, U3 promoter, and H1 promoter.

(40) The composition or kit of (38) or (39), wherein the promoter sequence for the fusion protein is selected from the group EFS promoter, EF-1α promoter, CMV promoter, CK8 promoter, MHC promoter, Des promoter, CAG promoter and MYOD promoter.

(41) The composition or kit of any of (38) to (40), wherein the guide RNA comprises the base sequence set forth in SEQ ID NO: 194, 195, or 197, or the base sequence set forth in SEQ ID NO: 194, 195, or 197 in which 1 to 3 bases are deleted, substituted, inserted, and/or added,
wherein the transcription activator comprises an amino acid sequence set forth in SEQ ID NO: 117, or an amino acid sequence which is at least 90% identical to the amino acid sequence set forth in SEQ ID NO: 117,
wherein the nuclease-deficient CRISPR effector protein is dCas9 derived from *Staphylococcus aureus*,
wherein the promoter sequence for the guide RNA is U6 promoter, and
wherein the promoter sequence for the fusion protein is CK8 promoter.

(42) The composition or kit of (41), wherein the guide RNA comprises the base sequence set forth in SEQ ID NO: 197, or the base sequence set forth in SEQ ID NO: 197 in which 1 to 3 bases are deleted, substituted, inserted, and/or added.

(43) A method for treating or preventing DUCHENNE muscular dystrophy or BECKER muscular dystrophy, comprising administering the following (e) and (f):

(e) a fusion protein of a nuclease-deficient CRISPR effector protein and a transcription activator, or a polynucleotide encoding the fusion protein, and (f) a guide RNA targeting a continuous region of 18 to 24 nucleotides in length in a region set forth in SEQ ID NO: 104, 105, 135, 141, 153, 167, or 172 in the expression regulatory region of human Utrophin gene, or a polynucleotide encoding the guide RNA.

(44) The method of (43), wherein the guide RNA comprises the base sequence set forth in SEQ ID NO: 194, 195, 196, 197, 198, 199, 200, 201, 202, 203, 204, 205, 206 or 207, or the base sequence set forth in SEQ ID NO: 194, 195, 196, 197, 198, 199, 200, 201, 202, 203, 204, 205, 206 or 207 in which 1 to 3 bases are deleted, substituted, inserted, and/or added, or a polynucleotide encoding the guide RNA.

(45) The method of (43) or (44), comprising at least two different guide RNAs.

(46) The method of any of (43) to (45), wherein the transcription activator is a peptide comprising VP64 and a transcription activation domain of RTA.

(47) The method of (46), wherein the transcription activator comprises an amino acid sequence set forth in SEQ ID NO: 117, or an amino acid sequence which is at least 90% identical to the amino acid sequence set forth in SEQ ID NO: 117.

(48) The method of any of (43) to (47), wherein the nuclease-deficient CRISPR effector protein is dCas9.

(49) The method of (48), wherein the dCas9 is derived from *Staphylococcus aureus*.

(50) The method of any of (43) to (49),
wherein the method comprises administering a polynucleotide encoding the fusion protein and a polynucleotide encoding the guide RNA and
wherein the polynucleotide encoding the fusion protein further comprises a promoter sequence for the fusion protein and/or the polynucleotide encoding the guide RNA further comprises a promoter sequence for the guide RNA.

(51) The method of (50), wherein the promoter sequence for the guide RNA is selected from the group U6 promoter, SNR6 promoter, SNR52 promoter, SCR1 promoter, RPR1 promoter, U3 promoter, and H1 promoter.

(52) The method of (50) or (51), wherein the promoter sequence for the fusion protein is selected from the group EFS promoter, EF-1a promoter, CMV promoter, CK8 promoter, MHC promoter, Des promoter, CAG promoter and MYOD promoter.

(53) The method of any of (50) to (52), wherein the guide RNA comprises the base sequence set forth in SEQ ID NO: 194, 195, or 197, or the base sequence set forth in SEQ ID NO: 194, 195, or 197 in which 1 to 3 bases are deleted, substituted, inserted, and/or added,
wherein the transcription activator comprises an amino acid sequence set forth in SEQ ID NO: 117, or an amino acid sequence which is at least 90% identical to the amino acid sequence set forth in SEQ ID NO: 117,
wherein the nuclease-deficient CRISPR effector protein is dCas9 derived from *Staphylococcus aureus*,
wherein the promoter sequence for the guide RNA is U6 promoter, and
wherein the promoter sequence for the fusion protein is CK8 promoter.

(54) The method of (53), wherein the guide RNA comprises the base sequence set forth in SEQ ID NO: 197, or the base sequence set forth in SEQ ID NO: 197 in which 1 to 3 bases are deleted, substituted, inserted, and/or added.

(55) Use of the following (e) and (f):
(e) a fusion protein of a nuclease-deficient CRISPR effector protein and a transcription activator, or a polynucleotide encoding the fusion protein, and
(f) a guide RNA targeting a continuous region of 18 to 24 nucleotides in length in a region set forth in SEQ ID NO: 104, 105, 135, 141, 153, 167, or 172 in the expression regulatory region of human Utrophin gene, or a polynucleotide encoding the guide RNA,
in the manufacture of a pharmaceutical composition for the treatment or prevention of DUCHENNE muscular dystrophy or BECKER muscular dystrophy.

(56) The use of (55), wherein the guide RNA comprises the base sequence set forth in SEQ ID NO: 194, 195, 196, 197, 198, 199, 200, 201, 202, 203, 204, 205, 206 or 207, or the base sequence set forth in SEQ ID NO: 194, 195, 196, 197, 198, 199, 200, 201, 202, 203, 204, 205, 206 or 207 in which 1 to 3 bases are deleted, substituted, inserted, and/or added.

(57) The use of (55) or (56), comprising at least two different guide RNAs.

(58) The use of any of (55) to (57), wherein the transcription activator is a peptide comprising VP64 and a transcription activation domain of RTA.

(59) The use of (58), wherein the transcription activator comprises an amino acid sequence set forth in SEQ ID NO: 117, or an amino acid sequence which is at least 90% identical to the amino acid sequence set forth in SEQ ID NO: 117.

(60) The use of any of (55) to (59), wherein the nuclease-deficient CRISPR effector protein is dCas9.

(61) The use of (60), wherein the dCas9 is derived from *Staphylococcus aureus*.

(62) The use of any of (55) to (61),
wherein the use comprises use of a polynucleotide encoding the fusion protein and use of a polynucleotide encoding the guide RNA and
wherein the polynucleotide encoding the fusion protein further comprises a promoter sequence for the fusion protein and/or the polynucleotide encoding the guide RNA further comprises a promoter sequence for the guide RNA.

(63) The use of (62), wherein the promoter sequence for the guide RNA is selected from the group U6 promoter, SNR6 promoter, SNR52 promoter, SCR1 promoter, RPR1 promoter, U3 promoter, and H1 promoter.

(64) The use of (62) or (63), wherein the promoter sequence for the fusion protein is selected from the group EFS promoter, EF-1a promoter, CMV promoter, CK8 promoter, MHC promoter, Des promoter, CAG promoter, and MYOD promoter.

(65) The use of any of (62) to (64), wherein the guide RNA comprises the base sequence set forth in SEQ ID NO: 194, 195, or 197, or the base sequence set forth in SEQ ID NO: 194, 195, or 197 in which 1 to 3 bases are deleted, substituted, inserted, and/or added,
wherein the transcription activator comprises an amino acid sequence set forth in SEQ ID NO: 117, or an amino acid sequence which is at least 90% identical to the amino acid sequence set forth in SEQ ID NO: 117,
wherein the nuclease-deficient CRISPR effector protein is dCas9 derived from *Staphylococcus aureus*,
wherein the promoter sequence for the guide RNA is U6 promoter, and
wherein the promoter sequence for the fusion protein is CK8 promoter.

(66) The use of (65), wherein the guide RNA comprises the base sequence set forth in SEQ ID NO: 197, or the base sequence set forth in SEQ ID NO: 197 in which 1 to 3 bases are deleted, substituted, inserted, and/or added.

Effect of the Invention

According to the present invention, the expression of the human Utrophin gene can be activated and, consequently, the present invention is expected to be able to treat DMD and BMD.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

In FIG. 1, the lower panel shows activation of human UTRN gene expression by using a combination of sgRNA comprising crRNA coded by the targeting sequences set forth in SEQ ID NOs: 129 to 152 and 3 kinds of different dSaCas9-transcription activator fusion proteins (dSaCas9-VP64 (SEQ ID NO: 188), dSaCas9-VPH (SEQ ID NO: 189), dSaCas9-VPR (SEQ ID NO: 190)) in HEK293FT cells (N=3. error bar shows standard deviation). When sgRNAs that specifically bind to a region comprising Guide #sgED3-6 and sgED3-7 (SEQ ID NOs: 134 and 135) (region A) and the other region comprising Guide #sgED3-13 (SEQ ID NO: 141) (region B) were used respectively, expression of human UTRN gene was strongly activated as compared to the case in which control sgRNA was used. The activation effect was the strongest when dSaCas9-VPR fusion protein was used out of 3 kinds of dSaCas9-transcription activator fusion proteins.

In FIG. 2, the lower panel shows activation of human UTRN gene expression by using a combination of sgRNA comprising crRNA coded by the targeting sequences Guide #sgED3-6, sgED3-13, sgED3-25 to sgED3-48 (SEQ ID NOs: 134, 141, 153 to 176) and dSaCas9-VPR in HEK293FT cells (N=3. error bar shows standard deviation). When sgRNAs that specifically bind to a region comprising the targeting sequences Guide #sgED3-6, sgED3-13, sgED3-25 to sgED3-32, sgED3-39, sgED3-40, sgED3-44 (SEQ ID NOs: 134, 141, 153 to 160, 167, 168, and 172) were used respectively, human UTRN gene expression was activated not less than two times as compared to the case in which the control sgRNA was used.

In FIG. 8, the upper panel shows homology with cynomolgus monkey (*Macaca fascicularis*) and located region of the 5 targeting sequences Guide #145, 146, 205, 208, 210 (SEQ ID NOs: 45, 46, 58, 59, and 60) respectively. The lower panel shows combinations of the 5 targeting sequences, their homology with cynomolgus monkey and located region.

DETAILED DESCRIPTION OF THE PREFERRED EMBODIMENTS

Figure 1:
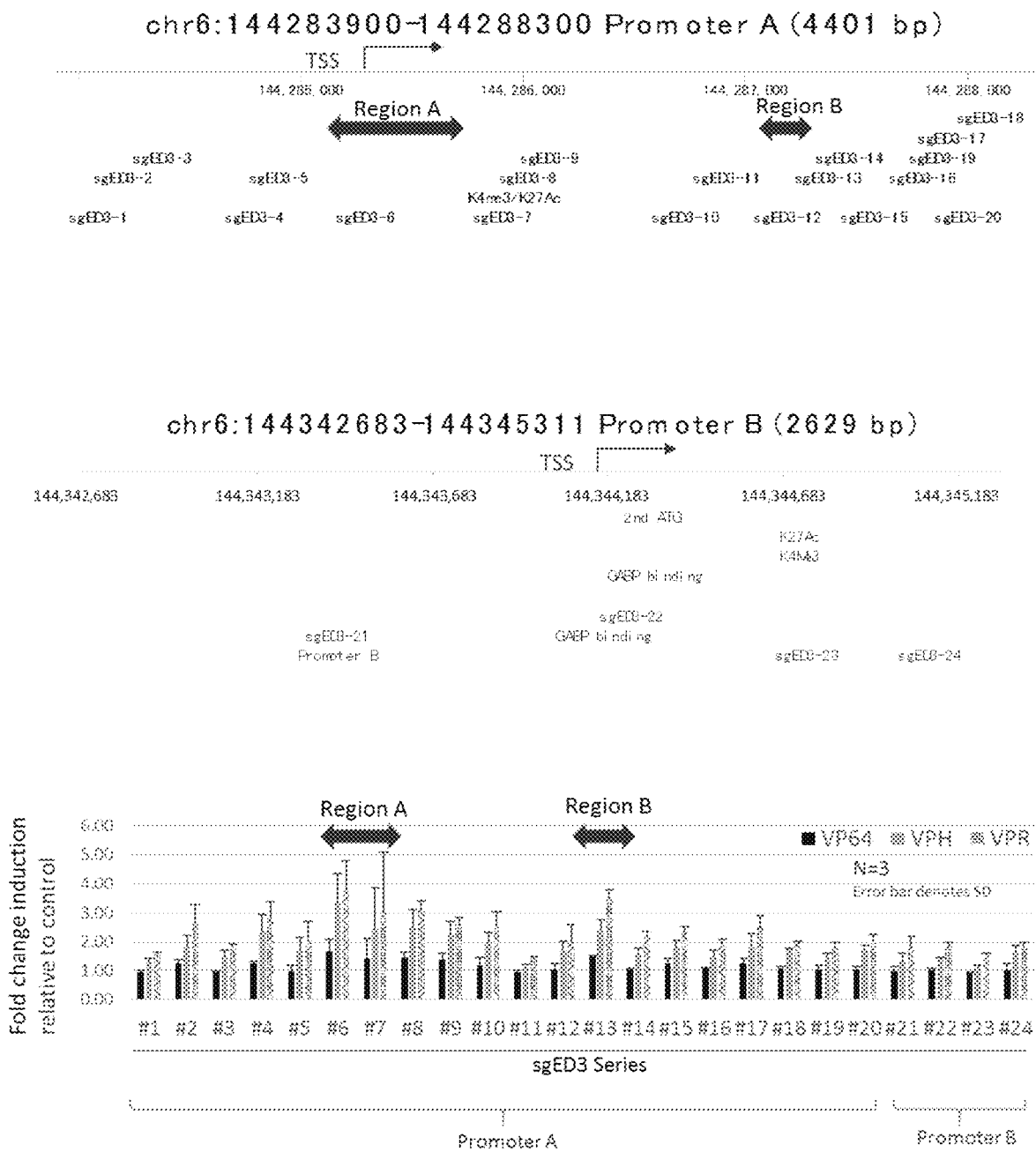
In FIG. 1, the upper panel shows the region of promoter A in human UTRN gene, and the middle panel shows the region of promoter B, and the positions of the 24 targeting sequences (Guide #sgED3-1 to sgED3-24 (SEQ ID NOs: 129 to 152)) determined in respective regions are shown.

The embodiments of the present invention are explained in detail below.

1. Polynucleotide

The present invention provides a polynucleotide comprising the following base sequences (hereinafter sometimes to be also referred to as "the polynucleotide of the present invention"):

(a) a base sequence encoding a fusion protein of a nuclease-deficient CRISPR effector protein and a transcription activator, and (b) a base sequence encoding a guide RNA targeting a continuous region of 18 to 24 nucleotides (i.e., 18 to 24 contiguous nucleotides) in length in a region set forth in SEQ ID NO: 104, 105, 135, 141, 153, 167, or 172 in the expression regulatory region of human Utrophin gene.

The polynucleotide of the present invention is introduced into a desired cell and transcribed to produce a fusion protein of a nuclease-deficient CRISPR effector protein and a transcription activator, and a guide RNA targeting a particular region of the expression regulatory region of the human UTRN gene. These fusion protein and guide RNA form a complex (hereinafter the complex is sometimes referred to as "ribonucleoprotein; RNP") and cooperatively act on the aforementioned particular region, thus activating transcription of the human UTRN gene.

(1) Definition

In the present specification, "the expression regulatory region of human Utrophin (UTRN) gene" means any region in which the expression of human UTRN gene can be activated by binding RNP to that region. That is, the expression regulatory region of human UTRN gene may exist in any region such as the promoter region, enhancer region, intron, and exon of the human UTRN gene, as long as the expression of the human UTRN gene is activated by the binding of RNP. In the present specification, when the expression regulatory region is shown by the particular sequence, the expression regulatory region includes both the sense strand sequence and the antisense strand sequence conceptually.

In the present invention, a fusion protein of a nuclease-deficient CRISPR effector protein and a transcription activator is recruited by a guide RNA into a particular region in the expression regulatory region of the human UTRN gene. In the present specification, the "guide RNA targeting . . . " means a "guide RNA recruiting a fusion protein into . . . ".

In the present specification, the "guide RNA (to be also referred to as 'gRNA')" is an RNA comprising a genome specific CRISPR-RNA (to be referred to as "crRNA"). crRNA is an RNA that binds to a complementary sequence of a targeting sequence (described later). When Cpf1 is used as the CRISPR effector protein, the "guide RNA" refers to an RNA comprising an RNA consisting of crRNA and a specific sequence attached to its 5'-terminal (for example, an RNA sequence set forth in SEQ ID NO: 106 in the case of FnCpf 1). When Cas9 is used as the CRISPR effector protein, the "guide RNA" refers to chimera RNA (to be referred to as "single guide RNA(sgRNA)") comprising crRNA and trans-activating crRNA attached to its 3'-terminal (to be referred to as "tracrRNA") (see, for example, Zhang F. et al., Hum Mol Genet. 2014 Sep. 15; 23(R1): R40-6 and Zetsche B. et al., Cell. 2015 Oct. 22; 163(3): 759-71, which are incorporated herein by reference in their entireties).

In the present specification, a sequence complementary to the sequence to which crRNA is bound in the expression regulatory region of the human UTRN gene is referred to as a "targeting sequence". That is, in the present specification, the "targeting sequence" is a DNA sequence present in the expression regulatory region of the human UTRN gene and adjacent to PAM (protospacer adjacent motif). PAM is adjacent to the 5'-side of the targeting sequence when Cpf1 is used as the CRISPR effector protein. PAM is adjacent to the 3'-side of the targeting sequence when Cas9 is used as the CRISPR effector protein. The targeting sequence may be present on either the sense strand sequence side or the antisense strand sequence side of the expression regulatory region of the human UTRN gene (see, for example, the aforementioned Zhang F. et al., Hum Mol Genet. 2014 Sep. 15; 23(R1): R40-6 and Zetsche B. et al., Cell. 2015 Oct. 22; 163(3): 759-71, which are incorporated herein by reference in their entireties).

(2) Nuclease-Deficient CRISPR Effector Protein

In the present invention, using a nuclease-deficient CRISPR effector protein, a transcriptional activator fused thereto is recruited to the expression regulatory region of the human UTRN gene. The nuclease-deficient CRISPR effector protein (hereinafter to be simply referred to as "CRISPR effector protein") to be used in the present invention is not particularly limited as long as it forms a complex with gRNA and is recruited to the expression regulatory region of the human UTRN gene. For example, nuclease-deficient Cas9 (hereinafter sometimes to be also referred to as "dCas9") or nuclease-deficient Cpf1 (hereinafter sometimes to be also referred to as "dCpf1") can be included.

Examples of the above-mentioned dCas9 include, but are not limited to, a nuclease-deficient variant of *Streptococcus pyogenes*-derived Cas9 (SpCas9; PAM sequence: NGG (N is A, G, T or C. hereinafter the same)), *Streptococcus thermophilus*-derived Cas9 (StCas9; PAM sequence: NNA-GAAW (W is A or T. hereinafter the same)), *Neisseria meningitidis*-derived Cas9 (NmCas9; PAM sequence: NNNNGATT), or *Staphylococcus aureus*-derived Cas9 (Sa-Cas9; PAM sequence: NNGRRT (R is A or G. hereinafter the same)) and the like (see, for example, Nishimasu et al., Cell. 2014 Feb. 27; 156(5): 935-49, Esvelt K M et al., Nat Methods. 2013 November; 10(11):1116-21, Zhang Y. Mol Cell. 2015 Oct. 15; 60(2):242-55, and Friedland A E et al., Genome Biol. 2015 Nov. 24; 16:257, which are incorporated herein by reference in their entireties). For example, in the case of SpCas9, a double mutant in which the 10th Asp residue is converted to Ala residue and the 840th His residue is converted to Ala residue (sometimes referred to as "dSpCas9") can be used (see, for example, the aforementioned Nishimasu et al., Cell. 2014). Alternatively, in the case of SaCas9, a double mutant in which the 10th Asp residue is converted to Ala residue and the 580th Asn residue is converted to Ala residue (SEQ ID NO: 107), or a double mutant in which the 10th Asp residue is converted to Ala residue and the 557th His residue is converted to Ala residue (SEQ ID NO: 108) (hereinafter any of these double mutants is sometimes to be referred to as "dSaCas9") can be used (see, for example, the aforementioned Friedland A E et al., Genome Biol. 2015, which is incorporated herein by reference in its entirety).

In addition, in one embodiment of the present invention, as dCas9, a variant obtained by modifying a part of the amino acid sequence of the aforementioned dCas9, which forms a complex with gRNA and is recruited to the expression regulatory region of the human UTRN gene, may also be used. Examples of such variants include a truncated variant with a partly deleted amino acid sequence. In one embodiment of the present invention, as dCas9, variants disclosed in PCT/JP2019/022795 and PCT/JP2019/041751, which are incorporated herein by reference in their entireties, can be used. Specifically, dSaCas9 obtained by deleting the 721st to 745th amino acids from dSaCas9 that is a double mutant in which the 10th Asp residue is converted to Ala residue and the 580th Asn residue is converted to Ala residue (SEQ ID NO: 109), or dSaCas9 in which the deleted part is substituted by a peptide linker (e.g., one in which the deleted part is substituted by GGSGGS linker (SEQ ID NO: 110) is set forth in SEQ ID NO: 111, and one in which the deleted part is substituted by SGGGS linker (SEQ ID NO: 213) is set forth in SEQ ID NO: 214, etc.) (hereinafter any of these double mutants is sometimes to be referred to as "dSaCas9[-25]"), or dSaCas9 obtained by deleting the 482nd to 648th amino acids from dSaCas9 that is the aforementioned double mutant (SEQ ID NO: 112), or dSaCas9 in which the deleted part is substituted by a peptide linker (one in which the deleted part is substituted by GGSGGS linker is set forth in SEQ ID NO: 113) may also be used.

Examples of the above-mentioned dCpf1 include, but are not limited to, a nuclease-deficient variant of *Francisella novicida*-derived Cpf1 (FnCpf1; PAM sequence: NTT),

*Acidaminococcus* sp.-derived Cpf1 (AsCpf1; PAM sequence: NTTT), or *Lachnospiraceae bacterium*-derived Cpf1 (LbCpf1; PAM sequence: NTTT) and the like (see, for example, Zetsche B. et al., Cell. 2015 Oct. 22; 163(3):759-71, Yamano T et al., Cell. 2016 May 5; 165(4):949-62, and Yamano T et al., Mol Cell. 2017 Aug. 17; 67(4):633-45, which are incorporated herein by reference in their entireties). For example, in the case of FnCpf1, a double mutant in which the 917th Asp residue is converted to Ala residue and the 1006th Glu residue is converted to Ala residue can be used (see, for example, the aforementioned Zetsche B et al., Cell. 2015, which is incorporated herein by reference in its entirety). In one embodiment of the present invention, as dCpf1, a variant obtained by modifying a part of the amino acid sequence of the aforementioned dCpf1, which forms a complex with gRNA and is recruited to the expression regulatory region of the human UTRN gene, may also be used.

In one embodiment of the present invention, dCas9 is used as the nuclease-deficient CRISPR effector protein. In one embodiment, the dCas9 is dSaCas9, and, in a particular embodiment, the dSaCas9 is dSaCas9[-25].

A polynucleotide comprising a base sequence encoding a CRISPR effector protein can be cloned by, for example, synthesizing an oligoDNA primer covering a region encoding a desired part of the protein based on the cDNA sequence information thereof, and amplifying the polynucleotide by PCR method using total RNA or mRNA fraction prepared from the cells producing the protein as a template. In addition, a polynucleotide comprising a base sequence encoding a nuclease-deficient CRISPR effector protein can be obtained by introducing a mutation into a nucleotide sequence encoding a cloned CRISPR effector protein by a known site-directed mutagenesis method to convert the amino acid residues (e.g., 10th Asp residue, 557th His residue, and 580th Asn residue in the case of SaCas9; 917th Asp residue and 1006th Glu residue in the case of FnCpf1, and the like can be included, but are not limited to these) at a site important for DNA cleavage activity to other amino acids.

Alternatively, a polynucleotide comprising a base sequence encoding nuclease-deficient CRISPR effector protein can be obtained by chemical synthesis or a combination of chemical synthesis and PCR method or Gibson Assembly method, based on the cDNA sequence information thereof, and can also be further constructed as a base sequence that underwent codon optimization to give codons suitable for expression in human.

(3) Transcription Activator

In the present invention, human UTRN gene expression is activated by the action of the transcription activator fused with the nuclease-deficient CRISPR effector protein. In the present specification, the "transcription activator" means a protein having the ability to activate gene transcription of human UTRN gene or a peptide fragment retaining the function thereof. The transcription activator to be used in the present invention is not particularly limited as long as it can activate the expression of human UTRN gene. For example, it includes VP64, VPH, VPR, miniVR, and microVR, a variant thereof having transcription activation ability and the like. VP64 is a peptide consisting of 50 amino acids set forth in SEQ ID NO: 114. VPH is a fusion protein of VP64, p65 and HSF1, specifically, a peptide consisting of 376 amino acids set forth in SEQ ID NO: 115. VPR is a fusion protein of VP64, p65, and a replication and transcription activator of Epstein-Barr virus (RTA), for example, a peptide consisting of 523 amino acids set forth in SEQ ID NO: 116, a peptide consisting of 519 amino acids set forth in SEQ ID NO: 216, and the like. VP64, VPH, and VPR are known and disclosed in detail in, for example, Chavez A. et al., Nat Methods. 2016 July; 13(7):563-7 and Chavez A. et al., Nat Methods. 2015 April; 12(4):326-8, which are incorporated herein by reference in their entireties. In one embodiment of the present invention, as a transcription activator, a peptide comprising VP64 and a transcription activation domain of RTA can be used.

The transcription activation domain of RTA is known and disclosed in, for example, J Virol. 1992 September; 66(9): 5500-8, which is incorporated herein by reference in its entirety and the like. As a sequence of such peptide, miniVR is a peptide consisting of 167 amino acids set forth in SEQ ID NO: 117, and microVR is a peptide consisting of 140 amino acids set forth in SEQ ID NO: 118. The amino acid sequence set forth in SEQ ID NO: 117 is composed of an amino acid sequence in which the 493rd -605th amino acid residues of RTA, which is a shorter transcription activation domain of RTA, and VP64 are linked with a G-S-G-S linker (SEQ ID NO: 209). The amino acid sequence set forth in SEQ ID NO: 118 is composed of an amino acid sequence in which the 520th -605th amino acid residues of RTA, which is a much shorter transcription activation domain of RTA, and VP64 are linked with a G-S-G-S linker. The detail of miniVR and microVR is described in PCT/JP2019/030972, which is incorporated herein by reference in its entirety. Any of the aforementioned transcriptional activators may be subjected to any modification and/or alteration as long as it maintains its transcription activation ability. For example, as a transcriptional activator in the present invention, (i) a peptide comprising an amino acid sequence set forth in SEQ ID NO: 117, (ii) a peptide comprising an amino acid sequence set forth in SEQ ID NO: 117 in which 1 or several (e.g., 2, 3, 4, 5 or more) amino acids are deleted, substituted, inserted and/or added, (iii) a peptide comprising an amino acid sequence not less than 90% (e.g., 90%, 91%, 92%, 93%, 94%, 95%, 96%, 97%, 98%, 99% or above) identical with the amino acid sequence set forth in SEQ ID NO: 117, (iv) a peptide consisting of the amino acid sequence set forth in SEQ ID NO: 117 in which 1 or several (e.g., 2, 3, 4, 5 or more) amino acids are deleted, substituted, inserted and/or added, or (v) a peptide consisting of an amino acid sequence not less than 90% (e.g., 90%, 91%, 92%, 93%, 94%, 95%, 96%, 97%, 98%, 99% or above) identical with the amino acid sequence set forth in SEQ ID NO: 117 can also be used, as long as it maintains its transcription activation ability. For example, as a transcriptional activator in the present invention, (i) a peptide comprising an amino acid sequence set forth in SEQ ID NO: 118, (ii) a peptide comprising an amino acid sequence set forth in SEQ ID NO: 118 in which 1 or several (e.g., 2, 3, 4, 5 or more) amino acids are deleted, substituted, inserted and/or added, (iii) a peptide consisting of an amino acid sequence not less than 90% (e.g., 90%, 91%, 92%, 93%, 94%, 95%, 96%, 97%, 98%, 99% or above) identical with the amino acid sequence shown in SEQ ID NO: 118, (iv) a peptide consisting of the amino acid sequence set forth in SEQ ID NO: 118 in which 1 or several (e.g., 2, 3, 4, 5 or more) amino acids are deleted, substituted, inserted and/or added, or (v) a peptide consisting of an amino acid sequence not less than 90% (e.g., 90%, 91%, 92%, 93%, 94%, 95%, 96%, 97%, 98%, 99% or above) identical with the amino acid sequence set forth in SEQ ID NO: 118 can also be used, as long as it maintains its transcription activation ability.

A polynucleotide comprising a base sequence encoding a transcription activator can be constructed by chemical synthesis or a combination of chemical synthesis and PCR method or Gibson Assembly method. Furthermore, a polynucleotide comprising a base sequence encoding a transcription activator can also be constructed as a codon-optimized DNA sequence to be codons suitable for expression in human.

A polynucleotide comprising a base sequence encoding a fusion protein of a transcription activator and a nuclease-deficient CRISPR effector protein can be prepared by ligating a base sequence encoding a nuclease-deficient CRISPR effector protein to a base sequence encoding a transcription activator directly or after adding a base sequence encoding a linker, NLS (nuclear localization signal), a tag and/or others. In the present invention, the transcription activator may be fused with either N-terminal or C-terminal of the CRISPR effector protein. As the linker, a linker with an amino acid number of about 2 to 50 can be used, and specific examples thereof include, but are not limited to, a G-S-G-S linker in which glycine (G) and serine (S) are alternately linked and the like.

(4) Guide RNA

In the present invention, a fusion protein of nuclease-deficient CRISPR effector protein and transcription activator can be recruited to the expression regulatory region of the human UTRN gene by guide RNA. As described in the aforementioned "(1) Definition", guide RNA comprises crRNA, and the crRNA binds to a complementary sequence of the targeting sequence. crRNA may not be completely complementary to the complementary sequence of the targeting sequence as long as the guide RNA can recruit the fusion protein to the target region, and may comprise a base sequence of the targeting sequence in which at least 1 to 3 bases are deleted, substituted, inserted and/or added.

When dCas9 is used as the nuclease-deficient CRISPR effector protein, for example, the targeting sequence can be determined using a published gRNA design web site (CRISPR Design Tool, CRISPR direct, etc.). To be specific, from the sequence of the target gene (i.e., human UTRN gene), candidate targeting sequences of about 20 nucleotides in length for which PAM (e.g., NNGRRT in the case of SaCas9) is adjacent to the 3'-side thereof are listed, and one having a small number of off-target sites in human genome from among these candidate targeting sequences can be used as the targeting sequence. The base length of the targeting sequence is 18 to 24 nucleotides in length, preferably 20 to 23 nucleotides in length, more preferably 21 to 23 nucleotides in length. As a primary screening for the prediction of the off-target site number, a number of bioinformatic tools are known and publicly available, and can be used to predict the targeting sequence with the lowest off-target effect. Examples thereof include bioinfoiivatics tools such as Benchling (Hypertext Transfer Protocol Secure://benchling.com), and COSMID (CRISPR Off-target Sites with Mismatches, Insertions, and Deletions) (Available on Hypertext Transfer Protocol Secure://crispr.bme.gatech.edu on the internet). Using these, the similarity to the base sequence targeted by gRNA can be summarized. When the gRNA design software to be used does not have a function to search for off-target site of the target genome, for example, the off-target site can be searched for by subjecting the target genome to Blast search with respect to 8 to 12 nucleotides on the 3'-side of the candidate targeting sequence (seed sequence with high discrimination ability of targeted nucleotide sequence).

In one embodiment of the present invention, in the region existing in the GRCh38.p12 position of human chromosome 6 (Chr 6), the following five regions can be the expression regulatory regions of the human UTRN gene. These regions are strongly suggested to be expression regulatory regions by histone modification patterns. Therefore, in one embodiment of the present invention, the targeting sequence can be 18 to 24 15 nucleotides in length, preferably 20 to 23 nucleotides in length, more preferably 21 to 23 nucleotides in length, in at least one region of the following five regions existing in the GRCh38.p12 position of human chromosome 6 (Chr 6):

(1) 144,215,500-144,217,000,
(2) 144,248,500-144,249,800,
(3) 144,264,000-144,267,000,
(4) 144,283,900-144,288,300,
(5) 144,292,500-144,295,500.

In one embodiment of the present invention, the targeting sequence can be continuous 18 to 24 nucleotides in length, preferably 20 to 23 nucleotides in length, more preferably 21 to 23 nucleotides in length, in the regions set forth in SEQ ID NO: 104 present in the above-mentioned region (3) or set forth in SEQ ID NO: 105, 135, 141, 153, 167, or 172 present in the above-mentioned region (4).

In another embodiment of the present invention, the targeting sequence can be the base sequence set forth in SEQ ID NO: 45, 46, 58, 59, 60, 135, 141, 153, 155, 156, 157, 159, 167, or 172. The base sequences set forth in SEQ ID NOs: 45 and 46 are targeting sequences comprised in the region set forth in the aforementioned SEQ ID NO: 104, and the base sequences set forth in SEQ ID NOs: 58, 59, 60, 155, 156, 157, and 159 are targeting sequences comprised in the region set forth in the aforementioned SEQ ID NO: 105.

In one embodiment of the present invention, a base sequence encoding crRNA may be the same base sequence as the targeting sequence. For example, when the targeting sequence set forth in SEQ ID NO: 4 (AGAAAAGCGGCCCCTAGGGGC) is introduced into the cell as a base sequence encoding crRNA, crRNA transcribed from the sequence is AGAAAAGCGGCCCCUAGGGGC (SEQ ID NO: 119) and is bound to GCCCCTAGGGGCCGCTTTTCT (SEQ ID NO: 120), which is a sequence complementary to the base sequence set forth in SEQ ID NO: 4 and is present in the expression regulatory region of the human UTRN gene. In another embodiment, a base sequence which is a targeting sequence in which at least 1 to 3 bases are deleted, substituted, inserted and/or added can be used as the base sequence encoding crRNA as long as guide RNA can recruit a fusion protein to the target region. Therefore, in one embodiment of the present invention, as a base sequence encoding crRNA, the base sequence set forth in SEQ ID NO: 45, 46, 58, 59, 60, 135, 141, 153, 155, 156, 157, 159, 167, or 172, or the base sequence set forth in SEQ ID NO: 45, 46, 58, 59, 60, 135, 141, 153, 155, 156, 157, 159, 167, or 172 in which 1 to 3 bases are deleted, substituted, inserted and/or added can be used.

In one embodiment of the present invention, the base sequence set forth in SEQ ID NO: 45, 46, 58, 59, 60, 135, 141, 153, 155, 156, 157, 159, 167, or 172 can be used as the base sequence encoding crRNA to produce gRNA comprising crRNA set forth in SEQ ID NO: 194, 195, 196, 197, 198, 199, 200, 201, 202, 203, 204, 205, 206, or 207, respectively. In another embodiment of the present invention, the gRNA can comprise the base sequence set forth in SEQ ID NO: 194, 195, 196, 197, 198, 199, 200, 201, 202, 203, 204, 205, 206 or 207, or the base sequence set forth in SEQ ID NO: 194, 195, 196, 197, 198, 199, 200, 201, 202, 203, 204, 205, 206 or 207 in which 1 to 3 bases are deleted, substituted, inserted, and/or added.

When dCpf1 is used as the nuclease-deficient CRISPR effector protein, a base sequence encoding gRNA can be designed as a DNA sequence encoding crRNA with particular RNA attached to the 5'-terminal. Such RNA attached to the 5'-terminal of crRNA and a DNA sequence encoding said RNA can be appropriately selected by those of ordinary skill in the art according to the dCpf1 to be used. For example, when dFnCpf1 is used, a base sequence in which SEQ ID NO: 121; AATT<u>TCTACTGTT</u>GTAGAT is attached to the 5'-side of the targeting sequence can be used as a base sequence encoding gRNA (when transcribed to RNA, the sequences of the underlined parts form a base pairs to form a stem-loop structure). The sequence to be added to the 5'-terminal may be a sequence generally used for various Cpf1 proteins in which at least 1 to 6 bases are deleted, substituted, inserted and/or added, as long as gRNA can recruit a fusion protein to the expression regulatory region after transcription.

When dCas9 is used as the CRISPR effector protein, a base sequence encoding gRNA can be designed as a DNA sequence in which a DNA sequence encoding known tracrRNA is linked to the 3'-terminal of a DNA sequence encoding crRNA. Such tracrRNA and a DNA sequence encoding the tracrRNA can be appropriately selected by those of ordinary skill in the art according to the dCas9 to be used. For example, when dSaCas9 is used, the base sequence set forth in SEQ ID NO: 122 is used as the DNA sequence encoding tracrRNA. The DNA sequence encoding tracrRNA may be a base sequence encoding tracrRNA generally used for various Cas9 proteins in which at least 1 to 6 bases are deleted, substituted, inserted and/or added, as long as gRNA can recruit a fusion protein to the expression regulatory region after transcription.

A polynucleotide comprising a base sequence encoding gRNA designed in this way can be chemically synthesized using a known DNA synthesis method.

In another embodiment of the present invention, the polynucleotide of the present invention may comprise at least two different base sequences encoding a gRNA. For example, the polynucleotide can comprise at least two different base sequences encoding the guide RNA, wherein the at least two different base sequences are selected from a base sequence comprising a sequence set forth in SEQ ID NO: 45, 46, 58, 59, 60, 135, 141, 153, 155, 156, 157, 159, 167, or 172. In one embodiment of the present invention, the polynucleotide can comprise at least two different base sequences encoding the guide RNA, wherein the at least two different base sequences are selected from a base sequence comprising the sequence set forth in SEQ ID NO: 45, 46, or 59.

(5) Promoter Sequence

In one embodiment of the present invention, a promoter sequence may be operably linked to the upstream of each of a base sequence encoding fusion protein of nuclease-deficient CRISPR effector protein and transcription activator and/or a base sequence encoding gRNA. The promoter to be possibly linked is not particularly limited as long as it shows a promoter activity in the target cell. Examples of the promoter sequence possibly linked to the upstream of the base sequence encoding the fusion protein include, but are not limited to, EFS promoter, EF-1α promoter, CMV (cytomegalovirus) promoter, CK8 promoter, MHC promoter, MLC promoter, Des promoter, cTnC promoter, MYOD promoter, hTERT promoter, SRα promoter, SV40 promoter, LTR promoter, CAG promoter, RSV (Rous sarcoma virus) promoter and the like. Examples of the promoter sequence possibly linked to the upstream of the base sequence encoding gRNA include, but are not limited to, U6 promoter, SNR6 promoter, SNR52 promoter, SCR1 promoter, RPR1 promoter, U3 promoter, H1 promoter, and tRNA promoter, which are pol III promoters, and the like. In one embodiment of the present invention, when a polynucleotide comprises two or more base sequences encoding the guide RNA, a single promoter sequence may be operably linked to the upstream of the two or more base sequences. In another embodiment, a promoter sequence may be operably linked to the upstream of each of the two or more base sequences, wherein the promoter sequence operably linked to each base sequence may be the same or different.

In one embodiment of the present invention, a muscle specific promoter can be used as the promoter sequence linked to the upstream of a base sequence encoding the aforementioned fusion protein. Examples of the muscle specific promoter include, but are not limited to, CK8 promoter, CK6 promoter, CK1 promoter, CK7 promoter, CK9 promoter, cardiac muscle troponin C promoter, a actin promoter, myosin heavy chain kinase (MHCK) promoter, myosin light chain 2A promoter, dystrophin promoter, muscle creatin kinase promoter, dMCK promoter, tMCK promoter, enh348 MCK promoter, synthetic C5-12(Syn) promoter, Myf5 promoter, MLC1/3f promoter, MYOD promoter, Myog promoter, Pax? promoter, Des promoter and the like (for the detail of the muscle specific promoter, see, for example, US2011/0212529A, McCarthy J J et al., Skeletal Muscle. 2012 May; 2(1):8, Wang B. et al., Gene Ther. 2008 Nov; 15(22):1489-99, which are incorporated herein by reference in their entireties and the like).

In one embodiment of the present invention, U6 promoter can be used as the promoter sequence for the base sequence encoding the gRNA, and CK8 promoter can be used as the promoter sequence for the base sequence encoding the fusion protein. Specifically, as for the U6 promoter, the following base sequences can be used; (i) the base sequence set forth in SEQ ID NO: 128, (ii) a base sequence set forth in SEQ ID NO: 128 wherein 1 or several (e.g., 2, 3, 4, 5 or more) bases are deleted, substituted, inserted and/or added with a promoter activity in the target cell, or (iii) a base sequence not less than 90% (e.g., 90%, 91%, 92%, 93%, 94%, 95%, 96%, 97%, 98%, 99% or above) identical with the base sequence set forth in SEQ ID NO: 128 showing a promoter activity in the target cell. As for the CK8 promoter, the following base sequences can be used; (i) the base sequence set forth in SEQ ID NO: 191, (ii) a base sequence set forth in SEQ ID NO: 191 wherein 1 or several (e.g., 2, 3, 4, 5 or more) bases are deleted, substituted, inserted and/or added with a promoter activity in the target cell, or (iii) a base sequence not less than 90% (e.g., 90%, 91%, 92%, 93%, 94%, 95%, 96%, 97%, 98%, 99% or above) identical with the base sequence set forth in SEQ ID NO: 191 showing a promoter activity in the target cell.

(6) Other Base Sequence

Furthermore, the polynucleotide of the present invention may further comprise known sequences such as Polyadenylation (polyA) signal, Kozak consensus sequence and the like besides those mentioned above for the purpose of improving the translation efficiency of mRNA produced by transcription of a base sequence encoding a fusion protein of nuclease-deficient CRISPR effector protein and transcription activator. For example, Polyadenylation signal in the present invention may include hGH polyA, bGH polyA, 2× sNRP-1 polyA (see US7557197B2, which is incorporated herein by reference in its entirety), and so on. In addition, the polynucleotide of the present invention may comprise a base sequence encoding a linker sequence, a base sequence encoding NLS and/or a base sequence encoding a tag.

(7) Exemplified Embodiments of the Present Invention

In one embodiment of the present invention, a polynucleotide is provided comprising:

a base sequence encoding a fusion protein of a nuclease-deficient CRISPR effector protein and a transcription activator, a promoter sequence for the base sequence encoding the fusion protein of the nuclease-deficient CRISPR effector protein and the transcription activator, one or two base sequences encoding a guide RNA, wherein the one or two base sequences are selected from a base sequence comprising a sequence set forth in SEQ ID NO: 45, 46, or 59, or the base sequence comprising a sequence set forth in SEQ ID NO: 45, 46, or 59 in which 1 to 3 bases are deleted, substituted, inserted, and/or added, and U6 promoter for the base sequence encoding the guide RNA, wherein the nuclease-deficient CRISPR effector protein is dSaCas9 or dSaCas9[-25], wherein the transcription activator is selected from the group VP64, VPH, VPR, miniVR, and microVR, and wherein the promoter sequence for the base sequence encoding the fusion protein is selected from the group EF-1α promoter, EFS promoter, and CK8 promoter. The polynucleotide may further comprise hGH polyA, bGH polyA or 2× sNRP-1 polyA.

In one embodiment of the present invention, a polynucleotide is provided comprising:

a base sequence encoding a fusion protein of a nuclease-deficient CRISPR effector protein and a transcription activator, CK8 promoter for the base sequence encoding the fusion protein of the nuclease-deficient CRISPR effector protein and the transcription activator, one or two base sequences encoding a guide RNA, wherein the one or two base sequences are selected from a base sequence comprising a sequence set forth in SEQ ID NO: 45, 46, or 59, or a base sequence comprising a sequence set forth in SEQ ID NO: 45, 46, or 59 in which 1 to 3 bases are deleted, substituted, inserted, and/or added, and U6 promoter for the base sequence encoding the guide RNA, wherein the nuclease-deficient CRISPR effector protein is dSaCas9 or dSaCas9[-25], and wherein the transcription activator is miniVR or microVR.

The polynucleotide may further comprise bGH polyA or 2× sNRP-1 polyA.

In one embodiment of the present invention, a polynucleotide is provided comprising:

a base sequence encoding a fusion protein of a nuclease-deficient CRISPR effector protein and a transcription activator, CK8 promoter for the base sequence encoding the fusion protein of the nuclease-deficient CRISPR effector protein and the transcription activator, one or two base sequences encoding a guide RNA, wherein the one or two base sequences are selected from a base sequence comprising a sequence set forth in SEQ ID NO: 45, 46, or 59, or a base sequence comprising a sequence set forth in SEQ ID NO: 45, 46, or 59 in which 1 to 3 bases are deleted, substituted, inserted, and/or added, and U6 promoter for the base sequence encoding the guide RNA, wherein the nuclease-deficient CRISPR effector protein is dSaCas9 and wherein the transcription activator is miniVR. The polynucleotide may further comprise bGH polyA or 2× sNRP-1 polyA.

In one embodiment of the present invention, a polynucleotide is provided comprising:

a base sequence encoding a fusion protein of a nuclease-deficient CRISPR effector protein and a transcription activator, CK8 promoter for the base sequence encoding the fusion protein of the nuclease-deficient CRISPR effector protein and the transcription activator, one or two base sequences encoding a guide RNA, wherein the one or two base sequences are selected from a base sequence comprising a sequence set forth in SEQ ID NO: 45, 46, or 59, or a base sequence comprising a sequence set forth in SEQ ID NO: 45, 46, or 59 in which 1 to 3 bases are deleted, substituted, inserted, and/or added, and U6 promoter for the base sequence encoding the guide RNA, wherein the nuclease-deficient CRISPR effector protein is dSaCas9 and wherein the transcription activator is microVR.

The polynucleotide may further comprise bGH polyA or 2× sNRP-1 polyA.

In one embodiment of the present invention, a polynucleotide is provided comprising:

a base sequence encoding a fusion protein of a nuclease-deficient CRISPR effector protein and a transcription activator, CK8 promoter for the base sequence encoding the fusion protein of the nuclease-deficient CRISPR effector protein and the transcription activator, a base sequence encoding a guide RNA comprising the base sequence set forth in SEQ ID NO: 59, or the base sequence set forth in SEQ ID NO: 59 in which 1 to 3 bases are deleted, substituted, inserted, and/or added, and U6 promoter for the base sequence encoding the guide RNA, wherein the nuclease-deficient CRISPR effector protein is dSaCas9 and wherein the transcription activator is miniVR. The polynucleotide may further comprise 2× sNRP-1 polyA.

In one embodiment of the present invention, a polynucleotide is provided comprising:

a base sequence encoding a fusion protein of a nuclease-deficient CRISPR effector protein and a transcription activator, CK8 promoter for the base sequence encoding the fusion protein of the nuclease-deficient CRISPR effector protein and the transcription activator, a base sequence encoding a guide RNA comprising the base sequence set forth in SEQ ID NO: 59, or the base sequence set forth in SEQ ID NO: 59 in which 1 to 3 bases are deleted, substituted, inserted, and/or added, and U6 promoter for the base sequence encoding the guide RNA, wherein the nuclease-deficient CRISPR effector protein is dSaCas9 and wherein the transcription activator is microVR. The polynucleotide may further comprise 2× sNRP-1 polyA.

In an embodiment of the polynucleotide of the present invention, the polynucleotide comprises in order from the 5'end (i) the base sequence encoding the fusion protein of the nuclease-deficient CRISPR effector protein and the transcription activator and (ii) the base sequence encoding the gRNA. In another embodiment, the polynucleotide comprises in order from the 5'end (ii) the base sequence encoding the gRNA and (i) the base sequence encoding the fusion protein of the nuclease-deficient CRISPR effector protein and the transcription activator.

2. Vector

The present invention provides a vector comprising the polynucleotide of the present invention (hereinafter sometimes referred to as "the vector of the present invention"). The vector of the present invention may be a plasmid vector or a viral vector.

When the vector of the present invention is a plasmid vector, the plasmid vector to be used is not particularly limited and may be any plasmid vector such as cloning plasmid vector and expression plasmid vector. The plasmid vector is prepared by inserting the polynucleotide of the present invention into a plasmid vector by a known method.

When the vector of the present invention is a viral vector, the viral vector to be used is not particularly limited and examples thereof include, but are not limited to, adenovirus vector, adeno-associated virus (AAV) vector, lentivirus vector, retrovirus vector, Sendaivirus vector and the like. In the present specification, the "virus vector" or "viral vector" also includes derivatives thereof. Considering the use in gene therapy, AAV vector is preferably used for the reasons such that it can express transgene for a long time, and it is derived from a non-pathogenic virus and has high safety.

A viral vector comprising the polynucleotide of the present invention can be prepared by a known method. In brief, a plasmid vector for virus expression into which the polynucleotide of the present invention has been inserted is prepared, the vector is transfected into an appropriate host cell to allow for transient production of a viral vector comprising the polynucleotide of the present invention, and the viral vector is collected.

In one embodiment of the present invention, when AAV vector is used, the serotype of the AAV vector is not particularly limited as long as expression of the human UTRN gene in the target can be activated, and any of AAV1, AAV2, AAV3, AAV4, AAV5, AAV6, AAV7, AAV8, AAV9, AAVrh.10 and the like may be used (for the various serotypes of AAV, see, for example, WO 2005/033321 and EP2341068 (A1), which are incorporated herein by reference in their entireties). Examples of the variants of AAV include, but are not limited to, new serotype with a modified capsid (e.g., WO 2012/057363, which is incorporated herein by reference in its entirety) and the like. For example, in one embodiment of the present invention, a new serotype with a modified capsid improving infectivity for muscle cells can be used, such as $AAV_{587}MTP$, $AAV_{588}MTP$, AAV-B1, AAVM41, AAVS1_P1, and AAVS10_P1, and the like (see Yu et al., Gene Ther. 2009 August; 16(8):953-62, Choudhury et al., Mol Ther. 2016 August; 24(7):1247-57, Yang et al., Proc Natl Acad Sci USA. 2009 Mar. 10; 106(10):3946-51, and WO2019/207132, which are incorporated herein by reference in their entireties).

When an AAV vector is prepared, a known method such as (1) a method using a plasmid, (2) a method using a baculovirus, (3) a method using a herpes simplex virus, (4) a method using an adenovirus, or (5) a method using yeast can be used (e.g., Appl Microbiol Biotechnol. 2018; 102(3): 1045-1054, etc., which is incorporated herein by reference in its entirety). For example, when an AAV vector is prepared by a method using a plasmid, first, a vector plasmid comprising inverted terminal repeat (ITR) at both ends of wild-type AAV genomic sequence and the polynucleotide of the present invention inserted in place of the DNA encoding Rep protein and capsid protein is prepared. On the other hand, the DNA encoding Rep protein and capsid protein necessary for forming virus particles are inserted into other plasmids. Furthermore, a plasmid comprising genes (E1A, E1B, E2A, VA and E4orf6) responsible for the helper action of adenovirus necessary for proliferation of AAV is prepared as an adenovirus helper plasmid. The co-transfection of these three kinds of plasmids into the host cell causes the production of recombinant AAV (i.e., AAV vector) in the cell. As the host cell, a cell capable of supplying a part of the gene products (proteins) of the genes responsible for the aforementioned helper action (e.g., 293 cell, etc.) is preferably used. When such cell is used, it is not necessary to carry the gene encoding a protein that can be supplied from the host cell in the aforementioned adenoviral helper plasmid. The produced AAV vector is present in the nucleus. Thus, a desired AAV vector is prepared by destroying the host cell with freeze-thawing, collecting the virus and then subjecting the virus fraction to separation and purification by density gradient ultracentrifugation method using cesium chloride, column method or the like.

AAV vector has great advantages in terms of safety, gene transduction efficiency and the like, and is used for gene therapy. However, it is known that the size of a polynucleotide that can be packaged in AAV vector is limited. For example, in one embodiment of the present invention, the entire length including the base length of a polynucleotide comprising a base sequence encoding a fusion protein of dSaCas9 and miniVR or microVR, a base sequence encoding gRNA targeting the expression regulatory region of the human UTRN gene, and EFS promoter sequence or CK8 promoter sequence and U6 promoter sequence as the promoter sequences, and ITR parts is about 4.85 kb, and they can be packaged in a single AAV vector.

3. Pharmaceutical Composition

The present invention also provides a pharmaceutical composition comprising the polynucleotide of the present invention or the vector of the present invention (hereinafter sometimes referred to as "the pharmaceutical composition of the present invention"). The pharmaceutical composition of the present invention can be used for treating or preventing DMD or BMD.

The pharmaceutical composition of the present invention comprises the polynucleotide of the present invention or the vector of the present invention as an active ingredient, and may be prepared as a formulation comprising such active ingredient (i.e., the polynucleotide of the present invention or the vector of the present invention) and, generally, a pharmaceutically acceptable carrier.

The pharmaceutical composition of the present invention is administered parenterally, and may be administered topically or systemically. The pharmaceutical composition of the present invention can be administered by, but are not limited to, for example, intravenous administration, intraarterial administration, subcutaneous administration, intraperitoneal administration, or intramuscular administration.

The dose of the pharmaceutical composition of the present invention to a subject is not particularly limited as long as it is an effective amount for the treatment and/or prevention. It may be appropriately optimized according to the active ingredient, dosage form, age and body weight of the subject, administration schedule, administration method and the like.

In one embodiment of the present invention, the pharmaceutical composition of the present invention can be not only administered to the subject affected with DMD or BMD but also prophylactically administered to subjects who may develop DMD or BMD in the future based on the genetic background analysis and the like. The term "treatment" in the present specification also includes remission of disease, in addition to the cure of diseases. In addition, the term "prevention" may also include delaying the onset of disease, in addition to prophylaxis of the onset of disease. The pharmaceutical composition of the present invention can also be referred to as "the agent of the present invention" or the like.

4. Method for Treatment or Prevention of DMD or BMD

The present invention also provides a method for treating or preventing DMD or BMD, comprising administering the polynucleotide of the present invention or the vector of the present invention to a subject in need thereof (hereinafter sometimes referred to as "the method of the present invention"). In addition, the present invention includes the polynucleotide of the present invention or the vector of the present invention for use in the treatment or prevention of DMD or BMD. Furthermore, the present invention includes use of the polynucleotide of the present invention or the vector of the present invention in the manufacture of a pharmaceutical composition for the treatment or prevention of DMD or BMD.

The method of the present invention can be practiced by administering the aforementioned pharmaceutical composition of the present invention to a subject affected with DMD or BMD, and the dose, administration route, subject and the like are the same as those mentioned above.

Measurement of the symptoms may be performed before the start of the treatment using the method of the present invention and at any timing after the treatment to determine the response of the subject to the treatment.

The method of the present invention can improve the functions of the skeletal muscle and/or cardiac muscle of the subject. Muscles to be improved in the function thereof are not particularly limited, and any muscles and muscle groups are exemplified.

5. Ribonucleoprotein

The present invention provides a ribonucleoprotein comprising the following (hereinafter sometimes referred to as "RNP of the present invention"):

(c) a fusion protein of a nuclease-deficient CRISPR effector protein and a transcription activator, and (d) a guide RNA targeting a continuous region of 18 to 24 nucleotides in length in a region set forth in SEQ ID NO: 104, 105, 135, 141, 153, 167, or 172 in the expression regulatory region of human Utrophin gene.

As the nuclease-deficient CRISPR effector protein, transcription activator, and guide RNA comprised in the RNP of the present invention, the nuclease-deficient CRISPR effector protein, transcription activator, and guide RNA explained in detail in the above-mentioned section of "1. Polynucleotide" can be used. The fusion protein of nuclease-deficient CRISPR effector protein and transcription activator to be comprised in the RNP of the present invention can be produced by, for example, introducing a polynucleotide encoding the fusion protein into the cell, bacterium, or other organism to allow for the expression, or an in vitro translation system by using the polynucleotide. In addition, guide RNA comprised in the RNP of the present invention can be produced by, for example, chemical synthesis or an in vitro transcription system by using a polynucleotide encoding the guide RNA. The thus-prepared fusion protein and guide RNA are mixed to prepare the RNP of the present invention. Where necessary, other substances such as gold particles may be mixed. To directly deliver the RNP of the present invention to the target cell, tissue and the like, the RNP may be encapsulated in a lipid nanoparticle (LNP) by a known method. The RNP of the present invention can be introduced into the target cell, tissue and the like by a known method. For example, Lee K., et al., Nat Biomed Eng. 2017; 1:889-901, WO 2016/153012, which are incorporated herein by reference in their entireties, and the like can be referred to for encapsulation in LNP and introduction method.

In one embodiment of the present invention, the guide RNA comprised in RNP of the present invention targets continuous 18 to 24 nucleotides in length, preferably 20 to 23 nucleotides in length, more preferably 21 to 23 nucleotides in length, in at least one region of the following five regions existing in the GRCh38.p12 position of human chromosome 6 (Chr 6):

(1) 144,215,500-144,217,000,
(2) 144,248,500-144,249,800,
(3) 144,264,000-144,267,000,
(4) 144,283,900-144,288,300,
(5) 144,292,500-144,295,500.

In one embodiment, the guide RNA targets a base sequence of continuous 18 to 24 nucleotides in length, preferably 20 to 23 nucleotides in length, more preferably 21 to 23 nucleotides in length, in the DNA sequence set forth in SEQ ID NO: 104, 105, 135, 141, 153, 167, or 172. In one embodiment, the guide RNA targets a region comprising all or a part of the sequence set forth in SEQ ID NO: 45, 46, 58, 59, 60, 135, 141, 153, 155, 156, 157, 159, 167, or 172. In one embodiment of the present invention, the guide RNA comprising crRNA set forth in SEQ ID NO: 194, 195, 196, 197, 198, 199, 200, 201, 202, 203, 204, 205, 206, or 207, or the base sequence set forth in SEQ ID NO: 194, 195, 196, 197, 198, 199, 200, 201, 202, 203, 204, 205, 206, or 207 in which 1 to 3 bases are deleted, substituted, inserted, and/or added respectively can be used.

6. Others

The present invention also provides a composition or kit comprising the following for activation of the expression of the human Utrophin gene:

(e) a fusion protein of a nuclease-deficient CRISPR effector protein and a transcription activator, or a polynucleotide encoding the fusion protein, and (f) a guide RNA targeting a continuous region of 18 to 24 nucleotides in length in a region set forth in SEQ ID NO: 104, 105, 135, 141, 153, 167, or 172 in the expression regulatory region of human Utrophin gene, or a polynucleotide encoding the guide RNA.

The present invention also provides a method for treating or preventing DUCHENNE muscular dystrophy or BECKER muscular dystrophy, comprising administering the following (e) and (f):

(e) a fusion protein of a nuclease-deficient CRISPR effector protein and a transcription activator, or a polynucleotide encoding the fusion protein, and (f) a guide RNA targeting a continuous region of 18 to 24 nucleotides in length in a region set forth in SEQ ID NO: 104, 105, 135, 141, 153, 167, or 172 in the expression regulatory region of human Utrophin gene, or a polynucleotide encoding the guide RNA.

The present invention also provides use of the following (e) and (f):

(e) a fusion protein of a nuclease-deficient CRISPR effector protein and a transcription activator, or a polynucleotide encoding the fusion protein, and (f) a guide RNA targeting a continuous region of 18 to 24 nucleotides in length in a region set forth in SEQ ID NO: 104, 105, 135, 141, 153, 167, or 172 in the expression regulatory region of human Utrophin gene, or a polynucleotide encoding the guide RNA, in the manufacture of a pharmaceutical composition for the treatment or prevention of DUCHENNE muscular dystrophy or BECKER muscular dystrophy.

As the nuclease-deficient CRISPR effector protein, transcription activator, guide RNA, as well as polynucleotides encoding them and vectors in which they are carried in these inventions, those explained in detail in the above-mentioned sections of "1. Polynucleotide", "2. Vector" and "5. Ribonucleoprotein" can be used. The dose, administration route, subject, formulation and the like of the above-mentioned (e) and (f) are the same as those explained in the section of "3. Treating or preventing agent for DMD or BMD".

Other features of the invention will become apparent in the course of the following descriptions of exemplary embodiments which are given for illustration of the invention and are not intended to be limiting thereof.

EXAMPLES

The examples describe the use of a fusion protein of dCas9 with a transcriptional activator to enhance gene expression, in the defined expression regulatory region of human UTRN gene that leads to the selective activation of human UTRN gene expression. The goal of the modification of the gene expression is to enhance the expression of wild-type human UTRN gene products that complements the function of a defective dystrophin gene product. The example also describes the definition of a specific genomic region that confers selective activation of the human UTRN gene without minimally affecting the expression of other genes. The method of the present invention to enhance human UTRN gene expression represents a novel therapeutic or preventive strategy for the amelioration of defective muscle function caused by defective dystrophin as described and illustrated herein.

Example 1

Screening of gRNAs for Human Utrophin Gene Using HEK293FT Cells

In this example, we illustrate use of the methods described herein to achieve the activation of the UTRN gene through targeting the defined expression regulatory region of the UTRN gene. The methods leverage the property of a complex of Cas9 and sgRNA to be recruited to a desired locus of the genome by designing an appropriate sgRNA sequence. The methods also leverage the nuclease-deficient form of the SaCas9 protein (D10A and N580A mutant (SEQ ID NO: 107), or D10A and H557A mutant (SEQ ID NO: 108); dSaCas9) to leave the genomic sequence intact, but tether various transcriptional/epigenetic functional domains or motifs to dSaCas9 to achieve desired modifications of the intended loci targeted by the sgRNA sequence, as described in Gilbert L A et al., Cell 2013 July; 154(2):442-51, and Gilbert LA et al., Cell 2014 October; 159(3):647-61, which are incorporated herein by reference in their entireties.

In this example, we illustrate that the methods described herein can be used to activate the expression of wild type UTRN. sgRNAs were designed to target the expression regulatory region of the UTRN gene that confers selective and effective gene activation. FIG. 1 shows the human UTRN locus and two predicted transcript start sites (TSSs) (top and middle). The TSSs of UTRN gene were identified by querying FANTOMS human prornoterome data base (world wide web.fantom.gsk.riken.jp, Nature 2014 Mar; 507(7493):462-70, which are incorporated herein by reference in their entireties). There are two promoter regions reported for UTRN gene (Promoter A and B), and we have tested both promoters for activation. Guide RNA sequences were designed to cover the regions above in order to determine the effective and selective therapeutic sequences within these regions.

(1) Experimental Methods
Selection of sgRNA Sequence

The sequences around the promoter regions of the UTRN gene (~4.4 kb for promoter A (Chr6: GRCh38/hg38; 144,283,900-144,288,300) and 2.6 kb for promoter B (Chr6: GRCh38/hg38; 144,342,683-144,345,311)) were scanned for potential recognition sequences where a complex of dSaCas9 and sgRNA would bind. The regions were scanned for protospacer adjacent motifs (PAMs) having the sequence NNGRRT. Targeting sequences adjacent to the PAMs were identified. The length of the targeting sequences (a portion of gRNA which hybridizes to the target DNA) was set to be 21 nucleotides. The targeting sequences were selected based on predicted specificity and efficiency generated by Benchling software (Hypertext Transfer Protocol Secure:// benchling.com), and to be evenly distributed across the selected region. Epigenetic information around the UTRN expression regulatory region from ENCODE study (The ENCODE Project Consortium, Nature. 2012 September; 489: 57-74, which is incorporated herein by reference in its entirety) was also referenced to select gRNAs with high likelihood of binding to a functional element of the gene.

The twenty-four targeting sequences listed in Table 1(Guide #sgED3-1 to sgED3-24 (SEQ ID Nos.: 129 through 152)) were tested for the modulation function of the UTRN gene expression (hereinafter the targeting sequences listed in Table 1 are sometimes referred to as "sgED3 Series").

The location of the targeting sequences in the UTRN gene is also shown in FIG. 1 (top and middle).

The selected 24 targeting sequences and a control non-targeting targeting sequence (SEQ ID NO: 177) were fused with the DNA sequence coding the tracr RNA (SEQ ID NO: 122) respectively to form sgRNA sequences, and were cloned into pCRISPR-LvSG03 vector (#pCRISPR-LvSG03) from Genecopoeia. The obtained vector denotes pCRISPR-LvSG03 sgRNA expressing vector in this specification. The sgRNA expression was driven by the U6 promoter, and the vector expressed mCherry-IRES-Puromycin gene under the SV40 promoter to facilitate the tracking and selection of the sgRNA expressing cells.

Cloning of Effector Molecules

Nuclease-deficient SaCas9 protein (D10A and N580A, or D10A and H557A; dSaCas9) serves as a main scaffold to tether functional domains/motifs in a form of direct fusion proteins. dSaCas9 was attached with two nuclear localization signal (NLS) in its N-terminus (amino acid sequence shown by SEQ ID NO: 178, DNA sequence shown by SEQ ID NO: 179) and C-terminus (amino acid sequence shown by SEQ ID NO: 180, DNA sequence shown by SEQ ID NO: 181) to enable efficient localization of the effector molecules to the nucleus.

In one example, DNA sequence encoding dSaCas9 with D10A and N580A mutations was fused with DNA sequence encoding VP64, VPH or VPR, which are the synthetic amino acid transcriptional activation moieties (see Chavez A et al., Nat Methods. 2016 July; 13(7):563-67 and Chavez A et al., Nat Methods. 2015 April; 12(4):326-8, which are incorporated herein by reference in their entireties), to its C-terminus (SEQ ID NO: 182, 183 or 184). The obtained fusion protein denotes dSaCas9-VP64, dSaCas9-VPH, or dSaCas9-VPR fusion protein respectively in this specification.

The fusion protein is recruited to the expression regulatory region of the UTRN gene and thereby exerts its transcriptional activation effect. As a consequence, the expression of UTRN gene is enhanced.

In one example, DNA sequence encoding dSaCas9 protein lacking amino acids 721-745 (dSaCas9[-25],(SEQ ID NO: 214)) was fused with DNA sequence encoding a synthetic amino acid transcriptional activator, miniVR (see PCT/JP2019/030972, which is incorporated herein by reference in its entirety), to its C-terminus (SEQ ID NO: 185). The obtained fusion protein denotes dSaCas9[-25]-miniVR fusion protein (SEQ ID NO: 186) in this specification.

For the expression of the dSaCas9-VP64, dSaCas9-VPH, dSaCas9-VPR, and dSaCas9[-25]-miniVR fusion proteins, DNA fragments encoding the fusion proteins were cloned into CP-LvC9NU-09 lentivirus expressing vector (Cat. #CP-LvC9NU-09) from Genecopoeia. The Cas9 coding sequence in the original vector was replaced with the fusion protein coding sequences, resulting in the generation of CP-LvC9NU-09 lentivirus expressing vector comprising a DNA fragment encoding the one of the four fusion proteins; dSaCas9-VP64, dSaCas9-VPH, dSaCas9-VPR or dSaCas9[-25]-miniVR. In this specification, the resulting vectors denote CP-LvdSaCas9-VP64-09, CP-LvdSaCas9-VPH-09, CP-LvdSaCas9-VPR-09, or CP-LvdSaCas9[-25]-miniVR-09 µlasmids, respectively. The vector uses EFla promoter for the expression of the effector molecules, and SV40 promoter to express eGFP-IRES-Neomycin gene.

Figure 5:
FIG. 5 shows a construct of pAAV-EFS-dSaCas9[-25]-miniVR-U6-sgRNA AIO plasmid.

For expression in adeno-associated virus vector, a DNA fragment encoding the dSaCas9[-25]-miniVR fusion protein, U6 promoter, and the sgRNA were cloned into pAAV-CMV vector (#6234) from Takara. The CMV promoter was replaced with EFS promoter (SEQ ID NO: 187). Beta-globin intron was removed from the original vector and hGH poly-A was replaced with bovine GH polyA (bGH polyA). The obtained vector comprises ITR, EFS promoter, dCas9, miniVR, bGH polyA, U6 promoter, sgRNA, and ITR, in order from its 5' end to its 3' end (FIG. 5), and denotes pAAV-EFS-dSaCas9[-25]-miniVR-U6-sgRNA AIO plasmid in this specification.

Cell Culture and Transfection

HEK293FT cells (Thermo Fisher #R70007) were seeded 24 hours prior to transfection in 24-well plates (CORNING #351147) at a density of 75,000 cells per well and cultured in DMEM media supplemented with 10% FBS and 2 mM fresh L-glutamine, 1 mM sodium pyruvate and non-essential amino acids (Thermo Fisher #11140050). For expression in lentivirus expressing vector, cells were transfected with 500 ng of CP-LvdSaCas9-VP64-09, CP-LvdSaCas9-VPH-09, CP-LvdSaCas9-VPR-09, or CP-LvdSaCas9[-25]-miniVR-09 µlasmids, and 500 ng of the pCRISPR-LvSGO3 sgRNA expressing vector using 1.5 µl of Lipofectamine 2000 (Life technologies #11668019), according to manufacturer's instructions. The transfected cells were selected with puromycin (1 µg/ml). For expression in adeno-associated virus vector, cells were transfected with 500 ng of pAAV-EFS-dSaCas9[-25]-miniVR-U6-sgRNA AIO plasmid using 1.5 µl of Lipofectamine 2000 (Life technologies #11668019), according to manufacturer's instructions. The transfected cells were not selected with puromycin.

For gene expression analysis, the transfected cells were cultured at 37° C. with 5% $CO_2$ and harvested at 72 h after transfection and lysed in RLT buffer (Qiagen #74104) to extract total RNA using RNeasy kit (Qiagen #74104).

Gene Expression Analysis

For Taqman analysis, 1.5 µg of total RNA was used to generate cDNA using TagMan™ High-Capacity RNA-to-cDNA Kit (Applied Biosystems #4387406) in 20 µl volume. The generated cDNA was diluted 20 fold with water and 6.33 µl was used per Taqman reaction. The Taqman primers and probes for the UTRN and HPRT gene were obtained from Applied Biosystems. Taqman reaction was run using Taqman gene expression master mix (Thermo Fisher #4369016) in Roche LightCycler 96 or LightCycler 480 and analyzed using LightCycler 96 analysis software. The expression level of UTRN gene was normalized by the expression level of HPRT gene.

Taqman probe product IDs:
UTRN: Hs01125994 ml (FAM)
HPRT: Hs99999909 ml (FAM, VIC)
Taqman QPCR condition:
Step 1; 95° C. for 10 min
Step 2; 95° C. for 15 sec
Step 3; 60° C. 30 for sec
Repeat Step 2 and 3; 40 times Adeno-Associated Virus (AAV) Production Adeno-associated virus serotype 2 (AAV2) particles were generated using AAVpro 293T cells (Takara #632273) seeded at a density of 9,000,000 cells per dish in 150 mm dishes (Corning) and cultured in DMEM media supplemented with 10% FBS, 2 mM fresh L-glutamine, 1 mM sodium pyruvate and non-essential amino acids (Thermo Fisher #11140050). Cells were transfected with 14.85 µg of pRC2-mi342 and pHelper vectors (Takara #6234) and 14.85 µg of pAAV-EFS-dsaCas9[-25]-miniVR-U6-sgRNA AIO plasmid with 81 µl TransIT-VirusGen (Mirus Bio #MIR6703). After 72 h, cells were harvested and crude AAV2 extracted in 550 µl per 150 mm dish according to the manufacturer's instructions in the AAV2 Helper Free System protocol (Takara #6230).

Cell Transduction with AAV2

In order to transduce HEK293FT cells (Thermo Fisher #R70007), 75,000 cells per well were seeded in 24-well plates (CORNING #351147) and incubated for 16 h in DMEM media supplemented with 10% FBS and 2 mM fresh L-glutamine, 1 mM sodium pyruvate and non-essential amino acids (Thermo Fisher #11140050). The media was replaced with 1000 µl fresh media, including 10 or 1 µl (1:100 or 1:1000 dilution, respectively) of crude AAV2. After a subsequent 72 h incubation, cells were lysed and total RNA extracted (RNeasy Plus 96 kit) according to manufacturer's instructions (Qiagen #74192) and over-expression of utrophin was determined as described in 'gene expression analysis' by Taqman.

TABLE 1

Targeting sequences used to screen the expression regulatory region of UTRN gene

| SEQ ID NO. | Guide # | Position | Strand | Targeting Sequence | PAM | Specificity | Efficiency |
|---|---|---|---|---|---|---|---|
| 129 | sgED3-1 | 144283943 | 1 | CTTGTTAAATGAATGAATGAA | GTGAAT | 21.67 | 24.07 |
| 130 | sgED3-2 | 144284051 | 1 | TGTCCTAGAAACCTTACAAGG | AAGAGT | 81.73 | 47.47 |

TABLE 1-continued

Targeting sequences used to screen the expression regulatory region of UTRN gene

| SEQ ID NO. | Guide # | Position | Strand | Targeting Sequence | PAM | Specificity | Efficiency |
|---|---|---|---|---|---|---|---|
| 131 | sgED3-3 | 144284216 | -1 | GGTTTATTGCTGGCTTAATAT | TTGAGT | 73.32 | 27.89 |
| 132 | sgED3-4 | 144284644 | 1 | ACGTCAGCAAACTGAGATGGG | GTGAGT | 72.28 | 29.99 |
| 133 | sgED3-5 | 144284753 | 1 | TTTTCGGATAATCTGAATAAG | GGGAAT | 73.39 | 26.71 |
| 134 | sgED3-6 | 144285129 | -1 | GGGGTCCGCTCTCCAGATGAG | AAGGGT | 86.65 | 25.53 |
| 135 | sgED3-7 | 144285744 | -1 | GGCTCCTCTAGGAGTTTGACA | CGGAGT | 88.25 | 85.15 |
| 136 | sgED3-8 | 144285873 | 1 | TAATGTGACTACAGCCCCCGA | GGGAAT | 93.52 | 70.61 |
| 137 | sgED3-9 | 144285972 | 1 | CCAAGTCCCAGAGTCGAAGAT | GGGAGT | 92.21 | 44.26 |
| 138 | sgED3-10 | 144286550 | -1 | TCAGTTGCAGCAAGAGATCCC | CAGAGT | 82.58 | 26.26 |
| 139 | sgED3-11 | 144286736 | 1 | CCTCCTCCTCGAAAAACGCAC | TGGAAT | 90.03 | 64.99 |
| 140 | sgED3-12 | 144287009 | -1 | GGGAGGGTCGGCTCAGACCTA | GGGAAT | 91.68 | 30.46 |
| 141 | sgED3-13 | 144287207 | 1 | GGGTAGTTCTGCGGTGACGGA | CAGGGT | 92.71 | 23.34 |
| 142 | sgED3-14 | 144287288 | -1 | ATTTTAGGTAAACACCCAAAG | GAGAGT | 70.86 | 46.61 |
| 143 | sgED3-15 | 144287397 | -1 | GAAACACAGTAAAAGAAAACG | GTGAGT | 51.32 | 53.15 |
| 144 | sgED3-16 | 144287614 | -1 | TAAGATTTTAGGAATTATACA | ATGAAT | 50.22 | 34.45 |
| 145 | sgED3-17 | 144287760 | 1 | AGCGTTCTGAAGGGAGAGTTA | GTGAAT | 75.62 | 42.44 |
| 146 | sgED3-18 | 144287920 | -1 | CAGAAGGCTAGGTGAGAAACT | GAGAAT | 64.29 | 34.34 |
| 147 | sgED3-19 | 144288078 | -1 | AATTTGAGTACACTTAAGGCA | AAGGAT | 74.85 | 24.36 |
| 148 | sgED3-20 | 144288193 | -1 | AGATACAGCAGAAAAGGTGAT | CAGAGT | 59.61 | 52 |
| 149 | sgED3-21 | 144343311 | 1 | GACACATGCAGAAGTGACAGC | AGGAGT | 62.51 | 64.83 |
| 150 | sgED3-22 | 144344138 | -1 | AGCAGCCTTCGAACTGCACAC | TGGGAT | 85.61 | 69.44 |
| 151 | sgED3-23 | 144344637 | -1 | TCTAGATGGCAGTAAACAGCA | CAGAGT | 72.98 | 81.01 |
| 152 | sgED3-24 | 144345218 | -1 | GGCTGCTCCAATCATTTTGGT | TTGAAT | 79.1 | 56.17 |
| 153 | sgED3-25 | 144284787 | -1 | GAGTCCGGAGACCGAACCAGA | ATGGAT | 91.54 | 23.9 |
| 154 | sgED3-26 | 144284810 | -1 | GAACCGTGCGTGCCGGGAGCC | GGGAGT | 86.09 | 1 |
| 155 | sgED3-27 | 144284837 | -1 | GCTGGCCTGGGGCGCGCGCTC | CAGAGT | 78.51 | 0.56 |
| 156 | sgED3-28 | 144285003 | -1 | AAGATCAGCCCCACTACGTTC | CCGGGT | 94.71 | 15.9 |
| 157 | sgED3-29 | 144285172 | 1 | CCGGAGGCGAGCCCCTTCCCG | GGGGGT | 82.7 | 14.59 |
| 158 | sgED3-30 | 144285207 | -1 | GGAGGGTGGGGCGCAGGACCG | CTGGGT | 68.11 | 4.19 |
| 159 | sgED3-31 | 144285227 | -1 | GAGCGCTGGAGGCGGAGGAGG | GAGGGT | 40.4 | 5.54 |
| 160 | sgED3-32 | 144285325 | 1 | CCTCTCTCGCGCACAAAGTTG | TGGAGT | 92.3 | 13.5 |
| 161 | sgED3-33 | 177285460 | 1 | GGGAGCGGCGCCCCCCTTCTT | TTGGGT | 92.82 | 3.72 |
| 162 | sgED3-34 | 144285496 | -1 | CACCAACTTTGCCAAACGCTA | CAGAGT | 90.69 | 15.32 |
| 163 | sgED3-35 | 144285722 | -1 | GGAGTAACCGCGGGGGTGTGT | GCGAGT | 90.76 | 15.84 |
| 164 | sgED3-36 | 144285896 | 1 | GAATGGGGCGGGGGCCGGGAG | GAGGAT | 47.73 | 3.79 |
| 165 | sgED3-37 | 144285926 | 1 | TCTTTCTGTGGTTCTTCCGCC | TGGGAT | 81.43 | 25.49 |
| 166 | sgED3-38 | 144286089 | -1 | TTTGGATCGTTCACAACTAGT | ACGGAT | 82.05 | 18.73 |
| 167 | sgED3-39 | 144286240 | 1 | AGAGGGGACGTGGCCTCTTAG | GAGAGT | 83.03 | 23.82 |

TABLE 1-continued

Targeting sequences used to screen the expression regulatory region of UTRN gene

| SEQ ID NO. | Guide # | Position | Strand | Targeting Sequence | PAM | Specificity | Efficiency |
|---|---|---|---|---|---|---|---|
| 168 | sgED3-40 | 144286311 | 1 | GTCCACAGGAGAGGGTGGGCA | GAGGGT | 38.6 | 8.03 |
| 169 | sgED3-41 | 144286418 | 1 | GCTCCCAAGGGTGGGGCTCCG | GAGAGT | 75.62 | 5.83 |
| 170 | sgED3-42 | 144286683 | 1 | TTTCAGATGGCAGGTTGTTCA | AAGGAT | 84.92 | 0.55 |
| 171 | sgED3-43 | 144286895 | 1 | CTTTCCCAGCCTTCAGGTCAG | CCGGAT | 70.16 | 23.24 |
| 172 | sgED3-44 | 144286993 | 1 | GCGCGCGGAGCTCGGGGGAGG | CCGGAT | 58.97 | 0.54 |
| 173 | sgED3-45 | 144287068 | -1 | TGAGGCCGGTGCAACTTACAA | AGGAAT | 94 | 33.46 |
| 174 | sgED3-46 | 144287139 | 1 | TGGGCGTGGGAGACGCAGCCT | GCGGAT | 73.4 | 1.47 |
| 175 | sgED3-47 | 144287184 | 1 | AGGTGGAGGAATGCGAAGCTT | GTGGGT | 87 | 21.29 |
| 176 | sgED3-48 | 144287284 | 1 | AGACAACTCTTTAACTCTCCT | TTGGGT | 78.9 | 15.46 |

In Table 1, "Position" indicates the cleavage position of a nucleotide in the strand where the targeting sequence exists, when SaCas9 is used.

In the item of "Strand" in Table 1, 1 shows sense strand, and −1 shows antisense strand.

(2) Results

FIG. 1 shows the activation of UTRN gene expression by the three different dSaCas9-activator fusion proteins (dSaCas9-VP64, dSaCas9-VPH, and dSaCas9-VPR) compared to the control sgRNA. The control sgRNA comprises ACGGAGGCUAAGCGUCGCAAG (SEQ ID NO: 215) and the tracrRNA sequence, and was designed as it has no targets on any sequences in the human genome. The sgRNAs comprising crRNA encoded by Guide #sgED3-6, sgED3-7, or sgED3-13 (SEQ ID NOs: 134, 135 or 141) respectively activated UTRN gene expression by recruiting dSaCas9-activator fusion proteins to expression regulatory region of UTRN gene. The activation effect was the strongest with dSaCas9-VPR fusion protein.

From the results above, the ~1.0 kb region (Region A) covered by Guide #sgED3-6 to sgED3-7(SEQ ID NOs 134 to 135) (Table 1), corresponding to Chr6: GRCh38/hg38; 144,285,000-144,286,000 (FIG. 1), and ~0.3 kb region (Region B) around Guide #sgED3-13 (SEQ ID NO 141), corresponding to Chr6: GRCh38/hg38; 144,287,000-144,287,300, confers efficient activation of UTRN gene expression. The promoter B confers relatively weak activation of UTRN gene compared with crRNA encoded by Guide #sgED3-6, sgED3-7, and sgED3-13 (SEQ ID NOs: 134, 135 and 141).

Figure 2:
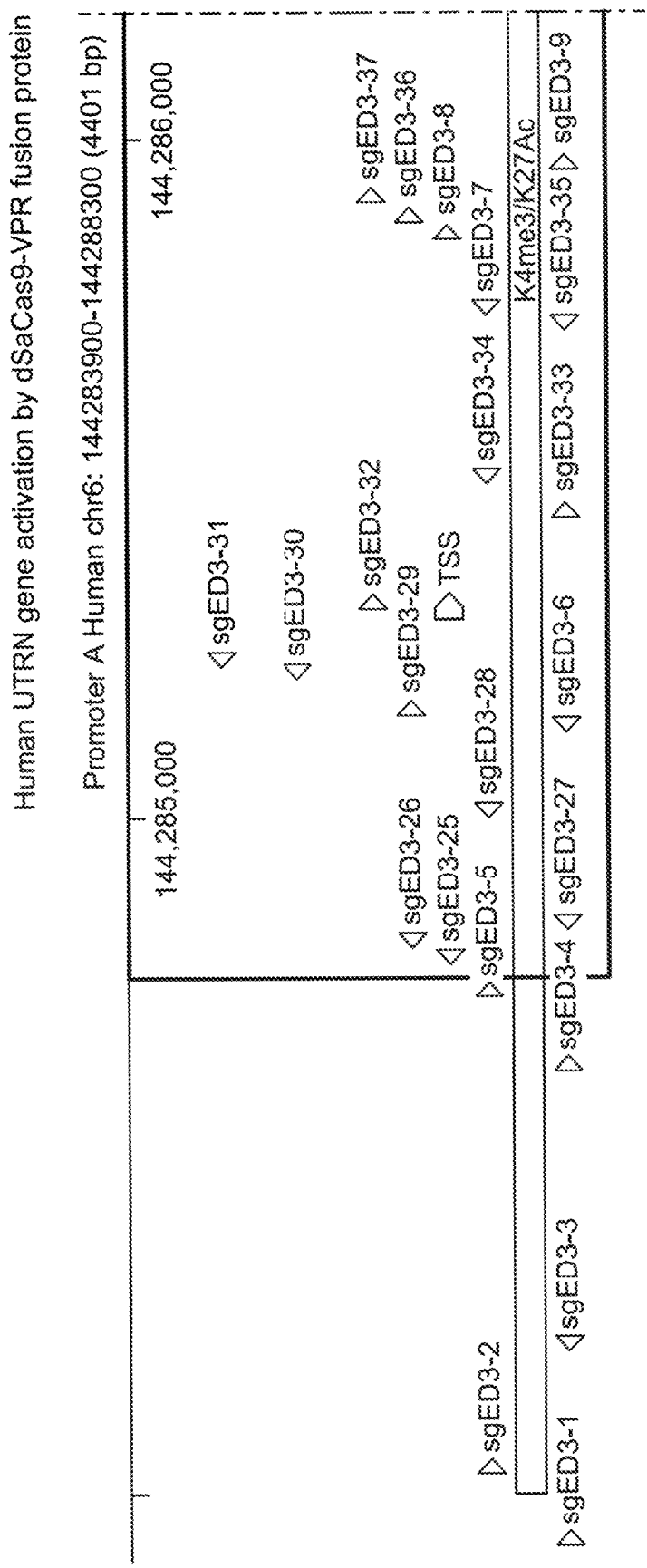
In FIG. 2, the upper panel shows the positions of the targeting sequences (Guide #sgED3-1 to sgED3-20 and sgED3-25 to sgED3-48 (SEQ ID NOs: 129 to 148 and 153 to 176)) determined in the regions of promoter A of human UTRN gene.
Figure 2:
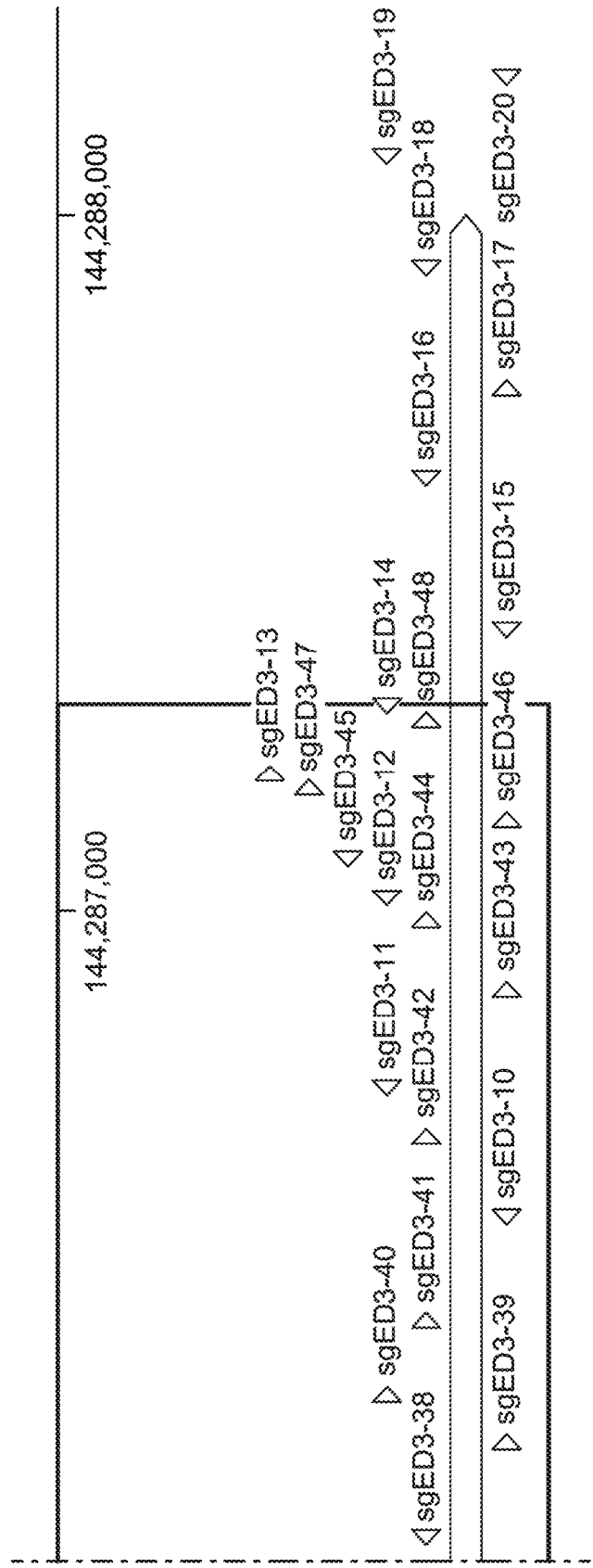
Figure 2:
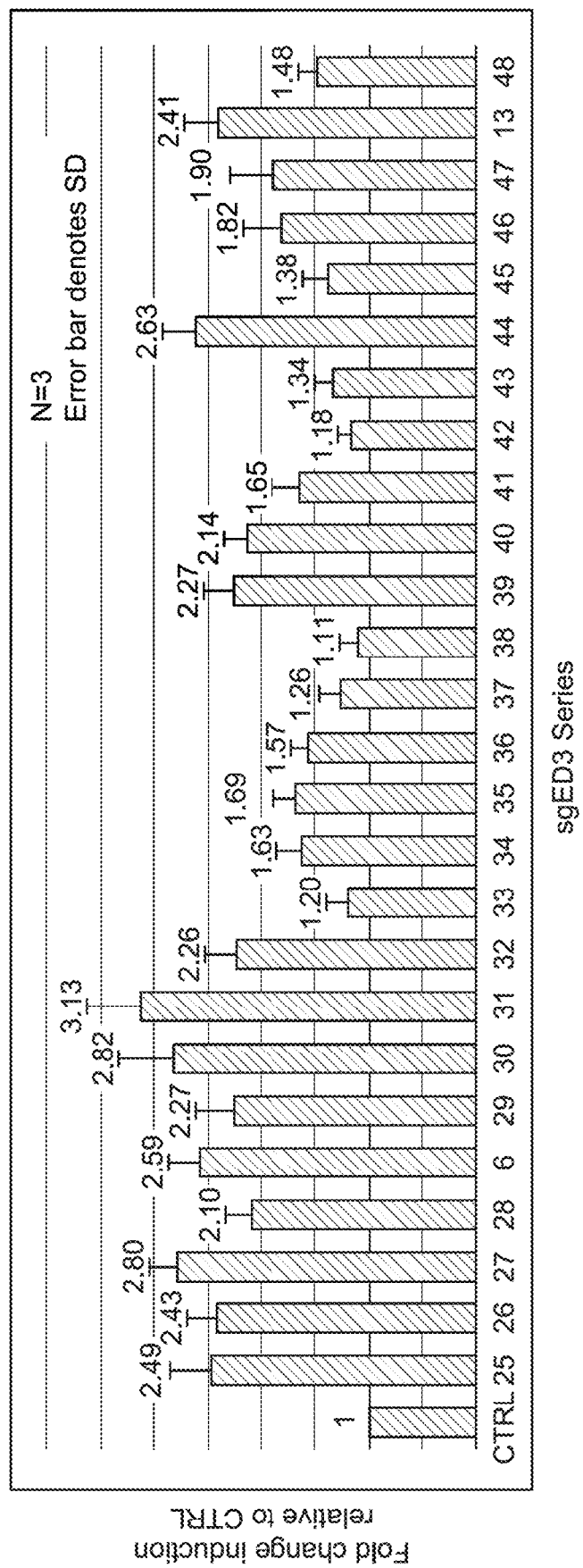

In FIG. 2, the region spanning Region A+B, corresponding to Chr6: GRCh38/hg38; 144,284,750-144,287,300, was further screened with additional twenty-four sgRNAs (Table 1, Guide #sgED3-25 to sgED3-48 (SEQ ID: Nos.153 to 176)) with dSaCas9-VPR for more potent activation of UTRN gene. The sgRNAs comprising crRNA encoded by Guide #sgED3-6, sgED3-13, sgED3-25 to sgED3-32, sgED3-39, sgED3-40 and sgED3-44 (SEQ ID NOs: 134, 141, 153 to 160, 167, 168 and 172), respectively, activated UTRN gene expression more than two fold compared to the aforementioned control sgRNA.

Figure 3:
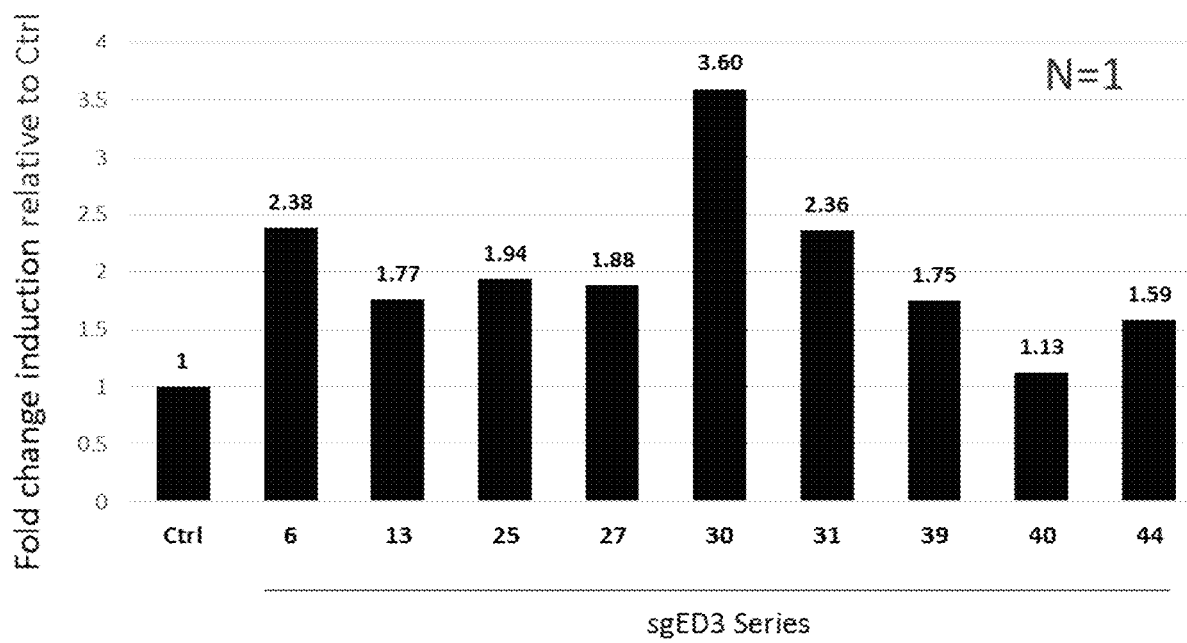
FIG. 3 shows validation results of the function of each sgRNA by using a plasmid vector (N=1). pAAV-EFS-dSaCas9[-25]-miniVR-U6-sgRNA AIO plasmid that expresses sgRNA comprising crRNA coded by the targeting sequence Guide #sgED3-6, sgED3-13, sgED3-25, sgED3-27, sgED3-30, sgED3-31, sgED3-39, sgED3-40, or sgED3-44 (SEQ ID NO: 134, 141, 153, 155, 158, 159, 167, 168 or 172) was prepared and transfected into HEK293FT cells, and the function thereof was verified. As compared to control sgRNA, when sgRNA comprising crRNA coded by the targeting sequence Guide #sgED3-6, sgED3-13, sgED3-25, sgED3-27, sgED3-30, sgED3-31, sgED3-39, sgED3-40, or sgED3-44 (SEQ ID NO: 134, 141, 153, 155, 158, 159, 167, 168 or 172) was used, activation of human UTRN gene expression was observed.

In FIG. 3, with regard to some of the potent sgRNAs comprising crRNA encoded by Guide #sgED3-6, sgED3-13, sgED3-25, sgED3-27, sgED3-30, sgED3-31, sgED3-39, sgED3-40, and sgED3-44 (SEQ ID Nos: 134, 141, 153, 155, 158, 159, 167, 168, and 172), respectively, pAAV-EFS-dSaCas9[-25]-miniVR-U6-sgRNA AIO plasmid were prepared and transfected into HEK293FT cells for validation of function, respectively. The induction of UTRN gene was observed, compared to the aforementioned control sgRNA, with the different sgRNAs with different extent.

Figure 4:
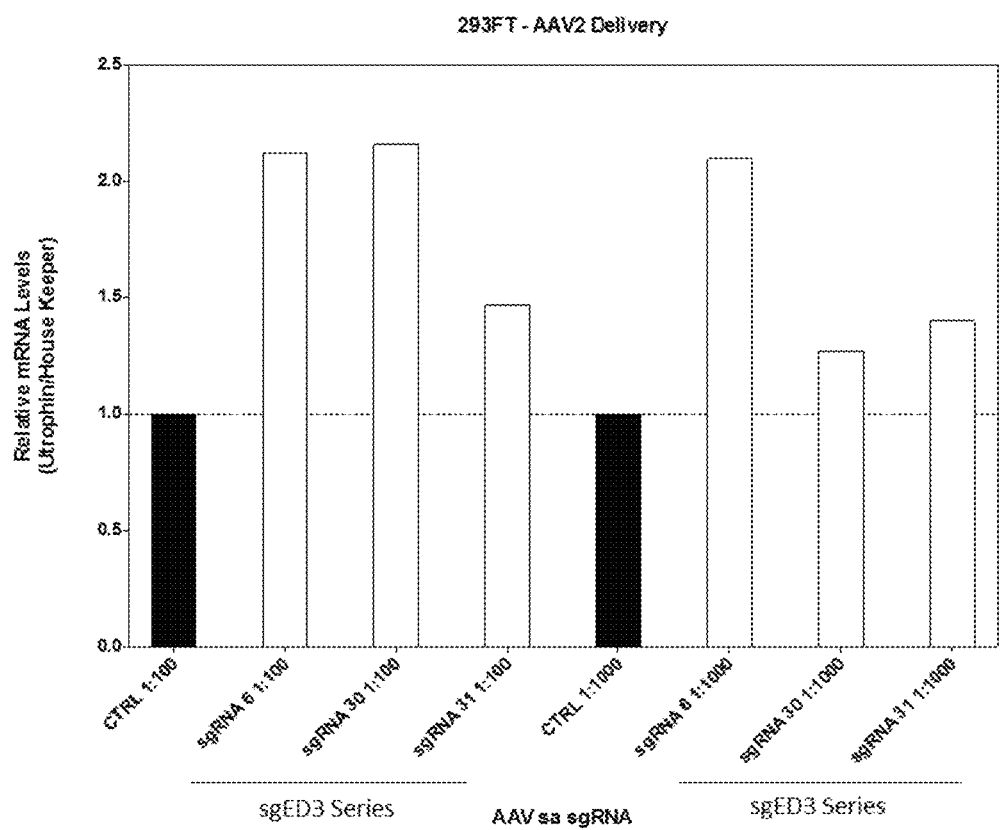
FIG. 4 shows the validation results of the function of each sgRNA by using an AAV vector (N=1). AAV2 produced using pAAV-EFS-dSaCas9[-25]-miniVR-U6-sgRNA AIO plasmid that expresses sgRNA comprising crRNA coded by the targeting sequence Guide #sgED3-6, sgED3-30, or sgED3-31 (SEQ ID NO: 134, 158 or 159) was transduced into HEK293FT cells. In all sgRNAs comprising crRNA coded by the targeting sequence Guide #sgED3-6, sgED3-30, or sgED3-31 (SEQ ID NO: 134, 158, or 159), activation of human UTRN gene was observed as compared to the control sgRNA.

In FIG. 4, AAV2 carrying EFS-dSaCas9[-25]-miniVR-U6-sgRNA were produced, and transduced HEK293FT cells. As sgRNA, sgRNAs comprising crRNA encoded by Guide #sgED3-6, sgED3-30, or sgED3-31 (SEQ ID NO: 134, 158, or 159), respectively, were used. UTRN gene induction was observed, compared to the aforementioned control sgRNA, regarding all the three sgRNAs.

Example 2

Figure 6:
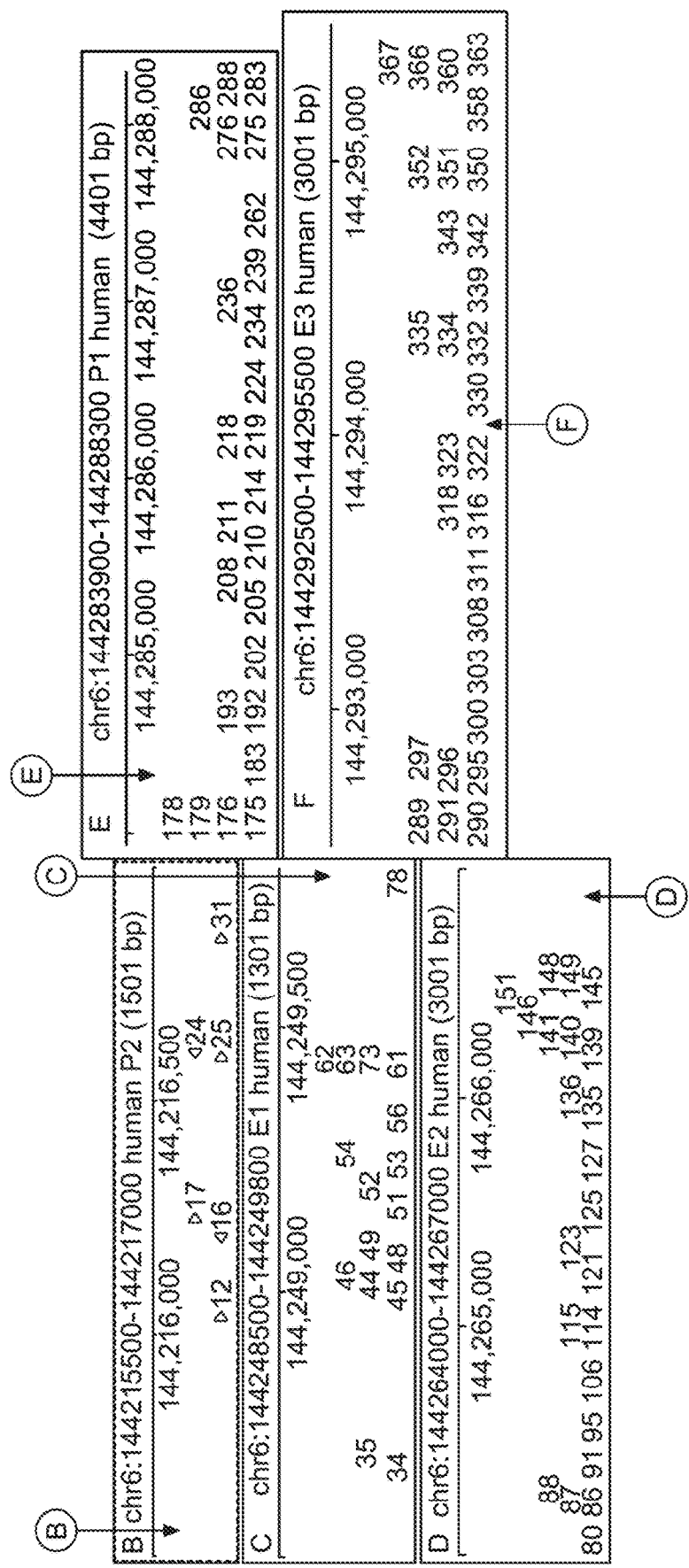
In FIG. 6, Panel A shows H3K4me3 and H3K27Ac pattern of genome in human skeletal muscle cells, and the putative enhancer region, E1, E2, and E3, and the putative promoter region, P1 and P2, of the human UTRN gene. Panels B to F show the positions of the targeting sequences set forth in each Guide #(sequences set forth in SEQ ID NOs: 4 to 103).
Figure 6:
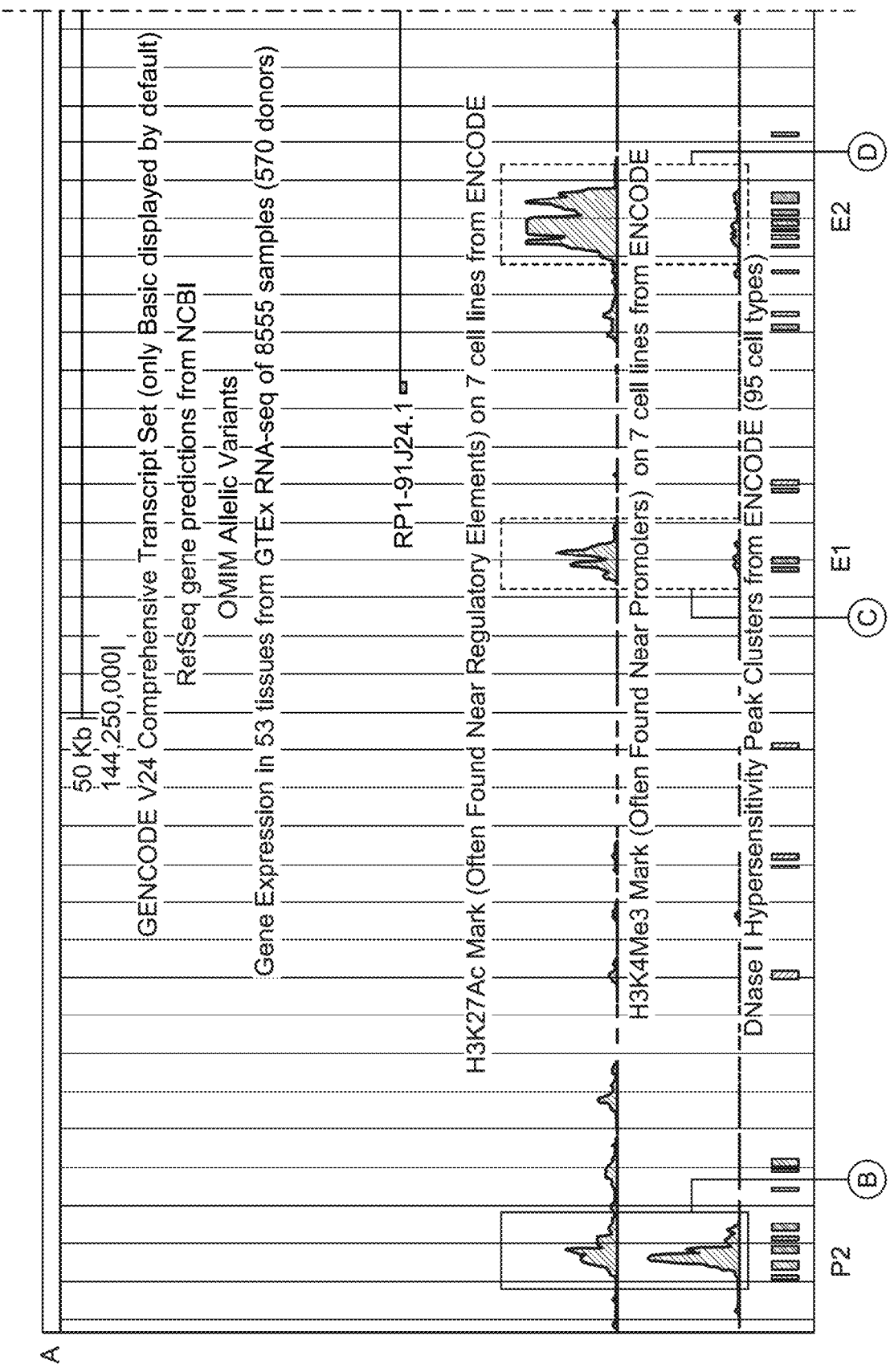
Figure 6:
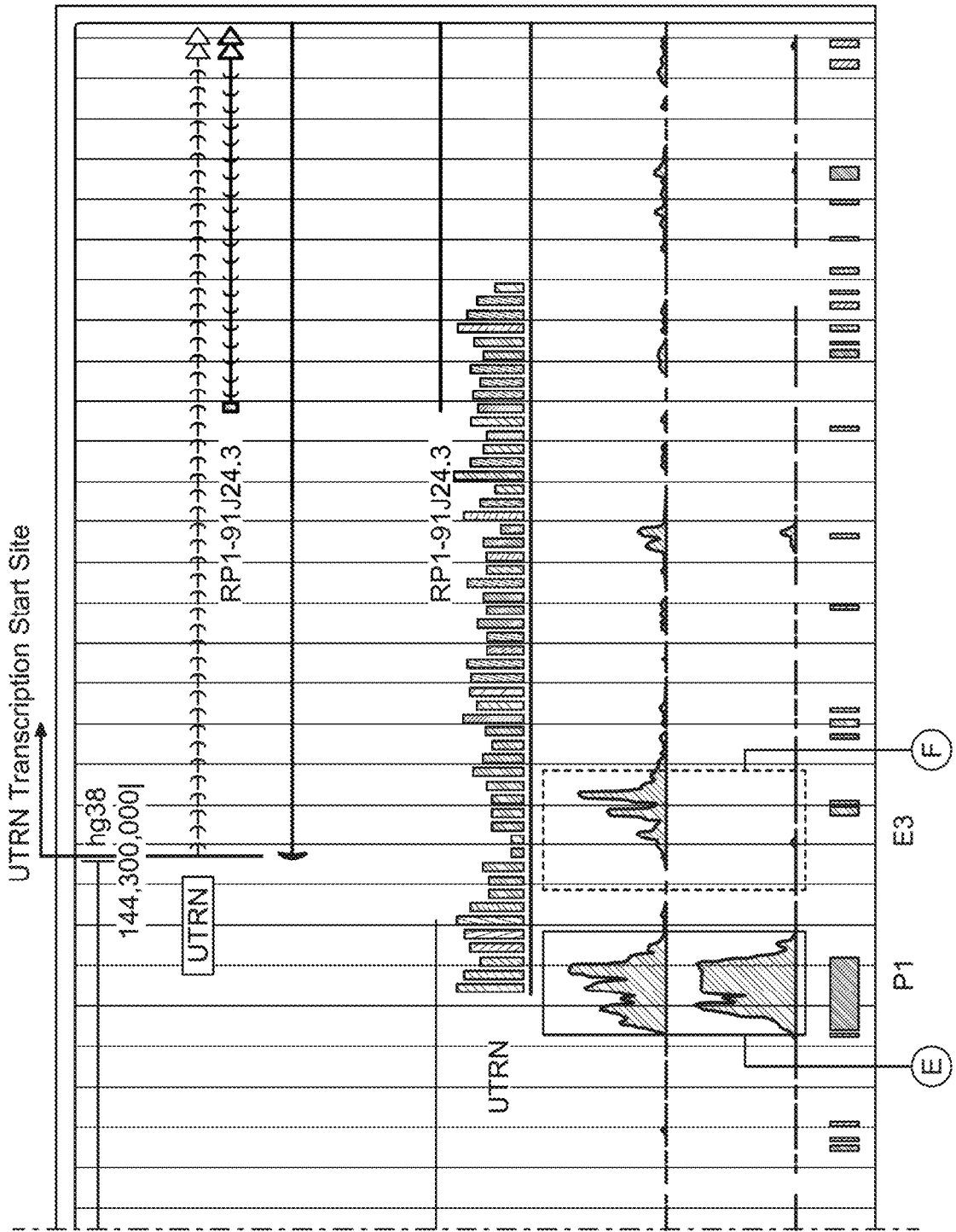

Screening of gRNAs for Human Utrophin Gene Using HSMM Cells (1) Experimental Methods
Selection of UTRN Targeting Sequences Based on the H3K4me3 and H3K27Ac pattern of genome in human skeletal muscle cells, roughly 13.2 kb of sequence around the putative enhancer (referred to as E) and promoter (referred to as P) regions of the human UTRN gene was scanned for sequences that can be targeted by a nuclease-deficient SaCas9 (D10A and N580A mutant; dSaCas9 [SEQ ID NO: 123 (Protein)]) complexed with gRNA, defined herein as a targeting sequence. Location of the targeted genome regions relative to UTRN gene is depicted in FIG. 6 and their coordinates for noted below:

1. Chr6: GRCh38.p12; 144215500-144217000->about 1.5kb (referred to as P2)
2. Chr6: GRCh38.p12; 144248500-144249800->about 1.3kb (referred to as E1)
3. Chr6: GRCh38.p12; 144264000-144267000->about 3.0kb (referred to as E2)
4. Chr6: GRCh38.p12; 144283900-144288300->about 4.4kb (referred to as P1)
5. Chr6: GRCh38.p12; 144292500-144295500->about 3.0kb (referred to as E3)

Targeting sequences were specified by the 21-nucleotide segment adjacent to a protospacer adjacent motif (PAM) having the sequence NNGRRT (5'-21nt targeting sequence-NNGRRT-3'), and were filtered to include mostly those with a perfect match (targeting sequence and PAM sequences) for the corresponding region of the cynomolgus monkey (*Macaca fascicularis*) genome (listed as "TRUE" in Table 3).

Construction of Lentiviral transfer plasmid (pED176)

pLentiCRISPR v2 was purchased from Genscript (Hypertext Transfer Protocol Secure://www.genscript.com) and the following modifications were made: the SpCas9 gRNA scaffold sequence was replaced by SaCas9 gRNA scaffold sequence (SEQ ID NO: 124); SpCas9 was replaced with dSaCas9 fused to codon optimized VP64-miniRTA (also referred to as miniVR) [SEQ ID NO: 125 (DNA) and 126 (Protein)]. MiniVR transcriptional activation domains can activate gene expression by activating transcription. MiniVR was tethered to the C-terminus of dSaCas9 (D10A and N580A mutant), which is referred to as dSaCas9-miniVR hereinafter (SEQ ID NO: 192 (DNA) and 193 (Protein)), and targeted to the putative enhancer or promoter regions of the human UTRN gene as directed by gRNA comprising crRNA encoded by each targeting sequence (FIG. 6). The generated backbone plasmid was named pED176.

gRNA Cloning

Three control non-targeting targeting sequences (Table 3, SEQ ID NOs: 1 through 3) and 100 targeting sequences (Table 3, SEQ ID NOs.: 4 through 103) were cloned into pED176. Forward and reverse oligos were synthesized by Integrated DNA Technologies in the following format: Forward; 5' CACC(G)-20-21 basepair targeting sequence-3', and Reverse: 5' AAAC-20-21 basepair reverse complement targeting sequence-(C)-3', where bases in parenthesis were added if the target did not begin with a G. Oligos were resuspended in Tris-EDTA buffer (pH 8.0) at 100 μM. 1 μl of each complementary oligo were combined in a 10 μl reaction in NE Buffer 3.1 (New England Biolabs (NEB) #B7203S). The reaction was heated to 95° C. and allowed to cool to 25° C. in a thermocycler, thus annealing oligos with sticky end overhangs compatible with cloning to pED176. Annealed oligos were combined with lentiviral transfer plasmid pED176 which had been digested with BsmBI and gel purified, and ligated with T4 DNA ligase (NEB #M0202S) according to manufacturer's protocol. 2 μl of the ligation reaction was transformed into 10 μl of NEB Stable Competent cells (NEB #C30401) according to the manufacturer's protocol. The resulting construct drives expression of sgRNAs comprising crRNA encoded by individual targeting sequences fused to their 3' end with tracrRNA (guuuuagua-cucuggaaacagaaucuacuaaaacaaggcaaaaugccguguuuaucuc-gucaa cuuguuggcgagauuuuuu (SEQ ID NO: 127)), which is encoded from the SaCas9 gRNA scaffold sequence added with a termination signal of U6 polymerase TTTTTT, by a U6 promoter (SEQ ID NO: 128).

Lentivirus Generation

HEK293TA cells (Genecopoeia #LT008) were seeded at $0.75 \times 10^6$ cells/well in 6 well cell culture dishes (VWR #10062-892) in 2 ml growth medium (DMEM media supplemented with 10% FBS and 2 mM fresh L-glutamine, 1 mM sodium pyruvate and non-essential amino acids (Thermo Fisher #11140050)) and incubated at 37° C./5% $CO_2$ for 24 hours. The next day, TransIT-VirusGEN transfection reactions (Mirus Bio #MIR6700) were set up according to manufacturer's protocol with 1.5 μg packaging plasmid mix [1 μg packaging plasmid (see pCMV delta R8.2; addgene #12263) and 0.5 μg envelope expression plasmid (see pCMV-VSV-G; addgene #8454)] and 1 μg of transfer plasmid containing sequence encoding dSaCas9-miniVR and indicated sgRNAs. Lentivirus was harvested 48 hours following transfection by passing media supernatant through a 0.45 μm PES filter (VWR #10218-488). Until ready to use, the purified and aliquoted lentiviruses were stored in −80° C. freezer.

Transduction of HSMM Cells

Primary skeletal muscle myoblast cells (HSMM) from 5 different human donors of age varying from 0-35 years were obtained from Lonza Inc, as shown in Table 2.

TABLE 2

| Donor # | Lot # | Age (Year) | Sex |
|---|---|---|---|
| 1 | 650386 | 35 | Male |
| 2 | 657512 | 34 | Female |
| 3 | 542368 | 0 | Female |
| 4 | 629287 | 19 | Female |
| 5 | 655307 | 18 | Male |

The cells were cultured in primary skeletal muscle cell growth medium [SkGM™-2 Skeletal Muscle Growth BulletKit medium (#CC-3245), which contains Culture system containing SkBM™-2 Basal Medium (#CC-3246) and SkGM™-2 SingleQuots™ supplements (#CC-3244) required for growth of skeletal muscle myoblasts)] from Lonza. CC-3246 contains 1× SkBM™-2 Basal Medium, 500 mL. 1×SkGM™-2 SingleQuots™ Supplement Pack (#CC-3244) contains:

1×Red Cap Vial with GA-1000, 0.50 mL
1×Green Cap Vial with hEGF, 0.50 mL
1×Natural Cap Vial with Dexamethasone, 0.50 mL
1×Bottle FBS, 50.00 mL
1×Bottle L-Glutamine, 10.00 mL Components of CC-3244 were added to the 500 ml culture medium (#CC-3246), according to manufacturer's instructions.

For transduction, cells were seeded at $0.125$-$0.33 \times 10^6$ cells/well in 6 well cell culture dishes (VWR #10062-894) containing growth medium and incubated at 37° C./5% $CO_2$ for 24 hours. The next day, 1.5 ml growth medium supplemented with 8 μg/ml Polybrene (Sigma #TR-1003-G) and 1.0 ml lentivirus supernatant (see above) corresponding to each sgRNA comprising crRNA encoded by individual targeting sequences (Table 3) fused with tracrRNA was added to each well. Lentivirus titrers ranged from $10^8$ to $10^9$ particles/ml, measured by using Lenti-X™ qRT-PCR Titration Kit (Clontech #631235). Cells were incubated with lentivirus for 6 hours before viral media were removed and replaced with fresh growth media. 72 hours after transduction, cells were fed selection media [growth media supplemented with 0.5 μg/ml puromycin (Sigma #P8833-100MG)]. Cells were given fresh selection media every 2-3 days. Following 7-10 days of cells being in selection media, cells were harvested and RNA was extracted with RNeasy 96 kit (Qiagen #74182) as directed by the manufacturer.

The co-transduction experiment of two viruses was conducted in the same way with the total amount of virus being equal to single virus transduction.

Gene Expression Analysis

For gene expression analysis, cDNA was generated from about 0.05-0.8 μg of total RNA according to High-Capacity cDNA Reverse Transcription Kit (Applied Biosystems; Thermo Fisher #4368813) protocol in a 10 μl volume. cDNA was diluted 10-fold and analyzed using Taqman Fast Advanced Master Mix (Thermo Fisher #4444557) according to the manufacturer's protocol. Taqman probes (UTRN: Assay Id Hs01125994_m1 FAM; HPRT: Assay Id Hs99999909_m1 VIC_PL) were obtained from Life Technologies. Taqman probe-based real-time PCR reactions were processed and analyzed by QuantStudio 5 Real-Time PCR system as directed by Taqman Fast Advanced Master Mix protocol.

Data Analysis For each sample and three controls, deltaCt values were calculated by subtracting the average Ct values from 3 technical replicates of the UTRN probe from the HPRT probe (Average Ct UTRN-Average Ct HPRT). Expression values were determined for each sample using the formula $2^{-(deltaCt)}$ Sample expression values (Table 3; SEQ ID NOs: 4 through 103) were then normalized to the average of 3 control expression values (Table 3; SEQ ID NOs: 1-3) for each experiment to determine the relative UTRN expression for each sample. Two biological replicates from each screen were analyzed and the average from all the experiments was calculated (Table 3).

(2) Results
Activation of UTRN Gene Expression by the RNP

Lentivirus was produced that deliver expression cassettes for dSaCas9-miniVR and sgRNAs for each targeting sequence to primary HSMM cells from the 5 different donors (Table 2). A majority of the assays were conducted on HSMM cells from donor #3 (Table 2) because of the growth speed of the cells. Transduced cells were selected for resistance to puromycin, and UTRN expression was quantitated using the Taqman Assay (Table 3). Expression values from each sample were normalized to an average of UTRN expression in cells transduced with control sgRNAs (Table 3; SEQ ID NOs: 1-3). Average expression levels were measured across duplicates of Donor #3 (Table 3; and FIG. 7).

TABLE 3

Targeting sequences used to screen expression regulatory region of UTRN gene.

| SEQ ID | Guide # | Coordinate (hg38/Chr.6) | nt length | plus or minus strand | Sequence | Cyno-Match | HSMMd3_screen1 | HSMMd3_screen2 |
|---|---|---|---|---|---|---|---|---|
| 1 | CtrlX3 | NA | 20 | – | ACGGAGGCTAAGCGTCGCAA | – | 1 | 1 |
| 2 | | NA | 20 | – | CGCTTCCGCGGCCCGTTCAA | – | | |
| 3 | | NA | 20 | – | GTAGGCGCGCCGCTCTCTAC | – | | |
| 4 | 12 | 144216047 | 21 | 1 | AGAAAAGCGGCCCCTAGGGC | TRUE | 1.42 | 0.55 |
| 5 | 16 | 144216199 | 21 | -1 | CAAACACACACCAGCAAACTT | TRUE | 1.27 | 0.53 |
| 6 | 17 | 144216257 | 21 | 1 | TGAAAGCGCAACTGGAGGGCC | TRUE | 0.99 | 0.73 |
| 7 | 24 | 144216593 | 21 | -1 | ACCCACGCGGACATATGTCCA | TRUE | 1.82 | 0.59 |
| 8 | 25 | 144216602 | 21 | 1 | ATCCAATGGACATATGTCCGC | TRUE | 1.41 | 0.68 |
| 9 | 31 | 144216855 | 21 | 1 | GAGGGGGAGGGCTGTGACCTG | TRUE | 1.35 | 0.56 |
| 10 | 34 | 144248644 | 21 | -1 | ATTTGGTGGTCAGGGAGCAAG | TRUE | 1.71 | 0.57 |
| 11 | 35 | 144248677 | 21 | 1 | AATGAAACCAAAGACAGCTTC | TRUE | 1.32 | 0.51 |
| 12 | 44 | 144248973 | 21 | -1 | CCAAAATCCTTTAATGAATCA | TRUE | 1.43 | 0.65 |
| 13 | 45 | 144248977 | 21 | 1 | TACAGATTCCATGATTCATTA | TRUE | 1.58 | 0.59 |
| 14 | 46 | 144248981 | 21 | -1 | GGAACAAACCAAAATCCTTTA | TRUE | 1.37 | 0.69 |
| 15 | 48 | 144249031 | 21 | -1 | ATCTGTTTGTGGGGAAATCTT | TRUE | 1.21 | 0.77 |
| 16 | 49 | 144249058 | 21 | 1 | CAAACAGATTTCAGTATTTTC | TRUE | 1.41 | 0.64 |
| 17 | 51 | 144249159 | 21 | 1 | GTGGTGATTTATGTTACTGGT | TRUE | 1.18 | 0.77 |
| 18 | 52 | 144249181 | 21 | 1 | TGAGTCTTTCAAGTTCCTTTC | TRUE | 1.5 | 0.72 |
| 19 | 53 | 144249211 | 21 | 1 | AGATCATTTTGGCTTCAAAC | TRUE | 1.63 | 0.71 |
| 20 | 54 | 144249221 | 21 | 1 | TGGCTTCAAACTAGAATGTCC | TRUE | 1.93 | 0.72 |
| 21 | 56 | 144249311 | 21 | 1 | GATCTATCTATAGACACCAAA | TRUE | 1.33 | 0.54 |
| 22 | 61 | 144249393 | 21 | -1 | TGCTTCTTCCAGGCTTGAGTG | TRUE | 1.39 | 0.75 |
| 23 | 62 | 144249400 | 21 | -1 | ACCGCTTTGCTTCTTCCAGGC | TRUE | 0.96 | 0.71 |
| 24 | 63 | 144249413 | 21 | 1 | AAGCCTGGAAGAAGCAAAGCG | TRUE | 1.51 | 0.98 |
| 25 | 73 | 144249669 | 21 | -1 | cttctgaatcagaattcctaa | TRUE | 1.04 | 0.66 |
| 26 | 78 | 144249756 | 21 | 1 | TGGTTCCAAGCTAGTACTTCA | TRUE | 1.03 | 0.78 |

TABLE 3-continued

Targeting sequences used to screen expression regulatory region of UTRN gene.

| SEQ ID | Guide # | Coordinate (hg38/Chr.6) | nt length | plus or minus strand | Sequence | Cyno-Match | HSMMd3_screen1 | HSMMd3_screen2 |
|---|---|---|---|---|---|---|---|---|
| 27 | 80 | 144264074 | 21 | 1 | ATGTTCACAAAATAAATTTAA | TRUE | 0.99 | 0.75 |
| 28 | 86 | 144264238 | 21 | 1 | CCTTTATGGTCACCTTCTCTG | TRUE | 1.2 | 0.79 |
| 29 | 87 | 144264250 | 21 | 1 | CCTTCTCTGCTGAGTAAAAAT | TRUE | 1.09 | .07 |
| 30 | 88 | 144264297 | 21 | 1 | AAGGTGGCCAAAAAGAACCC | FALSE | 1.28 | 1.37 |
| 31 | 91 | 144264318 | 21 | -1 | AAGGAAGAGAGAGGCAAGAAA | TRUE | 1.43 | 1.04 |
| 32 | 95 | 144264449 | 21 | -1 | TAAAGAATTCTAGCACTGGAA | TRUE | 0.62 | 0.51 |
| 33 | 106 | 144264745 | 21 | 1 | AAATGTGTCATGTGTTGGTTA | TRUE | 0.89 | 0.8 |
| 34 | 114 | 144265048 | 21 | 1 | AAAAATGAAAATTGCAACTTC | TRUE | 1.01 | 0.65 |
| 35 | 115 | 144265058 | 21 | 1 | ATTGCAACTTCTAGAATTTAA | TRUE | 0.79 | 0.57 |
| 36 | 121 | 144265214 | 21 | 1 | CAGCTGGAGTGGGCCACGTAA | TRUE | 1.19 | 1.25 |
| 37 | 123 | 144265304 | 21 | -1 | ATTTTTGCATATTTCTTTGGT | TRUE | 1.14 | 0.64 |
| 38 | 125 | 144265450 | 21 | -1 | AGTGACCTGCTGATTTCTCTA | TRUE | 1.38 | 0.74 |
| 39 | 127 | 144265606 | 21 | 1 | CTTTCCCCATTGTTCAGGACT | TRUE | 1.1 | 0.82 |
| 40 | 135 | 144265764 | 21 | 1 | TTGGTTGATAAATTTGTATAT | TRUE | 1.41 | 0.82 |
| 41 | 136 | 144265795 | 21 | -1 | TCTCTAGTTCATTTTTTAGCT | TRUE | 1.17 | 0.82 |
| 42 | 139 | 144266101 | 21 | -1 | TCCTTCAACTTCAAGACAACA | TRUE | 0.87 | 0.66 |
| 43 | 140 | 144266147 | 21 | -1 | GCTCCTCCTGCTGGATGGGGG | TRUE | 1.36 | 0.8 |
| 44 | 141 | 144266158 | 21 | -1 | CTCTATTTCCAGCTCCTCCTG | TRUE | 1.08 | 0.86 |
| 45 | 145 | 144266243 | 21 | 1 | GTACAGTTAGTGCTACTAGGA | TRUE | 3.2 | 1.43 |
| 46 | 146 | 144266254 | 21 | 1 | GCTACTAGGACAGGATGCTGG | TRUE | 2.5 | 1.23 |
| 47 | 148 | 144266287 | 21 | -1 | CCCCAGCTGTGCCTCTGTTTT | TRUE | 1.42 | 0.72 |
| 48 | 149 | 144266297 | 21 | 1 | TTCCCAAAACAGAGGCACAGC | TRUE | 1.36 | 0.87 |
| 49 | 151 | 144266338 | 21 | -1 | GTTTTGAAACTGGTAGCAGCT | TRUE | 1.52 | 1.2 |
| 50 | 175 | 144283934 | 21 | 1 | aaactgatgcttgttaaatga | TRUE | 1.05 | 0.91 |
| 51 | 176 | 144283943 | 21 | 1 | cttgttaaatgaatgaatGAA | TRUE | 1.34 | 0.89 |
| 52 | 178 | 144283973 | 21 | -1 | AATCCAAAGGATTAACTTGAA | TRUE | 1.48 | 1.09 |
| 53 | 179 | 144283981 | 21 | 1 | TACCCATTTCAAGTTAATCCT | TRUE | 1.3 | 1.02 |
| 54 | 183 | 144284099 | 21 | 1 | TGCCCCTCCCTGGAGCACTT | TRUE | 1.39 | 0.65 |
| 55 | 192 | 144284640 | 21 | 1 | AGCAACGTCAGCAAACTGAGA | TRUE | 1.06 | 0.96 |
| 56 | 193 | 144284644 | 21 | 1 | ACGTCAGCAAACTGAGATGGG | TRUE | 1.29 | 0.63 |
| 57 | 202 | 144284810 | 21 | -1 | GAACCGTGCGTGCCGGGAGCC | TRUE | 1.15 | 0.95 |
| 58 | 205 | 144285129 | 21 | -1 | GGGGTCCGCTCTCCAGATGAG | FALSE | 2.28 | 1.8 |
| 59 | 208 | 144285207 | 21 | -1 | GGAGGGTGGGGCGCAGGACCG | TRUE | 2.29 | 1.59 |
| 60 | 210 | 144285325 | 21 | 1 | CCTCTCTCGCGCACAAAGTTG | FALSE | 1.88 | 1.76 |
| 61 | 211 | 144285429 | 21 | 1 | TCTGGCTCCAGAAGCCGATTG | TRUE | 1.11 | 1.01 |
| 62 | 214 | 144285603 | 21 | 1 | ACAAGTAAGGGCGTTTTCAG | TRUE | 1.14 | 0.78 |

TABLE 3-continued

Targeting sequences used to screen expression regulatory region of UTRN gene.

| SEQ ID | Guide # | Coordinate (hg38/Chr.6) | nt length | plus or minus strand | Sequence | Cyno-Match | HSMMd3_screen1 | HSMMd3_screen2 |
|---|---|---|---|---|---|---|---|---|
| 63 | 218 | 144285756 | 21 | -1 | GAGCTGGCCAAGGGCTCCTCT | TRUE | 1.3 | 0.82 |
| 64 | 219 | 144285770 | 21 | 1 | TAGAGGAGCCCTTGGCCAGCT | TRUE | 1.34 | 0.86 |
| 65 | 224 | 144285972 | 21 | 1 | CCAAGTCCCAGAGTCGAAGAT | TRUE | 1.25 | 0.87 |
| 66 | 234 | 144286311 | 21 | 1 | GTCCACAGGAGAGGGTGGGCA | TRUE | 1.38 | 0.87 |
| 67 | 236 | 144286403 | 21 | 1 | CTCTGGGTGGTTGCTGCTCCC | TRUE | 1 | 0.73 |
| 68 | 239 | 144286550 | 21 | -1 | TCAGTTGCAGCAAGAGATCCC | TRUE | 1.12 | 0.92 |
| 69 | 262 | 144287288 | 21 | -1 | ATTTTAGGTAAACACCCAAAG | TRUE | 1.35 | 0.78 |
| 70 | 275 | 144287912 | 21 | -1 | taggtgagaaactgagaatca | TRUE | 1.45 | 0.77 |
| 71 | 276 | 144287920 | 21 | -1 | cagaaggctaggtgagaaact | TRUE | 1.3 | 0.69 |
| 72 | 283 | 144288096 | 21 | -1 | GCCATTAATGGCCAGAGGAAT | TRUE | 1.71 | 0.91 |
| 73 | 286 | 144288193 | 21 | -1 | AGATACAGCAGAAAAGGTGAT | TRUE | 1.13 | 0.92 |
| 74 | 288 | 144288268 | 21 | 1 | AATTTGAAAAATCACCTTGAG | TRUE | 1.47 | 0.81 |
| 75 | 289 | 144292526 | 21 | -1 | cagttgattcatctgtacagc | TRUE | 1.1 | 1.01 |
| 76 | 290 | 144292529 | 21 | 1 | tttttgactctggctgtacag | TRUE | 1.26 | 1.21 |
| 77 | 291 | 144292541 | 21 | 1 | gctgtacagatgaatcaactg | TRUE | 2.12 | 1.08 |
| 78 | 295 | 144292639 | 21 | -1 | ATCTCCCTTTGAGTTTGTCT | TRUE | 1.31 | 0.88 |
| 79 | 296 | 144292651 | 21 | -1 | CTGTTCAAAAATATCTCCCCT | TRUE | 1.31 | 1.03 |
| 80 | 297 | 144292708 | 21 | 1 | AAAATTACACAGAACTCCACC | TRUE | 1.69 | 1.06 |
| 81 | 300 | 144292779 | 21 | -1 | TTTTTTGTCTTTAAAGTGACA | TRUE | 1.12 | 0.7 |
| 82 | 303 | 144293063 | 21 | 1 | TCTTGTTTTAAAATATGCTTT | TRUE | 1.15 | 1.11 |
| 83 | 308 | 144293185 | 21 | -1 | CTCTGTTATATTTACATATGT | TRUE | 1.05 | 0.73 |
| 84 | 311 | 144293308 | 21 | -1 | TATAAATATCAAAGGTCTTAC | TRUE | 0.88 | 0.73 |
| 85 | 316 | 144293537 | 21 | -1 | cctagggaaaaactctagaaa | TRUE | 1.17 | 0.82 |
| 86 | 318 | 144293938 | 21 | 1 | acaccatgaaaatctaatatt | TRUE | 1.09 | 0.93 |
| 87 | 322 | 144293778 | 21 | -1 | agatgtgctagagtaaagaaa | TRUE | 1.25 | 0.93 |
| 88 | 323 | 144293791 | 21 | -1 | GTATGATCTGTTCagatgtgc | TRUE | 1.55 | 1.17 |
| 89 | 330 | 144294147 | 21 | 1 | TTTAAAGATTATCAAATTGCT | TRUE | 1.23 | 0.71 |
| 90 | 332 | 144294262 | 21 | 1 | ATATGAATCACATTCTTTTGG | TRUE | 1.33 | 0.93 |
| 91 | 334 | 144294294 | 21 | 1 | TGCAAAAGCCAGTAGATAAAT | TRUE | 1.01 | 0.81 |
| 92 | 335 | 144294300 | 21 | 1 | AGCCAGTAGATAAATTTGGAT | TRUE | 0.8 | 1.01 |
| 93 | 339 | 144294447 | 21 | 1 | TTTTAGTTTAGATTAAGTCAT | TRUE | 0.81 | 0.84 |
| 94 | 342 | 144294575 | 21 | -1 | AAGAAACCTGGAAGAGCAGAT | TRUE | 1.07 | 1.1 |
| 95 | 343 | 144294603 | 21 | 1 | GGTTTCTTTTTGGGGGGAAA | TRUE | 1.37 | 0.92 |
| 96 | 350 | 144294924 | 21 | 1 | TATGGTTGTAGTATACTTGCC | TRUE | 1.24 | 1.02 |
| 97 | 351 | 144294930 | 21 | 1 | TGTAGTATACTTGCCTTGGGT | TRUE | 1.07 | 0.83 |
| 98 | 352 | 144294934 | 21 | 1 | GTATACTTGCCTTGGGTTTGG | TRUE | 1.11 | 0.93 |

TABLE 3-continued

Targeting sequences used to screen expression regulatory region of UTRN gene.

| SEQ ID | Guide # | Coordinate (hg38/Chr.6) | nt length | plus or minus strand | Sequence | Cyno-Match | HSMMd3_screen1 | HSMMd3_screen2 |
|---|---|---|---|---|---|---|---|---|
| 99 | 358 | 144295231 | 21 | 1 | ACATGAAATAATAAAATGGTT | TRUE | 0.86 | 1.03 |
| 100 | 360 | 144295268 | 21 | -1 | ATTATTGAATGAAATAGCAGT | TRUE | 0.86 | 1.06 |
| 101 | 363 | 144295330 | 21 | -1 | ACAACACTGACAGCAACAGAA | TRUE | 0.89 | 0.97 |
| 102 | 366 | 144295418 | 21 | 1 | AGTGTGTCAGCTGGCTCCATG | TRUE | 1.09 | 1.14 |
| 103 | 367 | 144295435 | 21 | 1 | CATGTGGAGTTCTTGACAGTT | TRUE | 1.03 | 0.98 |

In Table 3, "Coordinate" indicates the potential SaCas9 cleavage site for all shown gRNAs when SaCas9 is used.

Figure 7:
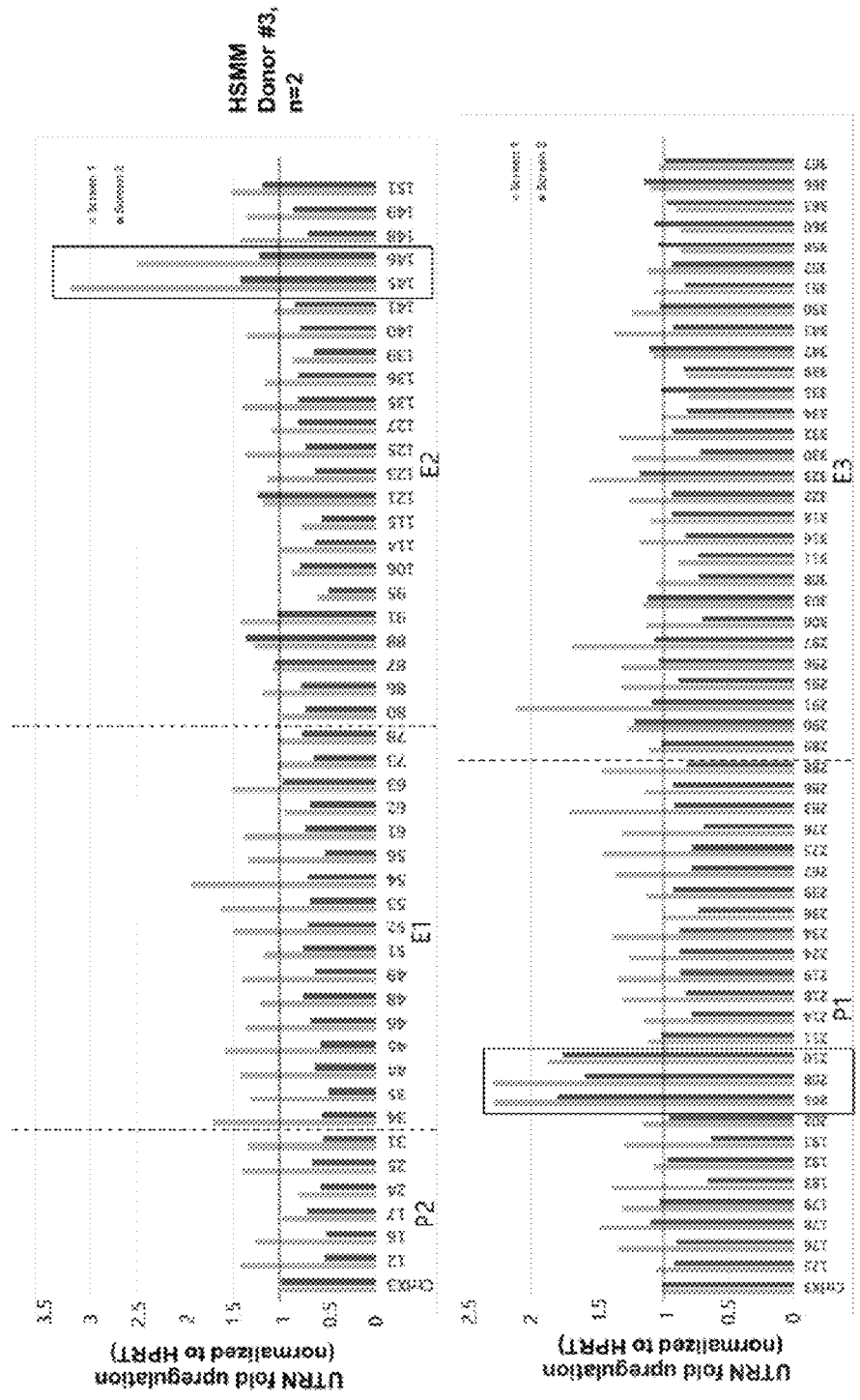
FIG. 7 shows the results of evaluating the activation of human UTRN gene expression by using sgRNA comprising crRNA coded by the targeting sequences set forth in each Guide #(sequences set forth in SEQ ID NOs: 4 to 103) and dSaCas9-miniVR in HSMM cells (N=2).

As shown in FIG. 7, out of tested 100 targeting sequences, 5 targeting sequences showed consistent upregulation of UTRN mRNA expression (Guide #145, 146, 205, 208, and 210 (SEQ ID NOs: 45, 46, 58, 59, and 60)) in HSMM Donor #3 cells. 2 of these sequences namely #145 (SEQ ID NO: 45), #146 (SEQ ID NO: 46) clustered in the enhancer E2 region, whereas the rest 3 namely #205 (SEQ ID NO: 58), #208 (SEQ ID NO: 59), and #210 (SEQ ID NO: 60) clustered in the promoter P1 region. Guide #205, 208, and 210 are same as #sgED3-6, sgED3-30, and sgED3-32 in Example 1 respectively.

Out of these 5 targeting sequences, 3 sequences namely #145, #146, and #208 match 100% with the corresponding region of the cynomolgus monkey genome. On the other hand, 2 of these sequences namely #205 and #210 do not match with the corresponding region of the cynomolgus monkey genome (FIG. 8).

Figure 9:
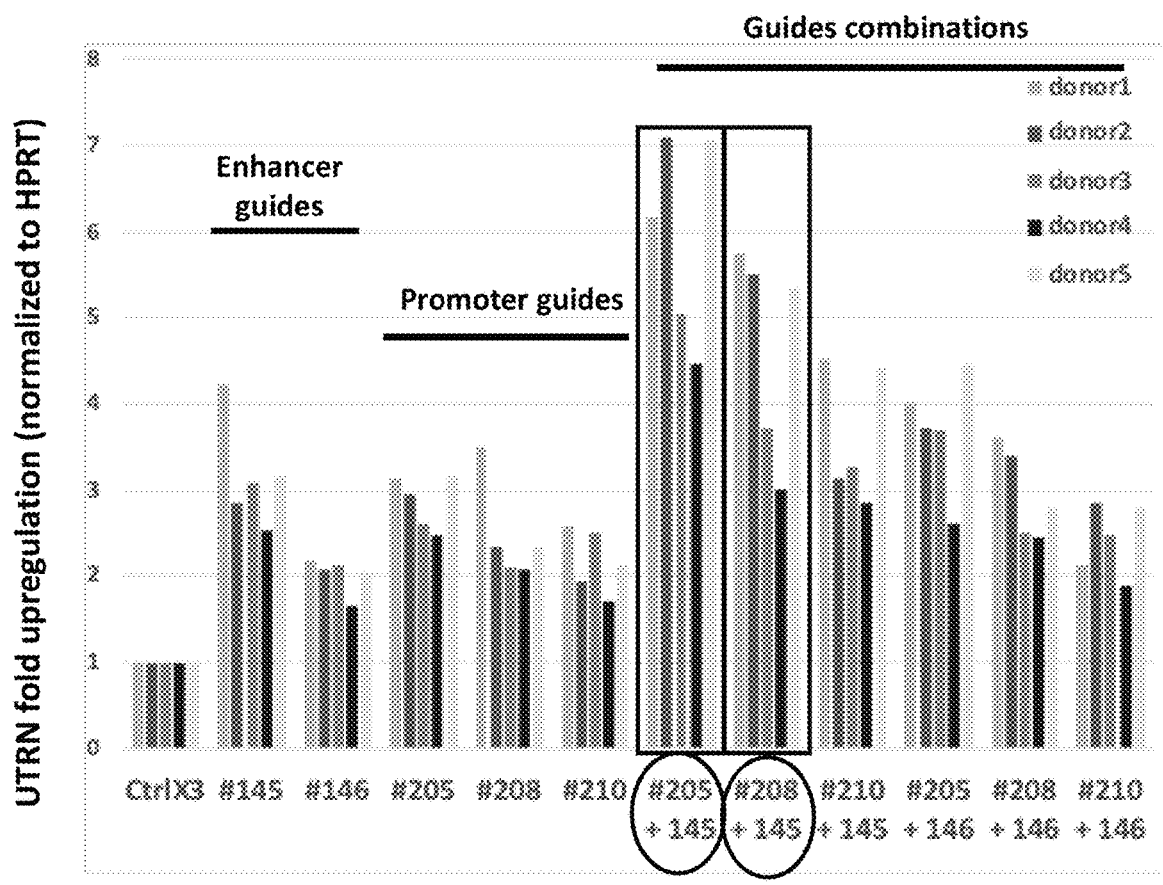
FIG. 9 shows activation of human UTRN gene expression by using sgRNA comprising crRNA coded by the targeting sequences Guide #145, 146, 205, 208, 210 (SEQ ID NOs: 45, 46, 58, 59, and 60) respectively , or combinations thereof, and dSaCas9-miniVR, in 5 different HSMM cells (N=2).

When tested individually, these 5 targeting sequences consistently showed about 2-4 fold upregulation of UTRN mRNA expression in the 5 different HSMM donors (FIG. 9). In the combinations of Guide #205, #208, or #210 in the promoter region and Guide #145 or #146 in the enhancer region (schematic shown in FIG. 8), 2 combinations, Guide #205 and #145 (#205+145) and Guide #208 and #145 (#208+145), led to about about 3-7 fold upregulation of UTRN expression in the 5 different HSMM donors (FIG. 9).

Example 3

Generation and Evaluation of AAV Cis-Plasmids (1) Experimental Methods
Construction of AAV AIO Cis-Plasmids As shown in Table 4, all the tested plasmid backbones pED260 (SEQ ID NO: 210), pED261 (SEQ ID NO: 211), and pED263 (SEQ ID NO: 212) contain same base sequence of full-length dSaCas9, CK8 promoter, and U6 promoter, replacing the sequence between ITRs of the pAAV-CMV vector (Takara #6234). They differ in activator moieties, polyA sequence-pED260, pED261 contain miniVR whereas pED263 contains microVR as activator moiety and pED260 has bGH polyA whereas pED261, pED263 have 2× sNRP-1 polyA sequence (SEQ ID NO: 208).

TABLE 4

| | promoter (dCas9) | dSaCas9 | activator | polyA | promoter (gRNA) | targeting sequence |
|---|---|---|---|---|---|---|
| plasmid pED260 (5171bp*) | CK8 | full length | miniVR | bGH polyA | U6 | SEQ ID NO: 45 (#145) |
| | CK8 | full length | miniVR | bGH polyA | U6 | SEQ ID NO: 46 (#146) |
| | CK8 | full length | miniVR | bGH polyA | U6 | SEQ ID NO: 59 (#208) |
| plasmid pED261 (4973bp*) | CK8 | full length | miniVR | 2 × sNRP-1 polyA | U6 | SEQ ID NO: 45 (#145) |
| | CK8 | full length | miniVR | 2 × sNRP-1 polyA | U6 | SEQ ID NO: 46 (#146) |
| | CK8 | full length | miniVR | 2 × sNRP-1 polyA | U6 | SEQ ID NO: 59 (#208) |
| plasmid pED263 (4883bp*) | CK8 | full length | microVR | 2 × sNRP-1 polyA | U6 | SEQ ID NO: 45 (#145) |
| | CK8 | full length | microVR | 2 × sNRP-1 polyA | U6 | SEQ ID NO: 46 (#146) |
| | CK8 | full length | microVR | 2 × sNRP-1 polyA | U6 | SEQ ID NO: 59 (#208) |

*nucleotide length between ITRs (including ITR nucleotides)

Each oligo for sgRNA comprising crRNA coded by the targeting sequences Guide #145, #146, or #208 was cloned into each of these backbones to create all-in-one (AIO) plasmids for testing. Each resulting AIO plasmid denotes pAAV-CK8-dSaCas9-miniVR-bGH polyA-U6-sgRNA#145 (pED260-145), pAAV-CK8-dSaCas9-miniVR-bGH polyA-U6-sgRNA#146 (pED260-146), pAAV-CK8-dSaCas9- miniVR-bGH polyA-U6-sgRNA#208 (pED260-208), pAAV-CK8-dSaCas9-miniVR-2× sNRP-1 polyA-U6-sgRNA#145 (pED261-145), pAAV-CK8-dSaCas9-miniVR-2× sNRP-1 polyA-U6-sgRNA#146 (pED261-146), pAAV-CK8-dSaCas9-miniVR-2× sNRP-1 polyA-U6-sgRNA#208 (pED261-208), pAAV-CK8-dSaCas9-microVR-2× sNRP-1 polyA-U6-sgRNA#145 (pED263-145), pAAV-CK8-dSaCas9-microVR-2× sNRP-1 polyA-U6-sgRNA#146 (pED263-146), or pAAV-CK8-dSaCas9-microVR-2× sNRP-1 polyA-U6-sgRNA#208 (pED263-208) as shown in Table 4.

Two different sequences known to be not homologous to any part of the human genome were used as negative controls and referred to as non-targeting guides (NTg1 (SEQ ID NO: 1), and NTg2 (SEQ ID NO: 2)). Each oligo for NTg1 or NTg2 was also cloned into the respective backbone, and used as control plasmids.

Transfection of HEK293FT Cells

HEK293FT cells (Thermo Fisher #R70007) were seeded at $5 \times 10^4$ cells/well in 24 well cell culture dishes (CORNING #351147) in 0.5 ml growth medium (DMEM media supplemented with 10% FBS and 2 mM fresh L-glutamine, 1 mM sodium pyruvate and non-essential amino acids (Thermo Fisher #11140050)) and incubated at 37° C./5% $CO_2$ for 24 hours. The next day lipofectamine-2000 transfection reactions (Thermo Fisher #11668019) were set up according to manufacturer's protocol with 0.5 µg plasmid containing sequence encoding dSaCas9-miniVR or dSaCas9-microVR and sgRNA comprising the targeting sequence selected in Example 2, i.e. Guide #145 (SEQ ID NO: 45), #146 (SEQ ID NO: 46), or #208 (SEQ ID NO: 59)) (Table 4).

48 hours post transfection, cells were harvested and RNA was extracted with RNeasy 96 kit (Qiagen #74182) as directed by the manufacturer.

Gene Expression Analysis

For gene expression analysis, cDNA was generated from ~0.5 µg of total RNA according to High-Capacity cDNA Reverse Transcription Kit (Applied Biosystems; Thermo Fisher #4368813) protocol in a 10 µl volume. cDNA was diluted 10-fold and analyzed using Taqman Fast Advanced Master Mix (Thermo Fisher #4444557) according to the manufacturer's protocol. Taqman probes (UTRN: Assay Id Hs01125994_m1 FAM; HPRT: Assay Id Hs99999909_m1 VIC_PL) were obtained from Thermo Fisher. Taqman probe-based real-time PCR reactions were processed and analyzed by QuantStudio 5 Real-Time PCR system as directed by Taqman Fast Advanced Master Mix protocol.

Data Analysis

For plasmid containing NTg1 or NTg2, the average of the results was shown as CtrlX2.

For each sample, delta Ct values for each probe were calculated by subtracting the average Ct values from 3 technical replicates for each sample from the average Ct values from 3 technical replicates of the non-targeting guide controls.

Delta Ct UTRN=Average control Ct UTRN−Average sample Ct UTRN.

Delta Ct HPRT=Average control Ct HPRT−Average sample Ct HPRT.

Delta delta Ct values were then calculated by subtracting delta Ct values of HPRT from delta Ct values of UTRN for each sample.

deltadeltaCt=delta Ct UTRN−delta Ct HPRT.

Expression values were determined for each sample using the formula $2^{(deltadeltaCt)}$.

(2) Results

Figure 10:
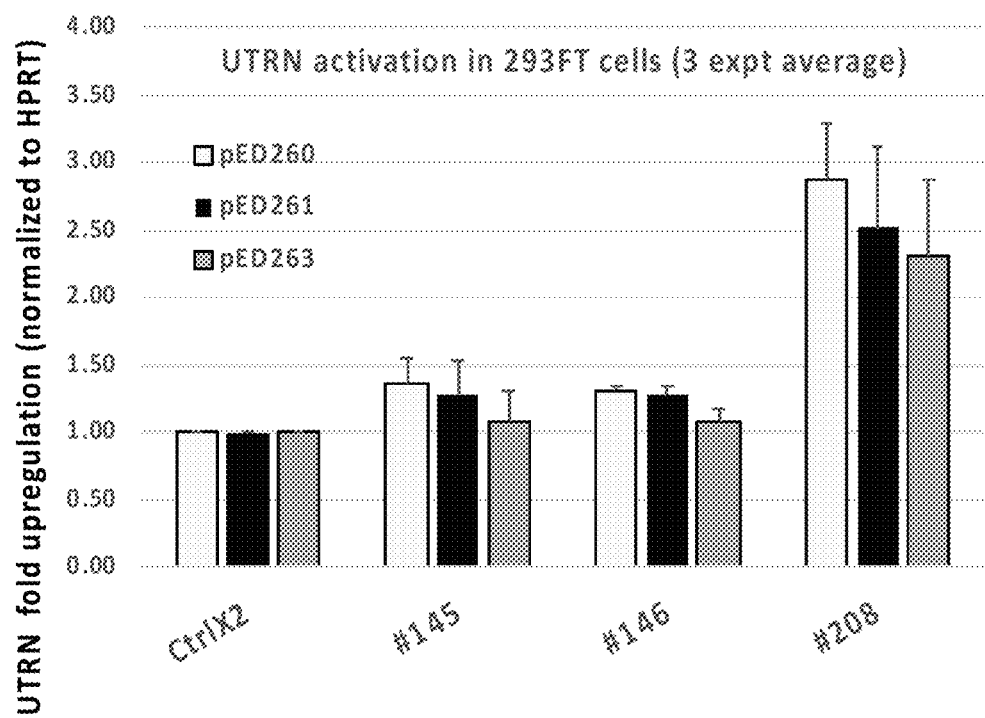
FIG. 10 shows sgRNA comprising crRNA coded by the targeting sequences Guides #145, #146, or #208 upregulates UTRN in pED260, pED261, or pED263 µlasmid backbones. Relative mRNA expression is determined from HEK293FT cells transiently expressing guides #145, #146, or #208 in pED260, pED261, or pED263 backbones, respectively. Data are represented as means+stdev from 3 repeats (N=3. error bar shows standard deviation).

In presence of sgRNA comprising crRNA coded by the targeting sequence Guide #145 (SEQ ID NO: 45), or #146 (SEQ ID NO: 46), or #208 (SEQ ID NO: 59), all 3 tested backbones (pED260, 261, and 263) were capable of upregulating UTRN in HEK293FT cells (FIG. 10).

Example 4

Generation of Recombinant AAV9 Carrying dSaCas9, Transcription Activator and sgRNA (1) Experimental Methods
Adeno-Associated Virus (AAV) Production Adeno-associated virus serotype 9 (AAV9) particles were generated using 293T cells (ATCC CRL-3216) seeded at a density of $0.96 \times 10^7 - 1.8 \times 10^7$ cells per T225 flask (Corning) and cultured in DMEM media supplemented with 10% FBS (Thermo Fisher #11995-065). The pRC9 µlasmid was constructed as follows: AAV9 capsid sequence (see JP5054975B) was subcloned into a pRC2-mi342 plasmid (Takara #6230) replacing with that of AAV2 capsid sequence. Cells were transfected with 20 µg of the pRC9 µlasmid and pHelper vector (Takara #6230) and 20 µg of one of 6 kinds of the AIO plasmid which was used in Example 3, pED261-145, pED261-146, pED261-208, pED263-145, pED263-146, or pED263-208, with 180 µl TransIT-293 Transfection Reagent (Mirus Bio #MIR2700) per T225 flask. A day after transfection, culture media was changed to DMEM media supplemented with 2% FBS. After 72 h, cells were harvested, and AAV was extracted and purified using AAVpro Purification Kit (All Serotypes) (Takara #6666) according to the manufacture's instructions. The titer of purified AAV was measured using AAVpro Titration Kit (for Real Time PCR) (Takara #6233). Each resulting AAV denotes AAV9-ED261-145, AAV9-ED261-146, AAV9-ED261-208, AAV9-ED263-145, AAV9-ED263-146, or AAV9-ED263-208.

Confirmation of AAV

AAV capsid proteins were checked by SDS-PAGE after AAV sample preparation with NuPAGE Sample Reducing Agent, antioxidant and Buffer (Thermo Fisher #NP0009, #NP0005, 190 NP0007) using NuPAGE 4-12% Bis-Tris Protein Gels 1.0 mm×12-well (Thermo Fisher #NP0322BOX). The applied amount of each AAV was $1.0 \times 10^{10}$ vg/lane. After the gel was stained with Oriole fluorescence gel stain solution (BioRad #161-0495), the image was captured by ChemiDoc™ Touch (BioRad) with UV excitation and 580 nm filter.

(2) Results

The titer values of the AAV9 which were produced in T225 flask were calculated as follows.

TABLE 5

| AAV name | Concentration (vg/mL) |
|---|---|
| AAV9-ED261-145 | $1.82 \times 10^{12}$ |
| AAV9-ED261-146 | $3.66 \times 10^{12}$ |
| AAV9-ED261-208 | $2.11 \times 10^{12}$ |
| AAV9-ED263-145 | $2.43 \times 10^{12}$ |
| AAV9-ED263-146 | $6.00 \times 10^{12}$ |
| AAV9-ED263-208 | $1.43 \times 10^{12}$ |

Figure 11:
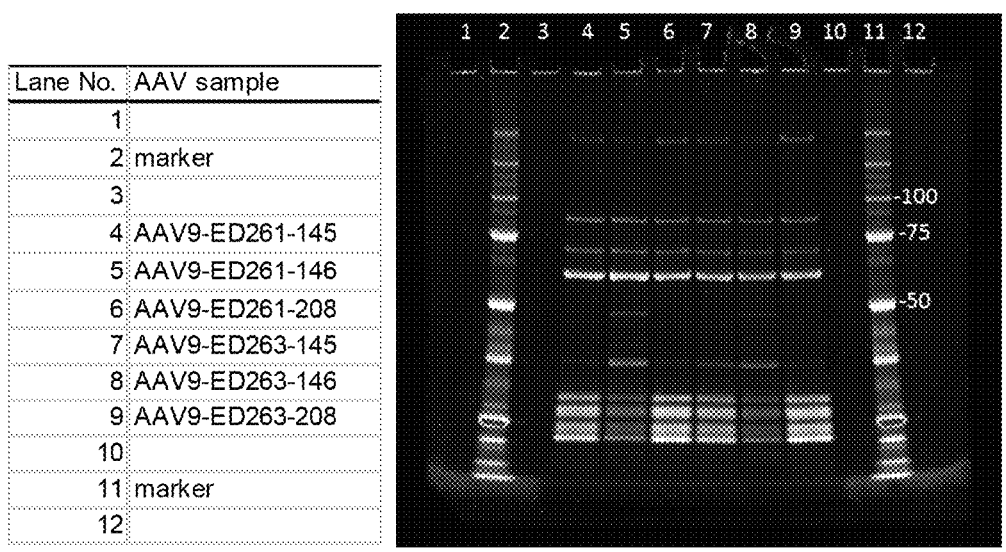
In FIG. 11, the left panel shows the lane layout of SDS-PAGE where each AAV9 sample and markers were applied, and the right panel shows the image of SDS-PAGE. The values next to lane 11 mean the molecular weight (kDa). Three capsid proteins (VP1, VP2, and VP3, which are 87, 72, and 62 kDa, respectively) were detected from each AAV sample. These results indicated that the genes of interest which were cloned into the plasmids (pED261-145, pED261-146, pED261-208, pED263-145, pED263-146, and pED263-208) can be packaged into AAV9.

In SDS-PAGE, 3 capsid proteins (VP1, VP2, and VP3, which are 87, 72, and 62 kDa, respectively) were detected from each AAV sample (FIG. 11). These results indicated the genes of interest including dSaCas9 and transcription activator which were cloned into AAV AIO cis-plasmid can be packaged into AAV9.

Example 5

In-Vitro Pharmacological Evaluation of Recombinant AAV9 carrying dSaCas9, transcription activator and sgRNA on utrophin upregulation (1) Experimental Methods
AAV9 Production Adeno-associated virus serotype 9 (AAV9) particles were generated using 293T cells (ATCC #CRL-3216) seeded at a density of $4.77 \times 10^7$ cell/700 mL/Cell Stack 5 flask (Corning) and cultured in DMEM media supplemented with 10% FBS (Hyclone #SH30070.03), 1% MEM (Sigma #M7145), 1% penicillin/streptomycin (Thermo Fisher #15070-063), and 2.5% HEPES (Sigma #H0887). Three days later, cells were transfected with 227.9 µg of the pRC9 plasmid which was constructed in Example 4, pHelper vector (Takara #6230) and one of the 3 AIO plasmids used in Example 3, pED261-145, pED261-208, or pED263-208, with 683.7 µl polyethyleneimine Max (2 mg/mL) (Polysciences #24765-2) per flask. Six days after transfection, cells were harvested with Triton X-100 (final 0.2%) (Roche #10789704001). AAV samples went through centrifugation, filtration, concentration, and purification using chromatography (AKTA avant 25, GE Healthcare and POROS CaptureSelect AAV Resins column, Thermo Fisher) and ultracentrifugation (Optima XE-90, Beckman Coulter) with CsCl. After the target fraction was dialyzed, the titer of AAV was measured using AAVpro Titration Kit (for Real Time PCR) (Takara #6233). AAV9-ED261-145, AAV9-ED261-208, and AAV9-ED263-208 were obtained.

Cell Culture and AAV Infection

Human skeletal muscle myoblasts (HSMM, Lonza #CC-2580, lot#18TL211617) were seeded into a collagen I-coated 24 well plate (IWAKI #4820-010) at a density of 100,000 cells per well and cultured in SkGM™-2 Skeletal Muscle Cell Growth Medium-2 BulletKit™ (Lonza #CC-3245) supplemented with 500 U/mL penicillin/streptomycin (Thermo Fisher #15070063) for 2 days at 37° C. with 5% $CO_2$. The media was replaced with differentiation media (DMEM media (Sigma #D6429) supplemented with 2% FBS (GE Healthcare #SH30070.03) and 500 U/mL penicillin/streptomycin) and the cells were cultured for 3 days at 37° C. with 5% $CO_2$. For AAV infection, the media was replaced with 500 µL fresh differentiation media containing 0.2, 1.0 or $5.0 \times 10^{11}$ vg/mL AAV9-ED261-145, AAV9-ED261-208, or AAV9-ED263-208. The infected cells were cultured for 3-4 days at 37° C. with 5% $CO_2$ after infection, and total RNA was extracted using RNeasy Plus Mini Kit (Qiagen #74134) according to the manufacturer's instruction. RNA from cells without AAV infection was set as control and shown as AAV (-).

Gene Expression Analysis

For Taqman qPCR, 250 ng of total RNA was converted to cDNA using SuperScript™ VILO™ cDNA Synthesis Kit (Thermo Fisher #11754250) in 20 µL reaction volume. The cDNA was diluted 5 fold with water and 2 µL was used for the qPCR. The qPCR was run in 10 µL final volume containing Taqman probes for UTRN (Thermo Fisher #Hs01125994_m1, FAM), HPRT1 (Thermo Fisher #Hs02800695_m1, FAM), and TaqMan™ Universal PCR Master Mix (Thermo Fisher #4324018) with QuantStudio™ 12K Flex Real-Time PCR System (Thermo Fisher). The qPCR cycling condition were as follows: 95° C. for 10 min followed by 45 cycles of 95° C. for 15 seconds and 60° C. for 1 min. The data were analyzed with QuantStudio™ 12K Flex software (Thermo Fisher). The expression values were analyzed with the standard curve for each gene and the expression level of UTRN gene was normalized to that of HPRT1 gene.

(2) Results

Figure 12:
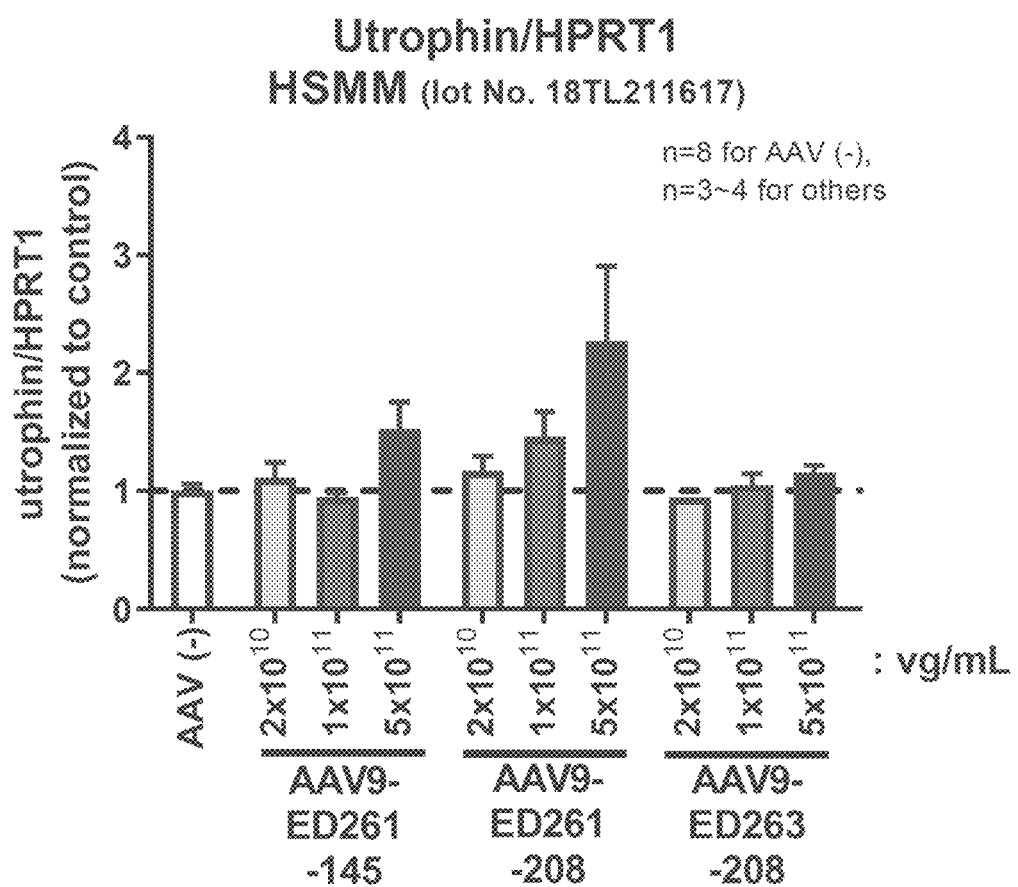
FIG. 12 shows activation of human UTRN gene expression by using 3 AAV9 (AAV9-ED261-145, AAV9-ED261-208, and AAV9-ED263-208) in HSMM cells (N=3-4 for AAV groups and N=8 for non-AAV control. Error bar shows standard error). Human UTRN gene expression was activated by these AAV9.

By applying AAV9-ED261-145, AAV9-ED261-208, or AAV9-ED263-208 into HSMM cells, utrophin mRNA upregulation was found, which suggests AAV9 carrying transgenes of dSaCas9, miniVR or microVR, and sgRNA comprising Guide #145 or #208 has a pharmacological effect on utrophin upregulation in human muscular cells (FIG. 12).

Example 6

Off-Target Analysis Using RNA-Seq Analysis (1) Experimental Methods
Lentivirus Generation HEK293TA cells (Genecopoeia #LT008) were seeded at $0.75 \times 10^6$ cells/well in 6 well cell culture dishes (VWR #10062-892) in 2 ml growth medium (DMEM media supplemented with 10% FBS and 2 mM fresh L-glutamine, 1 mM sodium pyruvate and non-essential amino acids (Thermo Fisher #11140050)) and incubated at 37° C./5% $CO_2$ for 24 hours. The next day TransIT-VirusGEN transfection reactions were set up according to manufacturer's protocol with 1.5 µg packaging plasmid mix [1 µg packaging plasmid (see pCMV delta R8.2; addgene #12263) and 0.5 µg envelope expression plasmid (see pCMV-VSV-G; addgene #8454)] and 1 µg of transfer plasmid containing base sequence encoding dSaCas9-miniVR and sgRNA comprising the targeting sequence selected in Example 2, i.e. Guide #145 (SEQ ID NO:45), #146 (SEQ ID NO: 46), #208 (SEQ ID NO: 59)), or NTg1 (non-targeting guide-1) (SEQ ID NO: 1). Lentivirus was harvested 48-72 hours following transfection by passing media supernatant through a 0.45 µm PES filter (VWR #10218-488). Until ready to use, the purified and aliquoted lentiviruses were stored in –80° C. freezer.

Transduction of HSMM Cells and RNA Sample Preparation

Primary skeletal muscle myoblast cells (HSMM) (Lot #542368) from a human donor of age 0 years were obtained from Lonza Inc. The cells were cultured in primary skeletal muscle cell growth medium [SkGM™-2 Skeletal Muscle Growth BulletKit medium (#CC-3245), which contains culture system containing SkBM™-2 Basal Medium (#CC-3246) and SkGM™-2 SingleQuots™ supplements (#CC-3244) required for growth of skeletal muscle myoblasts)] from Lonza. For transduction, cells were seeded at $0.125 \times 10^6$ cells/well in 6 well cell culture dishes (VWR #10062-894) containing the growth medium and incubated at 37° C./5% $CO_2$ for 24 hours. The next day, 1.5 ml growth medium supplemented with 8 µg/ml Polybrene (Sigma #TR-1003-G) and 1.0 ml lentivirus supernatant (titers ranging from $0.2-2 \times 10^9$ copies/ml, measured by using Lenti-X™ qRT-PCR Titration Kit (Clontech #631235)) corresponding to each sgRNA comprising crRNA encoded by individual targeting sequences (Guide #145 (SEQ ID NO: 45), #146 (SEQ ID NO: 46), or #208 (SEQ ID NO: 59)) and tracrRNA was added to each well. Cells were incubated with lentivirus for 6 hours before viral media was removed and replaced with fresh growth medium. 72 hours after transduction, cells were fed selection medium [growth media supplemented with 0.5 µg/ml puromycin (Sigma #P8833-100MG)]. Cells were given a fresh selection medium every 2-3 days. Following 7-10 days of cells being in the selection medium, cells were harvested and RNA extracted with RNeasy 96 kit (Qiagen #74182) as directed by the manufacturer. The sequence of NTg1 (non-targeting guide-1) guide used as control is ACGGAGGCTAAGCGTCGCAA (SEQ ID NO: 1).

Off-target analysis

Illumina sequencing was performed by GeneWiz, LLC, where RNA libraries were prepared using the NEBNext Ultra RNA Library Prep Kit (Ipswich, Mass., USA, NEB # E7530L) according to the manufacturer's protocol. Sequencing libraries were clustered on three lanes of an Illumina HiSeq flow cell and sequenced using a 2X150 Paired End configuration. Resulting raw sequence data (.bcl files) were converted to fastq files and demultiplexed using Illumina's bcl2fastq 2.17 software, where one mismatch was allowed for index sequence identification. Fastq files were aligned to the human genome assembly GRCh38.p12 using the STAR aligner. Differential analysis was conducted using DESeq2 and plots were generated with plotly (Hypertext Transfer Protocol Secure://plot.ly) using custom R scripts.

(2) Results

Figure 13A:
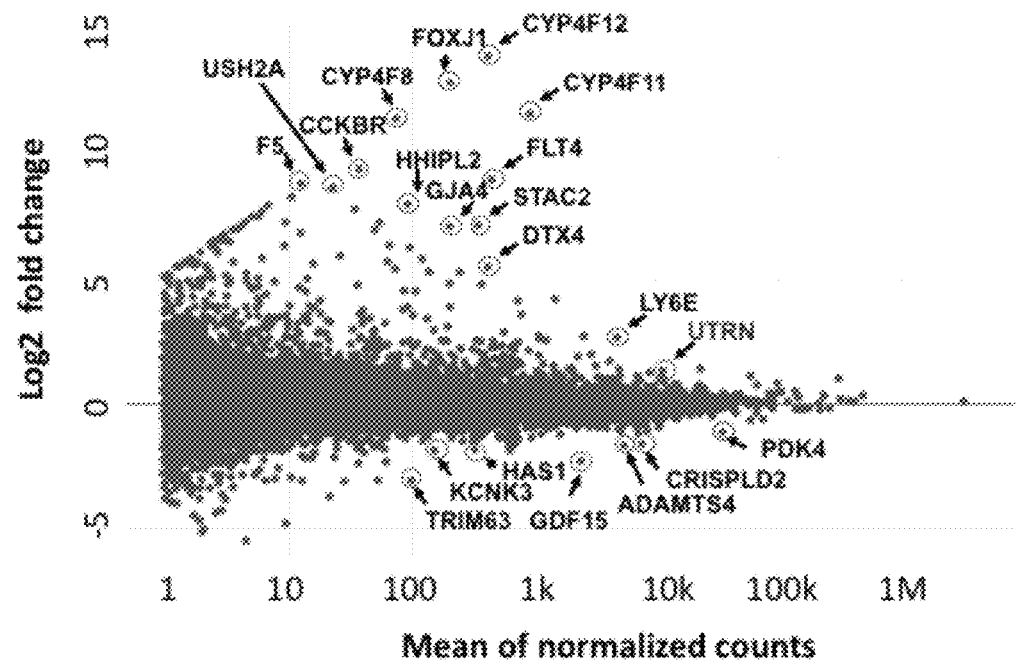
FIGS. 13A, 13B and 13C show RNA-seq results for target guide normalized against non-targeting guide plotted as log 2 fold change vs mean of normalized counts (FIG. 13A; Guide #145 vs NTg1, FIG. 13B; Guide #146 vs NTg1, and FIG. 13C; Guide #208 vs NTg1).
Figure 13B:
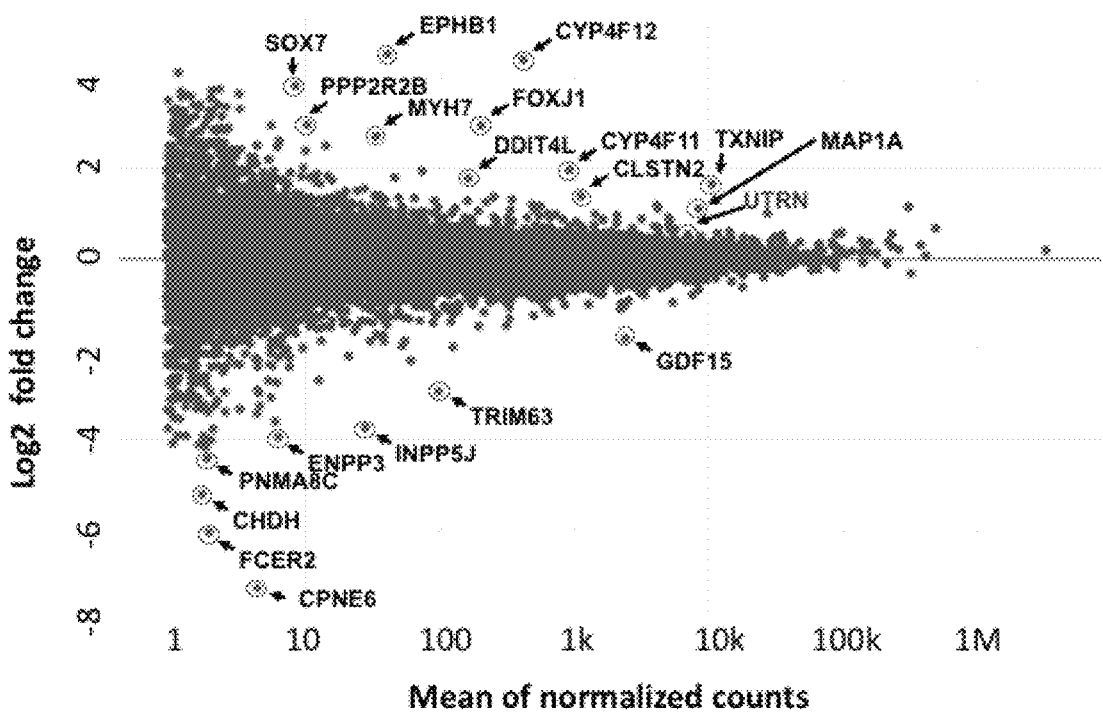
Figure 13C:
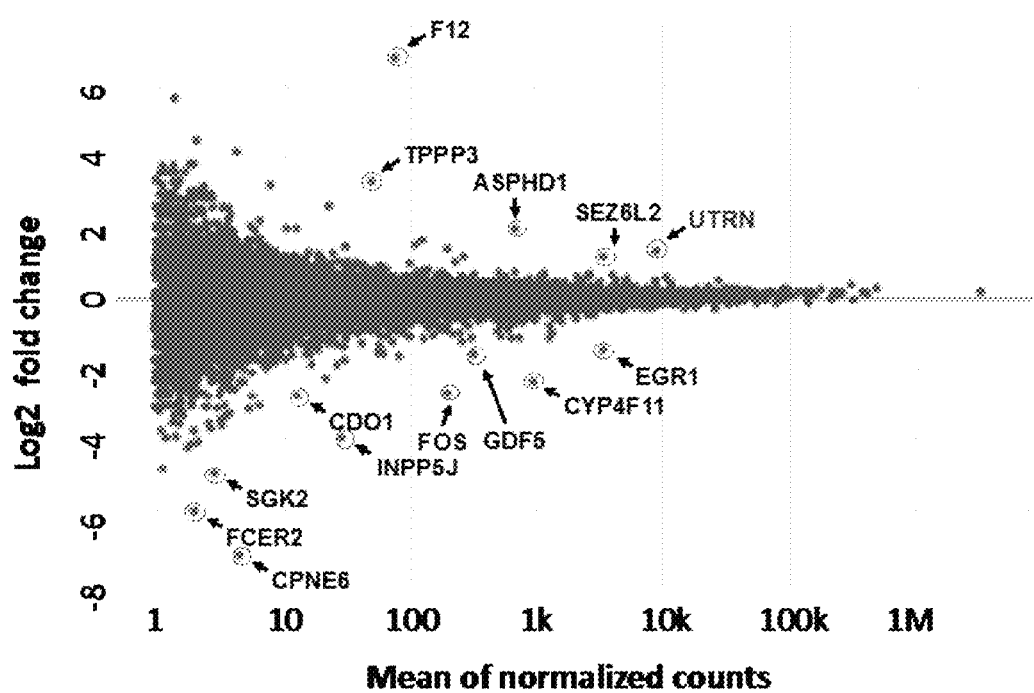

Genome-wide fold changes in mRNA levels for each guide normalized against a non-targeting guide 1 (NTg1). Each dot represents one gene. X-axis shows mean expression levels of the genes. Y-axis shows log-2 fold-changes of gene expression relative to the NTg1 sample. Genes above the horizontal Log2=0 indicate that the gene expression is higher in the experimental sample (e.g. Guide #145) than in the NTg1 sample, and genes below the horizontal Log2=0 indicate that the gene expression is lower in the experimental sample than in the NTg1 sample. Gene IDs are shown for the genes that are highly upregulated or down-regulated in the experimental samples than in the NTg1 sample. Different gRNA induces different gene expression changes (FIG. 13A: Guide #145, 13B: Guide #146, 13C: Guide #208). Guide #208 seems to trigger less other gene expression changes while showing good UTRN gene upregulation.

Example 7

In-Vivo Evaluation of Pharmacological Effect on Utrophin Upregulation (1) Experimental Methods
Animals and Immunosuppression Regimen AAV9-seronegative cynomolgus monkeys (male) are used in this study. One week after acclimatization, 0.75 mg/kg/day of prednisolone sodium phosphate (Abcam #ab142456) is orally administered to the cynomolgus monkeys. Dosing starts at 14 days before AAV administration and continues until sacrifice.

AAV9 Treatment and Muscle Tissue Sampling 1.0 or $6.0 \times 10^{13}$ vg/kg AAV9-ED261-208 (produced in SignaGen) are intravenously administered to the cynomolgus monkeys via the cephalic vein. For quadriceps biopsy, the monkeys are anesthetized by intramuscular administration of 10 mg/kg of Ketamine hydrochloride and 0.08 mg/kg Medetomidine Hydrochloride, and 50-200 mg of samples are obtained at 19 days before and 28 days after AAV administration. 56 days after AAV9 administration, monkeys are sacrificed, and each muscle and heart samples are obtained. The samples are frozen in liquid nitrogen and applied for gene and protein expression analysis.

Gene and Protein Expression Analysis of Muscle Tissue Samples

For Taqman qPCR, total RNA is extracted using RNeasy Fibrous Tissue Mini Kit (Qiagen #74704) from muscle samples, and converted to cDNA using SuperScript™ VILO™ cDNA Synthesis Kit (Thermo Fisher #11754250). The qPCR is run with Tagman probes for UTRN (Thermo Fisher #Mf01126001_m1, FAM), HPRT1 (Thermo Fisher, #Hs02800695_m1, FAM), and TagMan™ Universal PCR Master Mix (Thermo Fisher, #4324018) with QuantStudio™ 12K Flex Real-Time PCR System (Thermo Fisher). The expression level of UTRN gene is normalized to that of HPRT1 gene.

For protein expression analysis, whole muscle lysate is prepared with RIPA buffer (Millipore #20-188) containing protease and phosphatase inhibitor cocktail (Thermo Fisher #78441) and applied for SDS-PAGE and Western blot. Utrophin protein is detected using primary antibody for utrophin (SantaCruz #SC-33700) and horseradish peroxidase-labeled secondary antibodies (Cell Signaling #7076).

INDUSTRIAL APPLICABILITY

According to the present invention, the expression of UTRN gene in human cells can be activated. Thus, the present invention is expected to be extremely useful for the treatment and/or prevention of DMD and BMD.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is, therefore, to be understood that, within the scope of the appended claims, the invention may be practiced otherwise than as specifically described herein.

All patents and other references mentioned above are incorporated in full herein by this reference, the same as if set forth at length.

The invention claimed is:

1. A polynucleotide, comprising the following base sequences:
   (a) a base sequence encoding a fusion protein of a nuclease-deficient CRISPR effector protein and a transcription activator, and
   (b) a base sequence encoding a guide RNA comprising at least one base sequence selected from the group consisting of the base sequence of SEQ ID NO: 45, 46, 58, 59, 60, 135, 141, 153, 157, 159, and 167.

2. The polynucleotide according to claim 1, wherein the base sequence encoding the guide RNA comprises at least two different base sequences.

3. The polynucleotide according to claim 1, wherein the transcription activator is a peptide comprising VP64 and a transcription activation domain of RTA.

4. The polynucleotide according to claim 3, wherein the transcription activator comprises the amino acid sequence of SEQ ID NO: 117, or an amino acid sequence which is at least 90% identical to the amino acid sequence of SEQ ID NO: 117.

5. The polynucleotide according to claim 1, wherein the nuclease-deficient CRISPR effector protein is dCas9.

6. The polynucleotide according to claim 5, wherein the dCas9 is derived from *Staphylococcus aureus*.

7. The polynucleotide according to claim 1, further comprising a promoter sequence for the base sequence encoding the guide RNA, a promoter sequence for the base sequence encoding the fusion protein of the nuclease-deficient CRISPR effector protein and the transcription activator, or a combination thereof.

8. The polynucleotide according to claim 7, wherein the promoter sequence for the base sequence encoding the guide RNA is selected from the group consisting of U6 promoter, SNR6 promoter, SNR52 promoter, SCR1 promoter, RPR1 promoter, U3 promoter, and H1 promoter.

9. The polynucleotide according to claim 7, wherein the promoter sequence for the base sequence encoding the fusion protein of the nuclease-deficient CRISPR effector protein and the transcription activator is selected from the group consistinu of EFS promoter, EF-1α promoter, CMV promoter, CK8 promoter, MHC promoter, Des promoter, CAG promoter and MYOD promoter.

10. The polynucleotide according to claim 7, wherein the base sequence encoding the guide RNA comprises the base sequence of SEQ ID NO: 45, 46, or 59,
    the transcription activator comprises the amino acid sequence of SEQ ID NO: 117, or an amino acid sequence which is at least 90% identical to the amino acid sequence of SEQ ID NO: 117,
    the nuclease-deficient CRISPR effector protein is dCas9 derived from *Staphylococcus aureus*,
    the promoter sequence for the base sequence encoding the guide RNA is U6 promoter,
    the promoter sequence for the base sequence encoding the fusion protein of the nuclease-deficient CRISPR effector protein and the transcription activator is CK8 promoter.

11. The polynucleotide according to claim 10,
    wherein the base sequence encoding the guide RNA comprises the base sequence of SEQ ID NO: 59.

12. A vector comprising the polynucleotide of claim 1.

13. The vector according to claim 12, wherein the vector is a plasmid vector or a viral vector.

14. The vector according to claim 13, wherein the viral vector is selected from the group consisting of an adeno-associated virus (AAV) vector, adenovirus vector, and lentivirus vector.

15. The vector according to claim 14, wherein the AAV vector is selected from the group consisting of AAV1, AAV2, AAV6, AAV7, AAV8, AAV9, AAV$_{587}$MTP, AAV$_{588}$MTP, AAV-B1, AAVM41 AAVrh74, AAVS1_P1, and AAVS10_P1.

16. A method for treating or preventing DUCHENNE muscular dystrophy or BECKER muscular dystrophy, the method comprising administering the polynucleotide of claim 1 to a subject in need thereof.

17. A method for treating or preventing DUCHENNE muscular dystrophy or BECKER muscular dystrophy, the method comprising administering the vector of claim 12 to a subject in need thereof.

* * * * *

SEQUENCE LISTING

```
<160> NUMBER OF SEQ ID NOS: 216

<210> SEQ ID NO 1
<211> LENGTH: 20
<212> TYPE: DNA
<213> ORGANISM: Artificial Sequence
<220> FEATURE:
<223> OTHER INFORMATION: control non-targeting targeting sequence

<400> SEQUENCE: 1
```

```
acggaggcta agcgtcgcaa                                               20

<210> SEQ ID NO 2
<211> LENGTH: 20
<212> TYPE: DNA
<213> ORGANISM: Artificial Sequence
<220> FEATURE:
<223> OTHER INFORMATION: control non-targeting targeting sequence

<400> SEQUENCE: 2
cgcttccgcg gcccgttcaa                                               20

<210> SEQ ID NO 3
<211> LENGTH: 20
<212> TYPE: DNA
<213> ORGANISM: Artificial Sequence
<220> FEATURE:
<223> OTHER INFORMATION: control non-targeting targeting sequence

<400> SEQUENCE: 3
gtaggcgcgc cgctctctac                                               20

<210> SEQ ID NO 4
<211> LENGTH: 21
<212> TYPE: DNA
<213> ORGANISM: Homo sapiens

<400> SEQUENCE: 4
agaaaagcgg cccctagggg c                                             21

<210> SEQ ID NO 5
<211> LENGTH: 21
<212> TYPE: DNA
<213> ORGANISM: Homo sapiens

<400> SEQUENCE: 5
caaacacaca ccagcaaact t                                             21

<210> SEQ ID NO 6
<211> LENGTH: 21
<212> TYPE: DNA
<213> ORGANISM: Homo sapiens

<400> SEQUENCE: 6
tgaaagcgca actggagggc c                                             21

<210> SEQ ID NO 7
<211> LENGTH: 21
<212> TYPE: DNA
<213> ORGANISM: Homo sapiens

<400> SEQUENCE: 7
acccacgcgg acatatgtcc a                                             21

<210> SEQ ID NO 8
<211> LENGTH: 21
<212> TYPE: DNA
<213> ORGANISM: Homo sapiens

<400> SEQUENCE: 8
atccaatgga catatgtccg c                                             21

<210> SEQ ID NO 9
<211> LENGTH: 21
```

```
<212> TYPE: DNA
<213> ORGANISM: Homo sapiens

<400> SEQUENCE: 9
gagggggagg gctgtgacct g                                                21

<210> SEQ ID NO 10
<211> LENGTH: 21
<212> TYPE: DNA
<213> ORGANISM: Homo sapiens

<400> SEQUENCE: 10
atttggtggt cagggagcaa g                                                21

<210> SEQ ID NO 11
<211> LENGTH: 21
<212> TYPE: DNA
<213> ORGANISM: Homo sapiens

<400> SEQUENCE: 11
aatgaaacca aagacagctt c                                                21

<210> SEQ ID NO 12
<211> LENGTH: 21
<212> TYPE: DNA
<213> ORGANISM: Homo sapiens

<400> SEQUENCE: 12
ccaaaatcct ttaatgaatc a                                                21

<210> SEQ ID NO 13
<211> LENGTH: 21
<212> TYPE: DNA
<213> ORGANISM: Homo sapiens

<400> SEQUENCE: 13
tacagattcc atgattcatt a                                                21

<210> SEQ ID NO 14
<211> LENGTH: 21
<212> TYPE: DNA
<213> ORGANISM: Homo sapiens

<400> SEQUENCE: 14
ggaacaaacc aaaatccttt a                                                21

<210> SEQ ID NO 15
<211> LENGTH: 21
<212> TYPE: DNA
<213> ORGANISM: Homo sapiens

<400> SEQUENCE: 15
atctgtttgt ggggaaatct t                                                21

<210> SEQ ID NO 16
<211> LENGTH: 21
<212> TYPE: DNA
<213> ORGANISM: Homo sapiens

<400> SEQUENCE: 16
caaacagatt tcagtatttt c                                                21

<210> SEQ ID NO 17
```

```
<211> LENGTH: 21
<212> TYPE: DNA
<213> ORGANISM: Homo sapiens

<400> SEQUENCE: 17
gtggtgattt atgttactgg t                                              21

<210> SEQ ID NO 18
<211> LENGTH: 21
<212> TYPE: DNA
<213> ORGANISM: Homo sapiens

<400> SEQUENCE: 18
tgagtctttc aagttccttt c                                              21

<210> SEQ ID NO 19
<211> LENGTH: 21
<212> TYPE: DNA
<213> ORGANISM: Homo sapiens

<400> SEQUENCE: 19
agatcatttt tggcttcaaa c                                              21

<210> SEQ ID NO 20
<211> LENGTH: 21
<212> TYPE: DNA
<213> ORGANISM: Homo sapiens

<400> SEQUENCE: 20
tggcttcaaa ctagaatgtc c                                              21

<210> SEQ ID NO 21
<211> LENGTH: 21
<212> TYPE: DNA
<213> ORGANISM: Homo sapiens

<400> SEQUENCE: 21
gatctatcta tagacaccaa a                                              21

<210> SEQ ID NO 22
<211> LENGTH: 21
<212> TYPE: DNA
<213> ORGANISM: Homo sapiens

<400> SEQUENCE: 22
tgcttcttcc aggcttgagt g                                              21

<210> SEQ ID NO 23
<211> LENGTH: 21
<212> TYPE: DNA
<213> ORGANISM: Homo sapiens

<400> SEQUENCE: 23
accgctttgc ttcttccagg c                                              21

<210> SEQ ID NO 24
<211> LENGTH: 21
<212> TYPE: DNA
<213> ORGANISM: Homo sapiens

<400> SEQUENCE: 24
aagcctggaa gaagcaaagc g                                              21
```

```
<210> SEQ ID NO 25
<211> LENGTH: 21
<212> TYPE: DNA
<213> ORGANISM: Homo sapiens

<400> SEQUENCE: 25
cttctgaatc agaattccta a                                              21

<210> SEQ ID NO 26
<211> LENGTH: 21
<212> TYPE: DNA
<213> ORGANISM: Homo sapiens

<400> SEQUENCE: 26
tggttccaag ctagtacttc a                                              21

<210> SEQ ID NO 27
<211> LENGTH: 21
<212> TYPE: DNA
<213> ORGANISM: Homo sapiens

<400> SEQUENCE: 27
atgttcacaa aataaattta a                                              21

<210> SEQ ID NO 28
<211> LENGTH: 21
<212> TYPE: DNA
<213> ORGANISM: Homo sapiens

<400> SEQUENCE: 28
cctttatggt caccttctct g                                              21

<210> SEQ ID NO 29
<211> LENGTH: 21
<212> TYPE: DNA
<213> ORGANISM: Homo sapiens

<400> SEQUENCE: 29
ccttctctgc tgagtaaaaa t                                              21

<210> SEQ ID NO 30
<211> LENGTH: 21
<212> TYPE: DNA
<213> ORGANISM: Homo sapiens

<400> SEQUENCE: 30
aaggtggcca aaaagaacc c                                               21

<210> SEQ ID NO 31
<211> LENGTH: 21
<212> TYPE: DNA
<213> ORGANISM: Homo sapiens

<400> SEQUENCE: 31
aaggaagaga gaggcaagaa a                                              21

<210> SEQ ID NO 32
<211> LENGTH: 21
<212> TYPE: DNA
<213> ORGANISM: Homo sapiens

<400> SEQUENCE: 32
taaagaattc tagcactgga a                                              21
```

-continued

<210> SEQ ID NO 33
<211> LENGTH: 21
<212> TYPE: DNA
<213> ORGANISM: Homo sapiens

<400> SEQUENCE: 33
aaatgtgtca tgtgttggtt a                                              21

<210> SEQ ID NO 34
<211> LENGTH: 21
<212> TYPE: DNA
<213> ORGANISM: Homo sapiens

<400> SEQUENCE: 34
aaaaatgaaa attgcaactt c                                              21

<210> SEQ ID NO 35
<211> LENGTH: 21
<212> TYPE: DNA
<213> ORGANISM: Homo sapiens

<400> SEQUENCE: 35
attgcaactt ctagaattta a                                              21

<210> SEQ ID NO 36
<211> LENGTH: 21
<212> TYPE: DNA
<213> ORGANISM: Homo sapiens

<400> SEQUENCE: 36
cagctggagt gggccacgta a                                              21

<210> SEQ ID NO 37
<211> LENGTH: 21
<212> TYPE: DNA
<213> ORGANISM: Homo sapiens

<400> SEQUENCE: 37
atttttgcat atttctttgg t                                              21

<210> SEQ ID NO 38
<211> LENGTH: 21
<212> TYPE: DNA
<213> ORGANISM: Homo sapiens

<400> SEQUENCE: 38
agtgacctgc tgatttctct a                                              21

<210> SEQ ID NO 39
<211> LENGTH: 21
<212> TYPE: DNA
<213> ORGANISM: Homo sapiens

<400> SEQUENCE: 39
cttttcccat tgttcaggac t                                              21

<210> SEQ ID NO 40
<211> LENGTH: 21
<212> TYPE: DNA
<213> ORGANISM: Homo sapiens

<400> SEQUENCE: 40
ttggttgata aatttgtata t                                              21

```
<210> SEQ ID NO 41
<211> LENGTH: 21
<212> TYPE: DNA
<213> ORGANISM: Homo sapiens

<400> SEQUENCE: 41
tctctagttc attttttagc t                                              21

<210> SEQ ID NO 42
<211> LENGTH: 21
<212> TYPE: DNA
<213> ORGANISM: Homo sapiens

<400> SEQUENCE: 42
tccttcaact tcaagacaac a                                              21

<210> SEQ ID NO 43
<211> LENGTH: 21
<212> TYPE: DNA
<213> ORGANISM: Homo sapiens

<400> SEQUENCE: 43
gctcctcctg ctggatgggg g                                              21

<210> SEQ ID NO 44
<211> LENGTH: 21
<212> TYPE: DNA
<213> ORGANISM: Homo sapiens

<400> SEQUENCE: 44
ctctatttcc agctcctcct g                                              21

<210> SEQ ID NO 45
<211> LENGTH: 21
<212> TYPE: DNA
<213> ORGANISM: Homo sapiens

<400> SEQUENCE: 45
gtacagttag tgctactagg a                                              21

<210> SEQ ID NO 46
<211> LENGTH: 21
<212> TYPE: DNA
<213> ORGANISM: Homo sapiens

<400> SEQUENCE: 46
gctactagga caggatgctg g                                              21

<210> SEQ ID NO 47
<211> LENGTH: 21
<212> TYPE: DNA
<213> ORGANISM: Homo sapiens

<400> SEQUENCE: 47
ccccagctgt gcctctgttt t                                              21

<210> SEQ ID NO 48
<211> LENGTH: 21
<212> TYPE: DNA
<213> ORGANISM: Homo sapiens

<400> SEQUENCE: 48
```
ttcccaaaac agaggcacag c                                          21

<210> SEQ ID NO 49
<211> LENGTH: 21
<212> TYPE: DNA
<213> ORGANISM: Homo sapiens

<400> SEQUENCE: 49
gttttgaaac tggtagcagc t                                          21

<210> SEQ ID NO 50
<211> LENGTH: 21
<212> TYPE: DNA
<213> ORGANISM: Homo sapiens

<400> SEQUENCE: 50
aaactgatgc ttgttaaatg a                                          21

<210> SEQ ID NO 51
<211> LENGTH: 21
<212> TYPE: DNA
<213> ORGANISM: Homo sapiens

<400> SEQUENCE: 51
cttgttaaat gaatgaatga a                                          21

<210> SEQ ID NO 52
<211> LENGTH: 21
<212> TYPE: DNA
<213> ORGANISM: Homo sapiens

<400> SEQUENCE: 52
aatccaaagg attaacttga a                                          21

<210> SEQ ID NO 53
<211> LENGTH: 21
<212> TYPE: DNA
<213> ORGANISM: Homo sapiens

<400> SEQUENCE: 53
tacccatttc aagttaatcc t                                          21

<210> SEQ ID NO 54
<211> LENGTH: 21
<212> TYPE: DNA
<213> ORGANISM: Homo sapiens

<400> SEQUENCE: 54 tgcccctcc ctggagcact t                                           21

<210> SEQ ID NO 55
<211> LENGTH: 21
<212> TYPE: DNA
<213> ORGANISM: Homo sapiens

<400> SEQUENCE: 55
agcaacgtca gcaaactgag a                                          21

<210> SEQ ID NO 56
<211> LENGTH: 21
<212> TYPE: DNA
<213> ORGANISM: Homo sapiens

<400> SEQUENCE: 56

```
acgtcagcaa actgagatgg g                                             21

<210> SEQ ID NO 57
<211> LENGTH: 21
<212> TYPE: DNA
<213> ORGANISM: Homo sapiens

<400> SEQUENCE: 57
gaaccgtgcg tgccgggagc c                                             21

<210> SEQ ID NO 58
<211> LENGTH: 21
<212> TYPE: DNA
<213> ORGANISM: Homo sapiens

<400> SEQUENCE: 58
ggggtccgct ctccagatga g                                             21

<210> SEQ ID NO 59
<211> LENGTH: 21
<212> TYPE: DNA
<213> ORGANISM: Homo sapiens

<400> SEQUENCE: 59
ggagggtggg gcgcaggacc g                                             21

<210> SEQ ID NO 60
<211> LENGTH: 21
<212> TYPE: DNA
<213> ORGANISM: Homo sapiens

<400> SEQUENCE: 60
cctctctcgc gcacaaagtt g                                             21

<210> SEQ ID NO 61
<211> LENGTH: 21
<212> TYPE: DNA
<213> ORGANISM: Homo sapiens

<400> SEQUENCE: 61
tctggctcca gaagccgatt g                                             21

<210> SEQ ID NO 62
<211> LENGTH: 21
<212> TYPE: DNA
<213> ORGANISM: Homo sapiens

<400> SEQUENCE: 62
acaagtaagg ggcgttttca g                                             21

<210> SEQ ID NO 63
<211> LENGTH: 21
<212> TYPE: DNA
<213> ORGANISM: Homo sapiens

<400> SEQUENCE: 63
gagctggcca agggctcctc t                                             21

<210> SEQ ID NO 64
<211> LENGTH: 21
<212> TYPE: DNA
<213> ORGANISM: Homo sapiens
```

```
<400> SEQUENCE: 64
tagaggagcc cttggccagc t                                              21

<210> SEQ ID NO 65
<211> LENGTH: 21
<212> TYPE: DNA
<213> ORGANISM: Homo sapiens

<400> SEQUENCE: 65
ccaagtccca gagtcgaaga t                                              21

<210> SEQ ID NO 66
<211> LENGTH: 21
<212> TYPE: DNA
<213> ORGANISM: Homo sapiens

<400> SEQUENCE: 66
gtccacagga gagggtgggc a                                              21

<210> SEQ ID NO 67
<211> LENGTH: 21
<212> TYPE: DNA
<213> ORGANISM: Homo sapiens

<400> SEQUENCE: 67
ctctgggtgg ttgctgctcc c                                              21

<210> SEQ ID NO 68
<211> LENGTH: 21
<212> TYPE: DNA
<213> ORGANISM: Homo sapiens

<400> SEQUENCE: 68
tcagttgcag caagagatcc c                                              21

<210> SEQ ID NO 69
<211> LENGTH: 21
<212> TYPE: DNA
<213> ORGANISM: Homo sapiens

<400> SEQUENCE: 69
attttaggta aacacccaaa g                                              21

<210> SEQ ID NO 70
<211> LENGTH: 21
<212> TYPE: DNA
<213> ORGANISM: Homo sapiens

<400> SEQUENCE: 70
taggtgagaa actgagaatc a                                              21

<210> SEQ ID NO 71
<211> LENGTH: 21
<212> TYPE: DNA
<213> ORGANISM: Homo sapiens

<400> SEQUENCE: 71
cagaaggcta ggtgagaaac t                                              21

<210> SEQ ID NO 72
<211> LENGTH: 21
<212> TYPE: DNA
<213> ORGANISM: Homo sapiens
```

```
<400> SEQUENCE: 72
gccattaatg gccagaggaa t                                              21

<210> SEQ ID NO 73
<211> LENGTH: 21
<212> TYPE: DNA
<213> ORGANISM: Homo sapiens

<400> SEQUENCE: 73
agatacagca gaaaaggtga t                                              21

<210> SEQ ID NO 74
<211> LENGTH: 21
<212> TYPE: DNA
<213> ORGANISM: Homo sapiens

<400> SEQUENCE: 74
aatttgaaaa atcaccttga g                                              21

<210> SEQ ID NO 75
<211> LENGTH: 21
<212> TYPE: DNA
<213> ORGANISM: Homo sapiens

<400> SEQUENCE: 75
cagttgattc atctgtacag c                                              21

<210> SEQ ID NO 76
<211> LENGTH: 21
<212> TYPE: DNA
<213> ORGANISM: Homo sapiens

<400> SEQUENCE: 76
tttttgactc tggctgtaca g                                              21

<210> SEQ ID NO 77
<211> LENGTH: 21
<212> TYPE: DNA
<213> ORGANISM: Homo sapiens

<400> SEQUENCE: 77
gctgtacaga tgaatcaact g                                              21

<210> SEQ ID NO 78
<211> LENGTH: 21
<212> TYPE: DNA
<213> ORGANISM: Homo sapiens

<400> SEQUENCE: 78
atctcccctt tgagtttgtc t                                              21

<210> SEQ ID NO 79
<211> LENGTH: 21
<212> TYPE: DNA
<213> ORGANISM: Homo sapiens

<400> SEQUENCE: 79
ctgttcaaaa atatctcccc t                                              21

<210> SEQ ID NO 80
<211> LENGTH: 21
<212> TYPE: DNA
```

```
<213> ORGANISM: Homo sapiens

<400> SEQUENCE: 80
aaaattacac agaactccac c                                              21

<210> SEQ ID NO 81
<211> LENGTH: 21
<212> TYPE: DNA
<213> ORGANISM: Homo sapiens

<400> SEQUENCE: 81 tttttttgtct ttaaagtgac a                                             21

<210> SEQ ID NO 82
<211> LENGTH: 21
<212> TYPE: DNA
<213> ORGANISM: Homo sapiens

<400> SEQUENCE: 82
tcttgtttta aaatatgctt t                                              21

<210> SEQ ID NO 83
<211> LENGTH: 21
<212> TYPE: DNA
<213> ORGANISM: Homo sapiens

<400> SEQUENCE: 83
ctctgttata tttacatatg t                                              21

<210> SEQ ID NO 84
<211> LENGTH: 21
<212> TYPE: DNA
<213> ORGANISM: Homo sapiens

<400> SEQUENCE: 84
tataaatatc aaaggtctta c                                              21

<210> SEQ ID NO 85
<211> LENGTH: 21
<212> TYPE: DNA
<213> ORGANISM: Homo sapiens

<400> SEQUENCE: 85
cctagggaaa aactctagaa a                                              21

<210> SEQ ID NO 86
<211> LENGTH: 21
<212> TYPE: DNA
<213> ORGANISM: Homo sapiens

<400> SEQUENCE: 86
acaccatgaa aatctaatat t                                              21

<210> SEQ ID NO 87
<211> LENGTH: 21
<212> TYPE: DNA
<213> ORGANISM: Homo sapiens

<400> SEQUENCE: 87
agatgtgcta gagtaaagaa a                                              21

<210> SEQ ID NO 88
<211> LENGTH: 21
```

<212> TYPE: DNA
<213> ORGANISM: Homo sapiens

<400> SEQUENCE: 88
gtatgatctg ttcagatgtg c                                              21

<210> SEQ ID NO 89
<211> LENGTH: 21
<212> TYPE: DNA
<213> ORGANISM: Homo sapiens

<400> SEQUENCE: 89
tttaaagatt atcaaattgc t                                              21

<210> SEQ ID NO 90
<211> LENGTH: 21
<212> TYPE: DNA
<213> ORGANISM: Homo sapiens

<400> SEQUENCE: 90
atatgaatca cattcttttg g                                              21

<210> SEQ ID NO 91
<211> LENGTH: 21
<212> TYPE: DNA
<213> ORGANISM: Homo sapiens

<400> SEQUENCE: 91
tgcaaaagcc agtagataaa t                                              21

<210> SEQ ID NO 92
<211> LENGTH: 21
<212> TYPE: DNA
<213> ORGANISM: Homo sapiens

<400> SEQUENCE: 92
agccagtaga taaatttgga t                                              21

<210> SEQ ID NO 93
<211> LENGTH: 21
<212> TYPE: DNA
<213> ORGANISM: Homo sapiens

<400> SEQUENCE: 93
ttttagttta gattaagtca t                                              21

<210> SEQ ID NO 94
<211> LENGTH: 21
<212> TYPE: DNA
<213> ORGANISM: Homo sapiens

<400> SEQUENCE: 94
aagaaacctg gaagagcaga t                                              21

<210> SEQ ID NO 95
<211> LENGTH: 21
<212> TYPE: DNA
<213> ORGANISM: Homo sapiens

<400> SEQUENCE: 95
ggtttctttt ttgggggaa a                                               21

<210> SEQ ID NO 96

```
<211> LENGTH: 21
<212> TYPE: DNA
<213> ORGANISM: Homo sapiens

<400> SEQUENCE: 96
tatggttgta gtatacttgc c                                              21

<210> SEQ ID NO 97
<211> LENGTH: 21
<212> TYPE: DNA
<213> ORGANISM: Homo sapiens

<400> SEQUENCE: 97
tgtagtatac ttgccttggg t                                              21

<210> SEQ ID NO 98
<211> LENGTH: 21
<212> TYPE: DNA
<213> ORGANISM: Homo sapiens

<400> SEQUENCE: 98
gtatacttgc cttgggtttg g                                              21

<210> SEQ ID NO 99
<211> LENGTH: 21
<212> TYPE: DNA
<213> ORGANISM: Homo sapiens

<400> SEQUENCE: 99
acatgaaata ataaaatggt t                                              21

<210> SEQ ID NO 100
<211> LENGTH: 21
<212> TYPE: DNA
<213> ORGANISM: Homo sapiens

<400> SEQUENCE: 100
attattgaat gaaatagcag t                                              21

<210> SEQ ID NO 101
<211> LENGTH: 21
<212> TYPE: DNA
<213> ORGANISM: Homo sapiens

<400> SEQUENCE: 101
acaacactga cagcaacaga a                                              21

<210> SEQ ID NO 102
<211> LENGTH: 21
<212> TYPE: DNA
<213> ORGANISM: Homo sapiens

<400> SEQUENCE: 102
agtgtgtcag ctggctccat g                                              21

<210> SEQ ID NO 103
<211> LENGTH: 21
<212> TYPE: DNA
<213> ORGANISM: Homo sapiens

<400> SEQUENCE: 103
catgtggagt tcttgacagt t                                              21
```

-continued

```
<210> SEQ ID NO 104
<211> LENGTH: 32
<212> TYPE: DNA
<213> ORGANISM: Homo sapiens

<400> SEQUENCE: 104
gtacagttag tgctactagg acaggatgct gg                                    32

<210> SEQ ID NO 105
<211> LENGTH: 494
<212> TYPE: DNA
<213> ORGANISM: Homo sapiens

<400> SEQUENCE: 105
gagcgcgcgc cccaggccag ccaagcgccg agccgggctg ctgcgggctg ggagggcgcg      60
cagggccggc gctgattgac ggggcgcgca gtcaggtgac ttggggcgcc aagttcccga     120
cgcggtggcc gcggtgaccg ccgaggcccg gcagacgctg acccgggaac gtagtggggc     180
tgatcttccg gaacaaagtt gctgggccgg cggcggcggg gcgagagcgc cgaggggag      240 ccggagcgct gcagaggcgc gggccggagg gctggcgctg atctgcaccc ttctcatctg     300
gagagcggac ccctggctgc ccggaggcga gccccttccc gggggtgggg gcggcaacg      360 cgcgacccag cggtcctgcg ccccaccctc cctcctccgc ctccagcgct cggctccaac     420 aaagggcag gcccgcagcg gggaggagga ggaggagccg ccgaaggagc gagcctctct      480
cgcgcacaaa gttg                                                      494

<210> SEQ ID NO 106
<211> LENGTH: 19
<212> TYPE: RNA
<213> ORGANISM: Francisella novicida
<220> FEATURE:
<221> NAME/KEY: misc_feature
<222> LOCATION: (1)..(19)
<223> OTHER INFORMATION: 5'-handle of crRNA

<400> SEQUENCE: 106
aauuucuacu guuguagau                                                   19

<210> SEQ ID NO 107
<211> LENGTH: 1053
<212> TYPE: PRT
<213> ORGANISM: Staphylococcus aureus
<220> FEATURE:
<221> NAME/KEY: VARIANT
<222> LOCATION: (10)..(10)
<223> OTHER INFORMATION: conversion of Asp residue into Ala residue
<220> FEATURE:
<221> NAME/KEY: VARIANT
<222> LOCATION: (580)..(580)
<223> OTHER INFORMATION: conversion of Asn residue into Ala residue

<400> SEQUENCE: 107

Met Lys Arg Asn Tyr Ile Leu Gly Leu Ala Ile Gly Ile Thr Ser Val
1               5                  10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80
```

```
Ser Glu Leu Ser Gly Ile Asn Pro Tyr Glu Ala Arg Val Lys Gly Leu
             85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
            210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
            290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
            370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
            450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495
```

-continued

Arg Asn Arg Gln Thr Asn Glu Arg Ile Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Lys Val Leu Val Lys
            565                 570                 575

Gln Glu Glu Ala Ser Lys Lys Gly Asn Arg Thr Pro Phe Gln Tyr Leu
        580                 585                 590

Ser Ser Ser Asp Ser Lys Ile Ser Tyr Glu Thr Phe Lys Lys His Ile
    595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
            645                 650                 655

Met Asn Leu Leu Arg Ser Tyr Phe Arg Val Asn Asn Leu Asp Val Lys
        660                 665                 670

Val Lys Ser Ile Asn Gly Gly Phe Thr Ser Phe Leu Arg Arg Lys Trp
    675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
        740                 745                 750

Ile Phe Ile Thr Pro His Gln Ile Lys His Ile Lys Asp Phe Lys Asp
    755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
            805                 810                 815

Lys Lys Leu Ile Asn Lys Ser Pro Glu Lys Leu Leu Met Tyr His His
        820                 825                 830

Asp Pro Gln Thr Tyr Gln Lys Leu Lys Leu Ile Met Glu Gln Tyr Gly
    835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
        900                 905                 910

Arg Phe Asp Val Tyr Leu Asp Asn Gly Val Tyr Lys Phe Val Thr Val

-continued

```
                915                 920                 925
Lys Asn Leu Asp Val Ile Lys Lys Glu Asn Tyr Tyr Glu Val Asn Ser
        930                 935                 940
Lys Cys Tyr Glu Glu Ala Lys Lys Leu Lys Lys Ile Ser Asn Gln Ala
945                 950                 955                 960
Glu Phe Ile Ala Ser Phe Tyr Asn Asn Asp Leu Ile Lys Ile Asn Gly
                965                 970                 975
Glu Leu Tyr Arg Val Ile Gly Val Asn Asp Leu Leu Asn Arg Ile
            980                 985                 990
Glu Val Asn Met Ile Asp Ile Thr Tyr Arg Glu Tyr Leu Glu Asn Met
            995                 1000                1005
Asn Asp Lys Arg Pro Pro Arg Ile Ile Lys Thr Ile Ala Ser Lys
    1010                1015                1020
Thr Gln Ser Ile Lys Lys Tyr Ser Thr Asp Ile Leu Gly Asn Leu
    1025                1030                1035
Tyr Glu Val Lys Ser Lys Lys His Pro Gln Ile Ile Lys Lys Gly
    1040                1045                1050

<210> SEQ ID NO 108
<211> LENGTH: 1053
<212> TYPE: PRT
<213> ORGANISM: Staphylococcus aureus
<220> FEATURE:
<221> NAME/KEY: VARIANT
<222> LOCATION: (10)..(10)
<223> OTHER INFORMATION: conversion of Asp residue into Ala residue
<220> FEATURE:
<221> NAME/KEY: VARIANT
<222> LOCATION: (557)..(557)
<223> OTHER INFORMATION: conversion of His residue into Ala residue

<400> SEQUENCE: 108

Met Lys Arg Asn Tyr Ile Leu Gly Leu Ala Ile Gly Ile Thr Ser Val
1               5                   10                  15
Gly Tyr Gly Ile Ile Asp Tyr Glu Thr Arg Asp Val Ile Asp Ala Gly
            20                  25                  30
Val Arg Leu Phe Lys Glu Ala Asn Val Glu Asn Asn Glu Gly Arg Arg
        35                  40                  45
Ser Lys Arg Gly Ala Arg Arg Leu Lys Arg Arg Arg Arg His Arg Ile
    50                  55                  60
Gln Arg Val Lys Lys Leu Leu Phe Asp Tyr Asn Leu Leu Thr Asp His
65                  70                  75                  80
Ser Glu Leu Ser Gly Ile Asn Pro Tyr Glu Ala Arg Val Lys Gly Leu
                85                  90                  95
Ser Gln Lys Leu Ser Glu Glu Glu Phe Ser Ala Ala Leu Leu His Leu
            100                 105                 110
Ala Lys Arg Arg Gly Val His Asn Val Asn Glu Val Glu Glu Asp Thr
        115                 120                 125
Gly Asn Glu Leu Ser Thr Lys Glu Gln Ile Ser Arg Asn Ser Lys Ala
    130                 135                 140
Leu Glu Glu Lys Tyr Val Ala Glu Leu Gln Leu Glu Arg Leu Lys Lys
145                 150                 155                 160
Asp Gly Glu Val Arg Gly Ser Ile Asn Arg Phe Lys Thr Ser Asp Tyr
                165                 170                 175
Val Lys Glu Ala Lys Gln Leu Leu Lys Val Gln Lys Ala Tyr His Gln
            180                 185                 190
Leu Asp Gln Ser Phe Ile Asp Thr Tyr Ile Asp Leu Leu Glu Thr Arg
```

```
            195                 200                 205
Arg Thr Tyr Tyr Glu Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
            290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
            530                 535                 540

Asp Leu Leu Asn Asn Pro Phe Asn Tyr Glu Val Asp Ala Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
    610                 615                 620
```

```
Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
            645                 650                 655

Met Asn Leu Leu Arg Ser Tyr Phe Arg Val Asn Asn Leu Asp Val Lys
        660                 665                 670

Val Lys Ser Ile Asn Gly Gly Phe Thr Ser Phe Leu Arg Arg Lys Trp
    675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
        740                 745                 750

Ile Phe Ile Thr Pro His Gln Ile Lys His Ile Lys Asp Phe Lys Asp
    755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
            805                 810                 815

Lys Lys Leu Ile Asn Lys Ser Pro Glu Lys Leu Leu Met Tyr His His
        820                 825                 830

Asp Pro Gln Thr Tyr Gln Lys Leu Lys Leu Ile Met Glu Gln Tyr Gly
    835                 840                 845

Asp Glu Lys Asn Pro Leu Tyr Lys Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
        900                 905                 910

Arg Phe Asp Val Tyr Leu Asp Asn Gly Val Tyr Lys Phe Val Thr Val
    915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
            965                 970                 975

Glu Leu Tyr Arg Val Ile Gly Val Asn Asn Asp Leu Leu Asn Arg Ile
        980                 985                 990

Glu Val Asn Met Ile Asp Ile Thr Tyr Arg Glu Tyr Leu Glu Asn Met
    995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035
```

```
Tyr Glu  Val Lys Ser Lys Lys  His Pro Gln Ile Ile  Lys Lys Gly
        1040                 1045                 1050
```

<210> SEQ ID NO 109
<211> LENGTH: 1028
<212> TYPE: PRT
<213> ORGANISM: Artificial Sequence
<220> FEATURE:
<223> OTHER INFORMATION: amino acid residues  (721st to 745th amino acid
      residues of dSaCas9) deletion mutant
<220> FEATURE:
<221> NAME/KEY: VARIANT
<222> LOCATION: (10)..(10)
<223> OTHER INFORMATION: conversion of Asp residue into Ala residue
<220> FEATURE:
<221> NAME/KEY: VARIANT
<222> LOCATION: (580)..(580)
<223> OTHER INFORMATION: conversion of Asn residue into Ala residue

<400> SEQUENCE: 109

```
Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300
```

-continued

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
            325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
            405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
            485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
            565                 570                 575

Gln Glu Glu Ala Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
            645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
            690                 695                 700

Ala Leu Ile Ile Ala Asn Ala Asp Phe Ile Phe Lys Glu Trp Lys Lys
705                 710                 715                 720

Thr Glu Gln Glu Tyr Lys Glu Ile Phe Ile Thr Pro His Gln Ile Lys 725                 730                 735

His Ile Lys Asp Phe Lys Asp Tyr Lys Tyr Ser His Arg Val Asp Lys
                740                 745                 750

Lys Pro Asn Arg Glu Leu Ile Asn Asp Thr Leu Tyr Ser Thr Arg Lys
            755                 760                 765

Asp Asp Lys Gly Asn Thr Leu Ile Val Asn Asn Leu Asn Gly Leu Tyr
        770                 775                 780

Asp Lys Asp Asn Asp Lys Leu Lys Lys Leu Ile Asn Lys Ser Pro Glu
785                 790                 795                 800

Lys Leu Leu Met Tyr His His Asp Pro Gln Thr Tyr Gln Lys Leu Lys
                805                 810                 815

Leu Ile Met Glu Gln Tyr Gly Asp Glu Lys Asn Pro Leu Tyr Lys Tyr
            820                 825                 830

Tyr Glu Glu Thr Gly Asn Tyr Leu Thr Lys Tyr Ser Lys Lys Asp Asn
        835                 840                 845

Gly Pro Val Ile Lys Lys Ile Lys Tyr Tyr Gly Asn Lys Leu Asn Ala
850                 855                 860

His Leu Asp Ile Thr Asp Asp Tyr Pro Asn Ser Arg Asn Lys Val Val
865                 870                 875                 880

Lys Leu Ser Leu Lys Pro Tyr Arg Phe Asp Val Tyr Leu Asp Asn Gly
                885                 890                 895

Val Tyr Lys Phe Val Thr Val Lys Asn Leu Asp Val Ile Lys Lys Glu
            900                 905                 910

Asn Tyr Tyr Glu Val Asn Ser Lys Cys Tyr Glu Glu Ala Lys Lys Leu
        915                 920                 925

Lys Lys Ile Ser Asn Gln Ala Glu Phe Ile Ala Ser Phe Tyr Asn Asn
930                 935                 940

Asp Leu Ile Lys Ile Asn Gly Glu Leu Tyr Arg Val Ile Gly Val Asn
945                 950                 955                 960

Asn Asp Leu Leu Asn Arg Ile Glu Val Asn Met Ile Asp Ile Thr Tyr
                965                 970                 975

Arg Glu Tyr Leu Glu Asn Met Asn Asp Lys Arg Pro Pro Arg Ile Ile
            980                 985                 990

Lys Thr Ile Ala Ser Lys Thr Gln Ser Ile Lys Lys Tyr Ser Thr Asp
        995                1000                1005

Ile Leu Gly Asn Leu Tyr Glu Val Lys Ser Lys Lys His Pro Gln
    1010                1015                1020

Ile Ile Lys Lys Gly
    1025

<210> SEQ ID NO 110
<211> LENGTH: 6
<212> TYPE: PRT
<213> ORGANISM: Artificial Sequence
<220> FEATURE:
<223> OTHER INFORMATION: GGSGGS linker

<400> SEQUENCE: 110

Gly Gly Ser Gly Gly Ser
1               5

<210> SEQ ID NO 111
<211> LENGTH: 1034
<212> TYPE: PRT
<213> ORGANISM: Artificial Sequence
<220> FEATURE:
<223> OTHER INFORMATION: amino acid residues  (721st to 745th amino acid residues of dSaCas9) deletion mutant with GGSGGS linker
<220> FEATURE:
<221> NAME/KEY: VARIANT
<222> LOCATION: (10)..(10)
<223> OTHER INFORMATION: conversion of Asp residue into Ala residue
<220> FEATURE:
<221> NAME/KEY: VARIANT
<222> LOCATION: (580)..(580)
<223> OTHER INFORMATION: conversion of Asn residue into Ala residue
<220> FEATURE:
<221> NAME/KEY: SITE
<222> LOCATION: (721)..(726)
<223> OTHER INFORMATION: GGSGGS linker

<400> SEQUENCE: 111

```
Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335
```

```
Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
        370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Ala Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Gly Gly Ser Gly Gly Ser Thr Glu Gln Glu Tyr Lys Glu Ile Phe Ile
                725                 730                 735

Thr Pro His Gln Ile Lys His Ile Lys Asp Phe Lys Asp Tyr Lys Tyr
            740                 745                 750

Ser His Arg Val Asp Lys Lys Pro Asn Arg Glu Leu Ile Asn Asp Thr
```

```
                    755                 760                 765
Leu Tyr Ser Thr Arg Lys Asp Asp Lys Gly Asn Thr Leu Ile Val Asn
        770                 775                 780

Asn Leu Asn Gly Leu Tyr Asp Lys Asp Asn Asp Lys Leu Lys Lys Leu
785                 790                 795                 800

Ile Asn Lys Ser Pro Glu Lys Leu Leu Met Tyr His His Asp Pro Gln
                    805                 810                 815

Thr Tyr Gln Lys Leu Lys Leu Ile Met Glu Gln Tyr Gly Asp Glu Lys
                820                 825                 830

Asn Pro Leu Tyr Lys Tyr Tyr Glu Glu Thr Gly Asn Tyr Leu Thr Lys
            835                 840                 845

Tyr Ser Lys Lys Asp Asn Gly Pro Val Ile Lys Lys Ile Lys Tyr Tyr
        850                 855                 860

Gly Asn Lys Leu Asn Ala His Leu Asp Ile Thr Asp Asp Tyr Pro Asn
865                 870                 875                 880

Ser Arg Asn Lys Val Val Lys Leu Ser Leu Lys Pro Tyr Arg Phe Asp
                    885                 890                 895

Val Tyr Leu Asp Asn Gly Val Tyr Lys Phe Val Thr Val Lys Asn Leu
                900                 905                 910

Asp Val Ile Lys Lys Glu Asn Tyr Tyr Glu Val Asn Ser Lys Cys Tyr
            915                 920                 925

Glu Glu Ala Lys Lys Leu Lys Lys Ile Ser Asn Gln Ala Glu Phe Ile
        930                 935                 940

Ala Ser Phe Tyr Asn Asn Asp Leu Ile Lys Ile Asn Gly Glu Leu Tyr
945                 950                 955                 960

Arg Val Ile Gly Val Asn Asn Asp Leu Leu Asn Arg Ile Glu Val Asn
                    965                 970                 975

Met Ile Asp Ile Thr Tyr Arg Glu Tyr Leu Glu Asn Met Asn Asp Lys
                980                 985                 990

Arg Pro Pro Arg Ile Ile Lys Thr Ile Ala Ser Lys Thr Gln Ser Ile
            995                 1000                1005

Lys Lys Tyr Ser Thr Asp Ile Leu Gly Asn Leu Tyr Glu Val Lys
    1010                1015                1020

Ser Lys Lys His Pro Gln Ile Ile Lys Lys Gly
    1025                1030
```

<210> SEQ ID NO 112
<211> LENGTH: 886
<212> TYPE: PRT
<213> ORGANISM: Artificial Sequence
<220> FEATURE:
<223> OTHER INFORMATION: amino acid residues (482nd to 648th amino acid
      residues of dSaCas9) deletion mutant
<220> FEATURE:
<221> NAME/KEY: VARIANT
<222> LOCATION: (10)..(10)
<223> OTHER INFORMATION: conversion of Asp residue into Ala residue

<400> SEQUENCE: 112

```
Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60
```

```
Gln Arg Val Lys Lys Leu Leu Phe Asp Tyr Asn Leu Leu Thr Asp His
 65                  70                  75                  80

Ser Glu Leu Ser Gly Ile Asn Pro Tyr Glu Ala Arg Val Lys Gly Leu
                 85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
450                 455                 460

Ile Lys Lys Tyr Gly Leu Pro Asn Asp Ile Ile Ile Glu Leu Ala Arg
465                 470                 475                 480
```

```
Glu Thr Arg Tyr Ala Thr Arg Gly Leu Met Asn Leu Leu Arg Ser Tyr
                485                 490                 495

Phe Arg Val Asn Asn Leu Asp Val Lys Val Lys Ser Ile Asn Gly Gly
            500                 505                 510

Phe Thr Ser Phe Leu Arg Arg Lys Trp Lys Phe Lys Lys Glu Arg Asn
        515                 520                 525

Lys Gly Tyr Lys His His Ala Glu Asp Ala Leu Ile Ile Ala Asn Ala
    530                 535                 540

Asp Phe Ile Phe Lys Glu Trp Lys Lys Leu Asp Lys Ala Lys Lys Val
545                 550                 555                 560

Met Glu Asn Gln Met Phe Glu Glu Lys Gln Ala Glu Ser Met Pro Glu
                565                 570                 575

Ile Glu Thr Glu Gln Glu Tyr Lys Glu Ile Phe Ile Thr Pro His Gln
            580                 585                 590

Ile Lys His Ile Lys Asp Phe Lys Asp Tyr Lys Tyr Ser His Arg Val
        595                 600                 605

Asp Lys Lys Pro Asn Arg Glu Leu Ile Asn Asp Thr Leu Tyr Ser Thr
    610                 615                 620

Arg Lys Asp Asp Lys Gly Asn Thr Leu Ile Val Asn Asn Leu Asn Gly
625                 630                 635                 640

Leu Tyr Asp Lys Asp Asn Asp Lys Leu Lys Lys Leu Ile Asn Lys Ser
                645                 650                 655

Pro Glu Lys Leu Leu Met Tyr His His Asp Pro Gln Thr Tyr Gln Lys
            660                 665                 670

Leu Lys Leu Ile Met Glu Gln Tyr Gly Asp Glu Lys Asn Pro Leu Tyr
        675                 680                 685

Lys Tyr Tyr Glu Glu Thr Gly Asn Tyr Leu Thr Lys Tyr Ser Lys Lys
    690                 695                 700

Asp Asn Gly Pro Val Ile Lys Lys Ile Lys Tyr Tyr Gly Asn Lys Leu
705                 710                 715                 720

Asn Ala His Leu Asp Ile Thr Asp Asp Tyr Pro Asn Ser Arg Asn Lys
                725                 730                 735

Val Val Lys Leu Ser Leu Lys Pro Tyr Arg Phe Asp Val Tyr Leu Asp
            740                 745                 750

Asn Gly Val Tyr Lys Phe Val Thr Val Lys Asn Leu Asp Val Ile Lys
        755                 760                 765

Lys Glu Asn Tyr Tyr Glu Val Asn Ser Lys Cys Tyr Glu Glu Ala Lys
    770                 775                 780

Lys Leu Lys Lys Ile Ser Asn Gln Ala Glu Phe Ile Ala Ser Phe Tyr
785                 790                 795                 800

Asn Asn Asp Leu Ile Lys Ile Asn Gly Glu Leu Tyr Arg Val Ile Gly
                805                 810                 815

Val Asn Asn Asp Leu Leu Asn Arg Ile Glu Val Asn Met Ile Asp Ile
            820                 825                 830

Thr Tyr Arg Glu Tyr Leu Glu Asn Met Asn Asp Lys Arg Pro Pro Arg
        835                 840                 845

Ile Ile Lys Thr Ile Ala Ser Lys Thr Gln Ser Ile Lys Lys Tyr Ser
    850                 855                 860

Thr Asp Ile Leu Gly Asn Leu Tyr Glu Val Lys Ser Lys Lys His Pro
865                 870                 875                 880

Gln Ile Ile Lys Lys Gly
                885
```

-continued

```
<210> SEQ ID NO 113
<211> LENGTH: 892
<212> TYPE: PRT
<213> ORGANISM: Artificial Sequence
<220> FEATURE:
<223> OTHER INFORMATION: amino acid residues  (482nd to 648th amino acid
      residues of dSaCas9) deletion mutant with GGSGGS linker
<220> FEATURE:
<221> NAME/KEY: VARIANT
<222> LOCATION: (10)..(10)
<223> OTHER INFORMATION: conversion of Asp residue into Ala residue
<220> FEATURE:
<221> NAME/KEY: SITE
<222> LOCATION: (482)..(487)
<223> OTHER INFORMATION: GGSGGS linker

<400> SEQUENCE: 113

Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
```

```
                    325                 330                 335
Ala Arg Lys Glu Ile Ile Glu Asn Ala Glu Leu Leu Asp Gln Ile Ala
                340                 345                 350
Lys Ile Leu Thr Ile Tyr Gln Ser Ser Glu Asp Ile Gln Glu Glu Leu
                355                 360                 365
Thr Asn Leu Asn Ser Glu Leu Thr Gln Glu Glu Ile Glu Gln Ile Ser
370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
                420                 425                 430
Gln Lys Glu Ile Pro Thr Thr Leu Val Asp Asp Phe Ile Leu Ser Pro
                435                 440                 445
Val Val Lys Arg Ser Phe Ile Gln Ser Ile Lys Val Ile Asn Ala Ile
                450                 455                 460
Ile Lys Lys Tyr Gly Leu Pro Asn Asp Ile Ile Ile Glu Leu Ala Arg
465                 470                 475                 480
Glu Gly Gly Ser Gly Ser Thr Arg Tyr Ala Thr Arg Gly Leu Met
                    485                 490                 495
Asn Leu Leu Arg Ser Tyr Phe Arg Val Asn Asn Leu Asp Val Lys Val
                500                 505                 510
Lys Ser Ile Asn Gly Gly Phe Thr Ser Phe Leu Arg Arg Lys Trp Lys
                515                 520                 525
Phe Lys Lys Glu Arg Asn Lys Gly Tyr Lys His His Ala Glu Asp Ala
                530                 535                 540
Leu Ile Ile Ala Asn Ala Asp Phe Ile Phe Lys Glu Trp Lys Lys Leu
545                 550                 555                 560
Asp Lys Ala Lys Lys Val Met Glu Asn Gln Met Phe Glu Glu Lys Gln
                565                 570                 575
Ala Glu Ser Met Pro Glu Ile Glu Thr Glu Gln Glu Tyr Lys Glu Ile
                580                 585                 590
Phe Ile Thr Pro His Gln Ile Lys His Ile Lys Asp Phe Lys Asp Tyr
                595                 600                 605
Lys Tyr Ser His Arg Val Asp Lys Lys Pro Asn Arg Glu Leu Ile Asn
                610                 615                 620
Asp Thr Leu Tyr Ser Thr Arg Lys Asp Asp Lys Gly Asn Thr Leu Ile
625                 630                 635                 640
Val Asn Asn Leu Asn Gly Leu Tyr Asp Lys Asp Asn Asp Lys Leu Lys
                645                 650                 655
Lys Leu Ile Asn Lys Ser Pro Glu Lys Leu Leu Met Tyr His His Asp
                660                 665                 670
Pro Gln Thr Tyr Gln Lys Leu Lys Leu Ile Met Glu Gln Tyr Gly Asp
                675                 680                 685
Glu Lys Asn Pro Leu Tyr Lys Tyr Tyr Glu Glu Thr Gly Asn Tyr Leu
                690                 695                 700
Thr Lys Tyr Ser Lys Lys Asp Asn Gly Pro Val Ile Lys Lys Ile Lys
705                 710                 715                 720
Tyr Tyr Gly Asn Lys Leu Asn Ala His Leu Asp Ile Thr Asp Asp Tyr
                    725                 730                 735
Pro Asn Ser Arg Asn Lys Val Val Lys Leu Ser Leu Lys Pro Tyr Arg
                740                 745                 750
```

```
Phe Asp Val Tyr Leu Asp Asn Gly Val Tyr Lys Phe Val Thr Val Lys
            755                 760                 765

Asn Leu Asp Val Ile Lys Lys Glu Asn Tyr Tyr Glu Val Asn Ser Lys
        770                 775                 780

Cys Tyr Glu Glu Ala Lys Lys Leu Lys Lys Ile Ser Asn Gln Ala Glu
785                 790                 795                 800

Phe Ile Ala Ser Phe Tyr Asn Asn Asp Leu Ile Lys Ile Asn Gly Glu
                805                 810                 815

Leu Tyr Arg Val Ile Gly Val Asn Asn Asp Leu Leu Asn Arg Ile Glu
            820                 825                 830

Val Asn Met Ile Asp Ile Thr Tyr Arg Glu Tyr Leu Glu Asn Met Asn
            835                 840                 845

Asp Lys Arg Pro Pro Arg Ile Ile Lys Thr Ile Ala Ser Lys Thr Gln
            850                 855                 860

Ser Ile Lys Lys Tyr Ser Thr Asp Ile Leu Gly Asn Leu Tyr Glu Val
865                 870                 875                 880

Lys Ser Lys Lys His Pro Gln Ile Ile Lys Lys Gly
            885                 890

<210> SEQ ID NO 114
<211> LENGTH: 50
<212> TYPE: PRT
<213> ORGANISM: Artificial Sequence
<220> FEATURE:
<223> OTHER INFORMATION: VP64

<400> SEQUENCE: 114

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50

<210> SEQ ID NO 115
<211> LENGTH: 376
<212> TYPE: PRT
<213> ORGANISM: Artificial Sequence
<220> FEATURE:
<223> OTHER INFORMATION: VPH

<400> SEQUENCE: 115

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Ser Ser Gly Ser Pro Lys Lys Lys Arg Lys Val Gly Ser Pro
    50                  55                  60

Ser Gly Gln Ile Ser Asn Gln Ala Leu Ala Leu Ala Pro Ser Ser Ala
65                  70                  75                  80

Pro Val Leu Ala Gln Thr Met Val Pro Ser Ser Ala Met Val Pro Leu
                85                  90                  95

Ala Gln Pro Pro Ala Pro Ala Pro Val Leu Thr Pro Gly Pro Pro Gln
```

```
              100                 105                 110
Ser Leu Ser Ala Pro Val Pro Lys Ser Thr Gln Ala Gly Glu Gly Thr
        115                 120                 125

Leu Ser Glu Ala Leu Leu His Leu Gln Phe Asp Ala Asp Glu Asp Leu
    130                 135                 140

Gly Ala Leu Leu Gly Asn Ser Thr Asp Pro Gly Val Phe Thr Asp Leu
145                 150                 155                 160

Ala Ser Val Asp Asn Ser Glu Phe Gln Gln Leu Leu Asn Gln Gly Val
                165                 170                 175

Ser Met Ser His Ser Thr Ala Glu Pro Met Leu Met Glu Tyr Pro Glu
            180                 185                 190

Ala Ile Thr Arg Leu Val Thr Gly Ser Gln Arg Pro Pro Asp Pro Ala
        195                 200                 205

Pro Thr Pro Leu Gly Thr Ser Gly Leu Pro Asn Gly Leu Ser Gly Asp
    210                 215                 220

Glu Asp Phe Ser Ser Ile Ala Asp Met Asp Phe Ser Ala Leu Leu Ser
225                 230                 235                 240

Gln Ile Ser Ser Ser Gly Gln Gly Gly Gly Ser Gly Phe Ser Val
                245                 250                 255

Asp Thr Ser Ala Leu Leu Asp Leu Phe Ser Pro Ser Val Thr Val Pro
            260                 265                 270

Asp Met Ser Leu Pro Asp Leu Asp Ser Ser Leu Ala Ser Ile Gln Glu
        275                 280                 285

Leu Leu Ser Pro Gln Glu Pro Pro Arg Pro Pro Glu Ala Glu Asn Ser
    290                 295                 300

Ser Pro Asp Ser Gly Lys Gln Leu Val His Tyr Thr Ala Gln Pro Leu
305                 310                 315                 320

Phe Leu Leu Asp Pro Gly Ser Val Asp Thr Gly Ser Asn Asp Leu Pro
                325                 330                 335

Val Leu Phe Glu Leu Gly Glu Gly Ser Tyr Phe Ser Glu Gly Asp Gly
            340                 345                 350

Phe Ala Glu Asp Pro Thr Ile Ser Leu Leu Thr Gly Ser Glu Pro Pro
        355                 360                 365

Lys Ala Lys Asp Pro Thr Val Ser
    370                 375

<210> SEQ ID NO 116
<211> LENGTH: 523
<212> TYPE: PRT
<213> ORGANISM: Artificial Sequence
<220> FEATURE:
<223> OTHER INFORMATION: VPR

<400> SEQUENCE: 116

Glu Ala Ser Gly Ser Gly Arg Ala Asp Ala Leu Asp Asp Phe Asp Leu
1               5                   10                  15

Asp Met Leu Gly Ser Asp Ala Leu Asp Asp Phe Asp Leu Asp Met Leu
            20                  25                  30

Gly Ser Asp Ala Leu Asp Phe Asp Leu Asp Met Leu Gly Ser Asp
        35                  40                  45

Ala Leu Asp Asp Phe Asp Leu Asp Met Leu Ile Asn Ser Arg Ser Ser
    50                  55                  60

Gly Ser Ser Gln Tyr Leu Pro Asp Thr Asp Asp Arg His Arg Ile Glu
65                  70                  75                  80

Glu Lys Arg Lys Arg Thr Tyr Glu Thr Phe Lys Ser Ile Met Lys Lys
```

-continued

```
                 85                  90                  95
Ser Pro Phe Ser Gly Pro Thr Asp Pro Arg Pro Pro Arg Arg Ile
                100                 105                 110

Ala Val Pro Ser Arg Ser Ser Ala Ser Val Pro Lys Pro Ala Pro Gln
                115                 120                 125

Pro Tyr Pro Phe Thr Ser Ser Leu Ser Thr Ile Asn Tyr Asp Glu Phe
    130                 135                 140

Pro Thr Met Val Phe Pro Ser Gly Gln Ile Ser Gln Ala Ser Ala Leu
145                 150                 155                 160

Ala Pro Ala Pro Pro Gln Val Leu Pro Gln Ala Pro Ala Pro Ala Pro
                165                 170                 175

Ala Pro Ala Met Val Ser Ala Leu Ala Gln Ala Pro Ala Pro Val Pro
                180                 185                 190

Val Leu Ala Pro Gly Pro Pro Gln Ala Val Ala Pro Pro Ala Pro Lys
            195                 200                 205

Pro Thr Gln Ala Gly Glu Gly Thr Leu Ser Glu Ala Leu Leu Gln Leu
    210                 215                 220

Gln Phe Asp Asp Glu Asp Leu Gly Ala Leu Leu Gly Asn Ser Thr Asp
225                 230                 235                 240

Pro Ala Val Phe Thr Asp Leu Ala Ser Val Asp Asn Ser Glu Phe Gln
                245                 250                 255

Gln Leu Leu Asn Gln Gly Ile Pro Val Ala Pro His Thr Thr Glu Pro
                260                 265                 270

Met Leu Met Glu Tyr Pro Glu Ala Ile Thr Arg Leu Val Thr Gly Ala
            275                 280                 285

Gln Arg Pro Pro Asp Pro Ala Pro Ala Pro Leu Gly Ala Pro Gly Leu
    290                 295                 300

Pro Asn Gly Leu Leu Ser Gly Asp Glu Asp Phe Ser Ser Ile Ala Asp
305                 310                 315                 320

Met Asp Phe Ser Ala Leu Leu Gly Ser Gly Ser Gly Ser Arg Asp Ser
                325                 330                 335

Arg Glu Gly Met Phe Leu Pro Lys Pro Glu Ala Gly Ser Ala Ile Ser
            340                 345                 350

Asp Val Phe Glu Gly Arg Glu Val Cys Gln Pro Lys Arg Ile Arg Pro
    355                 360                 365

Phe His Pro Pro Gly Ser Pro Trp Ala Asn Arg Pro Leu Pro Ala Ser
    370                 375                 380

Leu Ala Pro Thr Pro Thr Gly Pro Val His Glu Pro Val Gly Ser Leu
385                 390                 395                 400

Thr Pro Ala Pro Val Pro Gln Pro Leu Asp Pro Ala Pro Ala Val Thr
                405                 410                 415

Pro Glu Ala Ser His Leu Leu Glu Asp Pro Asp Glu Glu Thr Ser Gln
            420                 425                 430

Ala Val Lys Ala Leu Arg Glu Met Ala Asp Thr Val Ile Pro Gln Lys
    435                 440                 445

Glu Glu Ala Ala Ile Cys Gly Gln Met Asp Leu Ser His Pro Pro Pro
    450                 455                 460

Arg Gly His Leu Asp Glu Leu Thr Thr Thr Leu Glu Ser Met Thr Glu
465                 470                 475                 480

Asp Leu Asn Leu Asp Ser Pro Leu Thr Pro Glu Leu Asn Glu Ile Leu
                485                 490                 495

Asp Thr Phe Leu Asn Asp Glu Cys Leu Leu His Ala Met His Ile Ser
                500                 505                 510
```

```
Thr Gly Leu Ser Ile Phe Asp Thr Ser Leu Phe
        515                 520
```

<210> SEQ ID NO 117
<211> LENGTH: 167
<212> TYPE: PRT
<213> ORGANISM: Artificial Sequence
<220> FEATURE:
<223> OTHER INFORMATION: miniVR

<400> SEQUENCE: 117

```
Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Gly Ser Gly Ser Pro Ala Pro Ala Val Thr Pro Glu Ala Ser
    50                  55                  60

His Leu Leu Glu Asp Pro Asp Glu Glu Thr Ser Gln Ala Val Lys Ala
65                  70                  75                  80

Leu Arg Glu Met Ala Asp Thr Val Ile Pro Gln Lys Glu Glu Ala Ala
                85                  90                  95

Ile Cys Gly Gln Met Asp Leu Ser His Pro Pro Arg Gly His Leu
            100                 105                 110

Asp Glu Leu Thr Thr Thr Leu Glu Ser Met Thr Glu Asp Leu Asn Leu
        115                 120                 125

Asp Ser Pro Leu Thr Pro Glu Leu Asn Glu Ile Leu Asp Thr Phe Leu
    130                 135                 140

Asn Asp Glu Cys Leu Leu His Ala Met His Ile Ser Thr Gly Leu Ser
145                 150                 155                 160

Ile Phe Asp Thr Ser Leu Phe
                165
```

<210> SEQ ID NO 118
<211> LENGTH: 140
<212> TYPE: PRT
<213> ORGANISM: Artificial Sequence
<220> FEATURE:
<223> OTHER INFORMATION: microVR

<400> SEQUENCE: 118

```
Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Phe Asp Leu Asp
        35                  40                  45

Met Leu Gly Ser Gly Ser Arg Glu Met Ala Asp Thr Val Ile Pro Gln
    50                  55                  60

Lys Glu Glu Ala Ala Ile Cys Gly Gln Met Asp Leu Ser His Pro Pro
65                  70                  75                  80

Pro Arg Gly His Leu Asp Glu Leu Thr Thr Thr Leu Glu Ser Met Thr
                85                  90                  95

Glu Asp Leu Asn Leu Asp Ser Pro Leu Thr Pro Glu Leu Asn Glu Ile
            100                 105                 110

Leu Asp Thr Phe Leu Asn Asp Glu Cys Leu Leu His Ala Met His Ile
```

Ser Thr Gly Leu Ser Ile Phe Asp Thr Ser Leu Phe
    130                 135                 140

<210> SEQ ID NO 119
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:4)

<400> SEQUENCE: 119
agaaaagcgg ccccuagggg c                                             21

<210> SEQ ID NO 120
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: sequence complementary to the target sequence
      (SEQ ID NO:4)

<400> SEQUENCE: 120
gcccctaggg gccgcttttc t                                             21

<210> SEQ ID NO 121
<211> LENGTH: 19
<212> TYPE: DNA
<213> ORGANISM: Francisella novicida
<220> FEATURE:
<221> NAME/KEY: misc_feature
<222> LOCATION: (1)..(19)
<223> OTHER INFORMATION: 5'-handle of crRNA

<400> SEQUENCE: 121
aatttctact gttgtagat                                                19

<210> SEQ ID NO 122
<211> LENGTH: 83
<212> TYPE: DNA
<213> ORGANISM: Staphylococcus aureus
<220> FEATURE:
<221> NAME/KEY: misc_feature
<222> LOCATION: (1)..(83)
<223> OTHER INFORMATION: sequence encoding tracrRNA

<400> SEQUENCE: 122
gttttagtac tctggaaaca gaatctacta aaacaaggca aaatgccgtg tttatctcgt   60
caacttgttg gcgagatttt ttt                                           83

<210> SEQ ID NO 123
<211> LENGTH: 1053
<212> TYPE: PRT
<213> ORGANISM: Staphylococcus aureus
<220> FEATURE:
<221> NAME/KEY: VARIANT
<222> LOCATION: (10)..(10)
<223> OTHER INFORMATION: conversion of Asp residue into Ala residue
<220> FEATURE:
<221> NAME/KEY: VARIANT
<222> LOCATION: (580)..(580)
<223> OTHER INFORMATION: conversion of Asn residue into Ala residue

<400> SEQUENCE: 123

```
Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415
```

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
                435                 440                 445

Val Val Lys Arg Ser Phe Ile Gln Ser Ile Lys Val Ile Asn Ala Ile
450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
                530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Ala Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
                610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
                690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
                770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

```
Asp Pro Gln Thr Tyr Gln Lys Leu Lys Leu Ile Met Glu Gln Tyr Gly
            835                 840                 845
Asp Glu Lys Asn Pro Leu Tyr Lys Tyr Tyr Glu Glu Thr Gly Asn Tyr
        850                 855                 860
Leu Thr Lys Tyr Ser Lys Lys Asp Asn Gly Pro Val Ile Lys Lys Ile
865                 870                 875                 880
Lys Tyr Tyr Gly Asn Lys Leu Asn Ala His Leu Asp Ile Thr Asp Asp
                885                 890                 895
Tyr Pro Asn Ser Arg Asn Lys Val Val Lys Leu Ser Leu Lys Pro Tyr
            900                 905                 910
Arg Phe Asp Val Tyr Leu Asp Asn Gly Val Tyr Lys Phe Val Thr Val
            915                 920                 925
Lys Asn Leu Asp Val Ile Lys Lys Glu Asn Tyr Tyr Glu Val Asn Ser
        930                 935                 940
Lys Cys Tyr Glu Glu Ala Lys Lys Leu Lys Lys Ile Ser Asn Gln Ala
945                 950                 955                 960
Glu Phe Ile Ala Ser Phe Tyr Asn Asn Asp Leu Ile Lys Ile Asn Gly
                965                 970                 975
Glu Leu Tyr Arg Val Ile Gly Val Asn Asn Asp Leu Leu Asn Arg Ile
            980                 985                 990
Glu Val Asn Met Ile Asp Ile Thr Tyr Arg Glu Tyr Leu Glu Asn Met
            995                 1000                1005
Asn Asp Lys Arg Pro Pro Arg Ile Ile Lys Thr Ile Ala Ser Lys
        1010                1015                1020
Thr Gln Ser Ile Lys Lys Tyr Ser Thr Asp Ile Leu Gly Asn Leu
        1025                1030                1035
Tyr Glu Val Lys Ser Lys Lys His Pro Gln Ile Ile Lys Lys Gly
        1040                1045                1050

<210> SEQ ID NO 124
<211> LENGTH: 76
<212> TYPE: DNA
<213> ORGANISM: Staphylococcus aureus
<220> FEATURE:
<221> NAME/KEY: misc_feature
<222> LOCATION: (1)..(76)
<223> OTHER INFORMATION: SaCas9 gRNA scaffold sequence

<400> SEQUENCE: 124
gttttagtac tctggaaaca gaatctacta aacaaggca aaatgccgtg tttatctcgt    60
caacttgttg gcgaga                                                   76

<210> SEQ ID NO 125
<211> LENGTH: 501
<212> TYPE: DNA
<213> ORGANISM: Artificial Sequence
<220> FEATURE:
<223> OTHER INFORMATION: miniVR DNA

<400> SEQUENCE: 125
gatgcactcg atgattttga cctcgatatg cttgggagtg atgcgctcga tgacttcgat    60 tggatatgc ttggatctga tgccctcgac gattcgacc ttgatatgct cgggtcagac    120
gctttggatg actttgacct tgacatgctg gggagcggct ccccgcacc ggcagttaca    180 ccggaggcca gtcacttgct cgaagatcct gacgaggaaa ccagccaggc cgtaaaggcg    240
ttgcgggaga tggctgacac agtaataccc caaaaagagg aggctgcgat tgtgggcag    300 atggatttgt cccacccctcc accgagaggt catcttgacg aattgacaac gacgctcgaa    360
```

```
tccatgaccg aggacctgaa cctcgatagc ccgctcaccc ccgagttgaa tgagatcctg    420
gatacatttc ttaatgatga gtgtttgctt cacgcaatgc atatttctac gggtcttagt    480
attttcgaca cgagcctgtt t                                              501
```

<210> SEQ ID NO 126
<211> LENGTH: 167
<212> TYPE: PRT
<213> ORGANISM: Artificial Sequence
<220> FEATURE:
<223> OTHER INFORMATION: miniVR protein

<400> SEQUENCE: 126

```
Asp Ala Leu Asp Asp Phe Asp Leu Asp Met Leu Gly Ser Asp Ala Leu
1               5                   10                  15
Asp Asp Phe Asp Leu Asp Met Leu Gly Ser Asp Ala Leu Asp Asp Phe
            20                  25                  30
Asp Leu Asp Met Leu Gly Ser Asp Ala Leu Asp Asp Phe Asp Leu Asp
        35                  40                  45
Met Leu Gly Ser Gly Ser Pro Ala Pro Ala Val Thr Pro Glu Ala Ser
    50                  55                  60
His Leu Leu Glu Asp Pro Asp Glu Glu Thr Ser Gln Ala Val Lys Ala
65                  70                  75                  80
Leu Arg Glu Met Ala Asp Thr Val Ile Pro Gln Lys Glu Glu Ala Ala
                85                  90                  95
Ile Cys Gly Gln Met Asp Leu Ser His Pro Pro Arg Gly His Leu
            100                 105                 110
Asp Glu Leu Thr Thr Thr Leu Glu Ser Met Thr Glu Asp Leu Asn Leu
        115                 120                 125
Asp Ser Pro Leu Thr Pro Glu Leu Asn Glu Ile Leu Asp Thr Phe Leu
    130                 135                 140
Asn Asp Glu Cys Leu Leu His Ala Met His Ile Ser Thr Gly Leu Ser
145                 150                 155                 160
Ile Phe Asp Thr Ser Leu Phe
                165
```

<210> SEQ ID NO 127
<211> LENGTH: 82
<212> TYPE: RNA
<213> ORGANISM: Staphylococcus aureus
<220> FEATURE:
<221> NAME/KEY: misc_feature
<222> LOCATION: (1)..(82)
<223> OTHER INFORMATION: tracrRNA

<400> SEQUENCE: 127

```
guuuuaguac ucuggaaaca gaaucuacua aacaaggca aaaugccgug uuuaucucgu    60
caacuuguug gcgagauuuu uu                                             82
```

<210> SEQ ID NO 128
<211> LENGTH: 241
<212> TYPE: DNA
<213> ORGANISM: Artificial Sequence
<220> FEATURE:
<223> OTHER INFORMATION: U6 promoter

<400> SEQUENCE: 128

```
gagggcctat ttcccatgat tccttcatat ttgcatatac gatacaaggc tgttagagag    60
ataattagaa ttaatttgac tgtaaacaca aagatattag tacaaaatac gtgacgtaga   120
```

```
aagtaataat ttcttgggta gtttgcagtt ttaaaattat gttttaaaat ggactatcat      180
atgcttaccg taacttgaaa gtatttcgat ttcttggctt tatatatctt gtggaaagga      240
c                                                                      241
```

<210> SEQ ID NO 129
<211> LENGTH: 21
<212> TYPE: DNA
<213> ORGANISM: Homo sapiens

<400> SEQUENCE: 129

```
cttgttaaat gaatgaatga a                                                 21
```

<210> SEQ ID NO 130
<211> LENGTH: 21
<212> TYPE: DNA
<213> ORGANISM: Homo sapiens

<400> SEQUENCE: 130

```
tgtcctagaa accttacaag g                                                 21
```

<210> SEQ ID NO 131
<211> LENGTH: 21
<212> TYPE: DNA
<213> ORGANISM: Homo sapiens

<400> SEQUENCE: 131

```
ggtttattgc tggcttaata t                                                 21
```

<210> SEQ ID NO 132
<211> LENGTH: 21
<212> TYPE: DNA
<213> ORGANISM: Homo sapiens

<400> SEQUENCE: 132

```
acgtcagcaa actgagatgg g                                                 21
```

<210> SEQ ID NO 133
<211> LENGTH: 21
<212> TYPE: DNA
<213> ORGANISM: Homo sapiens

<400> SEQUENCE: 133

```
ttttcggata atctgaataa g                                                 21
```

<210> SEQ ID NO 134
<211> LENGTH: 21
<212> TYPE: DNA
<213> ORGANISM: Homo sapiens

<400> SEQUENCE: 134

```
ggggtccgct ctccagatga g                                                 21
```

<210> SEQ ID NO 135
<211> LENGTH: 21
<212> TYPE: DNA
<213> ORGANISM: Homo sapiens

<400> SEQUENCE: 135

```
ggctcctcta ggagtttgac a                                                 21
```

<210> SEQ ID NO 136

```
<211> LENGTH: 21
<212> TYPE: DNA
<213> ORGANISM: Homo sapiens

<400> SEQUENCE: 136
taatgtgact acagccccg a                                              21

<210> SEQ ID NO 137
<211> LENGTH: 21
<212> TYPE: DNA
<213> ORGANISM: Homo sapiens

<400> SEQUENCE: 137
ccaagtccca gagtcgaaga t                                             21

<210> SEQ ID NO 138
<211> LENGTH: 21
<212> TYPE: DNA
<213> ORGANISM: Homo sapiens

<400> SEQUENCE: 138
tcagttgcag caagagatcc c                                             21

<210> SEQ ID NO 139
<211> LENGTH: 21
<212> TYPE: DNA
<213> ORGANISM: Homo sapiens

<400> SEQUENCE: 139
cctcctcctc gaaaaacgca c                                             21

<210> SEQ ID NO 140
<211> LENGTH: 21
<212> TYPE: DNA
<213> ORGANISM: Homo sapiens

<400> SEQUENCE: 140
gggagggtcg gctcagacct a                                             21

<210> SEQ ID NO 141
<211> LENGTH: 21
<212> TYPE: DNA
<213> ORGANISM: Homo sapiens

<400> SEQUENCE: 141
gggtagttct gcggtgacgg a                                             21

<210> SEQ ID NO 142
<211> LENGTH: 21
<212> TYPE: DNA
<213> ORGANISM: Homo sapiens

<400> SEQUENCE: 142
attttaggta aacacccaaa g                                             21

<210> SEQ ID NO 143
<211> LENGTH: 21
<212> TYPE: DNA
<213> ORGANISM: Homo sapiens

<400> SEQUENCE: 143
gaaacacagt aaagaaaac g                                              21
```

```
<210> SEQ ID NO 144
<211> LENGTH: 21
<212> TYPE: DNA
<213> ORGANISM: Homo sapiens

<400> SEQUENCE: 144 taagattttta ggaattatac a                                              21

<210> SEQ ID NO 145
<211> LENGTH: 21
<212> TYPE: DNA
<213> ORGANISM: Homo sapiens

<400> SEQUENCE: 145
agcgttctga agggagagtt a                                               21

<210> SEQ ID NO 146
<211> LENGTH: 21
<212> TYPE: DNA
<213> ORGANISM: Homo sapiens

<400> SEQUENCE: 146
cagaaggcta ggtgagaaac t                                               21

<210> SEQ ID NO 147
<211> LENGTH: 21
<212> TYPE: DNA
<213> ORGANISM: Homo sapiens

<400> SEQUENCE: 147
aatttgagta cacttaaggc a                                               21

<210> SEQ ID NO 148
<211> LENGTH: 21
<212> TYPE: DNA
<213> ORGANISM: Homo sapiens

<400> SEQUENCE: 148
agatacagca gaaaaggtga t                                               21

<210> SEQ ID NO 149
<211> LENGTH: 21
<212> TYPE: DNA
<213> ORGANISM: Homo sapiens

<400> SEQUENCE: 149
gacacatgca gaagtgacag c                                               21

<210> SEQ ID NO 150
<211> LENGTH: 21
<212> TYPE: DNA
<213> ORGANISM: Homo sapiens

<400> SEQUENCE: 150
agcagccttc gaactgcaca c                                               21

<210> SEQ ID NO 151
<211> LENGTH: 21
<212> TYPE: DNA
<213> ORGANISM: Homo sapiens

<400> SEQUENCE: 151
tctagatggc agtaaacagc a                                               21
```

<210> SEQ ID NO 152
<211> LENGTH: 21
<212> TYPE: DNA
<213> ORGANISM: Homo sapiens

<400> SEQUENCE: 152
ggctgctcca atcattttgg t                                              21

<210> SEQ ID NO 153
<211> LENGTH: 21
<212> TYPE: DNA
<213> ORGANISM: Homo sapiens

<400> SEQUENCE: 153
gagtccggag accgaaccag a                                              21

<210> SEQ ID NO 154
<211> LENGTH: 21
<212> TYPE: DNA
<213> ORGANISM: Homo sapiens

<400> SEQUENCE: 154
gaaccgtgcg tgccgggagc c                                              21

<210> SEQ ID NO 155
<211> LENGTH: 21
<212> TYPE: DNA
<213> ORGANISM: Homo sapiens

<400> SEQUENCE: 155
gctggcctgg ggcgcgcgct c                                              21

<210> SEQ ID NO 156
<211> LENGTH: 21
<212> TYPE: DNA
<213> ORGANISM: Homo sapiens

<400> SEQUENCE: 156
aagatcagcc ccactacgtt c                                              21

<210> SEQ ID NO 157
<211> LENGTH: 21
<212> TYPE: DNA
<213> ORGANISM: Homo sapiens

<400> SEQUENCE: 157
ccggaggcga gccccttccc g                                              21

<210> SEQ ID NO 158
<211> LENGTH: 21
<212> TYPE: DNA
<213> ORGANISM: Homo sapiens

<400> SEQUENCE: 158
ggagggtggg gcgcaggacc g                                              21

<210> SEQ ID NO 159
<211> LENGTH: 21
<212> TYPE: DNA
<213> ORGANISM: Homo sapiens

<400> SEQUENCE: 159
gagcgctgga ggcggaggag g                                              21

<210> SEQ ID NO 160
<211> LENGTH: 21
<212> TYPE: DNA
<213> ORGANISM: Homo sapiens

<400> SEQUENCE: 160
cctctctcgc gcacaaagtt g					21

<210> SEQ ID NO 161
<211> LENGTH: 21
<212> TYPE: DNA
<213> ORGANISM: Homo sapiens

<400> SEQUENCE: 161
gggagcggcg ccccccttct t					21

<210> SEQ ID NO 162
<211> LENGTH: 21
<212> TYPE: DNA
<213> ORGANISM: Homo sapiens

<400> SEQUENCE: 162
caccaacttt gccaaacgct a					21

<210> SEQ ID NO 163
<211> LENGTH: 21
<212> TYPE: DNA
<213> ORGANISM: Homo sapiens

<400> SEQUENCE: 163
ggagtaaccg cgggggtgtg t					21

<210> SEQ ID NO 164
<211> LENGTH: 21
<212> TYPE: DNA
<213> ORGANISM: Homo sapiens

<400> SEQUENCE: 164
gaatggggcg ggggccggga g					21

<210> SEQ ID NO 165
<211> LENGTH: 21
<212> TYPE: DNA
<213> ORGANISM: Homo sapiens

<400> SEQUENCE: 165
tctttctgtg gttcttccgc c					21

<210> SEQ ID NO 166
<211> LENGTH: 21
<212> TYPE: DNA
<213> ORGANISM: Homo sapiens

<400> SEQUENCE: 166
tttggatcgt tcacaactag t					21

<210> SEQ ID NO 167
<211> LENGTH: 21
<212> TYPE: DNA
<213> ORGANISM: Homo sapiens

<400> SEQUENCE: 167

```
agaggggacg tggcctctta g                                        21

<210> SEQ ID NO 168
<211> LENGTH: 21
<212> TYPE: DNA
<213> ORGANISM: Homo sapiens

<400> SEQUENCE: 168
gtccacagga gagggtgggc a                                        21

<210> SEQ ID NO 169
<211> LENGTH: 21
<212> TYPE: DNA
<213> ORGANISM: Homo sapiens

<400> SEQUENCE: 169
gctcccaagg gtggggctcc g                                        21

<210> SEQ ID NO 170
<211> LENGTH: 21
<212> TYPE: DNA
<213> ORGANISM: Homo sapiens

<400> SEQUENCE: 170
tttcagatgg caggttgttc a                                        21

<210> SEQ ID NO 171
<211> LENGTH: 21
<212> TYPE: DNA
<213> ORGANISM: Homo sapiens

<400> SEQUENCE: 171
ctttcccagc cttcaggtca g                                        21

<210> SEQ ID NO 172
<211> LENGTH: 21
<212> TYPE: DNA
<213> ORGANISM: Homo sapiens

<400> SEQUENCE: 172
gcgcgcggag ctcgggggag g                                        21

<210> SEQ ID NO 173
<211> LENGTH: 21
<212> TYPE: DNA
<213> ORGANISM: Homo sapiens

<400> SEQUENCE: 173
tgaggccggt gcaacttaca a                                        21

<210> SEQ ID NO 174
<211> LENGTH: 21
<212> TYPE: DNA
<213> ORGANISM: Homo sapiens

<400> SEQUENCE: 174
tgggcgtggg agacgcagcc t                                        21

<210> SEQ ID NO 175
<211> LENGTH: 21
<212> TYPE: DNA
<213> ORGANISM: Homo sapiens

<400> SEQUENCE: 175
```

```
aggtggagga atgcgaagct t                                              21

<210> SEQ ID NO 176
<211> LENGTH: 21
<212> TYPE: DNA
<213> ORGANISM: Homo sapiens

<400> SEQUENCE: 176
agacaactct ttaactctcc t                                              21

<210> SEQ ID NO 177
<211> LENGTH: 21
<212> TYPE: DNA
<213> ORGANISM: Artificial Sequence
<220> FEATURE:
<223> OTHER INFORMATION: sequence encoding crRNA of control sgRNA

<400> SEQUENCE: 177
acggaggcta agcgtcgcaa g                                              21

<210> SEQ ID NO 178
<211> LENGTH: 16
<212> TYPE: PRT
<213> ORGANISM: Artificial sequence
<220> FEATURE:
<223> OTHER INFORMATION: Nuclear localization signal

<400> SEQUENCE: 178

Ala Pro Lys Lys Lys Arg Lys Val Gly Ile His Gly Val Pro Ala Ala
1               5                   10                  15

<210> SEQ ID NO 179
<211> LENGTH: 48
<212> TYPE: DNA
<213> ORGANISM: Artificial sequence
<220> FEATURE:
<223> OTHER INFORMATION: DNA sequence encoding NLS of SEQ ID NO 178

<400> SEQUENCE: 179
gccccaaaga agaagcggaa ggtcggtatc cacggagtcc cagcagcc                 48

<210> SEQ ID NO 180
<211> LENGTH: 16
<212> TYPE: PRT
<213> ORGANISM: Artificial sequence
<220> FEATURE:
<223> OTHER INFORMATION: Nuclear localization signal

<400> SEQUENCE: 180

Lys Arg Pro Ala Ala Thr Lys Lys Ala Gly Gln Ala Lys Lys Lys Lys
1               5                   10                  15

<210> SEQ ID NO 181
<211> LENGTH: 48
<212> TYPE: DNA
<213> ORGANISM: Artificial sequence
<220> FEATURE:
<223> OTHER INFORMATION: DNA sequence encoding NLS of SEQ ID NO 180

<400> SEQUENCE: 181
aaaaggccgg cggccacgaa aaaggccggc caggcaaaaa agaaaaag                 48

<210> SEQ ID NO 182
<211> LENGTH: 3414
<212> TYPE: DNA
```

<213> ORGANISM: Artificial sequence
<220> FEATURE:
<223> OTHER INFORMATION: DNA sequence encoding dSaCas9(D10A, N580A)-VP64

<400> SEQUENCE: 182

```
atggccccaa agaagaagcg aaggtcggt atccacggag tcccagcagc caagcggaac      60
tacatcctgg gcctggccat cggcatcacc agcgtgggct acggcatcat cgactacgag     120
acacgggacg tgatcgatgc cggcgtgcgg ctgttcaaag aggccaacgt ggaaaacaac     180
gagggcaggc ggagcaagag aggcgccaga aggctgaagc ggcggaggcg gcatagaatc     240
cagagagtga agaagctgct gttcgactac aacctgctga ccgaccacag cgagctgagc     300
ggcatcaacc cctacgaggc cagagtgaag ggcctgagcc agaagctgag cgaggaagag     360
ttctctgccg ccctgctgca cctggccaag agaagaggcg tgcacaacgt gaacgaggtg     420
gaagaggaca ccggcaacga gctgtccacc aaagagcaga tcagccggaa cagcaaggcc     480
ctggaagaga aatacgtggc cgaactgcag ctggaacggc tgaagaaaga cggcgaagtg     540
cggggcagca tcaacagatt caagaccagc gactacgtga agaagccaa acagctgctg     600
aaggtgcaga aggcctacca ccagctggac cagagcttca tcgacaccta catcgacctg     660
ctggaaaccc ggcggaccta ctatgaggga cctggcgagg gcagcccctt cggctggaag     720
gacatcaaag aatggtacga gatgctgatg ggccactgca cctacttccc cgaggaactg     780
cggagcgtga gtacgcctac aacgccgac ctgtacaacg ccctgaacga cctgaacaat     840
ctcgtgatca ccagggacga gaacgagaag ctggaatatt acgagaagtt ccagatcatc     900
gagaacgtgt tcaagcagaa gaagaagccc accctgaagc agatcgccaa agaaatcctc     960
gtgaacgaag aggatattaa ggctacaga gtgaccagca ccggcaagcc cgagttcacc    1020
aacctgaagg tgtaccacga catcaaggac attaccgccc ggaaagagat tattgagaac    1080
gccgagctgc tggatcagat tgccaagatc ctgaccatct accagagcag cgaggacatc    1140
caggaagaac tgaccaatct gaactccgag ctgacccagg aagagatcga gcagatctct    1200
aatctgaagg gctataccgg cacccacaac ctgagcctga aggccatcaa cctgatcctg    1260
gacgagctgt ggcacaccaa cgacaaccag atcgctatct tcaaccggct gaagctggtg    1320
cccaagaagg tggacctgtc ccagcagaaa gagatcccca ccaccctggt ggacgacttc    1380
atcctgagcc ccgtcgtgaa agaagcttc atccagagca tcaaagtgat caacgccatc    1440
atcaagaagt acggcctgcc caacgacatc attatcgagc tggcccgcga gaagaactcc    1500
aaggacgccc agaaaatgat caacgagatg cagaagcgga accggcagac caacgagcgg    1560
atcgaggaaa tcatccggac caccggcaaa gagaacgcca agtacctgat cgagaagatc    1620
aagctgcacg acatgcagga aggcaagtgc ctgtacagcc tggaagccat ccctctggaa    1680
gatctgctga acaacccctt caactatgag gtggaccaca tcatcccag aagcgtgtcc    1740
ttcgacaaca gcttcaacaa caaggtgctc gtgaagcagg aagaagccag caagaagggc    1800
aaccggaccc cattccagta cctgagcagc agcgacagca gatcagcta cgaaaccttc    1860
aagaagcaca tcctgaatct ggccaagggc aagggcagaa tcagcaagac caagaaagag    1920
tatctgctgg aagaacggga catcaacagg ttctccgtgc agaaagactt catcaaccgg    1980
aacctggtgg ataccagata cgccaccaga ggcctgatga acctgctgcg agctacttc    2040
agagtgaaca acctggacgt gaaagtgaag tccatcaatg gcggcttcac cagctttctg    2100
cggcggaagt ggaagtttaa aaagagcgg aacaagggt acaagcacca cgccgaggac    2160
gccctgatca ttgccaacgc cgatttcatc ttcaaagagt ggaagaaact ggacaaggcc    2220
```

-continued

```
aaaaaagtga tggaaaacca gatgttcgag gaaaagcagg ccgagagcat gcccgagatc    2280
gaaaccgagc aggagtacaa agagatcttc atcaccccccc accagatcaa gcacattaag    2340
gacttcaagg actacaagta cagccaccgg gtggacaaga agcctaatag agagctgatt    2400
aacgacaccc tgtactccac ccggaaggac gacaagggca caccctgat cgtgaacaat     2460 ctgaacggcc tgtacgacaa ggacaatgac aagctgaaaa agctgatcaa caagagcccc    2520
gaaaagctgc tgatgtacca ccacgacccc cagacctacc agaaactgaa gctgattatg    2580
gaacagtacg gcgacgagaa gaatcccctg tacaagtact acgaggaaac cgggaactac    2640
ctgaccaagt actccaaaaa ggacaacggc cccgtgatca agaagattaa gtattacggc    2700
aacaaactga acgcccatct ggacatcacc gacgactacc ccaacagcag aaacaaggtc    2760
gtgaagctgt ccctgaagcc ctacagattc gacgtgtacc tggacaatgg cgtgtacaag    2820
ttcgtgaccg tgaagaatct ggatgtgatc aaaaagaaa actactacga agtgaatagc     2880
aagtgctatg aggaagctaa gaagctgaag aagatcagca accaggccga gtttatcgcc    2940
tccttctaca caacgatct gatcaagatc aacggcgagc tgtatagagt gatcggcgtg     3000
aacaacgacc tgctgaaccg gatcgaagtg aacatgatcg acatcaccta ccgcgagtac    3060
ctggaaaaca tgaacgacaa gaggcccccc aggatcatta agacaatcgc ctccaagacc    3120
cagagcatta agaagtacag cacagacatt ctgggcaacc tgtatgaagt gaaatctaag    3180
aagcaccctc agatcatcaa aaagggcaaa aggccggcgg ccacgaaaaa ggccggccag    3240
gcaaaaaaga aaaagtctag agatgcttta gacgattttg acttagatat gcttggttca    3300
gacgcgttag acgacttcga cctagacatg ttaggctcag atgcattgga cgacttcgat    3360
ttagatatgt tgggctccga tgccctagat gactttgatt tggatatgct ataa          3414
```

<210> SEQ ID NO 183
<211> LENGTH: 4392
<212> TYPE: DNA
<213> ORGANISM: Artificial sequence
<220> FEATURE:
<223> OTHER INFORMATION: DNA sequence encoding dSaCas9(D10A, N580A)-VPH

<400> SEQUENCE: 183

```
atggccccaa agaagaagcg gaaggtcggt atccacggag tcccagcagc caagcggaac     60
tacatcctgg gcctggccat cggcatcacc agcgtgggct acggcatcat cgactacgag    120
acacgggacg tgatcgatgc cggcgtgcgg ctgttcaaag aggccaacgt ggaaaacaac    180
gagggcaggc ggagcaagag aggcgccaga aggctgaagc ggcggaggcg gcatagaatc    240
cagagagtga agaagctgct gttcgactac aacctgctga ccgaccacag cgagctgagc    300
ggcatcaacc cctacgaggc cagagtgaag ggcctgagcc agaagctgag cgaggaagag    360
ttctctgccg ccctgctgca cctggccaag agaagaggcg tgcacaacgt gaacgaggtg    420
gaagaggaca ccggcaacga gctgtccacc aaagagcaga tcagccggaa cagcaaggcc    480
ctggaagaga atacgtggc cgaactgcag ctggaacggc tgaagaaaga cggcgaagtg    540
cggggcagca tcaacagatt caagaccagc gactacgtga agaagccaa acagctgctg    600 aaggtgcaga aggcctacca ccagctggac cagagcttca tcgacaccta catcgacctg    660
ctggaaaccc ggcggaccta ctatgaggga cctggcgagg gcagccccct cggctggaag    720
gacatcaaag aatggtacga gatgctgatg ggccactgca cctacttccc cgaggaactg    780
cggagcgtga agtacgccta caacgccgac ctgtacaacg ccctgaacga cctgaacaat    840
```

```
ctcgtgatca ccagggacga gaacgagaag ctggaatatt acgagaagtt ccagatcatc    900
gagaacgtgt tcaagcagaa gaagaagccc accctgaagc agatcgccaa agaaatcctc    960
gtgaacgaag aggatattaa gggctacaga gtgaccagca ccggcaagcc cgagttcacc   1020
aacctgaagg tgtaccacga catcaaggac attaccgccc ggaaagagat tattgagaac   1080
gccgagctgc tggatcagat tgccaagatc ctgaccatct accagagcag cgaggacatc   1140
caggaagaac tgaccaatct gaactccgag ctgacccagg aagagatcga gcagatctct   1200
aatctgaagg gctataccgg cacccacaac ctgagcctga aggccatcaa cctgatcctg   1260
gacgagctgt ggcacaccaa cgacaaccag atcgctatct tcaaccggct gaagctggtg   1320
cccaagaagg tggacctgtc ccagcagaaa gagatcccca ccaccctggt ggacgacttc   1380
atcctgagcc ccgtcgtgaa gagaagcttc atccagagca tcaaagtgat caacgccatc   1440
atcaagaagt acggcctgcc caacgacatc attatcgagc tggcccgcga agaactcc    1500 aaggacgccc agaaaatgat caacgagatg cagaagcgga accggcagac caacgagcgg   1560
atcgaggaaa tcatccggac caccggcaaa gagaacgcca agtacctgat cgagaagatc   1620
aagctgcacg acatgcagga aggcaagtgc ctgtacagcc tggaagccat ccctctggaa   1680
gatctgctga caaccccctt caactatgag gtggaccaca tcatccccag aagcgtgtcc   1740
ttcgacaaca gcttcaacaa caaggtgctc gtgaagcagg aagaagccag caagaagggc   1800
aaccggaccc cattccagta cctgagcagc agcgacagca gatcagcta cgaaaccttc   1860 aagaagcaca tcctgaatct ggccaagggc aagggcagaa tcagcaagac caagaaagag   1920
tatctgctgg aagaacggga catcaacagg ttctccgtgc agaaagactt catcaaccgg   1980
aacctggtgg ataccagata cgccaccaga ggcctgatga acctgctgcg gagctacttc   2040
agagtgaaca acctggacgt gaaagtgaag tccatcaatg gcggcttcac cagctttctg   2100
cggcggaagt ggaagtttaa aaagagcgg aacaaggggt acaagcacca cgccgaggac   2160
gccctgatca ttgccaacgc cgatttcatc ttcaaagagt ggaagaaact ggacaaggcc   2220
aaaaaagtga tggaaaacca gatgttcgag gaaaagcagg ccgagagcat gcccgagatc   2280
gaaaccgagc aggagtacaa agagatcttc atcaccccc accagatcaa gcacattaag   2340
gacttcaagg actacaagta cagccaccgg gtggacaaga gcctaatag agagctgatt   2400 aacgacaccc tgtactccac ccggaaggac gacaagggca caccctgat cgtgaacaat   2460 ctgaacggcc tgtacgacaa ggacaatgac aagctgaaaa agctgatcaa caagagcccc   2520
gaaaagctgc tgatgtacca ccacgacccc cagacctacc agaaactgaa gctgattatg   2580
gaacagtacg gcgacgagaa gaatccctg tacaagtact acgaggaaac cgggaactac   2640
ctgaccaagt actccaaaaa ggacaacggc ccgtgatca agaagattaa gtattacggc   2700
aacaaactga acgcccatct ggacatcacc gacgactacc caacagcag aaacaaggtc   2760 gtgaagctgt ccctgaagcc ctacagattc gacgtgtacc tggacaatgg cgtgtacaag   2820
ttcgtgaccg tgaagaatct ggatgtgatc aaaaagaaa actactacga agtgaatagc   2880
aagtgctatg aggaagctaa gaagctgaag aagatcagca accaggccga gtttatcgcc   2940
tccttctaca caacgatct gatcaagatc aacggcgagc tgtatagagt gatcggcgtg   3000
aacaacgacc tgctgaaccg gatcgaagtg aacatgatcg acatcaccta ccgcgagtac   3060
ctggaaaaca tgaacgacaa gaggcccccc aggatcatta agacaatcgc ctccaagacc   3120
cagagcatta agaagtacag cacagacatt ctgggcaacc tgtatgaagt gaaatctaag   3180 aagcacccctc agatcatcaa aaagggcaaa aggccggcgg ccacgaaaaa ggccggccag   3240
```

```
gcaaaaaaga aaaagtctag agatgcttta gacgattttg acttagatat gcttggttca   3300
gacgcgttag acgacttcga cctagacatg ttaggctcag atgcattgga cgacttcgat   3360
ttagatatgt tgggctccga tgccctagat gactttgatt tggatatgct aagttccgga   3420
tctccgaaaa agaaacgcaa agttggtagc ccttcagggc agatcagcaa ccaggccctg   3480
gctctggccc ctagctccgc tccagtgctg gcccagacta tggtgccctc tagtgctatg   3540
gtgcctctgg cccagccacc tgctccagcc cctgtgctga ccccaggacc accccagtca   3600
ctgagcgctc cagtgcccaa gtctacacag gccggcgagg ggactctgag tgaagctctg   3660
ctgcacctgc agttcgacgc tgatgaggac ctgggagctc tgctggggaa cagcaccgat   3720
cccggagtgt tcacagacct ggcctccgtg acaactctg agtttcagca gctgctgaat   3780
cagggcgtgt ccatgtctca tagtacagcc gaaccaatgc tgatggagta ccccgaagcc   3840
attacccggc tggtgaccgg cagccagcgg ccccccgacc ccgctccaac tcccctggga   3900
accagcggcc tgcctaatgg gctgtccgga gatgaagact tctcaagcat cgctgatatg   3960
gactttagtg ccctgctgtc acagatttcc tctagtgggc agggaggagg tggaagcggc   4020
ttcagcgtgg acaccagtgc cctgctggac ctgttcagcc cctcggtgac cgtgcccgac   4080
atgagcctgc ctgaccttga cagcagcctg gccagtatcc aagagctcct gtctccccag   4140
gagcccccca ggcctcccga ggcagagaac agcagcccgg attcagggaa gcagctggtg   4200
cactacacag cgcagccgct gttcctgctg gaccccggct ccgtggacac cgggagcaac   4260
gacctgccgg tgctgtttga gctggggagg ggctccctact tctccgaagg ggacggcttc   4320
gccgaggacc ccaccatctc cctgctgaca ggctcggagc ctcccaaagc caaggacccc   4380
actgtctcct ga                                                        4392
```

<210> SEQ ID NO 184
<211> LENGTH: 4821
<212> TYPE: DNA
<213> ORGANISM: Artificial sequence
<220> FEATURE:
<223> OTHER INFORMATION: DNA sequence encoding dSaCas9(D10A, N580A)-VPR

<400> SEQUENCE: 184

```
atggccccaa agaagaagcg gaaggtcggt atccacggag tcccagcagc caagcggaac    60
tacatcctgg gcctggccat cggcatcacc agcgtgggct acggcatcat cgactacgag   120
acacgggacg tgatcgatgc cggcgtgcgg ctgttcaaag aggccaacgt ggaaaacaac   180
gagggcaggc ggagcaagag aggcgccaga aggctgaagc ggcggaggcg gcatagaatc   240
cagagagtga agaagctgct gttcgactac aacctgctga ccgaccacag cgagctgagc   300
ggcatcaacc cctacgaggc agagtgaagg gcctgagcc agaagctgag cgaggaagag   360
ttctctgccg ccctgctgca cctggccaag agaagaggcg tgcacaacgt gaacgaggtg   420
gaagaggaca ccggcaacga gctgtccacc aaagagcaga tcagccggaa cagcaaggcc   480
ctggaagaga atacgtggc cgaactgcag ctggaacggc tgaagaaaga cggcgaagtg   540
cggggcagca tcaacagatt caagaccagc gactacgtga agaagccaa acagctgctg   600 aaggtgcaga aggcctacca ccagctggac cagagcttca tcgacaccta catcgacctg   660
ctggaaaccc ggcggaccta ctatgaggga cctggcgagg cagccccttc ggctggaag   720 gacatcaaag aatggtacga gatgctgatg ggccactgca cctacttccc cgaggaactg   780
cggagcgtga agtacgccta caacgccgac ctgtacaacg ccctgaacga cctgaacaat   840
```

-continued

```
ctcgtgatca ccagggacga gaacgagaag ctggaatatt acgagaagtt ccagatcatc    900
gagaacgtgt tcaagcagaa gaagaagccc accctgaagc agatcgccaa agaaatcctc    960
gtgaacgaag aggatattaa gggctacaga gtgaccagca ccggcaagcc cgagttcacc   1020
aacctgaagg tgtaccacga catcaaggac attaccgccc ggaaagagat tattgagaac   1080
gccgagctgc tggatcagat tgccaagatc ctgaccatct accagagcag cgaggacatc   1140
caggaagaac tgaccaatct gaactccgag ctgacccagg aagagatcga gcagatctct   1200
aatctgaagg gctataccgg cacccacaac ctgagcctga aggccatcaa cctgatcctg   1260
gacgagctgt ggcacaccaa cgacaaccag atcgctatct tcaaccggct gaagctggtg   1320
cccaagaagg tggacctgtc ccagcagaaa gagatcccca ccaccctggt ggacgacttc   1380
atcctgagcc ccgtcgtgaa gagaagcttc atccagagca tcaaagtgat caacgccatc   1440
atcaagaagt acggcctgcc caacgacatc attatcgagc tggcccgcga gaagaactcc   1500
aaggacgccc agaaaatgat caacgagatg cagaagcgga accggcagac caacgagcgg   1560
atcgaggaaa tcatccggac caccggcaaa gagaacgcca agtacctgat cgagaagatc   1620
aagctgcacg acatgcagga aggcaagtgc ctgtacagcc tggaagccat ccctctggaa   1680
gatctgctga acaaccccctt caactatgag gtggaccaca tcatccccag aagcgtgtcc   1740
ttcgacaaca gcttcaacaa caaggtgctc gtgaagcagg aagaagccag caagaagggc   1800
aaccggaccc cattccagta cctgagcagc agcgacagca gatcagcta cgaaaccttc   1860 aagaagcaca tcctgaatct ggccaagggc aagggcagaa tcagcaagac caagaaagag   1920
tatctgctgg aagaacggga catcaacagg ttctccgtgc agaaagactt catcaaccgg   1980
aacctggtgg ataccagata cgccaccaga ggcctgatga acctgctgcg gagctacttc   2040
agagtgaaca acctggacgt gaaagtgaag tccatcaatg gcggcttcac cagctttctg   2100
cggcggaagt ggaagtttaa gaaagagcgg aacaagggt acaagcacca cgccgaggac   2160
gccctgatca ttgccaacgc cgatttcatc ttcaaagagt ggaagaaact ggacaaggcc   2220
aaaaaagtga tggaaaacca gatgttcgag gaaaagcagg ccgagagcat gcccgagatc   2280
gaaaccgagc aggagtacaa agagatcttc atcaccccc accagatcaa gcacattaag   2340
gacttcaagg actacaagta cagccaccgg gtggacaaga gcctaatag agagctgatt   2400 aacgacaccc tgtactccac ccggaaggac gacaagggca cacccctgat cgtgaacaat   2460
ctgaacggcc tgtacgacaa ggacaatgac aagctgaaaa agctgatcaa caagagcccc   2520
gaaaagctgc tgatgtacca ccacgacccc cagacctacc agaaactgaa gctgattatg   2580
gaacagtacg gcgacgagaa gaatccctg tacaagtact acgaggaaac cgggaactac   2640
ctgaccaagt actccaaaaa ggacaacggc cccgtgatca agaagattaa gtattacggc   2700
aacaaactga acgcccatct ggacatcacc gacgactacc ccaacagcag aaacaaggtc   2760
gtgaagctgt ccctgaagcc ctacagattc gacgtgtacc tggacaatgg cgtgtacaag   2820
ttcgtgaccg tgaagaatct ggatgtgatc aaaaaagaaa actactacga agtgaatagc   2880
aagtgctatg aggaagctaa gaagctgaag aagatcagca accaggccga gtttatcgcc   2940
tccttctaca caacgatct gatcaagatc aacggcgagc tgtatagagt gatcggcgtg   3000
aacaacgacc tgctgaaccg gatcgaagtg aacatgatcg acatcaccta ccgcgagtac   3060
ctggaaaaca tgaacgacaa gaggccccccc aggatcatta gacaatcgc ctccaagacc   3120 cagagcatta agaagtacag cacagacatt ctgggcaacc tgtatgaagt gaaatctaag   3180 aagcacccte agatcatcaa aaagggcaaa aggccggcgg ccacgaaaaa ggccggccag   3240
```

```
gcaaaaaaga aaaagtctag agatgcttta gacgattttg acttagatat gcttggttca   3300
gacgcgttag acgacttcga cctagacatg ttaggctcag atgcattgga cgacttcgat   3360
ttagatatgt tgggctccga tgccctagat gactttgatt tggatatgct aagttccgga   3420
tctccgaaaa agaaacgcaa agttggtagc cagtacctgc ccgacaccga cgaccggcac   3480
cggatcgagg aaaagcggaa gcggacctac gagacattca agagcatcat gaagaagtcc   3540
cccttcagcg cccccaccga ccctagacct ccacctagaa gaatcgccgt gcccagcaga   3600
tccagcgcca gcgtgccaaa acctgccccc cagccttacc ccttcaccag cagcctgagc   3660
accatcaact acgacgagtt ccctaccatg gtgttcccca gcggccagat ctctcaggcc   3720
tctgctctgg ctccagcccc tcctcaggtg ctgcctcagg ctcctgctcc tgcaccagct   3780
ccagccatgt gtctgcact ggctcaggca ccagcacccg tgcctgtgct ggctcctgga   3840
cctccacagg ctgtggctcc accagcccct aaacctacac aggccggcga gggcacactg   3900
tctgaagctc tgctgcagct gcagttcgac gacgaggatc tgggagccct gctgggaaac   3960
agcaccgatc ctgccgtgtt caccgacctg gccagcgtgg acaacagcga gttccagcag   4020
ctgctgaacc agggcatccc tgtggcccct cacaccaccg agcccatgct gatggaatac   4080
cccgaggcca tcacccggct cgtgacaggc gctcagaggc tcctgatcc agctcctgcc   4140 cctctgggag caccaggcct gcctaatgga ctgctgtctg cgacgagga cttcagctct   4200 atcgccgata tggatttctc agccttgctg ggctctggca gcggcagccg ggattccagg   4260
gaagggatgt ttttgccgaa gcctgaggcc ggctccgcta ttagtgacgt gtttgagggc   4320
cgcgaggtgt gccagccaaa acgaatccgg ccatttcatc ctccaggaag tccatgggcc   4380
aaccgcccac tccccgccag cctcgcacca acaccaaccg gtccagtaca tgagccagtc   4440
gggtcactga ccccggcacc agtccctcag ccactcgatc cagcgcccgc agtgactccc   4500
gaggccagtc acctgttgga agatcccgat gaagagacca gccaggctgt caaagcccctt   4560 cgggagatgg ccgatactgt gattccccag aaggaagagg ctgcaatctg tggccaaatg   4620
gacctttccc atccgccccc aagggggcat ctggatgagc tgacaaccac acttgagtcc   4680
atgaccgagg atctgaacct ggactcaccc ctgacccctgg aattgaacga gattctggat   4740
accttcctga cgacgagtg cctcttgcat gccatgcata tcagcacagg actgtccatc   4800
ttcgacacat ctctgttttg a                                              4821

<210> SEQ ID NO 185
<211> LENGTH: 3726
<212> TYPE: DNA
<213> ORGANISM: Artificial sequence
<220> FEATURE:
<223> OTHER INFORMATION: DNA sequence encoding dSaCas9[-25](D10A,
      N580A)-miniVR with SGGGS linker

<400> SEQUENCE: 185
atggccccaa agaagaagcg gaaggtcggt atccacggag tcccagcagc caagcggaac     60
tacatcctgg gcctggccat cggcatcacc agcgtgggct acggcatcat cgactacgag   120
acacgggacg tgatcgatgc cggcgtgcgc ctgttcaaag aggccaacgt ggaaaacaac   180
gagggcaggc ggagcaagag aggcgccaga aggctgaagc ggcggaggcg catagaatc   240 cagagagtga gaagctgct gttcgactac aacctgctga ccgaccacag cgagctgagc   300
ggcatcaacc cctacgaggc cagagtgaag ggcctgagcc agaagctgag cgaggaagag   360
ttctctgccg ccctgctgca cctggccaag agaagaggcg tgcacaacgt gaacgaggtg   420
```

```
gaagaggaca ccggcaacga gctgtccacc aaagagcaga tcagccggaa cagcaaggcc    480
ctggaagaga aatacgtggc cgaactgcag ctggaacggc tgaagaaaga cggcgaagtg    540
cggggcagca tcaacagatt caagaccagc gactacgtga agaagccaa acagctgctg     600 aaggtgcaga aggcctacca ccagctggac cagagcttca tcgacaccta catcgacctg    660
ctggaaaccc ggcggaccta ctatgaggga cctggcgagg cagccccctt cggctggaag    720
gacatcaaag aatggtacga gatgctgatg ggccactgca cctacttccc cgaggaactg    780
cggagcgtga agtacgccta caacgccgac ctgtacaacg ccctgaacga cctgaacaat    840
ctcgtgatca ccagggacga gaacgagaag ctggaatatt acgagaagtt ccagatcatc    900
gagaacgtgt tcaagcagaa gaagaagccc accctgaagc agatcgccaa agaaatcctc    960
gtgaacgaag aggatattaa gggctacaga gtgaccagca ccggcaagcc cgagttcacc   1020
aacctgaagg tgtaccacga catcaaggac attaccgccc ggaaagagat tattgagaac   1080
gccgagctgc tggatcagat tgccaagatc ctgaccatct accagagcag cgaggacatc   1140
caggaagaac tgaccaatct gaactccgag ctgacccagg aagagatcga gcagatctct   1200
aatctgaagg gctataccgg cacccacaac ctgagcctga aggccatcaa cctgatcctg   1260
gacgagctgt ggcacaccaa cgacaaccag atcgctatct tcaaccggct gaagctggtg   1320
cccaagaagg tggacctgtc ccagcagaaa gagatcccca ccaccctggt ggacgacttc   1380
atcctgagcc ccgtcgtgaa gagaagcttc atccagagca tcaaagtgat caacgccatc   1440
atcaagaagt acggcctgcc caacgacatc attatcgagc tggcccgcga gaagaactcc   1500
aaggacgccc agaaaatgat caacgagatg cagaagcgga accggcagac caacgagcgg   1560
atcgaggaaa tcatccggac caccggcaaa gagaacgcca agtacctgat cgagaagatc   1620
aagctgcacg acatgcagga aggcaagtgc ctgtacagcc tggaagccat ccctctggaa   1680
gatctgctga acaacccctt caactatgag gtggaccaca tcatcccag aagcgtgtcc   1740 ttcgacaaca gcttcaacaa caaggtgctc gtgaagcagg aagaagccag caagaagggc   1800
aaccggaccc cattccagta cctgagcagc agcgacagca gatcagcta cgaaaccttc   1860 aagaagcaca tcctgaatct ggccaagggc aagggcagaa tcagcaagac caagaaagag   1920
tatctgctgg aagaacggga catcaacagg ttctccgtgc agaaagactt catcaaccgg   1980
aacctggtgg ataccagata cgccaccaga ggcctgatga acctgctgcg agctacttc    2040 agagtgaaca acctggacgt gaaagtgaag tccatcaatg gcggcttcac cagctttctg    2100
cggcggaagt ggaagtttaa gaaagagcgg aacaaggggt acaagcacca cgccgaggac    2160
gccctgatca ttgccaacgc cgatttcatc ttcaaagagt ggaagaaatc cggcggcggt   2220
tcgaccgagc aggagtacaa agatcttc atcaccccc accagatcaa gcacattaag      2280
gacttcaagg actacaagta cagccaccgg gtggacaaga gcctaatag agagctgatt    2340 aacgacaccc tgtactccac ccggaaggac gacaagggca caccctgat cgtgaacaat    2400 ctgaacggcc tgtacgacaa ggacaatgac aagctgaaaa agctgatcaa caagagcccc   2460
gaaaagctgc tgatgtacca ccacgacccc cagacctacc agaaactgaa gctgattatg    2520
gaacagtacg gcgacgagaa gaatcccctg tacaagtact acgaggaaac cgggaactac   2580
ctgaccaagt actccaaaaa ggacaacggc cccgtgatca agaagattaa gtattacggc   2640
aacaaactga acgcccatct ggacatcacc gacgactacc ccaacagcag aaacaaggtc   2700
gtgaagctgt ccctgaagcc ctacagattc gacgtgtacc tggacaatgg cgtgtacaag   2760
```

```
ttcgtgaccg tgaagaatct ggatgtgatc aaaaaagaaa actactacga agtgaatagc    2820
aagtgctatg aggaagctaa gaagctgaag aagatcagca accaggccga gtttatcgcc    2880
tccttctaca acaacgatct gatcaagatc aacggcgagc tgtatagagt gatcggcgtg    2940
aacaacgacc tgctgaaccg gatcgaagtg aacatgatcg acatcaccta ccgcgagtac    3000
ctggaaaaca tgaacgacaa gaggcccccc aggatcatta agacaatcgc ctccaagacc    3060
cagagcatta agaagtacag cacagacatt ctgggcaacc tgtatgaagt gaaatctaag    3120
aagcaccctc agatcatcaa aaagggcaaa aggccggcgg ccacgaaaaa ggccggccag    3180
gcaaaaaaga aaaagggatc cggtgctaga aagcttgatg ctttagacga ttttgactta    3240
gatatgcttg gttcagacgc gttagacgac ttcgacctag acatgttagg ctcagatgca    3300
ttggacgact tcgatttaga tatgttgggc tccgatgccc tagatgactt tgatttggat    3360
atgctaggat ctggtagccc agcgcccgca gtgactcccg aggccagtca cctgttggaa    3420
gatcccgatg aagaaaccag ccaggctgtc aaagcccttc gggagatggc cgatactgtg    3480
attccccaga aggaagaggc tgcaatctgt ggccaaatgg acctttccca tccgccccca    3540 agggccatc tggatgagct gacaaccaca cttgagtcca tgaccgagga tctgaacctg    3600
gactcacccc tgaccccgga attgaacgag attctggata ccttcctgaa cgacgagtgc    3660
ctcttgcatg ccatgcatat cagcacagga ctgtccatct tcgacacatc tctgtttgtc    3720
gactga                                                               3726

<210> SEQ ID NO 186
<211> LENGTH: 1241
<212> TYPE: PRT
<213> ORGANISM: Artificial Sequence
<220> FEATURE:
<223> OTHER INFORMATION: dSaCas9[-25](D10A and N580A)-miniVR with SGGGS
      linker
<220> FEATURE:
<221> NAME/KEY: SIGNAL
<222> LOCATION: (1)..(17)
<223> OTHER INFORMATION: nuclear localization signal
<220> FEATURE:
<221> NAME/KEY: PEPTIDE
<222> LOCATION: (18)..(1049)
<223> OTHER INFORMATION: dSaCas9[-25](D10A and N580A) with SGGGS linker
<220> FEATURE:
<221> NAME/KEY: VARIANT
<222> LOCATION: (26)..(26)
<223> OTHER INFORMATION: conversion of Asp residue into Ala residue
<220> FEATURE:
<221> NAME/KEY: VARIANT
<222> LOCATION: (596)..(596)
<223> OTHER INFORMATION: conversion of Asn residue into Ala residue
<220> FEATURE:
<221> NAME/KEY: PEPTIDE
<222> LOCATION: (737)..(741)
<223> OTHER INFORMATION: SGGGS linker
<220> FEATURE:
<221> NAME/KEY: SIGNAL
<222> LOCATION: (1050)..(1068)
<223> OTHER INFORMATION: nuclear localization signal
<220> FEATURE:
<221> NAME/KEY: PEPTIDE
<222> LOCATION: (1073)..(1239)
<223> OTHER INFORMATION: miniVR

<400> SEQUENCE: 186

Met Ala Pro Lys Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
            20                  25                  30
```

-continued

```
Gly Tyr Gly Ile Ile Asp Tyr Glu Thr Arg Asp Val Ile Asp Ala Gly
             35                  40                  45

Val Arg Leu Phe Lys Glu Ala Asn Val Glu Asn Glu Gly Arg Arg
 50                  55                  60

Ser Lys Arg Gly Ala Arg Arg Leu Lys Arg Arg Arg His Arg Ile
 65                  70                  75                  80

Gln Arg Val Lys Lys Leu Leu Phe Asp Tyr Asn Leu Leu Thr Asp His
                 85                  90                  95

Ser Glu Leu Ser Gly Ile Asn Pro Tyr Glu Ala Arg Val Lys Gly Leu
                100                 105                 110

Ser Gln Lys Leu Ser Glu Glu Phe Ser Ala Ala Leu Leu His Leu
                115                 120                 125

Ala Lys Arg Arg Gly Val His Asn Val Asn Glu Val Glu Glu Asp Thr
130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
                180                 185                 190

Val Lys Glu Ala Lys Gln Leu Leu Lys Val Gln Lys Ala Tyr His Gln
                195                 200                 205

Leu Asp Gln Ser Phe Ile Asp Thr Tyr Ile Asp Leu Leu Glu Thr Arg
210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
                260                 265                 270

Asn Ala Leu Asn Asp Leu Asn Asn Leu Val Ile Thr Arg Asp Glu Asn
                275                 280                 285

Glu Lys Leu Glu Tyr Tyr Glu Lys Phe Gln Ile Ile Glu Asn Val Phe
290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
                340                 345                 350

Ala Arg Lys Glu Ile Ile Glu Asn Ala Glu Leu Leu Asp Gln Ile Ala
                355                 360                 365

Lys Ile Leu Thr Ile Tyr Gln Ser Ser Glu Asp Ile Gln Glu Glu Leu
370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
                420                 425                 430

Ile Phe Asn Arg Leu Lys Leu Val Pro Lys Lys Val Asp Leu Ser Gln
                435                 440                 445

Gln Lys Glu Ile Pro Thr Thr Leu Val Asp Asp Phe Ile Leu Ser Pro
```

```
            450                 455                 460
Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Glu Leu Ala Arg
                485                 490                 495

Glu Lys Asn Ser Lys Asp Ala Gln Lys Met Ile Asn Glu Met Gln Lys
                500                 505                 510

Arg Asn Arg Gln Thr Asn Glu Arg Ile Glu Glu Ile Ile Arg Thr Thr
                515                 520                 525

Gly Lys Glu Asn Ala Lys Tyr Leu Ile Glu Lys Ile Lys Leu His Asp
                530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
                580                 585                 590

Gln Glu Glu Ala Ser Lys Lys Gly Asn Arg Thr Pro Phe Gln Tyr Leu
                595                 600                 605

Ser Ser Ser Asp Ser Lys Ile Ser Tyr Glu Thr Phe Lys Lys His Ile
                610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
                660                 665                 670

Met Asn Leu Leu Arg Ser Tyr Phe Arg Val Asn Asn Leu Asp Val Lys
                675                 680                 685

Val Lys Ser Ile Asn Gly Gly Phe Thr Ser Phe Leu Arg Arg Lys Trp
                690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Ser Gly Gly Gly Ser Thr Glu Gln Glu Tyr Lys Glu Ile Phe Ile Thr
                740                 745                 750

Pro His Gln Ile Lys His Ile Lys Asp Phe Lys Asp Tyr Lys Tyr Ser
                755                 760                 765

His Arg Val Asp Lys Lys Pro Asn Arg Glu Leu Ile Asn Asp Thr Leu
                770                 775                 780

Tyr Ser Thr Arg Lys Asp Asp Lys Gly Asn Thr Leu Ile Val Asn Asn
785                 790                 795                 800

Leu Asn Gly Leu Tyr Asp Lys Asp Asn Asp Lys Leu Lys Lys Leu Ile
                805                 810                 815

Asn Lys Ser Pro Glu Lys Leu Leu Met Tyr His His Asp Pro Gln Thr
                820                 825                 830

Tyr Gln Lys Leu Lys Leu Ile Met Glu Gln Tyr Gly Asp Glu Lys Asn
                835                 840                 845

Pro Leu Tyr Lys Tyr Tyr Glu Glu Thr Gly Asn Tyr Leu Thr Lys Tyr
                850                 855                 860

Ser Lys Lys Asp Asn Gly Pro Val Ile Lys Lys Ile Lys Tyr Tyr Gly
865                 870                 875                 880
```

```
Asn Lys Leu Asn Ala His Leu Asp Ile Thr Asp Asp Tyr Pro Asn Ser
                885                 890                 895

Arg Asn Lys Val Val Lys Leu Ser Leu Lys Pro Tyr Arg Phe Asp Val
            900                 905                 910

Tyr Leu Asp Asn Gly Val Tyr Lys Phe Val Thr Val Lys Asn Leu Asp
        915                 920                 925

Val Ile Lys Lys Glu Asn Tyr Tyr Glu Val Asn Ser Lys Cys Tyr Glu
930                 935                 940

Glu Ala Lys Lys Leu Lys Lys Ile Ser Asn Gln Ala Glu Phe Ile Ala
945                 950                 955                 960

Ser Phe Tyr Asn Asn Asp Leu Ile Lys Ile Asn Gly Glu Leu Tyr Arg
                965                 970                 975

Val Ile Gly Val Asn Asn Asp Leu Leu Asn Arg Ile Glu Val Asn Met
            980                 985                 990

Ile Asp Ile Thr Tyr Arg Glu Tyr Leu Glu Asn Met Asn Asp Lys Arg
        995                 1000                1005

Pro Pro Arg Ile Ile Lys Thr Ile Ala Ser Lys Thr Gln Ser Ile
    1010                1015                1020

Lys Lys Tyr Ser Thr Asp Ile Leu Gly Asn Leu Tyr Glu Val Lys
    1025                1030                1035

Ser Lys Lys His Pro Gln Ile Ile Lys Lys Gly Lys Arg Pro Ala
    1040                1045                1050

Ala Thr Lys Lys Ala Gly Gln Ala Lys Lys Lys Gly Ser Gly
    1055                1060                1065

Ala Arg Lys Leu Asp Ala Leu Asp Asp Phe Asp Leu Asp Met Leu
    1070                1075                1080

Gly Ser Asp Ala Leu Asp Asp Phe Asp Leu Asp Met Leu Gly Ser
    1085                1090                1095

Asp Ala Leu Asp Asp Phe Asp Leu Asp Met Leu Gly Ser Asp Ala
    1100                1105                1110

Leu Asp Asp Phe Asp Leu Asp Met Leu Gly Ser Gly Ser Pro Ala
    1115                1120                1125

Pro Ala Val Thr Pro Glu Ala Ser His Leu Leu Glu Asp Pro Asp
    1130                1135                1140

Glu Glu Thr Ser Gln Ala Val Lys Ala Leu Arg Glu Met Ala Asp
    1145                1150                1155

Thr Val Ile Pro Gln Lys Glu Glu Ala Ala Ile Cys Gly Gln Met
    1160                1165                1170

Asp Leu Ser His Pro Pro Arg Gly His Leu Asp Glu Leu Thr
    1175                1180                1185

Thr Thr Leu Glu Ser Met Thr Glu Asp Leu Asn Leu Asp Ser Pro
    1190                1195                1200

Leu Thr Pro Glu Leu Asn Glu Ile Leu Asp Thr Phe Leu Asn Asp
    1205                1210                1215

Glu Cys Leu Leu His Ala Met His Ile Ser Thr Gly Leu Ser Ile
    1220                1225                1230

Phe Asp Thr Ser Leu Phe Val Asp
    1235                1240

<210> SEQ ID NO 187
<211> LENGTH: 256
<212> TYPE: DNA
<213> ORGANISM: Artificial sequence
<220> FEATURE:
```

-continued

<223> OTHER INFORMATION: EFS promotor sequence

<400> SEQUENCE: 187

```
taggtcttga aaggagtggg aattggctcc ggtgcccgtc agtgggcaga gcgcacatcg    60
cccacagtcc ccgagaagtt gggggagggg gtcggcaatt gatccggtgc ctagagaagg   120
tggcgcgggg taaactggga aagtgatgtc gtgtactggc tccgcctttt tcccgagggt   180
gggggagaac cgtatataag tgcagtagtc gccgtgaacg ttcttttcg caacgggttt    240
gccgccagaa cacagg                                                    256
```

<210> SEQ ID NO 188
<211> LENGTH: 1137
<212> TYPE: PRT
<213> ORGANISM: Artificial Sequence
<220> FEATURE:
<223> OTHER INFORMATION: dSaCas9(D10A and N580A)-VP64
<220> FEATURE:
<221> NAME/KEY: SIGNAL
<222> LOCATION: (1)..(17)
<223> OTHER INFORMATION: nuclear localization signal
<220> FEATURE:
<221> NAME/KEY: PEPTIDE
<222> LOCATION: (18)..(1069)
<223> OTHER INFORMATION: dSaCas9(D10A and N580A)
<220> FEATURE:
<221> NAME/KEY: VARIANT
<222> LOCATION: (26)..(26)
<223> OTHER INFORMATION: conversion of Asp residue into Ala residue
<220> FEATURE:
<221> NAME/KEY: VARIANT
<222> LOCATION: (596)..(596)
<223> OTHER INFORMATION: conversion of Asn residue into Ala residue
<220> FEATURE:
<221> NAME/KEY: SIGNAL
<222> LOCATION: (1070)..(1085)
<223> OTHER INFORMATION: nuclear localization signal
<220> FEATURE:
<221> NAME/KEY: PEPTIDE
<222> LOCATION: (1088)..(1137)
<223> OTHER INFORMATION: VP64

<400> SEQUENCE: 188

```
Met Ala Pro Lys Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Glu Phe Ser Ala Ala Leu Leu His Leu
        115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
```

```
                165                 170                 175
Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
            195                 200                 205

Leu Asp Gln Ser Phe Ile Asp Thr Tyr Ile Asp Leu Leu Glu Thr Arg
            210                 215                 220

Arg Thr Tyr Tyr Glu Gly Pro Gly Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
            275                 280                 285

Glu Lys Leu Glu Tyr Tyr Glu Lys Phe Gln Ile Ile Glu Asn Val Phe
            290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
            355                 360                 365

Lys Ile Leu Thr Ile Tyr Gln Ser Ser Glu Asp Ile Gln Glu Glu Leu
            370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
            435                 440                 445

Gln Lys Glu Ile Pro Thr Thr Leu Val Asp Asp Phe Ile Leu Ser Pro
            450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Glu Leu Ala Arg
                485                 490                 495

Glu Lys Asn Ser Lys Asp Ala Gln Lys Met Ile Asn Glu Met Gln Lys
            500                 505                 510

Arg Asn Arg Gln Thr Asn Glu Arg Ile Glu Glu Ile Ile Arg Thr Thr
            515                 520                 525

Gly Lys Glu Asn Ala Lys Tyr Leu Ile Glu Lys Ile Lys Leu His Asp
            530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
            580                 585                 590
```

```
Gln Glu Glu Ala Ser Lys Lys Gly Asn Arg Thr Pro Phe Gln Tyr Leu
            595                 600                 605

Ser Ser Ser Asp Ser Lys Ile Ser Tyr Glu Thr Phe Lys Lys His Ile
610             615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
            660                 665                 670

Met Asn Leu Leu Arg Ser Tyr Phe Arg Val Asn Asn Leu Asp Val Lys
            675                 680                 685

Val Lys Ser Ile Asn Gly Gly Phe Thr Ser Phe Leu Arg Arg Lys Trp
690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
            740                 745                 750

Gln Ala Glu Ser Met Pro Glu Ile Glu Thr Glu Gln Glu Tyr Lys Glu
            755                 760                 765

Ile Phe Ile Thr Pro His Gln Ile Lys His Ile Lys Asp Phe Lys Asp
770                 775                 780

Tyr Lys Tyr Ser His Arg Val Asp Lys Lys Pro Asn Arg Glu Leu Ile
785                 790                 795                 800

Asn Asp Thr Leu Tyr Ser Thr Arg Lys Asp Asp Lys Gly Asn Thr Leu
                805                 810                 815

Ile Val Asn Asn Leu Asn Gly Leu Tyr Asp Lys Asp Asn Asp Lys Leu
            820                 825                 830

Lys Lys Leu Ile Asn Lys Ser Pro Glu Lys Leu Leu Met Tyr His His
            835                 840                 845

Asp Pro Gln Thr Tyr Gln Lys Leu Lys Leu Ile Met Glu Gln Tyr Gly
            850                 855                 860

Asp Glu Lys Asn Pro Leu Tyr Lys Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
            900                 905                 910

Tyr Pro Asn Ser Arg Asn Lys Val Val Lys Leu Ser Leu Lys Pro Tyr
            915                 920                 925

Arg Phe Asp Val Tyr Leu Asp Asn Gly Val Tyr Lys Phe Val Thr Val
930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
            980                 985                 990

Glu Leu Tyr Arg Val Ile Gly Val Asn Asn Asp Leu Leu Asn Arg Ile
            995                 1000                1005
```

```
Glu Val Asn Met Ile Asp Ile Thr Tyr Arg Glu Tyr Leu Glu Asn
    1010                1015                1020

Met Asn Asp Lys Arg Pro Pro Arg Ile Ile Lys Thr Ile Ala Ser
    1025                1030                1035

Lys Thr Gln Ser Ile Lys Lys Tyr Ser Thr Asp Ile Leu Gly Asn
    1040                1045                1050

Leu Tyr Glu Val Lys Ser Lys His Pro Gln Ile Ile Lys Lys
    1055                1060                1065

Gly Lys Arg Pro Ala Ala Thr Lys Lys Ala Gly Gln Ala Lys Lys
    1070                1075                1080

Lys Lys Ser Arg Asp Ala Leu Asp Asp Phe Asp Leu Asp Met Leu
    1085                1090                1095

Gly Ser Asp Ala Leu Asp Asp Phe Asp Leu Asp Met Leu Gly Ser
    1100                1105                1110

Asp Ala Leu Asp Asp Phe Asp Leu Asp Met Leu Gly Ser Asp Ala
    1115                1120                1125

Leu Asp Asp Phe Asp Leu Asp Met Leu
    1130                1135

<210> SEQ ID NO 189
<211> LENGTH: 1463
<212> TYPE: PRT
<213> ORGANISM: Artificial Sequence
<220> FEATURE:
<223> OTHER INFORMATION: dSaCas9(D10A and N580A)-VPH
<220> FEATURE:
<221> NAME/KEY: SIGNAL
<222> LOCATION: (1)..(17)
<223> OTHER INFORMATION: nuclear localization signal
<220> FEATURE:
<221> NAME/KEY: PEPTIDE
<222> LOCATION: (18)..(1069)
<223> OTHER INFORMATION: dSaCas9(D10A and N580A)
<220> FEATURE:
<221> NAME/KEY: VARIANT
<222> LOCATION: (26)..(26)
<223> OTHER INFORMATION: conversion of Asp residue into Ala residue
<220> FEATURE:
<221> NAME/KEY: VARIANT
<222> LOCATION: (596)..(596)
<223> OTHER INFORMATION: conversion of Asp residue into Ala residue
<220> FEATURE:
<221> NAME/KEY: SIGNAL
<222> LOCATION: (1070)..(1085)
<223> OTHER INFORMATION: nuclear localization signal
<220> FEATURE:
<221> NAME/KEY: PEPTIDE
<222> LOCATION: (1088)..(1463)
<223> OTHER INFORMATION: VPH

<400> SEQUENCE: 189

Met Ala Pro Lys Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
                20                  25                  30

Gly Tyr Gly Ile Ile Asp Tyr Glu Thr Arg Asp Val Ile Asp Ala Gly
            35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg Arg His Arg Ile
65                  70                  75                  80

Gln Arg Val Lys Lys Leu Leu Phe Asp Tyr Asn Leu Leu Thr Asp His
                85                  90                  95
```

```
Ser Glu Leu Ser Gly Ile Asn Pro Tyr Glu Ala Arg Val Lys Gly Leu
                100                 105                 110

Ser Gln Lys Leu Ser Glu Glu Phe Ser Ala Leu Leu His Leu
        115                 120                 125

Ala Lys Arg Arg Gly Val His Asn Val Asn Glu Val Glu Glu Asp Thr
130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
        180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
        260                 265                 270

Asn Ala Leu Asn Asp Leu Asn Asn Leu Val Ile Thr Arg Asp Glu Asn
        275                 280                 285

Glu Lys Leu Glu Tyr Tyr Glu Lys Phe Gln Ile Ile Glu Asn Val Phe
290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
        340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
        420                 425                 430

Ile Phe Asn Arg Leu Lys Leu Val Pro Lys Lys Val Asp Leu Ser Gln
        435                 440                 445

Gln Lys Glu Ile Pro Thr Thr Leu Val Asp Asp Phe Ile Leu Ser Pro
450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Ile Glu Leu Ala Arg
                485                 490                 495

Glu Lys Asn Ser Lys Asp Ala Gln Lys Met Ile Asn Glu Met Gln Lys
        500                 505                 510

Arg Asn Arg Gln Thr Asn Glu Arg Ile Glu Glu Ile Ile Arg Thr Thr
```

```
            515                 520                 525
Gly Lys Glu Asn Ala Lys Tyr Leu Ile Glu Lys Ile Lys Leu His Asp
            530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
                580                 585                 590

Gln Glu Glu Ala Ser Lys Lys Gly Asn Arg Thr Pro Phe Gln Tyr Leu
            595                 600                 605

Ser Ser Ser Asp Ser Lys Ile Ser Tyr Glu Thr Phe Lys Lys His Ile
            610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655

Phe Ile Asn Arg Asn Leu Val Asp Thr Arg Tyr Ala Thr Arg Gly Leu
                660                 665                 670

Met Asn Leu Leu Arg Ser Tyr Phe Arg Val Asn Asn Leu Asp Val Lys
            675                 680                 685

Val Lys Ser Ile Asn Gly Gly Phe Thr Ser Phe Leu Arg Arg Lys Trp
            690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
            740                 745                 750

Gln Ala Glu Ser Met Pro Glu Ile Glu Thr Glu Gln Glu Tyr Lys Glu
            755                 760                 765

Ile Phe Ile Thr Pro His Gln Ile Lys His Ile Lys Asp Phe Lys Asp
            770                 775                 780

Tyr Lys Tyr Ser His Arg Val Asp Lys Lys Pro Asn Arg Glu Leu Ile
785                 790                 795                 800

Asn Asp Thr Leu Tyr Ser Thr Arg Lys Asp Asp Lys Gly Asn Thr Leu
                805                 810                 815

Ile Val Asn Asn Leu Asn Gly Leu Tyr Asp Lys Asp Asn Asp Lys Leu
                820                 825                 830

Lys Lys Leu Ile Asn Lys Ser Pro Glu Lys Leu Leu Met Tyr His His
            835                 840                 845

Asp Pro Gln Thr Tyr Gln Lys Leu Lys Leu Ile Met Glu Gln Tyr Gly
            850                 855                 860

Asp Glu Lys Asn Pro Leu Tyr Lys Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
            900                 905                 910

Tyr Pro Asn Ser Arg Asn Lys Val Val Lys Leu Ser Leu Lys Pro Tyr
            915                 920                 925

Arg Phe Asp Val Tyr Leu Asp Asn Gly Val Tyr Lys Phe Val Thr Val
            930                 935                 940
```

```
Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
            965                 970                 975

Glu Phe Ile Ala Ser Phe Tyr Asn Asn Asp Leu Ile Lys Ile Asn Gly
        980                 985                 990

Glu Leu Tyr Arg Val Ile Gly Val Asn Asn Asp Leu Leu Asn Arg Ile
            995                 1000                1005

Glu Val Asn Met Ile Asp Ile Thr Tyr Arg Glu Tyr Leu Glu Asn
    1010                1015                1020

Met Asn Asp Lys Arg Pro Pro Arg Ile Ile Lys Thr Ile Ala Ser
    1025                1030                1035

Lys Thr Gln Ser Ile Lys Lys Tyr Ser Thr Asp Ile Leu Gly Asn
    1040                1045                1050

Leu Tyr Glu Val Lys Ser Lys Lys His Pro Gln Ile Ile Lys Lys
    1055                1060                1065

Gly Lys Arg Pro Ala Ala Thr Lys Lys Ala Gly Gln Ala Lys Lys
    1070                1075                1080

Lys Lys Ser Arg Asp Ala Leu Asp Asp Phe Asp Leu Asp Met Leu
    1085                1090                1095

Gly Ser Asp Ala Leu Asp Asp Phe Asp Leu Asp Met Leu Gly Ser
    1100                1105                1110

Asp Ala Leu Asp Asp Phe Asp Leu Asp Met Leu Gly Ser Asp Ala
    1115                1120                1125

Leu Asp Asp Phe Asp Leu Asp Met Leu Ser Ser Gly Ser Pro Lys
    1130                1135                1140

Lys Lys Arg Lys Val Gly Ser Pro Ser Gly Gln Ile Ser Asn Gln
    1145                1150                1155

Ala Leu Ala Leu Ala Pro Ser Ser Ala Pro Val Leu Ala Gln Thr
    1160                1165                1170

Met Val Pro Ser Ser Ala Met Val Pro Leu Ala Gln Pro Pro Ala
    1175                1180                1185

Pro Ala Pro Val Leu Thr Pro Gly Pro Pro Gln Ser Leu Ser Ala
    1190                1195                1200

Pro Val Pro Lys Ser Thr Gln Ala Gly Glu Gly Thr Leu Ser Glu
    1205                1210                1215

Ala Leu Leu His Leu Gln Phe Asp Ala Asp Glu Asp Leu Gly Ala
    1220                1225                1230

Leu Leu Gly Asn Ser Thr Asp Pro Gly Val Phe Thr Asp Leu Ala
    1235                1240                1245

Ser Val Asp Asn Ser Glu Phe Gln Gln Leu Leu Asn Gln Gly Val
    1250                1255                1260

Ser Met Ser His Ser Thr Ala Glu Pro Met Leu Met Glu Tyr Pro
    1265                1270                1275

Glu Ala Ile Thr Arg Leu Val Thr Gly Ser Gln Arg Pro Pro Asp
    1280                1285                1290

Pro Ala Pro Thr Pro Leu Gly Thr Ser Gly Leu Pro Asn Gly Leu
    1295                1300                1305

Ser Gly Asp Glu Asp Phe Ser Ser Ile Ala Asp Met Asp Phe Ser
    1310                1315                1320

Ala Leu Leu Ser Gln Ile Ser Ser Ser Gly Gln Gly Gly Gly Gly
    1325                1330                1335
```

-continued

```
Ser Gly Phe Ser Val Asp Thr Ser Ala Leu Leu Asp Leu Phe Ser
    1340                1345                1350

Pro Ser Val Thr Val Pro Asp Met Ser Leu Pro Asp Leu Asp Ser
    1355                1360                1365

Ser Leu Ala Ser Ile Gln Glu Leu Leu Ser Pro Gln Glu Pro Pro
    1370                1375                1380

Arg Pro Pro Glu Ala Glu Asn Ser Ser Pro Asp Ser Gly Lys Gln
    1385                1390                1395

Leu Val His Tyr Thr Ala Gln Pro Leu Phe Leu Leu Asp Pro Gly
    1400                1405                1410

Ser Val Asp Thr Gly Ser Asn Asp Leu Pro Val Leu Phe Glu Leu
    1415                1420                1425

Gly Glu Gly Ser Tyr Phe Ser Glu Gly Asp Gly Phe Ala Glu Asp
    1430                1435                1440

Pro Thr Ile Ser Leu Leu Thr Gly Ser Glu Pro Pro Lys Ala Lys
    1445                1450                1455

Asp Pro Thr Val Ser
    1460

<210> SEQ ID NO 190
<211> LENGTH: 1606
<212> TYPE: PRT
<213> ORGANISM: Artificial Sequence
<220> FEATURE:
<223> OTHER INFORMATION: dSaCas9(D10A and N580A)-VPR
<220> FEATURE:
<221> NAME/KEY: SIGNAL
<222> LOCATION: (1)..(17)
<223> OTHER INFORMATION: nuclear localization signal
<220> FEATURE:
<221> NAME/KEY: PEPTIDE
<222> LOCATION: (18)..(1069)
<223> OTHER INFORMATION: dSaCas9(D10A and N580A)
<220> FEATURE:
<221> NAME/KEY: VARIANT
<222> LOCATION: (26)..(26)
<223> OTHER INFORMATION: conversion of Asp residue into Ala residue
<220> FEATURE:
<221> NAME/KEY: VARIANT
<222> LOCATION: (596)..(596)
<223> OTHER INFORMATION: conversion of Asn residue into Ala residue
<220> FEATURE:
<221> NAME/KEY: SIGNAL
<222> LOCATION: (1070)..(1085)
<223> OTHER INFORMATION: nuclear localization signal
<220> FEATURE:
<221> NAME/KEY: PEPTIDE
<222> LOCATION: (1088)..(1606)
<223> OTHER INFORMATION: VPR

<400> SEQUENCE: 190

Met Ala Pro Lys Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
                20                  25                  30

Gly Tyr Gly Ile Ile Asp Tyr Glu Thr Arg Asp Val Ile Asp Ala Gly
            35                  40                  45

Val Arg Leu Phe Lys Glu Ala Asn Val Glu Asn Asn Glu Gly Arg Arg
        50                  55                  60

Ser Lys Arg Gly Ala Arg Arg Leu Lys Arg Arg Arg Arg His Arg Ile
65                  70                  75                  80

Gln Arg Val Lys Lys Leu Leu Phe Asp Tyr Asn Leu Leu Thr Asp His
                85                  90                  95
```

```
Ser Glu Leu Ser Gly Ile Asn Pro Tyr Glu Ala Arg Val Lys Gly Leu
            100                 105                 110

Ser Gln Lys Leu Ser Glu Glu Phe Ser Ala Leu Leu His Leu
        115                 120                 125

Ala Lys Arg Arg Gly Val His Asn Val Asn Glu Val Glu Glu Asp Thr
130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
        275                 280                 285

Glu Lys Leu Glu Tyr Tyr Glu Lys Phe Gln Ile Ile Glu Asn Val Phe
290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
        435                 440                 445

Gln Lys Glu Ile Pro Thr Thr Leu Val Asp Asp Phe Ile Leu Ser Pro
450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Ile Glu Leu Ala Arg
                485                 490                 495

Glu Lys Asn Ser Lys Asp Ala Gln Lys Met Ile Asn Glu Met Gln Lys
            500                 505                 510

Arg Asn Arg Gln Thr Asn Glu Arg Ile Glu Glu Ile Ile Arg Thr Thr
```

```
            515                 520                 525
Gly Lys Glu Asn Ala Lys Tyr Leu Ile Glu Lys Ile Lys Leu His Asp
    530                 535                 540
Met Gln Glu Gly Lys Cys Leu Tyr Ser Leu Glu Ala Ile Pro Leu Glu
545                 550                 555                 560
Asp Leu Leu Asn Asn Pro Phe Asn Tyr Glu Val Asp His Ile Ile Pro
                565                 570                 575
Arg Ser Val Ser Phe Asp Asn Ser Phe Asn Asn Lys Val Leu Val Lys
                580                 585                 590
Gln Glu Glu Ala Ser Lys Lys Gly Asn Arg Thr Pro Phe Gln Tyr Leu
            595                 600                 605
Ser Ser Ser Asp Ser Lys Ile Ser Tyr Glu Thr Phe Lys Lys His Ile
        610                 615                 620
Leu Asn Leu Ala Lys Gly Lys Gly Arg Ile Ser Lys Thr Lys Lys Glu
625                 630                 635                 640
Tyr Leu Leu Glu Glu Arg Asp Ile Asn Arg Phe Ser Val Gln Lys Asp
                645                 650                 655
Phe Ile Asn Arg Asn Leu Val Asp Thr Arg Tyr Ala Thr Arg Gly Leu
                660                 665                 670
Met Asn Leu Leu Arg Ser Tyr Phe Arg Val Asn Asn Leu Asp Val Lys
            675                 680                 685
Val Lys Ser Ile Asn Gly Gly Phe Thr Ser Phe Leu Arg Arg Lys Trp
690                 695                 700
Lys Phe Lys Lys Glu Arg Asn Lys Gly Tyr Lys His His Ala Glu Asp
705                 710                 715                 720
Ala Leu Ile Ile Ala Asn Ala Asp Phe Ile Phe Lys Glu Trp Lys Lys
                725                 730                 735
Leu Asp Lys Ala Lys Lys Val Met Glu Asn Gln Met Phe Glu Glu Lys
            740                 745                 750
Gln Ala Glu Ser Met Pro Glu Ile Glu Thr Glu Gln Glu Tyr Lys Glu
        755                 760                 765
Ile Phe Ile Thr Pro His Gln Ile Lys His Ile Lys Asp Phe Lys Asp
    770                 775                 780
Tyr Lys Tyr Ser His Arg Val Asp Lys Lys Pro Asn Arg Glu Leu Ile
785                 790                 795                 800
Asn Asp Thr Leu Tyr Ser Thr Arg Lys Asp Asp Lys Gly Asn Thr Leu
                805                 810                 815
Ile Val Asn Asn Leu Asn Gly Leu Tyr Asp Lys Asp Asn Asp Lys Leu
                820                 825                 830
Lys Lys Leu Ile Asn Lys Ser Pro Glu Lys Leu Leu Met Tyr His His
            835                 840                 845
Asp Pro Gln Thr Tyr Gln Lys Leu Lys Leu Ile Met Glu Gln Tyr Gly
        850                 855                 860
Asp Glu Lys Asn Pro Leu Tyr Lys Tyr Glu Glu Thr Gly Asn Tyr
865                 870                 875                 880
Leu Thr Lys Tyr Ser Lys Lys Asp Asn Gly Pro Val Ile Lys Lys Ile
                885                 890                 895
Lys Tyr Tyr Gly Asn Lys Leu Asn Ala His Leu Asp Ile Thr Asp Asp
            900                 905                 910
Tyr Pro Asn Ser Arg Asn Lys Val Val Lys Leu Ser Leu Lys Pro Tyr
        915                 920                 925
Arg Phe Asp Val Tyr Leu Asp Asn Gly Val Tyr Lys Phe Val Thr Val
    930                 935                 940
```

-continued

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
                980                 985                 990

Glu Leu Tyr Arg Val Ile Gly Val Asn Asn Asp Leu Leu Asn Arg Ile
            995                 1000                1005

Glu Val Asn Met Ile Asp Ile Thr Tyr Arg Glu Tyr Leu Glu Asn
    1010                1015                1020

Met Asn Asp Lys Arg Pro Arg Ile Ile Lys Thr Ile Ala Ser
    1025                1030                1035

Lys Thr Gln Ser Ile Lys Lys Tyr Ser Thr Asp Ile Leu Gly Asn
    1040                1045                1050

Leu Tyr Glu Val Lys Ser Lys His Pro Gln Ile Ile Lys Lys
    1055                1060                1065

Gly Lys Arg Pro Ala Ala Thr Lys Lys Ala Gly Gln Ala Lys Lys
    1070                1075                1080

Lys Lys Ser Arg Asp Ala Leu Asp Asp Phe Asp Leu Asp Met Leu
    1085                1090                1095

Gly Ser Asp Ala Leu Asp Phe Asp Leu Asp Met Leu Gly Ser
    1100                1105                1110

Asp Ala Leu Asp Asp Phe Asp Leu Asp Met Leu Gly Ser Asp Ala
    1115                1120                1125

Leu Asp Asp Phe Asp Leu Asp Met Leu Ser Ser Gly Ser Pro Lys
    1130                1135                1140

Lys Lys Arg Lys Val Gly Ser Gln Tyr Leu Pro Asp Thr Asp Asp
    1145                1150                1155

Arg His Arg Ile Glu Glu Lys Arg Lys Arg Thr Tyr Glu Thr Phe
    1160                1165                1170

Lys Ser Ile Met Lys Lys Ser Pro Phe Ser Gly Pro Thr Asp Pro
    1175                1180                1185

Arg Pro Pro Pro Arg Arg Ile Ala Val Pro Ser Arg Ser Ser Ala
    1190                1195                1200

Ser Val Pro Lys Pro Ala Pro Gln Pro Tyr Pro Phe Thr Ser Ser
    1205                1210                1215

Leu Ser Thr Ile Asn Tyr Asp Glu Phe Pro Thr Met Val Phe Pro
    1220                1225                1230

Ser Gly Gln Ile Ser Gln Ala Ser Ala Leu Ala Pro Ala Pro Pro
    1235                1240                1245

Gln Val Leu Pro Gln Ala Pro Ala Pro Ala Pro Ala Pro Ala Met
    1250                1255                1260

Val Ser Ala Leu Ala Gln Ala Pro Ala Pro Val Pro Val Leu Ala
    1265                1270                1275

Pro Gly Pro Pro Gln Ala Val Ala Pro Pro Ala Pro Lys Pro Thr
    1280                1285                1290

Gln Ala Gly Glu Gly Thr Leu Ser Glu Ala Leu Leu Gln Leu Gln
    1295                1300                1305

Phe Asp Asp Glu Asp Leu Gly Ala Leu Leu Gly Asn Ser Thr Asp
    1310                1315                1320

Pro Ala Val Phe Thr Asp Leu Ala Ser Val Asp Asn Ser Glu Phe
    1325                1330                1335

| | | | | | | | | | | |
|---|---|---|---|---|---|---|---|---|---|---|
| Gln | Gln | Leu | Leu | Asn | Gln | Gly | Ile | Pro | Val | Ala | Pro | His | Thr | Thr |
| | 1340 | | | | 1345 | | | | 1350 | |
| Glu | Pro | Met | Leu | Met | Glu | Tyr | Pro | Glu | Ala | Ile | Thr | Arg | Leu | Val |
| 1355 | | | | | 1360 | | | | | 1365 | |
| Thr | Gly | Ala | Gln | Arg | Pro | Pro | Asp | Pro | Ala | Pro | Ala | Pro | Leu | Gly |
| 1370 | | | | | 1375 | | | | | 1380 | |
| Ala | Pro | Gly | Leu | Pro | Asn | Gly | Leu | Leu | Ser | Gly | Asp | Glu | Asp | Phe |
| 1385 | | | | | 1390 | | | | | 1395 | |
| Ser | Ser | Ile | Ala | Asp | Met | Asp | Phe | Ser | Ala | Leu | Leu | Gly | Ser | Gly |
| 1400 | | | | | 1405 | | | | | 1410 | |
| Ser | Gly | Ser | Arg | Asp | Ser | Arg | Glu | Gly | Met | Phe | Leu | Pro | Lys | Pro |
| 1415 | | | | | 1420 | | | | | 1425 | |
| Glu | Ala | Gly | Ser | Ala | Ile | Ser | Asp | Val | Phe | Glu | Gly | Arg | Glu | Val |
| 1430 | | | | | 1435 | | | | | 1440 | |
| Cys | Gln | Pro | Lys | Arg | Ile | Arg | Pro | Phe | His | Pro | Pro | Gly | Ser | Pro |
| 1445 | | | | | 1450 | | | | | 1455 | |
| Trp | Ala | Asn | Arg | Pro | Leu | Pro | Ala | Ser | Leu | Ala | Pro | Thr | Pro | Thr |
| 1460 | | | | | 1465 | | | | | 1470 | |
| Gly | Pro | Val | His | Glu | Pro | Val | Gly | Ser | Leu | Thr | Pro | Ala | Pro | Val |
| 1475 | | | | | 1480 | | | | | 1485 | |
| Pro | Gln | Pro | Leu | Asp | Pro | Ala | Pro | Ala | Val | Thr | Pro | Glu | Ala | Ser |
| 1490 | | | | | 1495 | | | | | 1500 | |
| His | Leu | Leu | Glu | Asp | Pro | Asp | Glu | Glu | Thr | Ser | Gln | Ala | Val | Lys |
| 1505 | | | | | 1510 | | | | | 1515 | |
| Ala | Leu | Arg | Glu | Met | Ala | Asp | Thr | Val | Ile | Pro | Gln | Lys | Glu | Glu |
| 1520 | | | | | 1525 | | | | | 1530 | |
| Ala | Ala | Ile | Cys | Gly | Gln | Met | Asp | Leu | Ser | His | Pro | Pro | Pro | Arg |
| 1535 | | | | | 1540 | | | | | 1545 | |
| Gly | His | Leu | Asp | Glu | Leu | Thr | Thr | Thr | Leu | Glu | Ser | Met | Thr | Glu |
| 1550 | | | | | 1555 | | | | | 1560 | |
| Asp | Leu | Asn | Leu | Asp | Ser | Pro | Leu | Thr | Pro | Glu | Leu | Asn | Glu | Ile |
| 1565 | | | | | 1570 | | | | | 1575 | |
| Leu | Asp | Thr | Phe | Leu | Asn | Asp | Glu | Cys | Leu | Leu | His | Ala | Met | His |
| 1580 | | | | | 1585 | | | | | 1590 | |
| Ile | Ser | Thr | Gly | Leu | Ser | Ile | Phe | Asp | Thr | Ser | Leu | Phe | | |
| 1595 | | | | | 1600 | | | | | 1605 | |

<210> SEQ ID NO 191
<211> LENGTH: 450
<212> TYPE: DNA
<213> ORGANISM: Artificial Sequence
<220> FEATURE:
<223> OTHER INFORMATION: CK8 promotor sequence

<400> SEQUENCE: 191

```
ctagactagc atgctgccca tgtaaggagg caaggcctgg ggacacccga gatgcctggt      60
tataattaac ccagacatgt ggctgccccc cccccccaa cacctgctgc ctctaaaaat     120
aaccctgcat gccatgttcc cggcgaaggg ccagctgtcc cccgccagct agactcagca     180
cttagtttag gaaccagtga gcaagtcagc ccttggggca gcccatacaa ggccatgggg     240
ctgggcaagc tgcacgcctg gtccggggt gggcacggtg cccgggcaac gagctgaaag     300
ctcatctgct ctcaggggcc cctccctggg acagccccct cctggctagt cacaccctgt     360
aggtccctct atataaccca ggggcacagg ggctgccctc attctaccac cacctccaca     420
gcacagacag acactcagga gccagccagc                                      450
```

<210> SEQ ID NO 192
<211> LENGTH: 3762
<212> TYPE: DNA
<213> ORGANISM: Artificial Sequence
<220> FEATURE:
<223> OTHER INFORMATION: DNA sequence encoding dSaCas9(D10A, N580A)-miniVR

<400> SEQUENCE: 192

```
atggcccaa agaagaagcg aaggtcggt atccacggag tcccagcagc caagcggaac      60
tacatcctgg gcctggccat cggcatcacc agcgtgggct acggcatcat cgactacgag    120
acacgggacg tgatcgatgc cggcgtgcgg ctgttcaaag aggccaacgt ggaaaacaac    180
gagggcaggc ggagcaagag aggcgccaga aggctgaagc ggcggaggcg catagaatc     240
cagagagtga agaagctgct gttcgactac aacctgctga ccgaccacag cgagctgagc    300
ggcatcaacc cctacgaggc cagagtgaag ggcctgagcc agaagctgag cgaggaagag    360
ttctctgccg ccctgctgca cctggccaag agaagaggcg tgcacaacgt gaacgaggtg    420
gaagaggaca ccggcaacga gctgtccacc aaagagcaga tcagccggaa cagcaaggcc    480
ctggaagaga atacgtggc cgaactgcag ctggaacggc tgaagaaaga cggcgaagtg    540
cggggcagca tcaacagatt caagaccagc gactacgtga agaagccaa acagctgctg    600
aaggtgcaga aggcctacca ccagctggac cagagcttca tcgacaccta catcgacctg    660
ctggaaaccc ggcggaccta ctatgaggga cctggcgagg cagccccctt cggctggaag    720
gacatcaaag aatggtacga gatgctgatg ggccactgca cctacttccc cgaggaactg    780
cggagcgtga agtacgccta caacgccgac ctgtacaacg ccctgaacga cctgaacaat    840
ctcgtgatca ccagggacga gaacgagaag ctggaatatt acgagaagtt ccagatcatc    900
gagaacgtgt tcaagcagaa gaagaagccc accctgaagc agatcgccaa agaaatcctc    960
gtgaacgaag aggatattaa gggctacaga gtgaccagca ccggcaagcc cgagttcacc   1020
aacctgaagg tgtaccacga catcaaggac attaccgccc ggaaagagat tattgagaac   1080
gccgagctgc tggatcagat tgccaagatc ctgaccatct accagagcag cgaggacatc   1140
caggaagaac tgaccaatct gaactccgag ctgacccagg aagagatcga gcagatctct   1200
aatctgaagg gctataccgg cacccacaac ctgagcctga aggccatcaa cctgatcctg   1260
gacgagctgt ggcacaccaa cgacaaccag atcgctatct tcaaccggct gaagctggtg   1320
cccaagaagg tggacctgtc ccagcagaaa gagatcccca ccaccctggt ggacgacttc   1380
atcctgagcc ccgtcgtgaa gagaagcttc atccagagca tcaaagtgat caacgccatc   1440
atcaagaagt acggcctgcc caacgacatc attatcgagc tggcccgcga gaagaactcc   1500
aaggacgccc agaaaatgat caacgagatg cagaagcgga accggcagac aacgagcgg   1560
atcgaggaaa tcatccggac caccggcaaa gagaacgcca gtacctgat cgagaagatc   1620
aagctgcacg acatgcagga aggcaagtgc ctgtacagcc tggaagccat ccctctggaa   1680
gatctgctga caacccctt caactatgag gtggacgcca tcatccccag aagcgtgtcc   1740
ttcgacaaca gcttcaacaa caaggtgctc gtgaagcagg aagaagccag caagaagggc   1800
aaccggaccc cattccagta cctgagcagc agcgacagca gatcagcta cgaaaccttc   1860
aagaagcaca tcctgaatct ggccaagggc aagggcagaa tcagcaagac caagaaagag   1920
tatctgctga agaacggga catcaacagg ttctccgtgc agaaagactt catcaaccgg   1980
aacctggtgg ataccagata cgccaccaga ggcctgatga acctgctgcg gagctacttc   2040
```

```
agagtgaaca acctggacgt gaaagtgaag tccatcaatg gcggcttcac cagctttctg    2100
cggcggaagt ggaagtttaa gaaagagcgg aacaagggt acaagcacca cgccgaggac    2160
gccctgatca ttgccaacgc cgatttcatc ttcaaagagt ggaagaaact ggacaaggcc    2220
aaaaaagtga tggaaaacca gatgttcgag gaaaagcagg ccgagagcat gcccgagatc    2280
gaaaccgagc aggagtacaa agagatcttc atcacccccc accagatcaa gcacattaag    2340
gacttcaagg actacaagta cagccaccgg gtggacaaga agcctaatag agagctgatt    2400
aacgacaccc tgtactccac ccggaaggac gacaagggca cacccctgat cgtgaacaat    2460
ctgaacggcc tgtacgacaa ggacaatgac aagctgaaaa agctgatcaa caagagcccc    2520
gaaaagctgc tgatgtacca ccacgacccc cagacctacc agaaactgaa gctgattatg    2580
gaacagtacg gcgacgagaa gaatccctg tacaagtact acgaggaaac cgggaactac    2640
ctgaccaagt actccaaaaa ggacaacggc cccgtgatca agaagattaa gtattacggc    2700
aacaaactga acgcccatct ggacatcacc gacgactacc caacagcag aaacaaggtc    2760 gtgaagctgt ccctgaagcc ctacagattc gacgtgtacc tggacaatgg cgtgtacaag    2820
ttcgtgaccg tgaagaatct ggatgtgatc aaaaaagaaa actactacga agtgaatagc    2880
aagtgctatg aggaagctaa gaagctgaag aagatcagca ccaggccga gtttatcgcc    2940 tccttctaca caacgatct gatcaagatc aacggcgagc tgtatagagt gatcggcgtg    3000
aacaacgacc tgctgaaccg gatcgaagtg aacatgatcg acatcaccta ccgcgagtac    3060
ctggaaaaca tgaacgacaa gaggcccccc aggatcatta gacaatcgc ctccaagacc    3120 cagagcatta agaagtacag cacagacatt ctgggcaacc tgtatgaagt gaaatctaag    3180
aagcaccctc agatcatcaa aaagggcaaa aggccggcgg ccacgaaaaa ggccggccag    3240
gcaaaaaaga aaaaggctag cgatgcactc gatgattttg acctcgatat gcttgggagt    3300
gatgcgctcg atgacttcga tttggatatg cttggatctg atgccctcga cgatttcgac    3360
cttgatatgc tcgggtcaga cgctttggat gactttgacc ttgacatgct ggggagcggc    3420 tccccccgcac cggcagttac accggaggcc agtcacttgc tcgaagatcc tgacgaggaa    3480
accagccagg ccgtaaaggc gttgcgggag atggctgaca cagtaatacc ccaaaaagag    3540
gaggctgcga tttgtgggca gatggatttg tcccaccctc caccgagagg tcatcttgac    3600
gaattgacaa cgacgctcga atccatgacc gaggacctga acctcgatag cccgctcacc    3660
cccgagttga atgagatcct ggatacattt cttaatgatg agtgtttgct tcacgcaatg    3720
catatttcta cgggtcttag tattttcgac acgagcctgt tt                      3762
```

<210> SEQ ID NO 193
<211> LENGTH: 1254
<212> TYPE: PRT
<213> ORGANISM: Artificial Sequence
<220> FEATURE:
<223> OTHER INFORMATION: dSaCas9(D10A, N580A)-miniVR

<400> SEQUENCE: 193

```
Met Ala Pro Lys Lys Arg Lys Val Gly Ile His Gly Val Pro Ala
1               5                   10                  15

Ala Lys Arg Asn Tyr Ile Leu Gly Leu Ala Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
```

```
               50                  55                  60
Ser Lys Arg Gly Ala Arg Arg Leu Lys Arg Arg Arg His Arg Ile
 65                  70                  75                  80

Gln Arg Val Lys Lys Leu Leu Phe Asp Tyr Asn Leu Leu Thr Asp His
                 85                  90                  95

Ser Glu Leu Ser Gly Ile Asn Pro Tyr Glu Ala Arg Val Lys Gly Leu
                100                 105                 110

Ser Gln Lys Leu Ser Glu Glu Phe Ser Ala Ala Leu Leu His Leu
                115                 120                 125

Ala Lys Arg Arg Gly Val His Asn Val Asn Glu Val Glu Glu Asp Thr
130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
                180                 185                 190

Val Lys Glu Ala Lys Gln Leu Leu Lys Val Gln Lys Ala Tyr His Gln
                195                 200                 205

Leu Asp Gln Ser Phe Ile Asp Thr Tyr Ile Asp Leu Leu Glu Thr Arg
210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
                260                 265                 270

Asn Ala Leu Asn Asp Leu Asn Asn Leu Val Ile Thr Arg Asp Glu Asn
                275                 280                 285

Glu Lys Leu Glu Tyr Tyr Glu Lys Phe Gln Ile Ile Glu Asn Val Phe
                290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
                340                 345                 350

Ala Arg Lys Glu Ile Ile Glu Asn Ala Glu Leu Leu Asp Gln Ile Ala
                355                 360                 365

Lys Ile Leu Thr Ile Tyr Gln Ser Ser Glu Asp Ile Gln Glu Glu Leu
                370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
                420                 425                 430

Ile Phe Asn Arg Leu Lys Leu Val Pro Lys Lys Val Asp Leu Ser Gln
                435                 440                 445

Gln Lys Glu Ile Pro Thr Thr Leu Val Asp Asp Phe Ile Leu Ser Pro
                450                 455                 460

Val Val Lys Arg Ser Phe Ile Gln Ser Ile Lys Val Ile Asn Ala Ile
465                 470                 475                 480
```

-continued

Ile Lys Lys Tyr Gly Leu Pro Asn Asp Ile Ile Glu Leu Ala Arg
            485             490             495

Glu Lys Asn Ser Lys Asp Ala Gln Lys Met Ile Asn Glu Met Gln Lys
            500             505             510

Arg Asn Arg Gln Thr Asn Glu Arg Ile Glu Glu Ile Ile Arg Thr Thr
            515             520             525

Gly Lys Glu Asn Ala Lys Tyr Leu Ile Glu Lys Ile Lys Leu His Asp
    530             535             540

Met Gln Glu Gly Lys Cys Leu Tyr Ser Leu Glu Ala Ile Pro Leu Glu
545             550             555             560

Asp Leu Leu Asn Asn Pro Phe Asn Tyr Glu Val Asp Ala Ile Ile Pro
            565             570             575

Arg Ser Val Ser Phe Asp Asn Ser Phe Asn Asn Lys Val Leu Val Lys
            580             585             590

Gln Glu Glu Ala Ser Lys Lys Gly Asn Arg Thr Pro Phe Gln Tyr Leu
            595             600             605

Ser Ser Ser Asp Ser Lys Ile Ser Tyr Glu Thr Phe Lys Lys His Ile
    610             615             620

Leu Asn Leu Ala Lys Gly Lys Gly Arg Ile Ser Lys Thr Lys Lys Glu
625             630             635             640

Tyr Leu Leu Glu Glu Arg Asp Ile Asn Arg Phe Ser Val Gln Lys Asp
            645             650             655

Phe Ile Asn Arg Asn Leu Val Asp Thr Arg Tyr Ala Thr Arg Gly Leu
            660             665             670

Met Asn Leu Leu Arg Ser Tyr Phe Arg Val Asn Asn Leu Asp Val Lys
            675             680             685

Val Lys Ser Ile Asn Gly Gly Phe Thr Ser Phe Leu Arg Arg Lys Trp
    690             695             700

Lys Phe Lys Lys Glu Arg Asn Lys Gly Tyr Lys His His Ala Glu Asp
705             710             715             720

Ala Leu Ile Ile Ala Asn Ala Asp Phe Ile Phe Lys Glu Trp Lys Lys
            725             730             735

Leu Asp Lys Ala Lys Lys Val Met Glu Asn Gln Met Phe Glu Glu Lys
            740             745             750

Gln Ala Glu Ser Met Pro Glu Ile Glu Thr Glu Gln Glu Tyr Lys Glu
            755             760             765

Ile Phe Ile Thr Pro His Gln Ile Lys His Ile Lys Asp Phe Lys Asp
    770             775             780

Tyr Lys Tyr Ser His Arg Val Asp Lys Lys Pro Asn Arg Glu Leu Ile
785             790             795             800

Asn Asp Thr Leu Tyr Ser Thr Arg Lys Asp Asp Lys Gly Asn Thr Leu
            805             810             815

Ile Val Asn Asn Leu Asn Gly Leu Tyr Asp Lys Asp Asn Asp Lys Leu
            820             825             830

Lys Lys Leu Ile Asn Lys Ser Pro Glu Lys Leu Leu Met Tyr His His
            835             840             845

Asp Pro Gln Thr Tyr Gln Lys Leu Lys Leu Ile Met Glu Gln Tyr Gly
850             855             860

Asp Glu Lys Asn Pro Leu Tyr Lys Tyr Tyr Glu Glu Thr Gly Asn Tyr
865             870             875             880

Leu Thr Lys Tyr Ser Lys Lys Asp Asn Gly Pro Val Ile Lys Lys Ile
            885             890             895

Lys Tyr Tyr Gly Asn Lys Leu Asn Ala His Leu Asp Ile Thr Asp Asp
                900                 905                 910

Tyr Pro Asn Ser Arg Asn Lys Val Val Lys Leu Ser Leu Lys Pro Tyr
            915                 920                 925

Arg Phe Asp Val Tyr Leu Asp Asn Gly Val Tyr Lys Phe Val Thr Val
        930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
            980                 985                 990

Glu Leu Tyr Arg Val Ile Gly Val Asn Asn Asp Leu Leu Asn Arg Ile
        995                 1000                1005

Glu Val Asn Met Ile Asp Ile Thr Tyr Arg Glu Tyr Leu Glu Asn
        1010                1015                1020

Met Asn Asp Lys Arg Pro Pro Arg Ile Ile Lys Thr Ile Ala Ser
        1025                1030                1035

Lys Thr Gln Ser Ile Lys Lys Tyr Ser Thr Asp Ile Leu Gly Asn
        1040                1045                1050

Leu Tyr Glu Val Lys Ser Lys Lys His Pro Gln Ile Ile Lys Lys
        1055                1060                1065

Gly Lys Arg Pro Ala Ala Thr Lys Lys Ala Gly Gln Ala Lys Lys
        1070                1075                1080

Lys Lys Ala Ser Asp Ala Leu Asp Asp Phe Asp Leu Asp Met Leu
        1085                1090                1095

Gly Ser Asp Ala Leu Asp Asp Phe Asp Leu Asp Met Leu Gly Ser
        1100                1105                1110

Asp Ala Leu Asp Asp Phe Asp Leu Asp Met Leu Gly Ser Asp Ala
        1115                1120                1125

Leu Asp Asp Phe Asp Leu Asp Met Leu Gly Ser Gly Ser Pro Ala
        1130                1135                1140

Pro Ala Val Thr Pro Glu Ala Ser His Leu Leu Glu Asp Pro Asp
        1145                1150                1155

Glu Glu Thr Ser Gln Ala Val Lys Ala Leu Arg Glu Met Ala Asp
        1160                1165                1170

Thr Val Ile Pro Gln Lys Glu Glu Ala Ala Ile Cys Gly Gln Met
        1175                1180                1185

Asp Leu Ser His Pro Pro Arg Gly His Leu Asp Glu Leu Thr
        1190                1195                1200

Thr Thr Leu Glu Ser Met Thr Glu Asp Leu Asn Leu Asp Ser Pro
        1205                1210                1215

Leu Thr Pro Glu Leu Asn Glu Ile Leu Asp Thr Phe Leu Asn Asp
        1220                1225                1230

Glu Cys Leu Leu His Ala Met His Ile Ser Thr Gly Leu Ser Ile
        1235                1240                1245

Phe Asp Thr Ser Leu Phe
        1250

<210> SEQ ID NO 194
<211> LENGTH: 21
<212> TYPE: RNA
<213> ORGANISM: Homo sapiens
<220> FEATURE:
<221> NAME/KEY: misc_feature

```
<222> LOCATION: (1)..(21)
<223> OTHER INFORMATION: crRNA corresponding to the target sequence (SEQ
      ID NO:45)

<400> SEQUENCE: 194
guacaguuag ugcuacuagg a                                              21

<210> SEQ ID NO 195
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:46)

<400> SEQUENCE: 195
gcuacuagga caggaugcug g                                              21

<210> SEQ ID NO 196
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:58)

<400> SEQUENCE: 196
gggguccgcu cuccagauga g                                              21

<210> SEQ ID NO 197
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:59)

<400> SEQUENCE: 197 ggagggugggg gcgcaggacc g                                             21

<210> SEQ ID NO 198
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:60)

<400> SEQUENCE: 198
ccucucucgc gcacaaaguu g                                              21

<210> SEQ ID NO 199
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:135)
```

-continued

<400> SEQUENCE: 199
ggcuccucua ggaguuugac a                                              21

<210> SEQ ID NO 200
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:141)

<400> SEQUENCE: 200
ggguaguucu gcggugacgg a                                              21

<210> SEQ ID NO 201
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:153)

<400> SEQUENCE: 201
gaguccggag accgaaccag a                                              21

<210> SEQ ID NO 202
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:155)

<400> SEQUENCE: 202
gcuggccugg ggcgcgcgcu c                                              21

<210> SEQ ID NO 203
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:156)

<400> SEQUENCE: 203
aagaucagcc ccacuacguu c                                              21

<210> SEQ ID NO 204
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:157)

<400> SEQUENCE: 204
ccggaggcga gccccuuccc g                                              21

<210> SEQ ID NO 205
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:159)

<400> SEQUENCE: 205
gagcgcugga ggcggaggag g                                             21

<210> SEQ ID NO 206
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:167)

<400> SEQUENCE: 206
agaggggacg uggccucuua g                                             21

<210> SEQ ID NO 207
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: crRNA corresponding to the target sequence (SEQ
      ID NO:172)

<400> SEQUENCE: 207
gcgcgcggag cucgggggag g                                             21

<210> SEQ ID NO 208
<211> LENGTH: 34
<212> TYPE: DNA
<213> ORGANISM: Artificial Sequence
<220> FEATURE:
<223> OTHER INFORMATION: 2x sNRP-1 polyA sequence

<400> SEQUENCE: 208
aaataaaata cgaaatgaaa taaaatacga aatg                               34

<210> SEQ ID NO 209
<211> LENGTH: 4
<212> TYPE: PRT
<213> ORGANISM: Artificial Sequence
<220> FEATURE:
<223> OTHER INFORMATION: GSGS linker

<400> SEQUENCE: 209

Gly Ser Gly Ser
1

<210> SEQ ID NO 210
<211> LENGTH: 8288
<212> TYPE: DNA
<213> ORGANISM: Artificial Sequence
<220> FEATURE:
<223> OTHER INFORMATION: pED260 plasmid

<400> SEQUENCE: 210

-continued

```
cgctcgccgc agccgaacga ccgagcgcag cgagtcagtg agcgaggaag cggaagagcg    60
cccaatacgc aaaccgcctc tccccgcgcg ttggccgatt cattaatgca gctggcacga   120
caggtttccc gactggaaag cgggcagtga gcgcaacgca attaatgtga gttagctcac   180
tcattaggca ccccaggctt tacactttat gcttccggct cgtatgttgt gtggaattgt   240
gagcggataa caatttcaca caggaaacag ctatgaccat gattacgaat tgcctgcagg   300
cagctgcgcg ctcgctcgct cactgaggcc gcccgggcaa agcccgggcg tcgggcgacc   360
tttggtcgcc cggcctcagt gagcgagcga gcgcgcagag agggagtggc caactccatc   420
actagggttt cctatcgata tcactcgagg cgttgctaga ctagcatgct gcccatgtaa   480
ggaggcaagg cctggggaca cccgagatgc ctggttataa ttaacccaga catgtggctg   540 ccccccccccc cccaacacct gctgcctcta aaataacccc tgcatgccat gttcccggcg   600
aagggccagc tgtcccccgc cagctagact cagcacttag tttaggaacc agtgagcaag   660
tcagcccttg gggcagccca tacaaggcca tgggctgggg caagctgcac gcctgggtcc   720
ggggtgggca cggtgcccgg gcaacgagct gaaagctcat ctgctctcag ggcccctcc   780 ctggggacag cccctcctgg ctagtcacac cctgtaggct cctctatata acccaggggc   840 acagggctg ccctcattct accaccacct ccacagcaca gacagacact caggagccag   900
ccagcagagc tctctggcta actaccggtg ccaccatggc cccaaagaag aagcggaagg   960
tcggtatcca cggagtccca gcagccaagc ggaactacat cctgggcctg gccatcggca  1020
tcaccagcgt gggctacggc atcatcgact acgagacacg ggacgtgatc gatgccggcg  1080
tgcggctgtt caaagaggcc aacgtggaaa caacgagggg caggcggagc aagagaggcg  1140
ccagaaggct gaagcggcgg aggcggcata gaatccagag agtgaagaag ctgctgttcg  1200
actacaacct gctgaccgac cacagcgagc tgagcggcat caacccctac gaggccagag  1260
tgaagggcct gagccagaag ctgagcgagg aagagttctc tgccgccctg ctgcacctgg  1320
ccaagagaag aggcgtgcac aacgtgaacg aggtggaaga ggacaccggc aacgagctgt  1380
ccaccaaaga gcagatcagc cggaacagca aggccctgga agagaaatac gtggccgaac  1440
tgcagctgga acggctgaag aaagacgcg aagtgcgggg cagcatcaac agattcaaga  1500
ccagcgacta cgtgaaagaa gccaaacagc tgctgaaggt gcagaaggcc taccaccagc  1560
tggaccagag cttcatcgac acctacatcg acctgctgga aacccggcgg acctactatg  1620
agggacctgg cgagggcagc cccttcggct ggaaggacat caaagaatgg tacgagatgc  1680
tgatgggcca ctgcacctac ttccccgagg aactgcggag cgtgaagtac gcctacaacg  1740
ccgacctgta caacgccctg aacgacctga acaatctcgt gatcaccagg gacgagaacg  1800
agaagctgga atattacgag aagttccaga tcatcgagaa cgtgttcaag cagaagaaga  1860
agcccaccct gaagcagatc gccaaagaaa tcctcgtgaa cgaagaggat attaagggct  1920
acagagtgac cagcaccggc aagcccgagt tcaccaacct gaaggtgtac cacgacatca  1980
aggacattac cgcccggaaa gagattattg agaacgccga gctgctggat cagattgcca  2040
agatcctgac catctaccag agcagcgagg acatccagga agaactgacc aatctgaact  2100
ccgagctgac ccaggaagag atcgagcaga tctctaatct gaagggctat accggcaccc  2160
acaacctgag cctgaaggcc atcaacctga tcctggacga gctgtggcac accaacgaca  2220
accagatcgc tatcttcaac cggctgaagc tggtgcccaa gaaggtggac ctgtcccagc  2280
agaaagagat ccccaccacc ctggtggacg acttcatcct gagccccgtc gtgaagagaa  2340
```

| | |
|---|---|
| gcttcatcca gagcatcaaa gtgatcaacg ccatcatcaa gaagtacggc ctgcccaacg | 2400 |
| acatcattat cgagctggcc cgcgagaaga actccaagga cgcccagaaa atgatcaacg | 2460 |
| agatgcagaa gcggaaccgg cagaccaacg agcggatcga ggaaatcatc cggaccaccg | 2520 |
| gcaaagagaa cgccaagtac ctgatcgaga agatcaagct gcacgacatg caggaaggca | 2580 |
| agtgcctgta cagcctggaa gccatccctc tggaagatct gctgaacaac cccttcaact | 2640 |
| atgaggtgga cgccatcatc cccagaagcg tgtccttcga caacagcttc aacaacaagg | 2700 |
| tgctcgtgaa gcaggaagaa gccagcaaga agggcaaccg accccattc cagtacctga | 2760 |
| gcagcagcga cagcaagatc agctacgaaa ccttcaagaa gcacatcctg aatctggcca | 2820 |
| agggcaaggg cagaatcagc aagaccaaga aagagtatct gctggaagaa cgggacatca | 2880 |
| acaggttctc cgtgcagaaa gacttcatca accggaacct ggtggatacc agatacgcca | 2940 |
| ccagaggcct gatgaacctg ctgcggagct acttcagagt gaacaacctg gacgtgaaag | 3000 |
| tgaagtccat caatggcggc ttcaccagct ttctgcggcg gaagtggaag tttaagaaag | 3060 |
| agcggaacaa ggggtacaag caccacgccg aggacgccct gatcattgcc aacgccgatt | 3120 |
| tcatcttcaa agagtggaag aaactggaca aggccaaaaa agtgatggaa accagatgt | 3180 |
| tcgaggaaaa gcaggccgag agcatgcccg agatcgaaac cgagcaggag tacaaagaga | 3240 |
| tcttcatcac cccccaccag atcaagcaca ttaaggactt caaggactac aagtacagcc | 3300 |
| accgggtgga caagaagcct aatagagagc tgattaacga caccctgtac tccacccgga | 3360 |
| aggacgacaa gggcaacacc ctgatcgtga caatctgaa cggcctgtac gacaaggaca | 3420 |
| atgacaagct gaaaaagctg atcaacaaga gccccgaaaa gctgctgatg taccaccacg | 3480 |
| accccagac ctaccagaaa ctgaagctga ttatggaaca gtacggcgac gagaagaatc | 3540 |
| ccctgtacaa gtactacgag gaaaccggga actacctgac caagtactcc aaaaaggaca | 3600 |
| acggccccgt gatcaagaag attaagtatt acggcaacaa actgaacgcc catctggaca | 3660 |
| tcaccgacga ctaccccaac agcagaaaca aggtcgtgaa gctgtccctg aagcccctaca | 3720 |
| gattcgacgt gtacctggac aatggcgtgt acaagttcgt gaccgtgaag atctggatg | 3780 |
| tgatcaaaaa agaaaactac tacgaagtga atagcaagtg ctatgaggaa gctaagaagc | 3840 |
| tgaagaagat cagcaaccag gccgagttta tcgcctcctt ctacaacaac gatctgatca | 3900 |
| agatcaacgg cgagctgtat agagtgatcg gcgtgaacaa cgacctgctg aaccggatcg | 3960 |
| aagtgaacat gatcgacatc acctaccgcg agtacctgga aaacatgaac gacaagaggc | 4020 |
| cccccaggat cattaagaca atcgcctcca gacccagag cattaagaag tacagcacag | 4080 |
| acattctggg caacctgtat gaagtgaaat ctaagaagca ccctcagatc atcaaaaagg | 4140 |
| gcaaaaggcc ggcggccacg aaaaaggccg ccaggcaaa aaagaaaaag ggatccggtg | 4200 |
| ctagagatgc actcgatgat tttgacctcg atatgcttgg gagtgatgcg ctcgatgact | 4260 |
| tcgatttgga tatgcttgga tctgatgccc tcgacgattt cgaccttgat atgctcgggt | 4320 |
| cagacgcttt ggatgacttt gaccttgaca tgctggggag cggctccccc gcaccggcag | 4380 |
| ttacaccgga ggccagtcac ttgctcgaag atcctgacga ggaaaccagc caggccgtaa | 4440 |
| aggcgttgcg ggagatggct gacacagtaa taccccaaaa agaggaggct gcgatttgtg | 4500 |
| ggcagatgga tttgtcccac cctccaccga gaggtcatct tgacgaattg acaacgacgc | 4560 |
| tcgaatccat gaccgaggac ctgaacctcg atagcccgct cacccccgag ttgaatgaga | 4620 |
| tcctggatac atttcttaat gatgagtgtt tgcttcacgc aatgcatatt tctacgggtc | 4680 |
| ttagtatttt cgacacgagc ctgtttgtcg actgagaatt cctagagctc gctgatcagc | 4740 |

```
ctcgactgtg ccttctagtt gccagccatc tgttgtttgc ccctcccccg tgccttcctt      4800
gaccctggaa ggtgccactc ccactgtcct ttcctaataa aatgaggaaa ttgcatcgca      4860
ttgtctgagt aggtgtcatt ctattctggg gggtggggtg gggcaggaca gcaaggggga      4920
ggattgggaa gagaatagca ggcatgctgg ggaggtaccg agggcctatt tcccatgatt      4980
ccttcatatt tgcatatacg atacaaggct gttagagaga taattggaat taatttgact      5040
gtaaacacaa agatattagt acaaaatacg tgacgtagaa agtaataatt tcttgggtag      5100
tttgcagttt taaaattatg ttttaaaatg gactatcata tgcttaccgt aacttgaaag      5160
tatttcgatt tcttggcttt atatatcttg tggaaaggac gaaacaccgg agaccacggc      5220
aggtctcagt tttagtactc tggaaacaga atctactaaa acaaggcaaa atgccgtgtt      5280
tatctcgtca acttgttggc gagattttc cggccgcgat ctaggaaccc ctagtgatgg      5340
agttggccac tccctctctg cgcgctcgct cgctcactga ggccgggcga ccaaaggtcg      5400
cccgacgccc gggctttgcc cgggcggcct cagtgagcga gcgagcgcgc agctgcctgc      5460
aggcagcttg gcactggccg tcgttttaca acgtcgtgac tgggaaaacc ctggcgttac      5520
ccaacttaat cgccttgcag cacatccccc tttcgccagc tggcgtaata gcgaagaggc      5580
ccgcaccgat cgcccttccc aacagttgcg cagcctgaat ggcgaatggc gcctgatgcg      5640
gtattttctc cttacgcatc tgtgcggtat ttcacaccgc atacgtcaaa gcaaccatag      5700
tacgcgccct gtagcggcgc attaagcgcg gcgggtgtgg tggttacgcg cagcgtgacc      5760
gctacacttg ccagcgccct agcgcccgct cctttcgctt tcttcccttc ctttctcgcc      5820
acgttcgccg gctttccccg tcaagctcta aatcggggc tcccctttagg gttccgattt      5880 agtgctttac ggcacctcga cccaaaaaaa cttgatttgg gtgatggttc acgtagtggg      5940
ccatcgccct gatagacggt ttttcgccct ttgacgttgg agtccacgtt ctttaatagt      6000
ggactcttgt tccaaactgg aacaacactc aaccctatct cgggctattc ttttgattta      6060
taagggattt tgccgatttc ggcctattgg ttaaaaaatg agctgattta acaaaaattt      6120
aacgcgaatt ttaacaaaat attaacgttt acaattttat ggtgcactct cagtacaatc      6180
tgctctgatg ccgcatagtt aagccagccc cgacacccgc caacacccgc tgacgcgccc      6240
tgacgggctt gtctgctccc ggcatccgct tacagacaag ctgtgaccgt ctccgggagc      6300
tgcatgtgtc agaggttttc accgtcatca ccgaaacgcg cgagacgaaa gggcctcgtg      6360
atacgcctat ttttataggt taatgtcatg ataataatgg tttcttagac gtcaggtggc      6420
acttttcggg gaaatgtgcg cggaaccct atttgtttat ttttctaaat acattcaaat      6480
atgtatccgc tcatgagaca ataaccctga taaatgcttc aataatattg aaaaaggaag      6540
agtatgagta ttcaacattt ccgtgtcgcc cttattccct tttttgcggc attttgcctt      6600
cctgtttttg ctcacccaga aacgctggtg aaagtaaaag atgctgaaga tcagttgggt      6660
gcacgagtgg gttacatcga actggatctc aacagcggta agatccttga gagttttcgc      6720
cccgaagaac gttttccaat gatgagcact tttaaagttc tgctatgtgg cgcggtatta      6780
tcccgtattg acgccgggca agagcaactc ggtcgccgca tacactattc tcagaatgac      6840
ttggttgagt actcaccagt cacagaaaag catcttacgg atggcatgac agtaagagaa      6900
ttatgcagtg ctgccataac catgagtgat aacactgcgg ccaacttact tctgacaacg      6960
atcggaggac cgaaggagct aaccgctttt ttgcacaaca tgggggatca tgtaactcgc      7020
cttgatcgtt gggaaccgga gctgaatgaa gccataccaa acgacgagcg tgacaccacg      7080
```

```
atgcctgtag caatggcaac aacgttgcgc aaactattaa ctggcgaact acttactcta    7140
gcttcccggc aacaattaat agactggatg gaggcggata agttgcagg accacttctg     7200
cgctcggccc ttccggctgg ctggtttatt gctgataaat ctggagccgg tgagcgtgga    7260
agccgcggta tcattgcagc actggggcca gatggtaagc cctcccgtat cgtagttatc    7320
tacacgacgg ggagtcaggc aactatggat gaacgaaata gacagatcgc tgagataggt    7380
gcctcactga ttaagcattg gtaactgtca gaccaagttt actcatatat actttagatt    7440
gatttaaaac ttcatttta atttaaaagg atctaggtga agatccttt tgataatctc      7500
atgaccaaaa tcccttaacg tgagttttcg ttccactgag cgtcagaccc cgtagaaaag    7560
atcaaaggat cttcttgaga tccttttttt ctgcgcgtaa tctgctgctt gcaaacaaaa    7620
aaaccaccgc taccagcggt ggtttgtttg ccggatcaag agctaccaac tcttttccg     7680
aaggtaactg gcttcagcag agcgcagata ccaaatactg ttcttctagt gtagccgtag    7740
ttaggccacc acttcaagaa ctctgtagca ccgcctacat acctcgctct gctaatcctg    7800
ttaccagtgg ctgctgccag tggcgataag tcgtgtctta ccgggttgga ctcaagacga    7860
tagttaccgg ataaggcgca gcggtcgggc tgaacggggg gttcgtgcac acagcccagc    7920
ttggagcgaa cgacctacac cgaactgaga tacctacagc gtgagctatg agaaagcgcc    7980
acgcttcccg aagggagaaa ggcggacagg tatccggtaa gcggcagggt cggaacagga    8040
gagcgcacga gggagcttcc aggggggaaac gcctggtatc tttatagtcc tgtcgggttt    8100
cgccacctct gacttgagcg tcgatttttg tgatgctcgt caggggggcg gagcctatgg    8160
aaaaacgcca gcaacgcggc cttttacgg ttcctggcct tttgctggcc ttttgctcac      8220
atgttctttc ctgcgttatc ccctgattct gtggataacc gtattaccgc ctttgagtga    8280
gctgatac                                                               8288
```

<210> SEQ ID NO 211
<211> LENGTH: 8090
<212> TYPE: DNA
<213> ORGANISM: Artificial Sequence
<220> FEATURE:
<223> OTHER INFORMATION: pED261 plasmid

<400> SEQUENCE: 211

```
cgctcgccgc agccgaacga ccgagcgcag cgagtcagtg agcgaggaag cggaagagcg      60
cccaatacgc aaaccgcctc tccccgcgcg ttggccgatt cattaatgca gctggcacga    120
caggtttccc gactggaaag cgggcagtga gcgcaacgca attaatgtga gttagctcac    180
tcattaggca ccccaggctt tacactttat gcttccggct cgtatgttgt gtggaattgt    240
gagcggataa caatttcaca caggaaacag ctatgaccat gattacgaat tgcctgcagg    300
cagctgcgcg ctcgctcgct cactgaggcc gcccgggcaa agcccgggcg tcgggcgacc    360
tttggtcgcc cggcctcagt gagcgagcga gcgcgcagag agggagtggc caactccatc    420
actaggggtt cctatcgata tcactcgagg cgttgctaga ctagcatgct gcccatgtaa    480
ggaggcaagg cctggggaca cccgagatgc ctggttataa ttaacccaga catgtggctg    540
ccccccccc cccaacacct gctgcctcta aaaataaccc tgcatgccat gttcccggcg    600
aagggccagc tgtccccgc cagctagact cagcacttag tttaggaacc agtgagcaag    660
tcagccctgg ggcagccca tacaaggcca tgggctggg caagctgcac gcctgggtcc       720
ggggtgggca cggtgcccgg gcaacgagct gaaagctcat ctgctctcag ggccccctcc    780
ctggggacag cccctcctgg ctagtcacac cctgtaggct cctctatata acccaggggc    840
```

```
acaggggctg ccctcattct accaccacct ccacagcaca gacagacact caggagccag   900
ccagcagagc tctctggcta actaccggtg ccaccatggc cccaaagaag aagcggaagg   960
tcggtatcca cggagtccca gcagccaagc ggaactacat cctgggcctg gccatcggca  1020
tcaccagcgt gggctacggc atcatcgact acgagacacg ggacgtgatc gatgccggcg  1080
tgcggctgtt caaagaggcc aacgtggaaa caacgagggc aggcggagc aagagaggcg  1140
ccagaaggct gaagcggcgg aggcggcata gaatccagga gtgaagaag ctgctgttcg  1200
actacaacct gctgaccgac cacagcgagc tgagcggcat caaccctac gaggccagag  1260
tgaagggcct gagccagaag ctgagcgagg aagagttctc tgccgccctg ctgcacctgg  1320
ccaagagaag aggcgtgcac aacgtgaacg aggtggaaga ggacaccggc aacgagctgt  1380
ccaccaaaga gcagatcagc cggaacagca aggccctgga agagaaatac gtggccgaac  1440
tgcagctgga acggctgaag aaagacggcg aagtgcgggg cagcatcaac agattcaaga  1500
ccagcgacta cgtgaaagaa gccaaacagc tgctgaaggt gcagaaggcc taccaccagc  1560
tggaccagag cttcatcgac acctacatcg acctgctgga aacccggcgg acctactatg  1620
agggacctgg cgagggcagc cccttcggct ggaaggacat caaagaatgg tacgagatgc  1680
tgatgggcca ctgcacctac ttccccgagg aactgcggag cgtgaagtac gcctacaacg  1740
ccgacctgta caacgccctg aacgaccfga acaatctcgt gatcaccagg acgagaacg  1800
agaagctgga atattacgag aagttccaga tcatcgagaa cgtgttcaag cagaagaaga  1860
agcccaccct gaagcagatc gccaaagaaa tcctcgtgaa cgaagaggat attaagggct  1920
acagagtgac cagcaccggc aagcccgagt tcaccaacct gaaggtgtac cacgacatca  1980
aggacattac cgcccggaaa gagattattg agaacgccga gctgctggat cagattgcca  2040
agatcctgac catctaccag agcagcgagg acatccagga agaactgacc aatctgaact  2100
ccgagctgac ccaggaagag atcgagcaga tctctaatct gaagggctat accggcaccc  2160
acaacctgag cctgaaggcc atcaacctga tcctggacga gctgtggcac accaacgaca  2220
accagatcgc tatcttcaac cggctgaagc tggtgcccaa gaaggtggac ctgtcccagc  2280
agaaagagat ccccaccacc ctggtggacg acttcatcct gagccccgtc gtgaagagaa  2340
gcttcatcca gagcatcaaa gtgatcaacg ccatcatcaa gaagtacggc ctgcccaacg  2400
acatcattat cgagctggcc cgcgagaaga actccaagga cgcccagaaa atgatcaacg  2460
agatgcagaa gcggaaccgg cagaccaacg agcggatcga ggaaatcatc cggaccaccg  2520
gcaaagagaa cgccaagtac ctgatcgaga gatcaagct gcacgacatg caggaaggca  2580
agtgcctgta cagcctggaa gccatccctc tggaagatct gctgaacaac cccttcaact  2640
atgaggtgga cgccatcatc ccagaagcg tgtccttcga caacagcttc aacaacaagg  2700
tgctcgtgaa gcaggaagaa gccagcaaga agggcaaccg gaccccattc cagtacctga  2760
gcagcagcga cagcaagatc agctacgaaa ccttcaagaa gcacatcctg aatctggcca  2820
agggcaaggg cagaatcagc aagaccaaga aagagtatct gctggaagaa cgggacatca  2880
acaggttctc cgtgcagaaa gacttcatca accggaacct ggtggatacc agatacgcca  2940
ccagaggcct gatgaacctg ctgcggagct acttcagagt gaacaacctg gacgtgaaag  3000
tgaagtccat caatggcggc ttcaccagct ttctgcggcg gaagtggaag tttaagaaag  3060
agcggaacaa ggggtacaag caccacgccg gaacgccct gatcattgcc aacgccgatt  3120
tcatcttcaa agagtggaag aaactggaca aggccaaaaa agtgatggaa aaccagatgt  3180
```

```
tcgaggaaaa gcaggccgag agcatgcccg agatcgaaac cgagcaggag tacaaagaga   3240
tcttcatcac cccccaccag atcaagcaca ttaaggactt caaggactac aagtacagcc   3300
accgggtgga caagaagcct aatagagagc tgattaacga caccctgtac tccacccgga   3360
aggacgacaa gggcaacacc ctgatcgtga acaatctgaa cggcctgtac gacaaggaca   3420
atgacaagct gaaaaagctg atcaacaaga gccccgaaaa gctgctgatg taccaccacg   3480 accccagac ctaccagaaa ctgaagctga ttatggaaca gtacggcgac gagaagaatc   3540
ccctgtacaa gtactacgag gaaaccggga actacctgac caagtactcc aaaaaggaca   3600 acggcccgt gatcaagaag attaagtatt acggcaacaa actgaacgcc catctggaca   3660
tcaccgacga ctaccccaac agcagaaaca aggtcgtgaa gctgtccctg aagccctaca   3720
gattcgacgt gtacctggac aatggcgtgt acaagttcgt gaccgtgaag aatctggatg   3780
tgatcaaaaa agaaaactac tacgaagtga atagcaagtg ctatgaggaa gctaagaagc   3840
tgaagaagat cagcaaccag gccgagttta tcgcctcctt ctacaacaac gatctgatca   3900
agatcaacgg cgagctgtat agagtgatcg gcgtgaacaa cgacctgctg aaccggatcg   3960
aagtgaacat gatcgacatc acctaccgcg agtacctgga aaacatgaac gacaagaggc   4020
cccccaggat cattaagaca atcgcctcca agacccagag cattaagaag tacagcacag   4080
acattctggg caacctgtat gaagtgaaat ctaagaagca ccctcagatc atcaaaaagg   4140
gcaaaaggcc ggcggccacg aaaaaggcgg ccaggcaaa aagaaaaag ggatccggtg   4200 ctagagatgc actcgatgat tttgacctcg atatgcttgg gagtgatgcg ctcgatgact   4260
tcgatttgga tatgcttgga tctgatgccc tcgacgattt cgaccttgat atgctcgggt   4320
cagacgcttt ggatgacttt gaccttgaca tgctggggag cggctccccc gcaccggcag   4380
ttacaccgga ggccagtcac ttgctcgaag atcctgacga ggaaaccagc caggccgtaa   4440
aggcgttgcg ggagatggct gacacagtaa taccccaaaa agaggaggct gcgatttgtg   4500
ggcagatgga tttgtcccac cctccaccga gaggtcatct tgacgaattg acaacgacgc   4560
tcgaatccat gaccgaggac ctgaacctcg atagcccgct cacccccgag ttgaatgaga   4620
tcctggatac atttcttaat gatgagtgtt tgcttcacgc aatgcatatt tctacgggtc   4680
ttagtatttt cgacacgagc ctgtttgtcg actgagaatt caaataaaat acgaaatgaa   4740
ataaaatacg aaatgggtac cgagggccta tttcccatga ttccttcata tttgcatata   4800
cgatacaagg ctgttagaga gataattgga attaatttga ctgtaaacac aaagatatta   4860
gtacaaaata cgtgacgtag aaagtaataa tttcttgggt agtttgcagt tttaaaatta   4920
tgttttaaaa tggactatca tatgcttacc gtaacttgaa agtatttcga tttcttggct   4980
ttatatatct tgtggaaagg acgaaacacc ggagaccacg gcaggtctca gttttagtac   5040
tctggaaaca gaatctacta aaacaaggca aaatgccgtg tttatctcgt caacttgttg   5100
gcgagatttt tgcggccgcg atctaggaac ccctagtgat ggagttggcc actccctctc   5160
tgcgcgctcg ctcgctcact gaggccgggc gaccaaaggt cgcccgacgc ccgggctttg   5220
cccgggcggc ctcagtgagc gagcgagcgc gcagctgcct gcaggcagct tggcactggc   5280
cgtcgtttta acgtcgtg actgggaaaa ccctggcgtt acccaactta atcgccttgc   5340
agcacatccc cctttcgcca gctggcgtaa tagcgaagag gcccgcaccg atcgcccttc   5400
ccaacagttg cgcagcctga atggcgaatg gcgcctgatg cggtattttc tccttacgca   5460
tctgtgcggt atttcacacc gcatacgtca agcaaccat agtacgcgcc ctgtagcggc   5520
gcattaagcg cggcgggtgt ggtggttacg cgcagcgtga ccgctacact tgccagcgcc   5580
```

```
ctagcgcccg ctcctttcgc tttcttccct tcctttctcg ccacgttcgc cggctttccc    5640
cgtcaagctc taaatcgggg gctcccttta gggttccgat ttagtgcttt acggcacctc    5700
gaccccaaaa aacttgattt gggtgatggt tcacgtagtg ggccatcgcc ctgatagacg    5760 gttttcgcc ctttgacgtt ggagtccacg ttctttaata gtggactctt gttccaaact    5820
ggaacaacac tcaaccctat ctcgggctat tcttttgatt tataagggat tttgccgatt    5880
tcggcctatt ggttaaaaaa tgagctgatt taacaaaaat ttaacgcgaa ttttaacaaa    5940
atattaacgt ttacaatttt atggtgcact ctcagtacaa tctgctctga tgccgcatag    6000
ttaagccagc cccgacaccc gccaacaccc gctgacgcgc cctgacgggc ttgtctgctc    6060
ccggcatccg cttacagaca agctgtgacc gtctccggga gctgcatgtg tcagaggttt    6120
tcaccgtcat caccgaaacg cgcgagacga aagggcctcg tgatacgcct attttatag    6180 gttaatgtca tgataataat ggtttcttag acgtcaggtg gcacttttcg ggaaatgtg    6240 cgcggaaccc ctatttgttt atttttctaa atacattcaa atatgtatcc gctcatgaga    6300
caataaccct gataaatgct tcaataatat tgaaaaagga agagtatgag tattcaacat    6360
ttccgtgtcg cccttattcc cttttttgcg gcattttgcc ttcctgtttt tgctcaccca    6420
gaaacgctgg tgaaagtaaa agatgctgaa gatcagttgg gtgcacgagt gggttacatc    6480
gaactggatc tcaacagcgg taagatcctt gagagttttc gccccgaaga acgttttcca    6540
atgatgagca cttttaaagt tctgctatgt ggcgcggtat tatcccgtat tgacgccggg    6600
caagagcaac tcggtcgccg catacactat tctcagaatg acttggttga gtactcacca    6660
gtcacagaaa agcatcttac ggatggcatg acagtaagag aattatgcag tgctgccata    6720
accatgagtg ataacactgc ggccaactta cttctgacaa cgatcggagg accgaaggag    6780
ctaaccgctt ttttgcacaa catgggggat catgtaactc gccttgatcg ttgggaaccg    6840
gagctgaatg aagccatacc aaacgacgag cgtgacacca cgatgcctgt agcaatggca    6900
acaacgttgc gcaaactatt aactggcgaa ctacttactc tagcttcccg gcaacaatta    6960
atagactgga tggaggcgga taaagttgca ggaccacttc tgcgctcggc ccttccggct    7020
ggctggttta ttgctgataa atctggagcc ggtgagcgtg aagccgcgg tatcattgca    7080 gcactggggc cagatggtaa gccctcccgt atcgtagtta tctacacgac ggggagtcag    7140
gcaactatga tgaacgaaa tagacagatc gctgagatag gtgcctcact gattaagcat    7200
tggtaactgt cagaccaagt ttactcatat atactttaga ttgatttaaa acttcatttt    7260
taatttaaaa ggatctaggt gaagatcctt tttgataatc tcatgaccaa aatcccttaa    7320
cgtgagtttt cgttccactg agcgtcagac cccgtagaaa agatcaaagg atcttcttga    7380
gatccttttt ttctgcgcgt aatctgctgc ttgcaaacaa aaaaaccacc gctaccagcg    7440
gtggtttgtt tgccggatca agagctacca actctttttc cgaaggtaac tggcttcagc    7500
agagcgcaga taccaaatac tgttcttcta gtgtagccgt agttaggcca ccacttcaag    7560
aactctgtag caccgcctac atacctcgct ctgctaatcc tgttaccagt ggctgctgcc    7620
agtggcgata gtcgtgtct taccggggttg gactcaagac gatagttacc ggataaggcg    7680
cagcggtcgg gctgaacggg gggttcgtgc acacagccca gcttggagcg aacgacctac    7740
accgaactga gatacctaca gcgtgagcta tgagaaagcg ccacgcttcc cgaagggaga    7800
aaggcggaca ggtatccggt aagcggcagg gtcggaacag gagagcgcac gagggagctt    7860 ccaggggaa acgcctggta tctttatagt cctgtcgggt ttcgccacct ctgacttgag    7920
```

| | |
|---|---:|
| cgtcgatttt tgtgatgctc gtcagggggg cggagcctat ggaaaaacgc cagcaacgcg | 7980 |
| gccttttac ggttcctggc cttttgctgg ccttttgctc acatgttctt tcctgcgtta | 8040 |
| tcccctgatt ctgtggataa ccgtattacc gcctttgagt gagctgatac | 8090 |

<210> SEQ ID NO 212
<211> LENGTH: 8000
<212> TYPE: DNA
<213> ORGANISM: Artificial Sequence
<220> FEATURE:
<223> OTHER INFORMATION: pED263 plasmid

<400> SEQUENCE: 212

| | |
|---|---:|
| cgctcgccgc agccgaacga ccgagcgcag cgagtcagtg agcgaggaag cggaagagcg | 60 |
| cccaatacgc aaaccgcctc tccccgcgcg ttggccgatt cattaatgca gctggcacga | 120 |
| caggttttcc cgactggaaag cgggcagtga gcgaacgca attaatgtga gttagctcac | 180 |
| tcattaggca ccccaggctt tacactttat gcttccggct cgtatgttgt gtggaattgt | 240 |
| gagcggataa caatttcaca caggaaacag ctatgaccat gattacgaat tgcctgcagg | 300 |
| cagctgcgcg ctcgctcgct cactgaggcc gcccgggcaa agcccgggcg tcgggcgacc | 360 |
| tttggtcgcc cggcctcagt gagcgagcga gcgcgcagag agggagtggc caactccatc | 420 |
| actaggggtt cctatcgata tcactcgagg cgttgctaga ctagcatgct gcccatgtaa | 480 |
| ggaggcaagg cctggggaca cccgagatgc ctggttataa ttaacccaga catgtggctg | 540 |
| ccccccccc cccaacacct gctgcctcta aaaataaccc tgcatgccat gttcccggcg | 600 |
| aagggccagc tgtcccccgc cagctagact cagcacttag tttaggaacc agtgagcaag | 660 |
| tcagcccttg gggcagccca tacaaggcca tggggctggg caagctgcac gcctgggtcc | 720 |
| ggggtgggca cggtgcccgg gcaacgagct gaaagctcat ctgctctcag ggcccctcc | 780 |
| ctggggacag cccctcctgg ctagtcacac cctgtaggct cctctatata acccagggc | 840 |
| acaggggctg ccctcattct accaccacct ccacagcaca gacagacact caggagccag | 900 |
| ccagcagagc tctctggcta actaccggtg ccaccatggc cccaaagaag aagcggaagg | 960 |
| tcggtatcca cggagtccca gcagccaagc ggaactacat cctgggcctg gccatcggca | 1020 |
| tcaccagcgt gggctacggc atcatcgact acgagacacg ggacgtgatc gatgccggcg | 1080 |
| tgcggctgtt caaagaggcc aacgtggaaa caacgagggg caggcggagc aagagaggcg | 1140 |
| ccagaaggct gaagcggcgg aggcggcata gaatccagag agtgaagaag ctgctgttcg | 1200 |
| actacaacct gctgaccgac cacagcgagc tgagcggcat caaccctac gaggccagag | 1260 |
| tgaagggcct gagccagaag ctgagcgagg aagagttctc tgccgccctg ctgcacctgg | 1320 |
| ccaagagaag aggcgtgcac aacgtgaacg aggtggaaga ggacaccggc aacgagctgt | 1380 |
| ccaccaaaga gcagatcagc cggaacagca aggccctgga agagaaatac gtggccgaac | 1440 |
| tgcagctgga acggctgaag aaagacggcg aagtgcgggg cagcatcaac agattcaaga | 1500 |
| ccagcgacta cgtgaaagaa gccaaacagc tgctgaaggt gcagaaggcc taccaccagc | 1560 |
| tggaccagag cttcatcgac acctacatcg acctgctgga aacccggcgg acctactatg | 1620 |
| agggacctgg cgagggcagc cccttcggct ggaaggacat caaagaatgg tacgagatgc | 1680 |
| tgatgggcca ctgcacctac ttccccgagg aactgcggag cgtgaagtac gcctacaacg | 1740 |
| ccgacctgta caacgccctg aacgacctga acaatctcgt gatcaccagg gacgagaacg | 1800 |
| agaagctgga atattacgag aagttccaga tcatcgagaa cgtgttcaag cagaagaaga | 1860 |
| agcccaccct gaagcagatc gccaaagaaa tcctcgtgaa cgaagaggat attaagggct | 1920 |

```
acagagtgac cagcaccggc aagcccgagt tcaccaacct gaaggtgtac cacgacatca   1980
aggacattac cgcccggaaa gagattattg agaacgccga gctgctggat cagattgcca   2040
agatcctgac catctaccag agcagcgagg acatccagga gaactgacc aatctgaact    2100
ccgagctgac ccaggaagag atcgagcaga tctctaatct gaagggctat accggcaccc   2160
acaacctgag cctgaaggcc atcaacctga tcctggacga gctgtggcac accaacgaca   2220
accagatcgc tatcttcaac cggctgaagc tggtgcccaa gaaggtggac ctgtcccagc   2280
agaaagagat ccccaccacc ctggtggacg acttcatcct gagccccgtc gtgaagagaa   2340
gcttcatcca gagcatcaaa gtgatcaacg ccatcatcaa gaagtacggc ctgcccaacg   2400
acatcattat cgagctggcc cgcgagaaga actccaagga cgcccagaaa atgatcaacg   2460
agatgcagaa gcggaaccgg cagaccaacg agcggatcga ggaaatcatc cggaccaccg   2520
gcaaagagaa cgccaagtac ctgatcgaga agatcaagct gcacgacatg caggaaggca   2580
agtgcctgta cagcctggaa gccatccctc tggaagatct gctgaacaac cccttcaact   2640
atgaggtgga cgccatcatc cccagaagcg tgtccttcga caacagcttc aacaacaagg   2700
tgctcgtgaa gcaggaagaa gccagcaaga agggcaaccg gacccccattc cagtacctga   2760
gcagcagcga cagcaagatc agctacgaaa ccttcaagaa gcacatcctg aatctggcca   2820
agggcaaggg cagaatcagc aagaccaaga aagagtatct gctggaagaa cgggacatca   2880
acaggttctc cgtgcagaaa gacttcatca accggaacct ggtggatacc agatacgcca   2940
ccagaggcct gatgaacctg ctgcggagct acttcagagt gaacaacctg gacgtgaaag   3000
tgaagtccat caatggcggc ttcaccagct ttctgcggcg gaagtggaag tttaagaaag   3060
agcggaacaa ggggtacaag caccacgccg aggacgccct gatcattgcc aacgccgatt   3120
tcatcttcaa agagtggaag aaactggaca aggccaaaaa agtgatggaa aaccagatgt   3180
tcgaggaaaa gcaggccgag agcatgcccg agatcgaaac cgagcaggag tacaaagaga   3240
tcttcatcac cccccaccag atcaagcaca ttaaggactt caaggactac aagtacagcc   3300
accgggtgga caagaagcct aatagagagc tgattaacga caccctgtac tccacccgga   3360
aggacgacaa gggcaacacc ctgatcgtga acaatctgaa cggcctgtac gacaaggaca   3420
atgacaagct gaaaaagctg atcaacaaga gccccgaaaa gctgctgatg taccaccacg   3480
accccccaga ctaccagaaa ctgaagctga ttatggaaca gtacggcgac gagaagaatc   3540
ccctgtacaa gtactacgag gaaaccggga ctacctgac caagtactcc aaaaaggaca   3600
acggcccccgt gatcaagaag attaagtatt acggcaacaa actgaacgcc catctggaca   3660
tcaccgacga ctaccccaac agcagaaaca aggtcgtgaa gctgtccctg aagcccctaca   3720
gattcgacgt gtacctggac aatggcgtgt acaagttcgt gaccgtgaag aatctggatg   3780
tgatcaaaaa agaaaactac tacgaagtga atagcaagtg ctatgaggaa gctaagaagc   3840
tgaagaagat cagcaaccag gccgagttta tcgcctcctt ctacaacaac gatctgatca   3900
agatcaacgg cgagctgtat agagtgatcg gcgtgaacaa cgacctgctg aaccggatcg   3960
aagtgaacat gatcgacatc acctaccgcg agtacctgga aaacatgaac gacaagaggc   4020
cccccaggat cattaagaca atcgcctcca agacccagag cattaagaag tacagcacag   4080
acattctggg caacctgtat gaagtgaaat ctaagaagca ccctcagatc atcaaaaagg   4140
gcaaaaggcc ggcggccacg aaaaaggccg gccaggcaaa aaagaaaaag ggatccgatg   4200
cactcgatga ttttgacctc gatatgcttg ggagtgatgc gctcgatgac ttcgatttgg   4260
```

```
atatgcttgg atctgatgcc ctcgacgatt tcgaccttga tatgctcggg tcagacgctt    4320
tggatgactt tgaccttgac atgctgggga gcggctcccg ggagatggct gacacagtaa    4380
taccccaaaa agaggaggct gcgatttgtg ggcagatgga tttgtcccac cctccaccga    4440
gaggtcatct tgacgaattg acaacgacgc tcgaatccat gaccgaggac ctgaacctcg    4500
atagcccgct cacccccgag ttgaatgaga tcctggatac atttcttaat gatgagtgtt    4560
tgcttcacgc aatgcatatt tctacgggtc ttagtatttt cgacacgagc ctgtttgtcg    4620
actgagaatt caaataaaat acgaaatgaa ataaaatacg aaatgggtac cgagggccta    4680
tttcccatga ttccttcata tttgcatata cgatacaagg ctgttagaga gataattgga    4740
attaatttga ctgtaaacac aaagatatta gtacaaaata cgtgacgtag aaagtaataa    4800
tttcttgggt agtttgcagt tttaaaatta tgttttaaaa tggactatca tatgcttacc    4860
gtaacttgaa agtatttcga tttcttggct ttatatatct tgtggaaagg acgaaacacc    4920
ggagaccacg gcaggtctca gttttagtac tctggaaaca gaatctacta aaacaaggca    4980
aaatgccgtg tttatctcgt caacttgttg gcgagatttt tgcggccgcg atctaggaac    5040
ccctagtgat ggagttggcc actccctctc tgcgcgctcg ctcgctcact gaggccgggc    5100
gaccaaaggt cgcccgacgc ccgggctttg cccgggcggc ctcagtgagc gagcgagcgc    5160
gcagctgcct gcaggcagct tggcactggc cgtcgtttta caacgtcgtg actgggaaaa    5220
ccctggcgtt acccaactta atcgccttgc agcacatccc cctttcgcca gctggcgtaa    5280
tagcgaagag gcccgcaccg atcgcccttc ccaacagttg cgcagcctga atggcgaatg    5340
gcgcctgatg cggtattttc tccttacgca tctgtgcggt atttcacacc gcatacgtca    5400
aagcaaccat agtacgcgcc ctgtagcggc gcattaagcg cggcgggtgt ggtggttacg    5460
cgcagcgtga ccgctacact tgccagcgcc ctagcgcccg ctcctttcgc tttcttccct    5520
tcctttctcg ccacgttcgc cggctttccc cgtcaagctc taaatcgggg ctccctttta    5580
gggttccgat ttagtgcttt acggcacctc gaccccaaaa aacttgattt gggtgatggt    5640
tcacgtagtg ggccatcgcc ctgatagacg ttttttcgcc ctttgacgtt ggagtccacg    5700
ttctttaata gtggactctt gttccaaact ggaacaacac tcaaccctat ctcgggctat    5760
tcttttgatt tataagggat tttgccgatt tcggcctatt ggttaaaaaa tgagctgatt    5820
taacaaaaat ttaacgcgaa ttttaacaaa atattaacgt ttacaatttt atggtgcact    5880
ctcagtacaa tctgctctga tgccgcatag ttaagccagc cccgacaccc gccaacaccc    5940
gctgacgcgc cctgacgggc ttgtctgctc ccggcatccg cttacagaca agctgtgacc    6000
gtctccggga gctgcatgtg tcagaggttt tcaccgtcat caccgaaacg cgcgagacga    6060
aagggcctcg tgatacgcct atttttatag gttaatgtca tgataataat ggtttcttag    6120
acgtcaggtg gcacttttcg ggaaatgtgc gcggaaccc ctatttgttt attttttctaa    6180
atacattcaa atatgtatcc gctcatgaga caataaccct gataaatgct tcaataatat    6240
tgaaaaagga agagtatgag tattcaacat ttccgtgtcg cccttattcc cttttttgcg    6300
gcatttttgcc ttcctgtttt tgctcaccca gaaacgctgg tgaaagtaaa agatgctgaa    6360
gatcagttgg gtgcacgagt gggttacatc gaactggatc tcaacagcgg taagatcctt    6420
gagagttttc gccccgaaga acgttttcca atgatgagca cttttaaagt tctgctatgt    6480
ggcgcggtat tatcccgtat tgacgccggg caagagcaac tcggtcgccg catacactat    6540
tctcagaatg acttggttga gtactcacca gtcacagaaa agcatcttac ggatggcatg    6600
acagtaagag aattatgcag tgctgccata accatgagtg ataacactgc ggccaactta    6660
```

```
cttctgacaa cgatcggagg accgaaggag ctaaccgctt ttttgcacaa catgggggat    6720
catgtaactc gccttgatcg ttgggaaccg gagctgaatg aagccatacc aaacgacgag    6780
cgtgacacca cgatgcctgt agcaatggca acaacgttgc gcaaactatt aactggcgaa    6840
ctacttactc tagcttcccg gcaacaatta atagactgga tggaggcgga taaagttgca    6900
ggaccacttc tgcgctcggc ccttccggct ggctggttta ttgctgataa atctggagcc    6960
ggtgagcgtg gaagccgcgg tatcattgca gcactgggc cagatggtaa gccctcccgt     7020
atcgtagtta tctacacgac ggggagtcag gcaactatgg atgaacgaaa tagacagatc    7080
gctgagatag gtgcctcact gattaagcat tggtaactgt cagaccaagt ttactcatat    7140
atactttaga ttgatttaaa acttcatttt taatttaaaa ggatctaggt gaagatcctt    7200
tttgataatc tcatgaccaa aatcccttaa cgtgagtttt cgttccactg agcgtcagac    7260
cccgtagaaa agatcaaagg atcttcttga gatccttttt ttctgcgcgt aatctgctgc    7320
ttgcaaacaa aaaaccacc gctaccagcg gtggtttgtt tgccggatca agagctacca     7380 actcttttc cgaaggtaac tggcttcagc agagcgcaga taccaaatac tgttcttcta    7440
gtgtagccgt agttaggcca ccacttcaag aactctgtag caccgcctac atacctcgct    7500
ctgctaatcc tgttaccagt ggctgctgcc agtggcgata agtcgtgtct taccgggttg    7560
gactcaagac gatagttacc ggataaggcg cagcggtcgg gctgaacggg gggttcgtgc    7620
acacagccca gcttggagcg aacgacctac accgaactga gatacctaca gcgtgagcta    7680
tgagaaagcg ccacgcttcc cgaagggaga aaggcggaca ggtatccggt aagcggcagg    7740
gtcggaacag gagagcgcac gagggagctt ccaggggaa acgcctggta tctttatagt      7800
cctgtcgggt ttcgccacct ctgacttgag cgtcgatttt tgtgatgctc gtcaggggg     7860 cggagcctat ggaaaaacgc cagcaacgcg gcctttttac ggttcctggc cttttgctgg     7920 cctttttgctc acatgttctt tcctgcgtta tcccctgatt ctgtggataa ccgtattacc     7980
gcctttgagt gagctgatac                                               8000
```

<210> SEQ ID NO 213
<211> LENGTH: 5
<212> TYPE: PRT
<213> ORGANISM: Artificial Sequence
<220> FEATURE:
<223> OTHER INFORMATION: SGGGS linker

<400> SEQUENCE: 213

Ser Gly Gly Gly Ser
1               5

<210> SEQ ID NO 214
<211> LENGTH: 1033
<212> TYPE: PRT
<213> ORGANISM: Artificial Sequence
<220> FEATURE:
<223> OTHER INFORMATION: amino acid residues (721st to 745th amino acid
      residues of dSaCas9) deletion mutant with SGGGS linker
<220> FEATURE:
<221> NAME/KEY: VARIANT
<222> LOCATION: (10)..(10)
<223> OTHER INFORMATION: conversion of Asp residue into Ala residue
<220> FEATURE:
<221> NAME/KEY: VARIANT
<222> LOCATION: (580)..(580)
<223> OTHER INFORMATION: conversion of Asn residue into Ala residue
<220> FEATURE:
<221> NAME/KEY: SITE
<222> LOCATION: (721)..(725)

<223> OTHER INFORMATION: SGGGS linker

<400> SEQUENCE: 214

Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

```
Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Arg Thr Thr
                500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
        530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Ala Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
        610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
        690                 695                 700

Ala Leu Ile Ile Ala Asn Ala Asp Phe Ile Phe Lys Glu Trp Lys Lys
705                 710                 715                 720

Ser Gly Gly Gly Ser Thr Glu Gln Glu Tyr Lys Glu Ile Phe Ile Thr
                725                 730                 735

Pro His Gln Ile Lys His Ile Lys Asp Phe Lys Asp Tyr Lys Tyr Ser
                740                 745                 750

His Arg Val Asp Lys Lys Pro Asn Arg Glu Leu Ile Asn Asp Thr Leu
            755                 760                 765

Tyr Ser Thr Arg Lys Asp Asp Lys Gly Asn Thr Leu Ile Val Asn Asn
        770                 775                 780

Leu Asn Gly Leu Tyr Asp Lys Asp Asn Asp Lys Leu Lys Lys Leu Ile
785                 790                 795                 800

Asn Lys Ser Pro Glu Lys Leu Leu Met Tyr His His Asp Pro Gln Thr
                805                 810                 815

Tyr Gln Lys Leu Lys Leu Ile Met Glu Gln Tyr Gly Asp Glu Lys Asn
```

```
                  820                 825                 830
Pro Leu Tyr Lys Tyr Tyr Glu Glu Thr Gly Asn Tyr Leu Thr Lys Tyr
            835                 840                 845

Ser Lys Lys Asp Asn Gly Pro Val Ile Lys Ile Lys Tyr Tyr Gly
    850                 855                 860

Asn Lys Leu Asn Ala His Leu Asp Ile Thr Asp Tyr Pro Asn Ser
865                 870                 875                 880

Arg Asn Lys Val Val Lys Leu Ser Leu Lys Pro Tyr Arg Phe Asp Val
                885                 890                 895

Tyr Leu Asp Asn Gly Val Tyr Lys Phe Val Thr Val Lys Asn Leu Asp
            900                 905                 910

Val Ile Lys Lys Glu Asn Tyr Glu Val Asn Ser Lys Cys Tyr Glu
        915                 920                 925

Glu Ala Lys Lys Leu Lys Lys Ile Ser Asn Gln Ala Glu Phe Ile Ala
            930                 935                 940

Ser Phe Tyr Asn Asn Asp Leu Ile Lys Ile Asn Gly Glu Leu Tyr Arg
945                 950                 955                 960

Val Ile Gly Val Asn Asn Asp Leu Leu Asn Arg Ile Glu Val Asn Met
                965                 970                 975

Ile Asp Ile Thr Tyr Arg Glu Tyr Leu Glu Asn Met Asn Asp Lys Arg
            980                 985                 990

Pro Pro Arg Ile Ile Lys Thr Ile Ala Ser Lys Thr Gln Ser Ile Lys
        995                 1000                1005

Lys Tyr Ser Thr Asp Ile Leu Gly Asn Leu Tyr Glu Val Lys Ser
    1010                1015                1020

Lys Lys His Pro Gln Ile Ile Lys Lys Gly
    1025                1030

<210> SEQ ID NO 215
<211> LENGTH: 21
<212> TYPE: RNA
<213> ORGANISM: Artificial Sequence
<220> FEATURE:
<223> OTHER INFORMATION: crRNA comprised in control sgRNA

<400> SEQUENCE: 215
acggaggcua agcgucgcaa g                                             21

<210> SEQ ID NO 216
<211> LENGTH: 519
<212> TYPE: PRT
<213> ORGANISM: Artificial Sequence
<220> FEATURE:
<223> OTHER INFORMATION: VPR

<400> SEQUENCE: 216

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Ser Ser Gly Ser Pro Lys Lys Lys Arg Lys Val Gly Ser Gln
    50                  55                  60

Tyr Leu Pro Asp Thr Asp Asp Arg His Arg Ile Glu Glu Lys Arg Lys
65                  70                  75                  80

Arg Thr Tyr Glu Thr Phe Lys Ser Ile Met Lys Lys Ser Pro Phe Ser
```

```
                    85                  90                  95
Gly Pro Thr Asp Pro Arg Pro Pro Arg Ile Ala Val Pro Ser
                100                 105                 110

Arg Ser Ser Ala Ser Val Pro Lys Pro Ala Pro Gln Pro Tyr Pro Phe
                115                 120                 125

Thr Ser Ser Leu Ser Thr Ile Asn Tyr Asp Glu Phe Pro Thr Met Val
            130                 135                 140

Phe Pro Ser Gly Gln Ile Ser Gln Ala Ser Ala Leu Ala Pro Ala Pro
145                 150                 155                 160

Pro Gln Val Leu Pro Gln Ala Pro Ala Pro Ala Pro Ala Pro Ala Met
                165                 170                 175

Val Ser Ala Leu Ala Gln Ala Pro Ala Pro Val Pro Val Leu Ala Pro
                180                 185                 190

Gly Pro Pro Gln Ala Val Ala Pro Ala Pro Lys Pro Thr Gln Ala
                195                 200                 205

Gly Glu Gly Thr Leu Ser Glu Ala Leu Leu Gln Leu Gln Phe Asp Asp
            210                 215                 220

Glu Asp Leu Gly Ala Leu Leu Gly Asn Ser Thr Asp Pro Ala Val Phe
225                 230                 235                 240

Thr Asp Leu Ala Ser Val Asp Asn Ser Glu Phe Gln Gln Leu Leu Asn
                245                 250                 255

Gln Gly Ile Pro Val Ala Pro His Thr Thr Glu Pro Met Leu Met Glu
                260                 265                 270

Tyr Pro Glu Ala Ile Thr Arg Leu Val Thr Gly Ala Gln Arg Pro Pro
                275                 280                 285

Asp Pro Ala Pro Ala Pro Leu Gly Ala Pro Gly Leu Pro Asn Gly Leu
            290                 295                 300

Leu Ser Gly Asp Glu Asp Phe Ser Ser Ile Ala Asp Met Asp Phe Ser
305                 310                 315                 320

Ala Leu Leu Gly Ser Gly Ser Gly Ser Arg Asp Ser Arg Glu Gly Met
                325                 330                 335

Phe Leu Pro Lys Pro Glu Ala Gly Ser Ala Ile Ser Asp Val Phe Glu
                340                 345                 350

Gly Arg Glu Val Cys Gln Pro Lys Arg Ile Arg Pro Phe His Pro Pro
                355                 360                 365

Gly Ser Pro Trp Ala Asn Arg Pro Leu Pro Ala Ser Leu Ala Pro Thr
            370                 375                 380

Pro Thr Gly Pro Val His Glu Pro Val Gly Ser Leu Thr Pro Ala Pro
385                 390                 395                 400

Val Pro Gln Pro Leu Asp Pro Ala Pro Ala Val Thr Pro Glu Ala Ser
                405                 410                 415

His Leu Leu Glu Asp Pro Asp Glu Glu Thr Ser Gln Ala Val Lys Ala
                420                 425                 430

Leu Arg Glu Met Ala Asp Thr Val Ile Pro Gln Lys Glu Glu Ala Ala
            435                 440                 445

Ile Cys Gly Gln Met Asp Leu Ser His Pro Pro Pro Arg Gly His Leu
            450                 455                 460

Asp Glu Leu Thr Thr Thr Leu Glu Ser Met Thr Glu Asp Leu Asn Leu
465                 470                 475                 480

Asp Ser Pro Leu Thr Pro Glu Leu Asn Glu Ile Leu Asp Thr Phe Leu
                485                 490                 495

Asn Asp Glu Cys Leu Leu His Ala Met His Ile Ser Thr Gly Leu Ser
                500                 505                 510
```

```
Ile Phe Asp Thr Ser Leu Phe
        515
```